US012746243B2

(12) United States Patent
Clare et al.

(10) Patent No.: US 12,746,243 B2
(45) Date of Patent: Sep. 29, 2026

(54) LOX ENZYME INHIBITING METHODS AND COMPOSITIONS

(71) Applicant: ANOVIA BIOSCIENCES, INC., New York, NY (US)

(72) Inventors: Michael Clare, New York, NY (US); Maria Kleppe, New York, NY (US); Xiang Li, Beijing (CN); Juan Du, Beijing (CN); Ronggang Liu, Berwyn, PA (US)

(73) Assignee: Anovia Biosciences, Inc., New York, NY (US)

( * ) Notice: Subject to any disclaimer, the term of this patent is extended or adjusted under 35 U.S.C. 154(b) by 911 days.

(21) Appl. No.: 17/920,382

(22) PCT Filed: Apr. 20, 2021

(86) PCT No.: PCT/US2021/028220

§ 371 (c)(1),
(2) Date: Oct. 20, 2022

(87) PCT Pub. No.: WO2021/216592

PCT Pub. Date: Oct. 28, 2021

(65) Prior Publication Data

US 2023/0310445 A1 Oct. 5, 2023

Related U.S. Application Data

(60) Provisional application No. 63/171,573, filed on Apr. 6, 2021, provisional application No. 63/013,049, filed on Apr. 21, 2020.

(51) Int. Cl.
*A61K 31/541* (2006.01)
*A61K 31/4545* (2006.01)
*A61K 31/497* (2006.01)
*A61K 31/5377* (2006.01)

(52) U.S. Cl.
CPC ........ *A61K 31/541* (2013.01); *A61K 31/4545* (2013.01); *A61K 31/497* (2013.01); *A61K 31/5377* (2013.01)

(58) Field of Classification Search
None
See application file for complete search history.

(56) References Cited

FOREIGN PATENT DOCUMENTS

| | | | | |
|---|---|---|---|---|
| EP | 21791992.7 | | 4/2021 | |
| JP | 2022-564596 | | 10/2022 | |
| WO | WO 2008/140810 | | 11/2008 | |
| WO | WO-2008140810 | A1 * | 11/2008 | ........... C07D 211/60 |
| WO | WO 2016/144703 | A1 | 9/2016 | |
| WO | WO 2017/003862 | | 1/2017 | |
| WO | WO 2017/141049 | | 8/2017 | |
| WO | WO 2019/073251 | A1 | 4/2019 | |
| WO | WO 2019/234418 | A1 | 12/2019 | |
| WO | WO PCT/US2021/028220 | | 4/2020 | |
| WO | WO 2021/216592 | | 10/2021 | |
| WO | WO PCT/US2022/048180 | | 10/2021 | |

OTHER PUBLICATIONS

Kumari et al. Lysyl Oxidase: Its Diversity in Health and Diseases Indian J Clin Biochem. May 11, 2016;32(2):134-141. (Year: 2016).*
Xu, H. et a. Experimental & Molecular Medicine (2019) 51:20 (Year: 2019).*
Leung, L. et al. J Med Chem. May 9, 2019;62(12):5863-5884 (Year: 2019).*
U.S. Appl. No. 63/013,049, filed Apr. 21, 2020, Michael Clare.
U.S. Appl. No. 63/171,573, filed Apr. 6, 2021, Michael Clare.
U.S. Appl. No. 63/273,090, filed Oct. 28, 2021, Michael Clare.
U.S. Appl. No. 18/265,422, filed Jun. 5, 2023, Michael Clare.
PubChem SID 308221703 Deposit Date: Jan. 30, 2016, pp. 1-5, p. 2.
PubChem SID 348802764 Deposit Date: Dec. 18, 2017, pp. 1-6, p. 2.
Abbonante, V., et al. (2017). "Upregulation of lysyl oxidase and adhesion to collagen of human megakaryocytes and platelets in primary myelofibrosis." Blood 130(6): 829-831.
Abourbih, D. A., et al. (2010). "Lysyl oxidase expression and inhibition in uveal melanoma." Melanoma Res 20(2): 97-106.
Al-U'datt, D., et al. (2019). "Role of the lysyl oxidase enzyme family in cardiac function and disease." Cardiovasc Res 115(13): 1820-1837.
Albinger-Hegyi, A., et al. (2010). "Lysyl oxidase expression is an independent marker of prognosis and a predictor of lymph node metastasis in oral and oropharyngeal squamous cell carcinoma (OSCC)." Int J Cancer 126(11): 2653-2662.
Almassian, B., et al. (1991). "Induction of lung lysyl oxidase activity and lysyl oxidase protein by exposure of rats to cadmium chloride: properties of the induced enzyme." Connect Tissue Res 25(3-4): 197-208.
Amendola, P. G., et al. (2019). "Interplay Between LOX Enzymes and Integrins in the Tumor Microenvironment." Cancers (Basel) 11(5).
Aumiller, V., et al. (2017). "Comparative analysis of lysyl oxidase (like) family members in pulmonary fibrosis." Sci Rep 7(1): 149.
Baker, A. M., et al. (2013). "Lysyl oxidase enzymatic function increases stiffness to drive colorectal cancer progression through FAK." Oncogene 32(14): 1863-1868.
Barker, H. E., et al. (2012). "The rationale for targeting the LOX family in cancer." Nat Rev Cancer 12(8): 540-552.

(Continued)

*Primary Examiner* — Clinton A Brooks
*Assistant Examiner* — Nicola Maria Bauer
(74) *Attorney, Agent, or Firm* — Ballard Spahr LLC

(57) ABSTRACT

This invention relates to compounds, pharmaceutical compositions and their use for treating fibrotic disorders, proliferative disorders, cardiovascular diseases, acute and chronic inflammatory disorders, primary and metastatic cancer, pulmonary conditions, ocular diseases, or neurological and neuropsychiatric conditions. One particular aspect of the inventions relates to inhibitors of the family of lysyl oxidase enzymes and their use as therapeutics for fibrotic disorders.

16 Claims, 3 Drawing Sheets

(56) References Cited

OTHER PUBLICATIONS

Figure 1A:
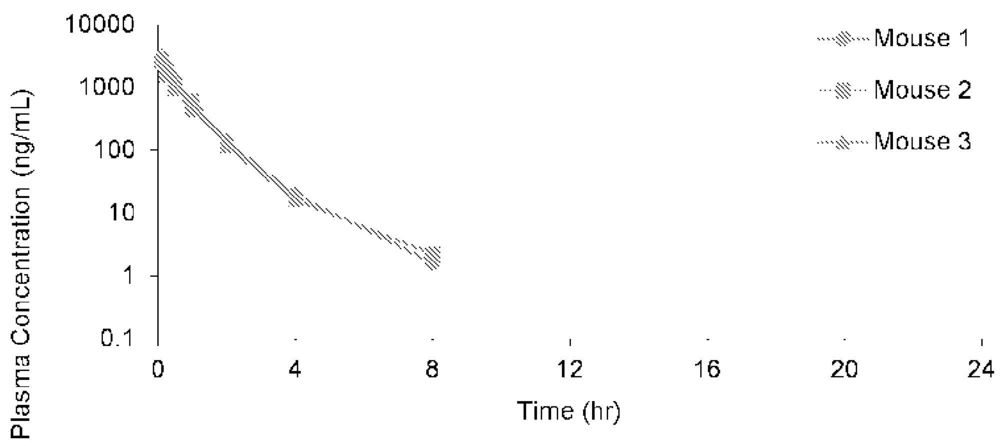

Borel, A., et al. (2001). "Lysyl oxidase-like protein from bovine aorta. Isolation and maturation to an active form by bone morphogenetic protein-1." J Biol Chem 276(52): 48944-48949.
Burke, A. A., et al. (2017). "Comparing hydrazine-derived reactive groups as inhibitors of quinone-dependent amine oxidases." J Enzyme Inhib Med Chem 32(1): 496-503.
Carter, E. A., et al. (1982). "Lysyl oxidase and collagenase in experimental acute and chronic liver injury." Gastroenterology 82(3): 526-534.
Chang, J., et al. (2017). "Pre-clinical evaluation of small molecule LOXL2 inhibitors in breast cancer." Oncotarget 8(16): 26066-26078.
Cheng, T., et al. (2014). "Lysyl oxidase promotes bleomycin-induced lung fibrosis through modulating inflammation." J Mol Cell Biol 6(6): 506-515.
Cheon, D. J., et al. (2014). "A collagen-remodeling gene signature regulated by TGF-beta signaling is associated with metastasis and poor survival in serous ovarian cancer." Clin Cancer Res 20(3): 711-723.
Chou, T. F., et al. (2007). "Engineered monomeric human histidine triad nucleotide-binding protein 1 hydrolyzes fluorogenic acyl-adenylate and lysyl-tRNA synthetase-generated lysyl- adenylate." J Biol Chem 282(20): 15137-15147.
Cosgrove, D., et al. (2018). "Lysyl oxidase like-2 contributes to renal fibrosis in Col4alpha3/Alport mice." Kidney Int 94(2): 303-314.
Counts, D. F., et al. (1981). "Collagen lysyl oxidase activity in the lung increases during bleomycin-induced lung fibrosis." J Pharmacol Exp Ther 219(3): 675-678.
De Bruyn, J. R., et al. (2018). "Fibrostenotic Phenotype of Myofibroblasts in Crohn's Disease is Dependent on Tissue Stiffness and Reversed by LOX Inhibition." J Crohns Colitis 12(7): 849-859.
Dentillo, D. B., et al. (2010). "Deregulation of LOXL1 and HTRA1 gene expression in endometriosis." Reprod Sci 17(11): 1016-1023.
Erler, J. T., et al. (2006). "Lysyl oxidase is essential for hypoxia-induced metastasis." Nature 440(7088): 1222-1226.
Gilad, G. M., et al. (2001). "Lysyl oxidase, the extracellular matrix-forming enzyme, in rat brain injury sites." Neurosci Lett 310(1): 45-48.
Gilad, G. M., et al. (2005). "Evidence for increased lysyl oxidase, the extracellular matrix-forming enzyme, in Alzheimer's disease brain." Neurosci Lett 376(3): 210-214.
Gorogh, T., et al. (2015). ""Characterisation of seven newly established head and neck squamous cell carcinoma cell lines."" Eur Arch Otorhinolaryngol 272(5): 1251-1258.
Goto, Y., et al. (2005). "Transforming growth factor-betal mediated up-regulation of lysyl oxidase in the kidneys of hereditary nephrotic mouse with chronic renal fibrosis." Virchows Arch 447(5): 859-868.
Hajdu, I., et al. (2018). "Inhibition of the LOX enzyme family members with old and new ligands. Selectivity analysis revisited." Bioorg Med Chem Lett 28(18): 3113-3118.
Halberg, N., et al. (2009). "Hypoxia-inducible factor lalpha induces fibrosis and insulin resistance in white adipose tissue." Mol Cell Biol 29(16): 4467-4483.
Hase, H., et al. (2014). "LOXL2 status correlates with tumor stage and regulates integrin levels to promote tumor progression in ccRCC." Mol Cancer Res 12(12): 1807-1817.
Hutchinson, J. H., et al. (2017). "Small Molecule Lysyl Oxidase-like 2 (LOXL2) Inhibitors: The Identification of an Inhibitor Selective for LOXL2 over LOX." ACS Med Chem Lett 8(4): 423-427.
Kagan, H. M. and W. Li (2003). "Lysyl oxidase: properties, specificity, and biological roles inside and outside of the cell." J Cell Biochem 88(4): 660-672.
Kagan, H. M., et al. (1981). "Changes in aortic lysyl oxidase activity in diet-induced atherosclerosis in the rabbit." Arteriosclerosis 1(4): 287-291.
Kagan, H. M., et al. (1979). "Purification and properties of four species of lysyl oxidase from bovine aorta." Biochem J 177(1): 203-214.
Kim, D., et al. (2015). "Impaired osteogenesis in Menkes disease-derived induced pluripotent stem cells." Stem Cell Res Ther 6: 160.
Kim, Y., et al. (2009). "Differential expression of the LOX family genes in human colorectal adenocarcinomas." Oncol Rep 22(4): 799-804.
Kirschmann, D. A., et al. (2002). "A molecular role for lysyl oxidase in breast cancer invasion." Cancer Res 62(15): 4478-4483.
Kumar, P., et al. (2018). "Periostin promotes liver fibrogenesis by activating lysyl oxidase in hepatic stellate cells." J Biol Chem 293(33): 12781-12792.
Lapointe, J., et al. (2004). "Gene expression profiling identifies clinically relevant subtypes of prostate cancer." Proc Natl Acad Sci U S A 101(3): 811-816.
Le, Q. T., et al. (2009). "Validation of lysyl oxidase as a prognostic marker for metastasis and Survival in head and neck squamous cell carcinoma: Radiation Therapy Oncology Group trial 90-03." J Clin Oncol 27(26): 4281-4286.
Leiva, 0., et al. (2019). ""Novel lysyl oxidase inhibitors attenuate hallmarks of primary myelofibrosis in mice."" Int J Hematol 110(6): 699-708.
Leung et al., "Anti-metastatic Inhibitors of Lysyl Oxidate (LOX): Design and Structure-Activity Relationships" Journal of Medicinal Chemistry, 2019, vol. 62, pp. 5863-5884.
Li, P. A., et al. (2004). "Up-regulation and altered distribution of lysyl oxidase in the central nervous system of mutant SOD1 transgenic mouse model of amyotrophic lateral sclerosis." Brain Res Mol Brain Res 120(2): 115-122.
Li, W., et al. (2003). "Lysyl oxidase oxidizes basic fibroblast growth factor and inactivates its mitogenic potential." J Cell Biochem 88(1): 152-164.
Liu, N., et al. (2017). "Nuclear expression of lysyl oxidase enzyme is an independent prognostic factor in rectal cancer patients." Oncotarget 8(36): 60015-60024.
Liu, S. B., et al. (2016). "Lysyl oxidase activity contributes to collagen stabilization during liver fibrosis progression and limits spontaneous fibrosis reversal in mice." FASEB J 30(4): 1599-1609.
Lopez, B., et al. (2009). "Impact of treatment on myocardial lysyl oxidase expression and collagen cross-linking in patients with heart failure." Hypertension 53(2): 236-242.
Lu, J., et al. (2018). "Hypoxia-inducible factor-lalpha regulates epithelial-to-mesenchymal transition in paraquat-induced pulmonary fibrosis by activating lysyl oxidase." Exp Ther Med 15(3): 2287-2294.
Lu, M., et al. (2019). "Induction of LOX by TGF-betal/Smad/AP-1 signaling aggravates rat myocardial fibrosis and heart failure." IUBMB Life 71(11): 1729-1739.
Lucero, H. A. and H. M. Kagan (2006). "Lysyl oxidase: an oxidative enzyme and effector of cell function." Cell Mol Life Sci 63(19-20): 2304-2316.
Lucero, H. A., et al. (2008). "Lysyl oxidase oxidizes cell membrane proteins and enhances the chemotactic response of vascular smooth muscle cells." J Biol Chem 283(35): 24103-24117.
Mambetsariev, I., et al. (2014). "Stiffness-activated GEF-HI expression exacerbates LP S-induced lung inflammation." PLoS One 9(4): e92670.
Martin, A., et al. (2015). "Lysyl oxidase-like 2 represses Notchl expression in the skin to promote squamous cell carcinoma progression." Embo J 34(8): 1090-1109.
Mesarwi, 0. A., et al. (2015). "Lysyl Oxidase as a Serum Biomarker of Liver Fibrosis in Patients with Severe Obesity and Obstructive Sleep Apnea." Sleep 38(10): 1583-1591.
Miana, M., et al. (2015). "The lysyl oxidase inhibitor beta-aminopropionitrile reduces body weight gain and improves the metabolic profile in diet-induced obesity in rats." Dis Model Mech 8(6): 543-551.
Miller, B. W., et al. (2015). "Targeting the LOX/hypoxia axis reverses many of the features that make pancreatic cancer deadly: inhibition of LOX abrogates metastasis and enhances drug efficacy." EMBO Mol Med 7(8): 1063-1076.

(56) References Cited

OTHER PUBLICATIONS

Min, C., et al. (2007). "The tumor suppressor activity of the lysyl oxidase propeptide reverses the invasive phenotype of Her-2/neu-driven breast cancer." Cancer Res 67(3): 1105-1112.
Murawaki, Y., et al. (1991). "Serum lysyl oxidase activity in chronic liver disease in comparison with serum levels of prolyl hydroxylase and laminin." Hepatology 14(6): 1167-1173.
Ovchinnikova, 0. A., et al. (2014). "The collagen cross-linking enzyme lysyl oxidase is associated with the healing of human atherosclerotic lesions." J Intern Med 276(5): 525-536.
Papadantonakis, N., et al. (2012). "Megakaryocyte pathology and bone marrow fibrosis: the lysyl oxidase connection." Blood 120(9): 1774-1781.
Rivera, A. D. and A. M. Butt (2019). "Astrocytes are direct cellular targets of lithium treatment: novel roles for lysyl oxidase and peroxisome-proliferator activated receptor-gamma as astroglial targets of lithium." Transl Psychiatry 9(1): 211.
Rowbottom, M. W., et al. (2017). "Identification of 4-(Aminomethyl)-6-(trifluoromethyl)-2-(phenoxy)pyridine Derivatives as Potent, Selective, and Orally Efficacious Inhibitors of the Copper-Dependent Amine Oxidase, Lysyl Oxidase-Like 2 (LOXL2)." J Med Chem 60(10): 4403-4423.
Ruiz, L. A., et al. (2011). "Single-nucleotide polymorphisms in the lysyl oxidase-like protein 4 and complement component 3 genes are associated with increased risk for endometriosis and endometriosis-associated infertility." Fertil Steril 96(2): 512-515.
Ryner, L., et al. (2015). "Upregulation of Periostin and Reactive Stroma Is Associated with Primary Chemoresistance and Predicts Clinical Outcomes in Epithelial Ovarian Cancer." Clin Cancer Res 21(13): 2941-2951.
Saifi, M. A. and C. Godugu (2020). "Inhibition of lysyl oxidase ameliorates renal injury by inhibiting CD44-mediated pericyte detachment and loss of peritubular capillaries." Life Sci 243: 117294.
Salvador, F., et al. (2017). "Lysyl Oxidase-like Protein LOXL2 Promotes Lung Metastasis of Breast Cancer." Cancer Res 77(21): 5846-5859.
Sasaki, T., et al. (2016). "Loss of fibulin-4 results in abnormal collagen fibril assembly in bone, caused by impaired lysyl oxidase processing and collagen cross-linking." Matrix Biol 50: 53-66.
Sato, S., et al. (2011). "The Ras signaling inhibitor LOX-PP interacts with Hsp70 and c-Raf to reduce Erk activation and transformed phenotype of breast cancer cells." Mol Cell Biol 31(13): 2683-2695.
Schilter, H., et al. (2019). "The lysyl oxidase like 2/3 enzymatic inhibitor, PXS-5153A, reduces crosslinks and ameliorates fibrosis." J Cell Mol Med 23(3): 1759-1770.
Siegel, R. C., et al. (1978). "Biochemical and immunochemical study of lysyl oxidase in experimental hepatic fibrosis in the rat." Proc Natl Acad Sci U S A 75(6): 2945-2949.
Smithen, D. A., et al. (2020). "2-Aminomethylene-5-sulfonylthiazole Inhibitors of Lysyl Oxidase (LOX) and LOXL2 Show Significant Efficacy in Delaying Tumor Growth." J Med Chem 63(5): 2308-2324.
Stangenberg, S., et al. (2018). "Lysyl oxidase-like 2 inhibition ameliorates glomerulosclerosis and albuminuria in diabetic nephropathy." Sci Rep 8(1): 9423.
Tadmor, T., et al. (2013). "The expression of lysyl-oxidase gene family members in myeloproliferative neoplasms." Am J Hematol 88(5): 355-358.
Tang, H., et al. (2017). "Lysyl oxidase drives tumour progression by trapping EGF receptors at the cell surface." Nat Commun 8: 14909.
Tjin, G., et al. (2017). "Lysyl oxidases regulate fibrillar collagen remodelling in idiopathic pulmonary fibrosis." Dis Model Mech 10(11): 1301-1312.
Uzel, M. I., et al. (2001). "Multiple bone morphogenetic protein 1-related mammalian metalloproteinases process pro-lysyl oxidase at the correct physiological site and control lysyl oxidase activation in mouse embryo fibroblast cultures." J Biol Chem 276(25): 22537-22543.
Van Bergen, T., et al. (2015). "The Role of LOX and LOXL2 in the Pathogenesis of an Experimental Model of Choroidal Neovascularization." Invest Ophthalmol Vis Sci 56(9): 5280-5289.
Virani, S. S., et al. (2020). "Heart Disease and Stroke Statistics-2020 Update: A Report From the American Heart Association." Circulation 141(9): el39-e596.
Vulpe, C., et al. (1993). "Isolation of a candidate gene for Menkes disease and evidence that it encodes a copper-transporting ATPase." Nat Genet 3(1): 7-13.
Wakasaki, H. and A. Ooshima (1990). "Synthesis of lysyl oxidase in experimental hepatic fibrosis." Biochem Biophys Res Commun 166(3): 1201-1204.
Wilhelmus, M. M., et al. (2013). "Extracellular matrix modulator lysyl oxidase colocalizes with amyloid-beta pathology in Alzheimer's disease and hereditary cerebral hemorrhage with amyloidosis—Dutch type." Exp Gerontol 48(2): 109-114.
Xia et al. "Design, synthesis and SAR of piperidyl-oxadiazoles as 11beta-hydroxysteroid dehydrogenase 1 inhibitors", European Journal of Medicinal Chemistry, 2013. vol. 62, pp. 1-10.
Yang, J., et al. (2016). "Targeting LOXL2 for cardiac interstitial fibrosis and heart failure treatment." Nat Commun 7: 13710.

* cited by examiner

LOX ENZYME INHIBITING METHODS AND COMPOSITIONS

CROSS-REFERENCE TO RELATED APPLICATIONS

This application is a U.S. National Phase of International Application No. PCT/US2021/028220, filed on Apr. 20, 2021, which claims the benefit of U.S. Provisional Patent Application No. 63/013,049, filed on Apr. 21, 2020, and U.S. Provisional Patent Application No. 63/171,573, filed on Apr. 6, 2021, the contents of which are incorporated herein by reference in their entireties.

STATEMENT REGARDING FEDERALLY SPONSORED RESEARCH

This invention was made with government support under Grant No. R43 HL147651, awarded by the National Institutes of Health. The government has certain rights in the invention.

FIELD OF THE INVENTION

This invention relates to compounds, pharmaceutical compositions and their use for treating fibrotic disorders, proliferative disorders, cardiovascular diseases, acute and chronic inflammatory disorders, primary and metastatic cancer, pulmonary conditions, ocular diseases, or neurological and neuropsychiatric conditions. One particular aspect of the inventions relates to inhibitors of the family of lysyl oxidase enzymes and their use as therapeutics for fibrotic disorders.

BACKGROUND

Prototypic LOX (protein-6-lysine-oxidase; EC 1.4.3.13) is a copper and quinone-cofactor containing amine oxidase, which is expressed in various cell types such as basal and suprabasal keratinocytes, fibroblasts, adipocytes, osteoblasts, smooth muscle cells, and endothelial cells. The most well known function of LOX is the initiation of the cross-linking of collagens and elastins. More specifically, LOX catalyzes oxidative deamination of the primary amines of lysine and hydroxylysine in proteins such as collagen and tropoelastin to generate peptidyl aminoadipic-δ-semialdehyde, an aldehyde that spontaneously condenses to form inter- and intra-chain crosslinks (Lucero and Kagan 2006). Such modifications of structural components of the extracellular matrix (ECM) stabilize fibrous deposits and contribute to tissue strength and integrity in the connective tissue. Other proteins have been reported as substrates for oxidation by LOX, such as basic fibroblast growth factor, PDGFR-β and other globular proteins with basic isoelectric points such histones H1, H2, and H3 (Kagan and Li 2003, Li, Nugent et al. 2003, Lucero and Kagan 2006, Lucero, Ravid et al. 2008).

The LOX mRNA is translated to a pre-pro-protein (pre-pro-LOX), 48 kDa), followed by incorporation of copper, cleavage of 21 amino acids, glycosylation of the N-terminus, and tertiary folding, to form the inactive LOX pro-protein (pro-LOX, 50 kDa). Pro-LOX is then secreted out of the cell and cleaved to a mature active form by procollagen C-proteinases (bone morphogenetic protein 1, BMP-1) and mammalian tolloid-like protein (mTLL-1) (Uzel, Scott et al. 2001) to become LOX pro-peptide (PP-LOX, 18 kDa) and the 32-kDa mature active LOX enzyme (Lucero and Kagan 2006). The catalytic domain contains a lysine-tyrosylquinone (LTQ) cofactor. LTQ is formed by post-translational oxidation of a catalytic site tyrosine (Tyr349), which then condenses onto a lysine, also within the catalytic site (Lys314), to form a stable covalent modification that is an essential part of the catalytic mechanism (Lucero and Kagan 2006, Kagan and Li 2003).

LOX is part of a protein family which consists of five enzymes, LOX, LOX-like 1 [LOXL1], LOX-like 2 [LOXL2], LOX-like 3 [LOXL3] and LOX-like 4 [LOXL4]), all containing a highly conserved C-terminal region containing the copper binding domain, residues for lysine tryosylquinone (LTQ), cofactor formation, and a cytokine receptor-like (CRL) domain. Although the C-terminal regions of the members of this family are conserved, the N-terminal portions are variable. Accordingly, this family is divided into two groups based on the N-terminal similarities. LOX and LOXL1 have N-terminals with pro-sequences, which confer their secretion as inactive pro-enzymes, whereas LOXL2, LOXL3, and LOXL4 contain scavenger receptor cysteine-rich (SRCR) domains.

LOX enzymes play a crucial role in maintaining ECM stability, by initiating and regulating the crosslinking of collagens and elastin within the ECM. The function of these enzymes is key to maintaining the normal tensile and elastic features of connective tissue of many organ systems within the body and as such is required for the structural integrity of many tissues. LOX expression decreases during ageing indicating that its activity is especially important during development. Inappropriate expression of these enzymes has been observed in a number of human diseases (many involving a fibrotic response), in particular primary and metastatic cancer. LOX family members are reported to have both intracellular and extracellular functions.

LOX was first proposed to be a tumor suppressor gene owing to its inhibitory effects on oncogenic HRAS-mediated transformation. There is now compelling evidence that the 18-kDa LOX-PP can suppress the neoplastic transformation of normal rat kidney fibroblasts and is capable of suppressing transformation and xenograft tumor formation of mammary epithelial cells that express HRAS or HER2 (Min et al. 2007, Sato et al 2011). Currently, evidence only exists to support tumor suppressive roles for LOX-PP, which adds extra complexity to the role of this family member in tumorigenesis.

Alteration in LOX and LOX-like (e.g. LOXL1, LOXL2, LOXL3, or LOXL4) enzyme activity is implicated in many diseases and disorders including but not limited to inflammation and acute and chronic inflammatory diseases, fibrosis of distinct organs and fibrotic disorders, cancer promotion and progression, and cardiovascular diseases.

LOX and LOX-like enzymes are implicated in fibrotic diseases, such as liver fibrosis (Siegel et al., 1978; Carter et al., 1982; Wakasaki et al., 1990; Murawaki et al., 1991; Mesarwi et al., 2015, Liu et al., 2016, Kumar et al., 2018), lung fibrosis (Counts et al., 1981; Almassian et al., 1991; Cheng et al., 2014; Tijn, et al., 2017, Aumiller et al., 2017, Lu et al., 2018), kidney fibrosis (Goto et al., 2005, Cosgrove et al., 2018, Stangenberg, et al., 2018, Saifi et al., 2020), cardiac fibrosis (Lopez et al., 2009, Yang et al., 2016, Lu et al., 2019), myelofibrosis (Papadantonakis et al, 2012, Tadmor et al., 2013, Leiva, et al., 2017, Abbonante et al., 2017, Leiva et al., 2019) and scleroderma, and can contribute to atherosclerosis (Kagan et al., 1981; Ovchinnikova et al., 2014). Decreased LOX activity is involved in disorders such as Menkes disease (Vulpe et al., 1993; Kim et al., 2015), osteoporosis, and cutis laxa (Sasaki et al., 2016).

In the United States, heart failure (HF) is a major public health problem and the leading cause of morbidity and mortality, resulting in 800,000 hospitalizations and 80,000 deaths per year [REF]. About one million people are newly diagnosed with HF every year, and >6 million people in the US are now afflicted with this disease, with annual treatment cost exceeding $30 billion. The HF epidemic is worsening. In 10 years (by 2030), >8 million adults in the US (near 3% of the adult population) are projected to be afflicted with HF, and the treatment cost will rise to $70 billion. Despite the huge socioeconomic expenses, the 1- and 5-year mortality rates of HF remain high at 30% and 50%, respectively. Such persistently high mortality of HF reflects inadequacy of current medical therapies and calls for new mechanistic paradigms for treatment. The LOX enzyme family plays also a role in cardiac function and disease. Fibrosis impairs myocardial relaxation and causes diastolic dysfunction, increasing the probability of heart failure (HF) development. HF is associated with substantial morbidity and mortality. Cardiac fibrosis also impedes propagation of the cardiac impulse, leading to arrhythmias such as atrial fibrillation (AF). AF is the most common sustained arrhythmia and is associated with adverse outcomes such as stroke, HF, and death. LOXL2 expression is increased in the cardiac interstitium and correlates with collagen cross-linking and cardiac dysfunction in failing human hearts. LOXL2 is also increased in the serum of HF-patients, correlating with biomarkers of HF, collagen cross-linking, and cardiac dysfunction (Yang et al., 2016; Al-u'datt, et al., 2019). As discussed in the detailed description of the invention, LOXL2 inhibition may prove beneficial in the treatment or prevention of cardiovascular conditions, including hypertensive heart disease, pressure overload, myocardial ischemia, heart failure, cardiac hypertrophy, and atherosclerosis.

LOX is associated with the amyloid-beta (Aβ) related pathological hallmarks (such as cerebral amyloid angiopathy and senile plaques) of both Alzheimer's disease (AD) and hereditary cerebral hemorrhage with amyloidosis of the Dutch type (HCHWA-D) pathogenesis (Wilhelmus, Bol et al. 2013). LOX activity is increased in the hippocampal samples of AD and also in non-Alzheimer's dementia (Gilad, Kagan et al. 2005). LOX is increased at the site of brain injury (Gilad, Kagan et al. 2001) and spinal cord injury and its inhibition lead to accelerated functional recovery in an unilateral spinal cord dissection model (Gilad and Gilad 2001). Increased LOX is associated with pathological progression of ALS, where it is a potential biomarker (Li et al., 2004). Genomic analyses identified the enzyme LOX as the most highly regulated lithium-responsive astroglial gene and as a common factor and potential surrogate biomarker in bipolar disease, schizophrenia and AD (Rivera, Butt, 2019).

LOX inhibition may be beneficial in the treatment of various ocular conditions. Inhibition of LOX and/or LOXL2 prevents neovascularization and fibrosis following laser-induced choroidal neovascularization (Van Bergen, et al., 2015). Therefore targeting LOX and LOX-like proteins can be useful in the treatment of conditions characterized by neovascularization, such as age-related macular degeneration, diabetic retinopathy and retinopathy of prematurity.

Another medical condition that may benefit from ECM remodeling factors-based therapeutics is IBD-associated fibrosis, considered an irreversible self-propagating process, currently treated mainly by mechanical means (e.g. surgical resection or balloon dilation). As increase in matrix stiffness seems to be an early event in tissue fibrosis, targeting collagen cross-linking enzymes, such as the LOX family, may be of therapeutic significance (de Bruyn, et al., 2018).

LOX is implicated in inflammatory conditions and may be useful in the treatment of other conditions such as acute respiratory distress syndrome (ARDS) (Mambetsariev, Tian et al. 2014).

In recent years, fibrosis has been recognized as a crucial player in adipose tissue dysfunction in obesity. LOX is the main LOX family enzyme expressed in human adipose tissue and its expression is strongly upregulated in samples from obese patients. BAPN, a pan-LOX inhibitor, reduces body weight gain, improves the metabolic profile in diet-induced obesity in rats (Miana, Galan et al. 2015), and reduces local adipose tissue inflammation (Halberg, Khan et al. 2009). BAPN has also been shown to reduce leptin pro-fibrotic effects and ameliorates cardiovascular remodeling in diet-induced obesity in rats.

LOX is upregulated in endometriosis and may be implicated in the establishment and progression of endometriotic lesions (Ruiz, Dutil et al. 2011; Dentillo, Meola et al. 2010).

Aberrant expression and activity of LOX and LOX-like enzymes has been reported in several cancer types (reviewed by Barker et al., 2012 and Amendola et al., 2019). For example, a functional role of LOX proteins has been described in breast (Erler et al., 2006; Kirschmann et al, 2002; Salvador et al., 2017), colorectal (Kim et al., 2009; Baker et al., 2011; Baker et al., 2013), pancreatic (Miller et al., 2015), prostate (Lapointe et al., 2004), and ovarian (Cheon et al., 2014; Chang et al., 2007) cancers, in head and neck squamous cell carcinoma (Le et al., 2009; Gorogh et al., 2015; Albinger-Hegyi et al., 2010), renal cells carcinoma (Hase et al., 2014), uveal melanoma (Abourbih et al., 2010), and squamous cell skin carcinoma (Martin et al., 2015). The precise contribution to each LOX protein however still remains to be fully elucidated. Of note, while LOX and LOXL2 are involved in similar extra-cellular processes, it appears that they have distinct roles.

LOX enzymes represent exciting targets for the treatment of fibrotic disorders, proliferative disorders, cardiovascular diseases, acute and chronic inflammatory disorders, primary and metastatic cancer, pulmonary conditions, ocular diseases, or neurological and neuropsychiatric conditions. Targeting LOX proteins with small molecule inhibitors is very challenging owing to the lack of crystal structures useful for drug design for any of the isoforms (except LOXL2) and the high degree of homology of the catalytic domain and difficulties associated with isolating several of the enzymes in an active form, particularly LOX, LOXL1, and LOXL4.

A number of small molecule LOX inhibitors are known (reviewed by Hajdn et al, 2018). However, in general these compounds are either non-selective (e.g. the prototypical pan-LOX inhibitor BAPN and copper chelator molecules, such as D-penicillamin), lack potency, or are unsuitable for use in patients. More recently a variety of LOX protein inhibitors have been described. For example, LOX inhibitors containing hydrazine and hydrazide groups (Burke et al, 2017); LOXL2 inhibitors: derivatives of haloallylamine (Chang et al, 2017, Stangenberg et al, 2018, Schilter et al, 2019), pyridines (Rowbottom et al, 2016a; Rowbottom et al, 2016b), pyrimidines (Rowbottom & Hutchinson, 2017a) chromenones (Rowbottom & Hutchinson, 2017b), and 2-Aminomethylene-5-sulfonylthiazole (Tang et al., 2017; Smithen et al., 2019; Springer et al, 2017). LOXL2/3 inhibitors PAT-1251 and PXS-5153A, pan-LOX inhibitor PXS-5505A, and the LOXL2-selective inhibitor PXS-4878A are in early clinical development.

There is therefore a need for new LOX inhibitors.

SUMMARY OF THE INVENTION

Provided are compounds, pharmaceutical compositions and methods of treating or preventing diseases associated with aberrant LOX family enzyme expression, particularly fibrotic disorders, including more specifically proliferative disorders, chronic and acute inflammatory disorders, cardiovascular diseases, primary or metastatic cancer, ocular diseases, pulmonary conditions, neurological ad neuropsychiatric conditions, or other diseases and medical conditions for which inhibiting one or more enzyme of the family of lysyl oxidases (LOX) provides a therapeutic effect.

In a particular embodiment, provided are LOX enzyme-inhibiting compounds in accordance with Formula I, or a pharmaceutically acceptable salt and/or hydrate thereof:

I

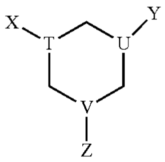

wherein:

T, U, and V are nitrogen or carbon and only one of T, U, and V is nitrogen.

X is independently selected from —$OR^1$, —$SO_2R^1$, and —C(═O)$R^1$

Y is independently selected from —$OR^2$, —$SO_2R^2$, and —C(═O)$R^2$

Z is independently selected from —$R^3$, —$CH_2$—$R^3$, —$SO_2R^3$, —C(═O)$R^3$, and —$OR^3$ $R^1$ is phenyl or heteroaryl containing 1 to 2 heteroatom(s) each independently selected from N, O, and S, wherein said phenyl or heteroaryl is substituted with —$CR^4R^5NH_2$ and optionally halogen or lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl.

$R^2$ is substituted or unsubstituted phenyl, substituted or unsubstituted benzyl, substituted or unsubstituted heteroaryl containing 1 to 2 heteroatom(s) each independently selected from N, O, and S, ($C_1$-$C_8$) alkyl, ($C_1$-$C_8$) cycloalkyl, mono-, di-, or trihalo($C_1$-$C_4$)alkyl, —$NR^6R^7$, where $R^6$ and $R^7$ are independently selected from H and lower alkyl or where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is substituted or unsubstituted, wherein substituent is lower alkyl or —$SO_2R^8$ or —$OR^8$, and wherein S is unsubstituted or forms sulfonyl, wherein said substituted phenyl, benzyl, or heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl.

$R^3$ is unsubstituted or substituted phenyl, substituted or unsubstituted benzyl, or substituted or unsubstituted heteroaryl containing 1 to 2 heteroatom(s) each independently selected from N, O, and S, mono-, di-, or trihalo($C_1$-$C_4$)alkyl, ($C_1$-$C_8$) cycloalkyl, ($C_1$-$C_8$) alkyl, —$NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with a lower alkyl or —$SO_2R^{13}$ or —$OR^{13}$, and wherein S is unsubstituted or forms sulfonyl, wherein said substituted phenyl, benzyl, or heteroaryl has at least one substituent being halogen, mono-, di- or trihalo($C_1$-$C_4$) alkyl, —$SO_2R^{14}$ or —$OR^{14}$ where $R^{14}$ is lower alkyl, cyano, lower alkyl, or —$SO_2NR^{15}R^{16}$, where $R^{15}$ and $R^{16}$ are independently selected from H and lower alkyl; or a tautomer or stereoisomer thereof.

Also provided herein are methods of treating or preventing a disease associated with aberrant LOX family enzyme expression for which inhibiting one or more enzyme of the family of lysyl oxidases provides a therapeutic effect, comprising administering to a subject in need thereof an effective amount of a lysyl oxidase (LOX) enzyme-inhibiting compound or a pharmaceutically acceptable salt and/or hydrate thereof as described herein.

Also provided herein are pharmaceutical compositions comprising a LOX enzyme-inhibiting compound described herein and a pharmaceutically acceptable carrier.

Also provided are methods of synthesizing the LOX enzyme inhibiting compounds described herein.

DRAWINGS OF THE INVENTION

Figure 1B:
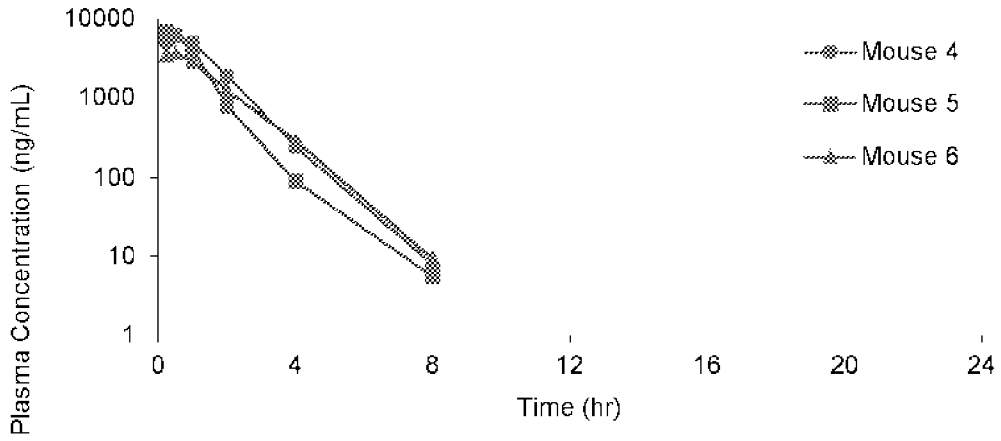

FIGS. 1A-B depicts plasma concentration over time of PH-AOV-0074 after i.v. (A) or p.o. (B) administration in male CD1 mice.

Figures 2A, 2B:
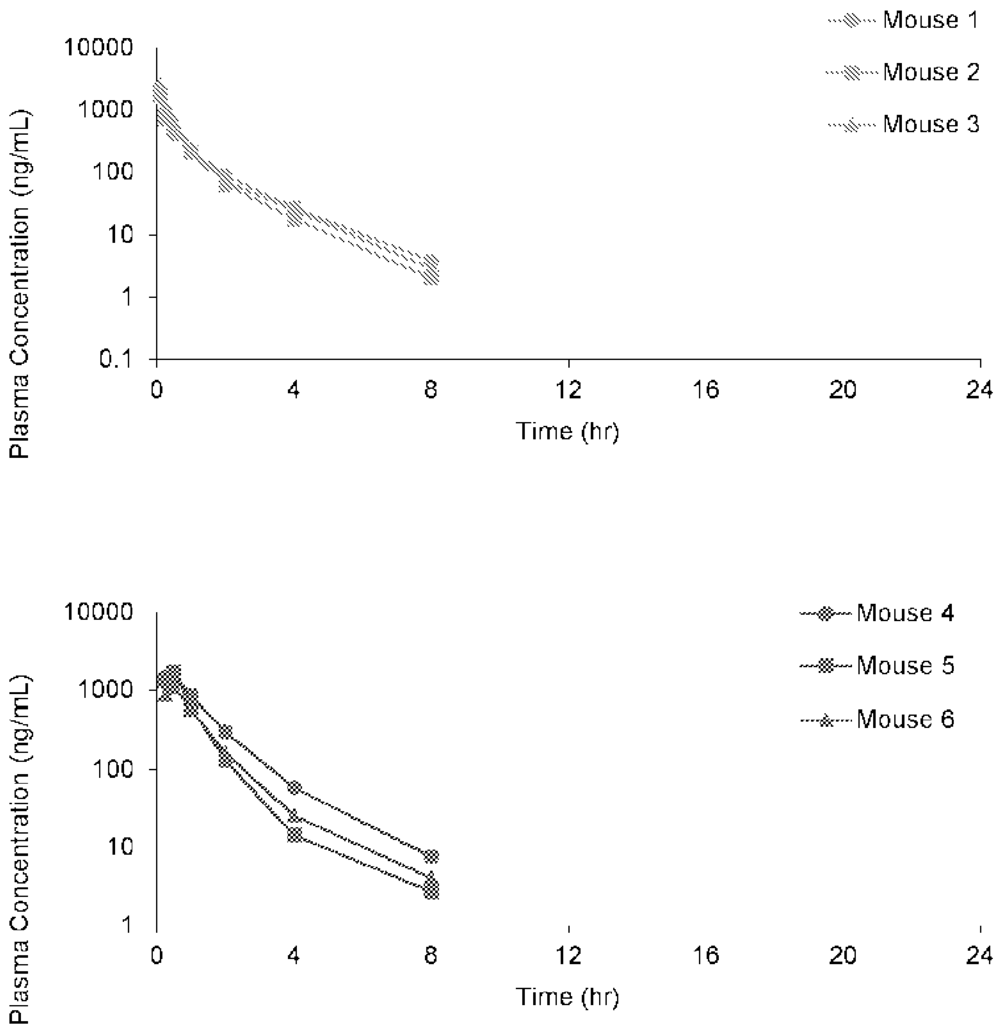

FIGS. 2A-B depicts plasma concentration over time of PH-AOV-0122 after i.v. (A) or p.o. (B) administration in male CD1 mice.

Figure 3A:
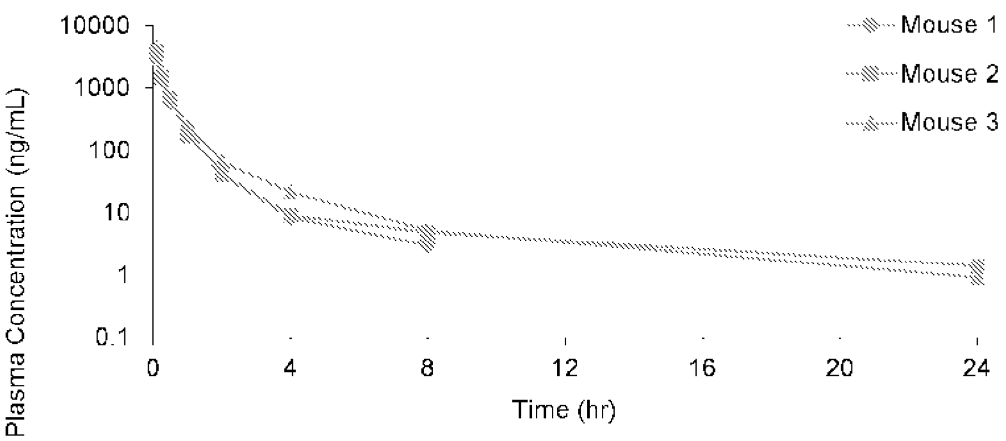
Figure 3B:
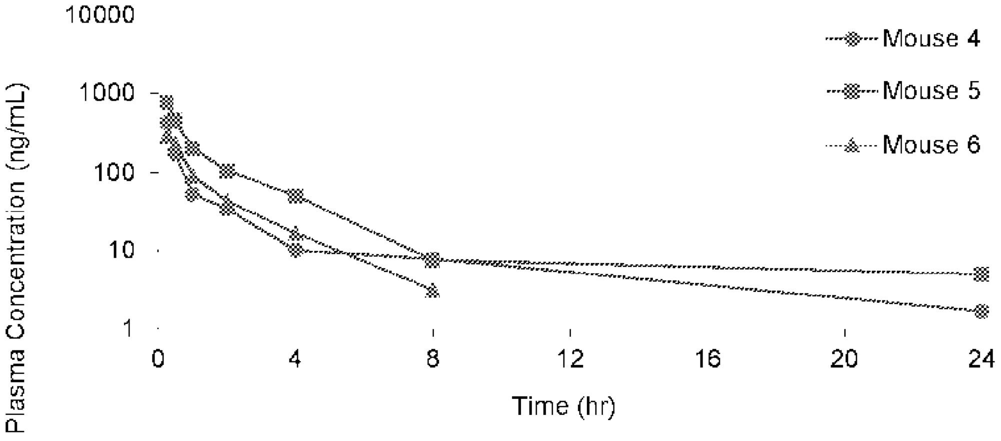

FIGS. 3A-B depicts plasma concentration over time of PH-AOV-0146 after i.v. (A) or p.o. (B) administration in male CD1 mice.

DETAILED DESCRIPTION OF THE INVENTION

I. Definitions

The terms below, when used herein, have the following meanings unless indicated otherwise.

As used in this specification and the appended claims, the singular forms "a", "an" and "the" include plural references unless the content clearly dictates otherwise.

The term "heteroatom" means O, S or N, selected on an independent basis.

"Halogen" and "halo" refer to fluorine, chlorine, bromine and iodine.

The term "lower alkyl" refers to methyl, ethyl, propyl, butyl and their various branched isomers.

When any variable (e.g. aryl, heterocycle, R', etc.) occurs more than one time in any constituent, its definition on each occurrence is independent at every other occurrence.

The nomenclature "$C_x$-$C_y$", for example, "$C_1$-$C_6$", species corresponds to the number of carbon atoms of a hydrocarbon. For example, $C_1$-$C_6$ indicates a hydrocarbon containing 1, 2, 3, 4, 5, or 6 carbon atoms.

"Alkyl" refers to a saturated hydrocarbon chain. Such hydrocarbon chains may be branched or linear. Unless specified otherwise, "Alkyl" groups may be substituted by one or more substituents selected from halogen, amido, aryl or $C_1$-$C_4$ alkoxy. Nonlimiting examples include methyl, trifluoromethyl, ethyl, propyl, butyl, pentyl, 1-methylbutyl, 1-ethylpropyl, 3-methylpentyl, octyl and the like.

"Cycloalkyl" refers to a saturated or unsaturated cyclic hydrocarbon radical, including bridged, fused, or spiro cyclic compounds, preferably having 3 to 8 carbon atoms. Non-limiting examples of "$C_3$-$C_i$ cycloalkyl" groups according to the present invention are cyclopropyl, cyclopentyl, cyclohexyl and the like. In some embodiments, the cycloalkyl has 3 to 8 carbon atoms. In some embodiments, the cycloalkyl has 3 to 6 carbon atoms.

The term "aryl" refers to a moiety derived from an aromatic ring or polycyclic ring, such as phenyl, naphthyl, or quinolinyl. An aryl can be a $C_3$-$C_i$ aryl.

The term "heteroaryl" refers to an aromatic moiety having at least one heteroatom as part of the aromatic ring. A heteroaryl can be a $C_3$-$C_{10}$ aryl. Non-limiting examples of "$C_3$-$C_{10}$ heteroaryl" groups according to the present invention are thiophenyl, thiazolyl, pyridinyl, pyrimidinyl, imidazolyl, pyrrolyl, oxazolyl, and the like.

The term "alkoxy" refers to an alkyl singularly bonded to an oxygen, thus R—O—.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric/chiral centers and may thus occur as racemates, racemic mixtures, single enantiomers, diastereomeric mixtures, and individual diastereomers.

All configurational isomers of the compounds of the present invention are contemplated, either in admixture or in pure or substantially pure form. "Substantially pure" is at least 90%, at least 95%, at least 98% or at least 99%. The definition of compounds of the present invention embraces both cis (Z) and trans (E) alkene isomers, as well as cis and trans isomers of cyclic hydrocarbon or heterocyclo rings.

The term "LOX family enzymes", "LOX enzymes", or "LOX and LOX-like enzymes" refers, except indicated otherwise, to the protein family of lysyl oxidases, which consist of five enzymes: LOX, LOXL1, LOXL2, LOXL3, and LOXL4.

The term "LOX", "prototypic LOX", or "LOX enzyme" refers to the prototypic member of the LOX enzyme family: LOX, protein-6-lysine-oxidase; EC 1.4.3.13.

The term "LOX enzyme-inhibiting compound(s)" refers to compounds of this invention, which inhibit one or more LOX enzymes.

In embodiments, provided are compounds that selectively or specifically inhibit one or more of the LOX enzymes. A compound with an IC50 below or equal to 500 nM in LOX, LOXL2, and LOXL3 activity assays, for example, specifically, as described in the Examples 1 and 2 below, is an unselective, pan-LOX enzyme inhibitor. A compound with an IC50 below or equal to 500 nM in a LOXL2 activity assay and greater than 30 μM in both LOX and LOXL3 assays, for example, specifically, as described in the Examples below, is a specific LOXL2 inhibitor. A compound with an IC50 below or equal to 500 nM in the LOXL2 assay and greater than 30 μM in LOX and an IC50 which is at least 10-fold greater in the LOXL3 assay than the LOXL2 assay, for example, as described in the Examples below, is a selective LOXL2 inhibitor. A compound with an IC50 below or equal to 500 nM in the LOXL2 assay and an IC50, which is at least 10-fold greater in the LOX and LOXL3 activity assays than the LOXL2 assay, for example, as described in the Examples below, is a selective LOXL2 inhibitor. A compound with an IC50 below or equal to 500 nM in a LOX activity assay and greater than 30 μM in LOXL2 and LOXL3 activity assays, for example, specifically, as described in the Examples below, is a specific inhibitor of prototypic LOX. A compound with an IC50 below or equal to 500 nM in the LOX assay and an IC50, which is at least 10-fold greater in the LOXL2 and LOXL3 activity assays than the LOX assay, for example, as described in the Examples below, is a selective inhibitor of prototypic LOX. A compound with an IC50 below or equal to 500 nM in both the LOXL2 and LOXL3 activity assay and greater than 30 μM in the LOX assay, for example, specifically as described in the Examples below, is a dual (specific) LOXL2/LOXL3 inhibitor. A compound with an IC50 below or equal to 500 nM in both the LOXL2 and LOXL3 activity assay and an IC50, which is at least 10-fold greater in the LOX activity assay than the LOXL2 and LOXL3 activity assays, for example, specifically as described in the Examples below, is a dual (selective) LOXL2/LOXL3 inhibitor. A compound with an IC50 below or equal to 500 nM in the LOXL3 assay and greater than 30 μM in the LOX and LOXL2 assay, for example, specifically, as described in the Examples below, is a specific LOXL3 inhibitor. A compound with an IC50 below or equal to 500 nM in the LOXL3 assay and an IC50, which is at least 10-fold greater in the LOX and LOXL2 activity assays than the LOXL3 assay, for example, specifically, as described in the Examples below, is a selective LOXL3 inhibitor.

In general, specific inhibitors are compounds with an IC50 below or equal to 500 nM in only one of the LOX, LOXL1, LOXL2, LOXL3, and LOXL4 activity assays, as described in the Examples below, and greater than 30 μM in the activity assays of the other LOX family enzymes. Dual-specific inhibitors are compounds with an IC50 below or equal to 500 nM in two of the LOX, LOXL1, LOXL2, LOXL3, and LOXL4 activity assays, as described in the Examples below, and greater than 30 μM in the activity assays of the other LOX family enzymes. Any compound with an IC50 below or equal to 500 nM in only one of the LOX, LOXL1, LOXL2, LOXL3, and LOXL4 activity assays, as described in the Examples below, and an IC50, which is 10-fold greater in the other LOX enzyme activity assays, is deemed a selective inhibitor. Dual-selective inhibitors are compounds with an IC50 below or equal to 500 nM in two of the LOX, LOXL1, LOXL2, LOXL3, and LOXL4 activity assays, as described in the Examples below, and an IC50 which is 10-fold greater in the other LOX enzyme activity assays.

It will be understood that, as used herein, references to the compounds disclosed herein are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamme, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

A "pharmaceutically acceptable excipient" or "pharmaceutically acceptable carrier" refers to an excipient that can be included in the compositions of the invention and that causes no significant adverse toxicological effects to the subject or patient to which the composition is administered. "Pharmacologically effective amount," "physiologically effective amount," and "therapeutically effective amount" are used interchangeably herein to mean the amount of an active agent present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

The term "mammal" "mammalian" or "mammals" includes humans, as well as animals, such as dogs, cats, horses, pigs and cattle.

The term "patient" refers to a living organism suffering from or prone to a condition that can be prevented or treated by administration of an active agent as described herein, and includes both humans and animals. In one embodiment, the patient is a human patient.

As used herein, "individual" (as in the subject of the treatment) means a mammal. Mammals include, for example, humans; non-human primates, e.g., apes and monkeys; and non-primates, e.g., dogs, cats, rats, mice, cattle, horses, sheep, and goats. Non-mammals include, for example, fish and birds.

The term "disease" or "disorder" are used interchangeably, and are used to refer to diseases or conditions wherein lack of or reduced amounts of a specific gene product, e.g., a lysosomal storage enzyme, plays a role in the disease such that a therapeutically beneficial effect can be achieved by supplementing, e.g., to at least 1% of normal levels.

Without being bound by theory, the administration of compounds according to the invention in an "effective amount" or "therapeutically effective amount" provides a concentration of the compound that functions as an inhibitor of one or more LOX enzymes sufficient to inhibit the effect of one or more LOX enzymes.

"Treating" or "treatment" of a disease state includes: 1) inhibiting the disease state, i.e., arresting the development of the disease state or its clinical symptoms; 2) attenuating the disease state, i.e. reducing the number or intensity of one or more symptoms associated with the disease state, such that one or more symptoms is reduced but may, or may not be completely eliminated; and/or 3) relieving the disease state, i.e., causing temporary or permanent regression of the disease state or its clinical symptoms.

"Prevent" or "preventing" a disease state includes: preventing the disease state, i.e. causing the clinical symptoms of the disease state not to develop in a subject that may be exposed to or predisposed to the disease state, but does not yet experience or display symptoms of the disease states.

All patents, patent applications and publications cited herein, whether supra or infra, are hereby incorporated by reference in their entirety.

II. Compounds

The derivatives of 1,3,5-tri-substituted piperidine described herein are preferably inhibitors of one or more of the LOX proteins selected from LOX, LOXL1, LOXL2, LOXL3, or LOXL4, and useful in the treatment or prevention or reduction in the likelihood of fibrotic disorders, cardiovascular diseases, acute or chronic inflammatory disorders, primary and metastatic cancer, pulmonary conditions, ocular diseases, or neurological and neuropsychiatric conditions or diseases in which one or more LOX proteins are involved. The compounds of the invention can be characterized by their activity to inhibit one or more of the enzyme family of lysyl oxidases.

In some embodiments, the compounds of Formula I, Formula Ia, Formula Ib, Formula Ic, Formula Id, Formula Ie, Formula If, Formula Ig, Formula Ih, or Table 1 are effective to inhibit one or more of the LOX enzymes, as determined using an assay which determines the inhibitory concentration (IC50) for the conversion of primary amine substrates to aldehydes as described herein, with a IC50 superior or equal to 30 μM. In preferred embodiments, the IC50 as so determined is superior or equal to 1 μM. In an embodiment, the IC50 as so determined is superior or equal to 500 nM.

The ability of compounds within the scope of this disclosure to inhibit the activity of one or more LOX enzymes may be determined by methods known to those in the art for measuring LOX enzymes inhibition. One method for measuring LOX activity uses a fluorometric assay (kit from Abcam). This assay measures the release of hydrogen peroxide ($H_2O_2$) by the substrate upon transformation of the primary amine to the reactive aldehyde. In turn, $H_2O_2$ is detected using a red fluorescence substrate for HRP-coupled reactions. Using this assay, preferred compounds of the invention have an IC50 superior or equal to 30 μM. In increasingly preferred embodiments, the IC50 as so determined is superior or equal to 1 μM. In a more preferred embodiment, the IC50 as so determined is superior or equal to 500 nM.

In some embodiments, the compounds disclosed herein or a pharmaceutically acceptable salt and/or hydrate thereof, may be used in the selective or specific inhibition of LOX, LOXL1, LOXL2, LOXL3 or LOXL4. In other embodiments, it may be advantageous to selectively or specifically inhibit two or more enzymes of the LOX family. Accordingly in another embodiment, the compounds disclosed herein or pharmaceutically acceptable salt and/or hydrate thereof, may be used in the selective inhibition of two or more members of the LOX family selected from LOX, LOXL1, LOXL2, LOXL3 or LOXL4. In one embodiment, a compound of Formula Id, Formula Ig, or Formula Ih selectively or specifically inhibits LOXL2. In another embodiment, a compound of Formula Ie or Formula If inhibits selectively or specifically LOX and LOXL2 and optionally inhibits LOXL3 and/or LOXL4. In another embodiment, provided is a compound of Formula I, which selectively or specifically inhibits LOX.

Other embodiments are prodrugs of the compounds described herein. The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce the active compounds.

Prodrugs may be prepared by any variety of synthetic methods or appropriate adaptations presented in the chemical literature or as in synthetic or organic chemistry text books, such as those provide in Green's Protective Groups in Organic Synthesis, Wiley, 4$^{th}$ Edition (2007) Peter G. M. Wuts and Theodora W. Green; March's Advanced Organic Chemistry: Reactions, Mechanisms, and Structure, Wiley, 6th Edition (2007) Michael B. Smith and Domino Reactions in Organic Synthesis, Wiley (2006) Lutz F. Tietze, hereby incorporated by reference. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association), also hereby incorporated by reference.

Prodrugs in accordance with this disclosure can, for example, be produced by replacing appropriate functionalities present in the compounds disclosed herein with certain moieties known to those skilled in the art as 'pro-moieties' as described, for example, in Design of Prodrugs by H. Bundgaard (Elsevier, 1985), incorporated by reference in its entirety.

Some non-limiting examples of prodrugs in accordance with this disclosure include: (i) where the exemplary compound contains a carboxylic acid functionality which is functionalized into a suitably metabolically labile group (esters, carbamates, etc.); (ii) where the exemplary compound contains an alcohol functionality which is functionalized into a suitably metabolically labile group (ethers, esters, carbamates, acetals, ketals, etc.); and (iii) where the exemplary compound contains a primary or secondary amino functionality, or an amide which are functionalized into a suitably metabolically labile group, e.g., a hydrolysable group (amides, carbamates, ureas, phosphonates, sulfonates, etc.). Further examples of replacement groups in accordance with the foregoing examples and examples of other prodrug types may be found in the aforementioned references.

III. Compositions and Methods

The provided are methods of treating or preventing diseases associated with aberrant LOX family enzyme expression, particularly fibrotic disorders, including more specifically proliferative disorders, chronic and acute inflammatory disorders, cardiovascular diseases, primary or metastatic cancer, ocular diseases, pulmonary conditions, neurological ad neuropsychiatric conditions, or other diseases and medical conditions for which inhibiting one or more enzyme of the family of lysyl oxidases provides a therapeutic effect in a subject in need thereof by administering to the subject a LOX enzyme-inhibiting compound described herein, particularly a therapeutically effective amount of a pharmaceutical composition comprising the LOX enzyme-inhibiting compound disclosed herein.

One aspect of this disclosure it a method of treating, managing, ameliorating the symptoms of or preventing fibrotic disorders, proliferative disorders, inflammatory disorders, cardiovascular diseases, ocular diseases, primary or metastatic cancers, neurological and neuropsychiatric conditions, pulmonary conditions, or other diseases or medical conditions for which inhibiting any one of LOX, LOXL1, LOXL2, LOXL3, or LOXL4 provides a therapeutic benefit in a subject in need thereof by administering to the subject a LOX enzyme-inhibiting compound described herein, particularly a therapeutically effective amount of a pharmaceutical composition comprising the LOX enzyme-inhibiting compound disclosed herein.

Another aspect of this disclosure is a method of treating and preventing diseases associated with fibrosis, or treating symptoms associated with fibrotic diseases, and in particular such disorders for which inhibiting one or more LOX enzymes provides a therapeutic effect in a subject in need thereof by administering to the subject a LOX enzyme-inhibiting compound described herein, particularly a therapeutically effective amount of a pharmaceutical composition comprising the LOX enzyme-inhibiting compound disclosed herein. Without being bound by theory, the therapeutic effect provided is achieved by inhibiting oxidative deamination of lysine and hydroxylysine residues by LOX enzymes. Accordingly, embodiments herein include methods of treating and/or preventing a disease for which inhibiting of oxidative deamination of lysine and hydroxylysine residues in, for example but not limited to, collagen and elastin, provides a beneficial therapeutic effect by administering to a subject in need thereof a LOX enzyme-inhibiting compound described herein.

Embodiments herein include compounds of Formula I and methods of inhibiting one or more LOX enzymes in a subject in need thereof by administering to said subject an effective amount of LOX enzyme-inhibiting compound in accordance with Formula I, or a pharmaceutically acceptable salt or hydrate thereof. Formula I is as follows:

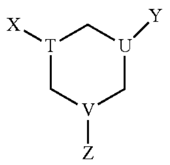

I wherein:

T, U, and V are nitrogen or carbon and only one of T, U, and V is nitrogen.

X is independently selected from $—OR^1$, $—SO_2R^1$, and $—C(=O)R^1$;

Y is independently selected from $—OR^2$, $—SO_2R^2$, and $—C(=O)R^2$;

Z is independently selected from $—R^3$, $—CH_2—R^3$, $—SO_2R^3$, $—C(=O)R^3$, and $—OR^3$;

$R^1$ is phenyl or heteroaryl containing 1 to 2 heteroatom(s) each independently selected from N, O, and S, wherein said phenyl or heteroaryl is substituted with $—CR^4R^5NH_2$ and optionally halogen or lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl;

$R^2$ is substituted or unsubstituted phenyl, substituted or unsubstituted benzyl, substituted or unsubstituted heteroaryl containing 1 to 2 heteroatom(s) each independently selected from N, O, and S, ($C_1$-$C_8$) alkyl, ($C_1$-$C_8$) cycloalkyl, mono-, di-, or trihalo($C_1$-$C_4$)alkyl, $—NR^6R^7$, where $R^6$ and $R^7$ are independently selected from H and lower alkyl or where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is substituted or unsubstituted, wherein substituent is lower alkyl or $—SO_2R^8$ or $—OR^8$, and wherein S is unsubstituted or forms sulfonyl, wherein said substituted phenyl, benzyl, or heteroaryl has at least one substituent being halogen, mono-, di- or trihalo($C_1$-$C_4$)alkyl, $—SO_2R^8$ or $—OR^8$ where $R^8$ is lower alkyl, cyano, lower alkyl, or $—SO_2NR^9R^{10}$, where $R^9$ and $R^{10}$ are independently selected from H and lower alkyl;

$R^3$ is unsubstituted or substituted phenyl, substituted or unsubstituted benzyl, or substituted or unsubstituted heteroaryl containing 1 to 2 heteroatom(s) each independently selected from N, O, and S, mono-, di-, or trihalo($C_1$-$C_4$)alkyl, ($C_1$-$C_8$) cycloalkyl, ($C_1$-$C_8$) alkyl, $—NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with a lower alkyl or $—SO_2R^{13}$ or $—OR^{13}$, and wherein S is unsubstituted or forms sulfonyl, wherein said substituted phenyl, benzyl, or heteroaryl has at least one substituent being halogen, mono-, di- or trihalo($C_1$-$C_4$) alkyl, $—SO_2R^{14}$ or $—OR^{14}$ where $R^{14}$ is lower alkyl, cyano, lower alkyl, or $—SO_2NR^{15}R^{16}$, where $R^{15}$ and $R^{16}$ are independently selected from H and lower alkyl;

including a tautomer, stereoisomer or racemic mixture thereof.

In embodiments, T, U, and V are nitrogen or carbon and only one of T, U, and V is nitrogen. In some embodiments, T is nitrogen and U and V are carbon. In some embodiments, U is nitrogen and T and V are carbon. In some embodiments, V is nitrogen and T and U are carbon.

In particular embodiments, X is $—OR^1$, $—SO_2R^1$, and $—C(=O)R^1$ where $R^1$ is phenyl or heteroaryl, wherein said phenyl or heteroaryl is substituted with $—CR^4R^5NH_2$ and optionally a halogen or lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl. In preferred embodiment, $R^4$ and $R^5$ are both hydrogen. In embodiments, $R^4$ and $R^5$ are independently H or methyl or $R^4$ and $R^5$ form cyclohexyl, 1,1-dioxidotetrahydro-2H-thiopyran-4-yl, or tetrahydropyran-4-yl.

In preferred embodiments, X is $—SO_2R^1$ where $R^1$ is phenyl or 4-, 5-, or 6-membered heteroaryl, wherein said phenyl or 4-, 5-, or 6-membered heteroaryl is substituted being methylamine and optionally a halogen or lower alkyl. In preferred embodiments, $R^1$ is phenyl, thiophen-2-yl, pyridin-4-yl, pyridin-2-yl, thiazol-2-yl, or pyrimidin-2-yl, wherein phenyl, thiophen-2-yl, pyridin-4-yl, pyridin-2-yl, thiazol-2-yl, or pyrimidin-2-yl is substituted with $—CR^4R^5NH_2$ and optionally halogen or lower alkyl, where $R^4$ and $R^5$ are both hydrogen.

In embodiments, Y is selected from $—OR^2$, $—SO_2R^2$, and $—C(=O)R^2$. In embodiments, when U is nitrogen, Y is preferably $—SO_2R^2$ or $—C(=O)R^2$.

In some embodiments, $R^2$ is lower alkyl, but preferably methyl, or $NR^6R^7$ where $R^6$ and $R^7$ are independently selected from H or lower alkyl. In preferred embodiments, Y is $—C(=O)R^2$ where $R^2$ is lower alkyl or $NR^6R^7$ where $R^6$ and $R^7$ are independently selected from H and lower alkyl. In other embodiments, $R^2$ is $NR^6R^7$ where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or $—SO_2R^8$ or $—OR^8$ where $R^8$ is lower alkyl, and wherein S is unsubstituted or forms sulfonyl. In preferred embodiments, $R^6$ and $R^7$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In some embodiments, $R^2$ is unsubstituted or substituted phenyl or unsubstituted or substituted benzyl, wherein substituted phenyl or benzyl is substituted with lower alkyl, halogen, mono-, di- or trihalo($C_1$-$C_4$)alkyl, cyano, or $—OR^9$, $—SO_2R^9$, or $—SO_2NR^9R^{10}$ where $R^9$ and $R^{10}$ are independently selected from H and lower alkyl.

In embodiments, Z is independently selected from $—R^3$, $—CH_2—R^3$, $—SO_2R^3$, $—C(=O)R^3$, and $—OR^3$. In some embodiments, when V is nitrogen, Z is $—CH_2—R^3$ or $—C(=O)R^3$.

In some embodiments, $R^3$ is mono-, di-, or trihalo($C_1$-$C_4$) alkyl, ($C_3$-$C_6$) cycloalkyl, lower alkyl, or $—NR^{11}R^{12}$ where $R^{11}$ and $R^{12}$ are independently selected from lower alkyl. In some embodiments, $R^3$ is $—NR^{11}R^{12}$ where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl, $—SO_2R^{13}$ or $—OR^{13}$, and wherein S is unsubstituted or forms sulfonyl. In some embodiments, $R^{11}$ and $R^{12}$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In some embodiments, $R^3$ is unsubstituted or substituted phenyl, unsubstituted or substituted benzyl, or unsubstituted or substituted heteroaryl containing 1 to 2 heteroatom(s) each independently selected from N, O, and S, wherein said substituted phenyl, benzyl, or heteroaryl has at least one substituent being halogen, mono-, di- or trihalo($C_1$-$C_4$)alkyl, $—SO_2R^{14}$ or $—OR^{14}$, where $R^{14}$ is lower alkyl, cyano, lower alkyl, or $—SO_2NR^{15}R^{16}$, where $R^{15}$ and $R^{16}$ are independently selected from H and lower alkyl;

In preferred embodiments, $R^3$ is substituted or unsubstituted phenyl, unsubstituted or substituted pyrimindin-2-yl, unsubstituted or substituted pyridin-4-yl, methoxy, halogen, cyclohexyl, methylsulfonyl, dimethylaminosulfonyl, or trifluoromethyl, wherein said phenyl, pyrimidin-2-yl, or pyridine-4-yl is substituted with halogen, cyano, lower alkyl, or methylsulfonyl. In some embodiments, when V is nitrogen, Z is methyl, methylcarbonyl, or unsubstituted or substituted benzyl or unsubstituted or substituted benzoyl, wherein said substituted benzyl or benzoyl is substituted with lower alkyl, methoxy, halogen, cyano, dimethylaminosulfonyl, or methylsulfonyl.

Some embodiments include compounds of Formula Ia and methods of inhibiting one or more LOX enzymes in a subject in need thereof by administering to said subject an effective amount of a LOX enzyme-inhibiting compound in accordance with Formula Ia, or a pharmaceutically acceptable salt or hydrate thereof. Formula Ia is as follows:

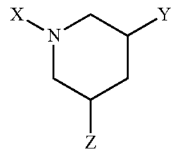

Ia wherein:

X is independently selected from —$OR^1$, —$SO_2R^1$, and —C(═O)$R^1$

Y is independently selected from —$OR^2$, —$SO_2R^2$, and —C(═O)$R^2$

Z is independently selected from —$R^3$, —$SO_2R^3$, and —$OR^3$ $R^1$ is phenyl or 4, 5, or 6-membered heteroaryl containing 1 to 2 heteroatom(s) each independently selected from N, O, and S, wherein said phenyl or 4, 5, or 6-membered heteroaryl is substituted with —$CR^4R^5NH_2$ and optionally halogen or lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl.

$R^2$ is substituted or unsubstituted phenyl, unsubstituted or substituted benzyl, unsubstituted or substituted 4-, 5-, or 6-membered heteroaryl containing 1 to 2 heteroatom(s) each independently selected from N, O, and S, ($C_1$-$C_8$) alkyl, ($C_1$-$C_8$) cycloalkyl, mono-, di-, or trihalo ($C_1$-$C_4$)alkyl, —$NR^6R^7$, where $R^6$ and $R^7$ are independently selected from H and lower alkyl or where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^8$ or —$OR^8$, and wherein S is unsubstituted or forms sulfonyl, wherein said substituted phenyl, benzyl, or 4, 5, or 6-membered heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl.

$R^3$ is unsubstituted or substituted phenyl or unsubstituted or substituted 4-, 5-, or 6-membered heteroaryl containing 1 to 2 heteroatom(s) each independently selected from N, O, and S, mono-, di-, or trihalo($C_1$-$C_4$)alkyl, ($C_1$-$C_8$) cycloalkyl, ($C_1$-$C_8$) alkyl, —$NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^{13}$ or —$OR^{13}$, and wherein S is unsubstituted or forms sulfonyl, wherein said substituted phenyl or 4-, 5-, or 6-membered heteroaryl has at least one substituent being halogen, mono-, di- or trihalo($C_1$-$C_4$)alkyl, —$SO_2R^{14}$ or —$OR^{14}$ where $R^{14}$ is lower alkyl, cyano, lower alkyl, or —$SO_2NR^{15}R^{16}$, where $R^{15}$ and $R^{16}$ are independently selected from H and lower alkyl;

including a tautomer, stereoisomer or racemic mixture thereof.

In some embodiments, X is independently selected from —$OR^1$, —$SO_2R^1$, and —C(═O)$R^1$ where $R^1$ is phenyl or 4, 5, or 6-membered heteroaryl containing 1 to 2 heteroatom(s) each independently selected from N, O, and S, wherein said phenyl or 4, 5, or 6-membered heteroaryl is substituted with —$CR^4R^5NH_2$ and optionally halogen or lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl. In preferred embodiments, $R^4$ and $R^5$ are both hydrogen. In some embodiments, $R^4$ and $R^5$ are independently H or methyl or $R^4$ and $R^5$ form cyclohexyl, 1,1-dioxidotetrahydro-2H-thiopyran-4-yl, or tetrahydropyran-4-yl.

In particular embodiments, X is —$SO_2R^1$ where $R^1$ is phenyl, thiophen-2-yl, pyridin-4-yl, pyridin-2-yl, thiazol-2-yl, or pyrimidin-2-yl, wherein said phenyl, thiophen-2-yl, pyridin-4-yl, pyridin-2-yl, thiazol-2-yl, or pyrimidin-2-yl is substituted with —$CR^4R^5NH_2$ and optionally halogen or lower alkyl, where $R^4$ and $R^5$ are both hydrogen.

In embodiments, Y is selected from —$OR^2$, —$SO_2R^2$, and —C(═O)$R^2$. In preferred embodiments, Y is —$SO_2R^2$ where $R^2$ is lower alkyl, but preferably methyl, or —$NR^6R^7$, where $R^6$ and $R^7$ are independently selected from H and lower alkyl. In some embodiments, Y is —C(═O)$R^2$ where $R^2$ is lower alkyl or $NR^6R^7$ where $R^6$ and $R^7$ are independently selected from H and lower alkyl. In other embodiments, Y is —C(═O)$R^2$ or —$SO_2R^2$ where $R^2$ is $NR^6R^7$ where $R^6$ and $R^7$ form a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^8$ or —$OR^8$ where $R^8$ is lower alkyl, and wherein S is unsubstituted or forms sulfonyl. In preferred embodiments, $R^6$ and $R^7$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In some embodiments, $R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, wherein said substituted phenyl, benzyl, or 4, 5, or 6-membered heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl.

In some embodiments, Z is selected from —$R^3$, —$SO_2R^3$, and —$OR^3$. In some embodiments, $R^3$ is unsubstituted or substituted phenyl or unsubstituted or substituted 4, 5, or 6-membered heteroaryl containing 1 to 2 heteroatom(s) each independently selected from N, O, and S, wherein said substituted phenyl or 4-, 5-, or 6-membered heteroaryl has at least one substituent being halogen, mono-, di- or trihalo ($C_1$-$C_4$)alkyl, —$SO_2R^{14}$ or —$OR^{14}$ where $R^{14}$ is lower alkyl, cyano, lower alkyl, or $—SO_2NR^{15}R^{16}$, where $R^{15}$ and $R^{16}$ are independently selected from H and lower alkyl. In preferred embodiments, Z is phenyl. In some embodiments, $R^3$ is mono-, di-, or trihalo($C_1$-$C_4$)alkyl, ($C_1$-$C_8$) cycloalkyl, ($C_1$-$C_8$) alkyl, or $—NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or $—SO_2R^{13}$ or $—OR^{13}$, and wherein S is unsubstituted or forms sulfonyl. In some embodiments, $R^{11}$ and $R^{12}$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In preferred embodiments, $R^3$ is substituted or unsubstituted phenyl, substituted or unsubstituted pyrimindin-2-yl, substituted or unsubstituted pyridin-4-yl, methoxy, halogen, cyclohexyl, methylsulfonyl, dimethylaminosulfonyl, or trifluoromethyl, wherein said phenyl, pyrimindin-2-yl, or pyridin-4-yl is substituted with halogen, cyano, lower alkyl, or methylsulfonyl.

Some embodiments include compounds of Formula Ib and methods of inhibiting one or more LOX enzymes in a subject in need thereof by administering to said subject an effective amount of a LOX enzyme-inhibiting compound in accordance with Formula Ib, or a pharmaceutically acceptable salt or hydrate thereof. Formula Ib is as follows:

Ib

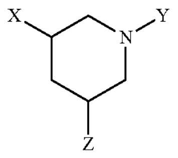

wherein:

X is independently selected from $—OR^1$, $—SO_2R^1$, and $—C(═O)R^1$

Y is independently selected from $—OR^2$, $—SO_2R^2$, and $—C(═O)R^2$

Z is independently selected from $—R^3$, $—SO_2R^3$, and $—OR^3$ $R^1$ is phenyl or 4, 5, or 6-membered heteroaryl containing 1 to 2 heteroatom(s) each independently selected from N, O, and S, wherein said phenyl or 4, 5, or 6-membered heteroaryl is substituted with $—CR^4R^5NH_2$ and optionally halogen or lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl.

$R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, ($C_1$-$C_8$) alkyl, ($C_1$-$C_8$) cycloalkyl, mono-, di-, or trihalo($C_1$-$C_4$)alkyl, $—NR^6R^7$, where $R^6$ and $R^7$ are independently selected from H and lower alkyl or where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or $—SO_2R^8$ or $—OR^8$, and wherein S is unsubstituted or forms sulfonyl, wherein said substituted phenyl, benzyl, or 4, 5, or 6-membered heteroaryl has at least one substituent being halogen, mono-, di- or trihalo($C_1$-$C_4$)alkyl, $—SO_2R^8$ or $—OR^8$ where $R^8$ is lower alkyl, cyano, lower alkyl, or $—SO_2NR^9R^{10}$, where $R^9$ and $R^{10}$ are independently selected from H and lower alkyl.

$R^3$ is unsubstituted or substituted phenyl or unsubstituted or substituted 4-, 5-, or 6-membered heteroaryl containing 1 to 2 heteroatom(s) each independently selected from N, O, and S, mono-, di-, or trihalo($C_1$-$C_4$)alkyl, ($C_1$-$C_8$) cycloalkyl, ($C_1$-$C_8$) alkyl, $—NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N optionally substituted with lower alkyl or $—SO_2R^{13}$ or $—OR^{13}$, and wherein S is unsubstituted or forms sulfonyl, wherein said substituted phenyl or 4-, 5-, or 6-membered heteroaryl has at least one substituent being halogen, mono-, di- or trihalo($C_1$-$C_4$)alkyl, $—SO_2R^{14}$ or $—OR^{14}$ where $R^{14}$ is lower alkyl, cyano, lower alkyl, or $—SO_2NR^{15}R^{16}$, where $R^{15}$ and $R^{16}$ are independently selected from H and lower alkyl;

including a tautomer, stereoisomer or racemic mixture thereof.

In some embodiments, X is independently selected from $—OR^1$, $—SO_2R^1$, and $—C(═O)R^1$ where $R^1$ is phenyl or 4, 5, or 6-membered heteroaryl containing 1 to 2 heteroatom(s) each independently selected from N, O, and S, wherein said phenyl or 4, 5, or 6-membered heteroaryl is substituted with $—CR^4R^5NH_2$ and optionally halogen optionally lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl. In preferred embodiments, $R^4$ and $R^5$ are both hydrogen. In some embodiments, $R^4$ and $R^5$ are independently H or methyl or $R^4$ and $R^5$ form cyclohexyl, 1,1-dioxidotetrahydro-2H-thiopyran-4-yl, or tetrahydropyran-4-yl.

In particular embodiments, X is $—SO_2R^1$ where $R^1$ is phenyl, thiophen-2-yl, pyridin-4-yl, pyridin-2-yl, thiazol-2-yl, or pyrimidin-2-yl, wherein said phenyl, thiophen-2-yl, pyridin-4-yl, pyridin-2-yl, thiazol-2-yl, or pyrimidin-2-yl is substituted with $—CR^4R^5NH_2$ and optionally halogen or lower alkyl, where $R^4$ and $R^5$ are both hydrogen. In some embodiments, X is $—OR^1$ where $R^1$ is phenyl, wherein said phenyl is substituted with $—CR^4R^5NH_2$ where $R^4$ and $R^5$ are both hydrogen.

In embodiments, Y is independently selected from $—OR^2$, $—SO_2R^2$, and $—C(═O)R^2$. In embodiments, Y is preferably $—SO_2R^2$ or $—C(═O)R^2$. In preferred embodiments, Y is $—SO_2R^2$ where $R^2$ is lower alkyl, but preferably methyl, or $—NR^6R^7$, where $R^6$ and $R^7$ are independently selected from H and lower alkyl. In some embodiments, Y is $—C(═O)R^2$ where $R^2$ is lower alkyl or $NR^6R^7$ where $R^6$ and $R^7$ are independently selected from H and lower alkyl. In other embodiments, Y is $—C(═O)R^2$ or $—SO_2R^2$ where $R^2$ is $NR^6R^7$ where $R^6$ and $R^7$ form a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or $—SO_2R^8$ or $—OR^8$ where $R^8$ is lower alkyl, and wherein S is unsubstituted or forms sulfonyl. In preferred embodiments, $R^6$ and $R^7$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In some embodiments, $R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, wherein said substituted phenyl, benzyl, or 4, 5, or 6-membered heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl.

In some embodiments, Z is elected from —$R^3$, —$SO_2R^3$, and —$OR^3$. In some embodiments, $R^3$ is unsubstituted or substituted phenyl or unsubstituted or substituted 4, 5, or 6-membered heteroaryl containing 1 to 2 heteroatom(s) each independently selected from N, O, and S, wherein said substituted phenyl or 4-, 5-, or 6-membered heteroaryl has at least one substituent being halogen, mono-, di- or trihalo ($C_1$-$C_4$)alkyl, —$SO_2R^{14}$ or —$OR^{14}$ where $R^{14}$ is lower alkyl, cyano, lower alkyl, or —$SO_2NR^{15}R^{16}$, where $R^{15}$ and $R^{16}$ are independently selected from H and lower alkyl. In preferred embodiments, Z is phenyl. In some embodiments, $R^3$ is mono-, di-, or trihalo($C_1$-$C_4$)alkyl, ($C_1$-$C_8$) cycloalkyl, ($C_1$-$C_8$) alkyl, or —$NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^{13}$ or —$OR^{13}$, and wherein S is unsubstituted or forms sulfonyl. In some embodiments, $R^{11}$ and $R^{12}$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In preferred embodiments, $R^3$ is substituted or unsubstituted phenyl, substituted or unsubstituted pyrimindin-2-yl, substituted or unsubstituted pyridin-4-yl, methoxy, halogen, cyclohexyl, methylsulfonyl, dimethylaminosulfonyl, or trifluoromethyl, wherein said phenyl, pyrimidin-2-yl, or pyridine-4-yl is substituted with halogen, cyano, lower alkyl, or methylsulfonyl.

Some embodiments include compounds of Formula Ic and methods of inhibiting one or more LOX enzymes in a subject in need thereof by administering to said subject an effective amount of a LOX enzyme-inhibiting compound in accordance with Formula Ic, or a pharmaceutically acceptable salt or hydrate thereof. Formula Ic is as follows:

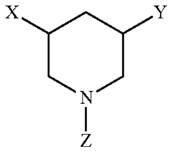

Ic wherein:

X is independently selected from —$OR^1$, —$SO_2R^1$, and —$C(=O)R^1$

Y is independently selected from —$OR^2$, —$SO_2R^2$, and —$C(=O)R^2$

Z is independently selected from —$R^3$, —$CH_2$—$R^3$, —$SO_2R^3$, —$C(=O)R^3$, and —$OR^3$ $R^1$ is phenyl or 4-, 5-, or 6-membered heteroaryl containing 1 to 2 heteroatom(s) each independently selected from N, O, and S, wherein said phenyl or 4-, 5-, or 6-membered heteroaryl is substituted with —$CR^4R^5NH_2$ and optionally halogen or lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl.

$R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, ($C_1$-$C_8$) alkyl, ($C_1$-$C_8$) cycloalkyl, mono-, di-, or trihalo($C_1$-$C_4$)alkyl, —$NR^6R^7$, where $R^6$ and $R^7$ are independently selected from H and lower alkyl or where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^8$ or —$OR^8$, and wherein S is unsubstituted or forms sulfonyl, wherein said substituted phenyl, benzyl, or 4, 5, or 6-membered heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl.

$R^3$ is unsubstituted or substituted phenyl or unsubstituted or substituted 4-, 5-, or 6-membered heteroaryl containing 1 to 2 heteroatom(s) each independently selected from N, O, and S, mono-, di-, or trihalo($C_1$-$C_4$)alkyl, ($C_1$-$C_8$) cycloalkyl, ($C_1$-$C_8$) alkyl, —$NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^{13}$ or —$OR^{13}$, and wherein S is unsubstituted or forms sulfonyl, wherein said substituted phenyl or 4-, 5-, or 6-membered heteroaryl has at least one substituent being halogen, mono-, di- or trihalo($C_1$-$C_4$)alkyl, —$SO_2R^{14}$ or —$OR^{14}$ where $R^{14}$ is lower alkyl, cyano, lower alkyl, or —$SO_2NR^{15}R^{16}$, where $R^{15}$ and $R^{16}$ are independently selected from H and lower alkyl;

including a tautomer, stereoisomer or racemic mixture thereof.

In some embodiments, X is selected from —$OR^1$, —$SO_2R^1$, and —$C(=O)R^1$ where $R^1$ is phenyl or 4, 5, or 6-membered heteroaryl containing 1 to 2 heteroatom(s) each independently selected from N, O, and S, wherein said phenyl or 4, 5, or 6-membered heteroaryl is substituted with —$CR^4R^5NH_2$ and optionally halogen or lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl. In preferred embodiments, $R^4$ and $R^5$ are both hydrogen. In some embodiments, $R^4$ and $R^5$ are independently H or methyl or $R^4$ and $R^5$ form cyclohexyl, 1,1-dioxidotetrahydro-2H-thiopyran-4-yl, or tetrahydropyran-4-yl.

In particular embodiments, X is —$SO_2R^1$ where $R^1$ is phenyl, thiophen-2-yl, pyridin-4-yl, pyridin-2-yl, thiazol-2-yl, or pyrimidin-2-yl, wherein said phenyl, thiophen-2-yl, pyridin-4-yl, pyridin-2-yl, thiazol-2-yl, or pyrimidin-2-yl is substituted with —$CR^4R^5NH_2$ and optionally halogen or lower alkyl, where $R^4$ and $R^5$ are both hydrogen. In some embodiments, X is —$OR^1$ where $R^1$ is phenyl, wherein said phenyl is substituted with —$CR^4R^5NH_2$ where $R^4$ and $R^5$ are both hydrogen.

In embodiments, Y is selected from —$OR^2$, —$SO_2R^2$, and —$C(=O)R^2$, but preferably $SO_2R^2$ and —$C(=O)R^2$. In preferred embodiments, Y is —$SO_2R^2$ where $R^2$ is lower alkyl, but preferably methyl, or —$NR^6R^7$, where $R^6$ and $R^7$ are independently selected from H and lower alkyl. In some embodiments, Y is —C(=O)$R^2$ where $R^2$ is lower alkyl or $NR^6R^7$ where $R^6$ and $R^7$ are independently selected from H and lower alkyl. In other embodiments, Y is —C(=O)$R^2$ or —$SO_2R^2$ where $R^2$ is $NR^6R^7$ where $R^6$ and $R^7$ form a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^8$ or —$OR^8$ where $R^8$ is lower alkyl, and wherein S is unsubstituted or forms sulfonyl. In preferred embodiments, $R^6$ and $R^7$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In some embodiments, $R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, wherein said substituted phenyl, benzyl, or 4, 5, or 6-membered heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl.

In some embodiments, Z is selected from —$R^3$, —$SO_2R^3$, —C(=O)$R^3$, —$CH_2R^3$, and —$OR^3$. In some embodiments, Z is benzyl or benzoyl. In some embodiments, $R^3$ is unsubstituted or substituted phenyl or unsubstituted or substituted 4, 5, or 6-membered heteroaryl containing 1 to 2 heteroatom(s) each independently selected from N, O, and S, wherein said substituted phenyl or 4-, 5-, or 6-membered heteroaryl has at least one substituent being halogen, mono-, di- or trihalo($C_1$-$C_4$)alkyl, —$SO_2R^{14}$ or —$OR^{14}$ where $R^{14}$ is lower alkyl, cyano, lower alkyl, or —$SO_2NR^{15}R^{16}$, where $R^{15}$ and $R^{16}$ are independently selected from H and lower alkyl. In preferred embodiments, Z is phenyl. In some embodiments, $R^3$ is mono-, di-, or trihalo($C_1$-$C_4$)alkyl, ($C_1$-$C_8$) cycloalkyl, ($C_1$-$C_8$) alkyl, or —$NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^{13}$ or —$OR^{13}$, and wherein S is unsubstituted or forms sulfonyl. In some embodiments, $R^{11}$ and $R^{12}$ form together a ($C_3$-$C_6$) hetero-cycloalkyl, wherein the ($C_3$-$C_6$) hetero-cycloalkyl is piperidinyl, piperazine, 4-methylpiperazin-1-yl, 4-(methylsulfonyl)piperazinyl, 4-morpholinyl, 1,1-dioxidothiomorpholinyl. In preferred embodiments, $R^3$ is substituted or unsubstituted phenyl, substituted or unsubstituted benzyl, substituted or unsubstituted benzoyl, substituted or unsubstituted pyrimindin-2-yl, substituted or unsubstituted pyridin-4-yl, methoxy, halogen, cyclohexyl, methylsulfonyl, dimethylaminosulfonyl, or trifluoromethyl, wherein said phenyl, benzyl, benzoyl, pyrimidin-2-yl, or pyridine-4-yl is substituted with halogen, cyano, lower alkyl, or methylsulfonyl.

Some embodiments include compounds of Formula Id and methods of inhibiting one or more LOX enzymes in a subject in need thereof by administering to said subject an effective amount of a LOX enzyme-inhibiting compound in accordance with Formula Id, or a pharmaceutically acceptable salt or hydrate thereof. Formula Id is as follows:

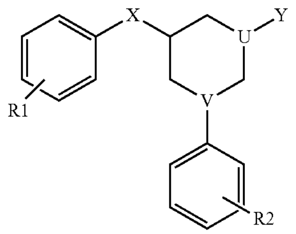

Id wherein:

U and V is nitrogen or carbon, wherein only U or V is nitrogen.

X is independently selected from —O—, —$SO_2$—, and —C(=O)—.

Y is independently selected from —$OR^3$, —$SO_2R^3$, and —C(=O)$R^3$ $R^1$ is —$CR^4R^5NH_2$ and optionally halogen or lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl.

$R^2$ is at halogen, mono-, di- or trihalo($C_1$-$C_4$)alkyl, —$SO_2R^{11}$ or —$OR^{11}$ where $R^{11}$ is lower alkyl, cyano, lower alkyl, or —$SO_2NR^{12}R^{13}$, where $R^2$ and $R^{13}$ are independently selected from H and lower alkyl.

$R^3$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, ($C_1$-$C_8$) alkyl, ($C_1$-$C_8$) cycloalkyl, mono-, di-, or trihalo($C_1$-$C_4$)alkyl, —$NR^6R^7$, where $R^6$ and $R^7$ are independently selected from H and lower alkyl or where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^8$ or —$OR^8$, and wherein S is unsubstituted or forms sulfonyl, wherein said substituted phenyl, benzyl, or 4, 5, or 6-membered heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl;

including a tautomer, stereoisomer or racemic mixture thereof.

In some embodiments, U is nitrogen and V is carbon. In other embodiments, V is nitrogen and U is carbon.

In embodiments, X is selected from —O—, —$SO_2$—, and —C(=O)—.

In some embodiments, $R^1$ is —$CR^4R^5NH_2$ and optionally halogen or lower alkyl, where $R^4$ and $R^5$ are independently H or lower alkyl or $R^4$ and $R^5$ form a ($C_1$-$C_8$) cycloalkyl or ($C_1$-$C_8$) hetero-cycloalkyl. In preferred embodiments, $R^4$ and $R^5$ are both hydrogen. In some embodiments, $R^4$ and $R^5$ are independently H or methyl or $R^4$ and $R^5$ form cyclohexyl, 1,1-dioxidotetrahydro-2H-thiopyran-4-yl, or tetrahydropyran-4-yl. In particular embodiments, X is —$SO_2$— or —O— and $R^1$ is —$CR^4R^5NH_2$ and optionally halogen or lower alkyl, where $R^4$ and $R^5$ are both hydrogen In some embodiments, $R^2$ is at halogen, mono-, di- or trihalo($C_1$-$C_4$)alkyl, —$SO_2R^1$ or —$OR^{11}$ where $R^{11}$ is lower alkyl, cyano, lower alkyl, or —$SO_2NR^{12}R^{13}$, where $R^2$ and $R^{13}$ are independently selected from H and lower alkyl.

In embodiments, Y is selected from —$OR^3$, —$SO_2R^3$, and —C(═O)$R^3$. In embodiments, when U is nitrogen and V is carbon, Y is preferably —$SO_2R^3$ or —C(═O)$R^3$. In preferred embodiments, Y is —$SO_2R^3$ where $R^3$ is lower alkyl, but preferably methyl, or —$NR^6R^7$, where $R^6$ and $R^7$ are independently selected from H and lower alkyl. In some embodiments, Y is —C(═O)$R^3$ where $R^3$ is lower alkyl or $NR^6R^7$ where $R^6$ and $R^7$ are independently selected from H and lower alkyl. In other embodiments, Y is —C(═O)$R^3$ or —$SO_2R^3$ where $R^2$ is $NR^6R^7$ where $R^6$ and $R^7$ form a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^8$ or —$OR^8$ where $R^8$ is lower alkyl, and wherein S is unsubstituted or forms sulfonyl. In preferred embodiments, $R^6$ and $R^7$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl) piperazinyl, 4-morpholinyl, 1,1-dioxidothiomorpholinyl. In some embodiments, $R^3$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, wherein said substituted phenyl, benzyl, or 4, 5, or 6-membered heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl.

Other embodiments include compounds of Formula Ie and methods of inhibiting one or more LOX enzymes in a subject in need thereof by administering to said subject such Formula Ie compound. These methods comprise administering to a subject in need thereof an effective amount of a LOX enzyme-inhibiting compound in accordance with Formula Ie, or a pharmaceutically acceptable salt or hydrate thereof. Formula Ie is as follows:

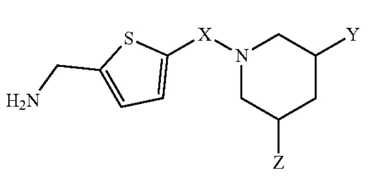

Ie wherein:

X is independently selected from —O—, —$SO_2$—, and —C(═O)—.

Y is independently selected from —$OR^2$, —$SO_2R^2$, and —C(═O)$R^2$

Z is independently selected from —$R^3$, —$CH_2$—$R^3$, —$SO_2R^3$, —C(═O)$R^3$, and —$OR^3$ $R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, ($C_1$-$C_8$) alkyl, ($C_1$-$C_8$) cycloalkyl, mono-, di-, or trihalo($C_1$-$C_4$)alkyl, —$NR^6R^7$, where $R^6$ and $R^7$ are independently selected from H and lower alkyl or where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^8$ or —$OR^8$, and wherein S is unsubstituted or forms sulfonyl, wherein said substituted phenyl, benzyl, or 4, 5, or 6-membered heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl.

$R^3$ is unsubstituted or substituted phenyl or substituted or unsubstituted 4-, 5-, or 6-membered heteroaryl containing 1 to 2 heteroatom(s) each independently selected from N, O, and S, mono-, di-, or trihalo($C_1$-$C_4$)alkyl, ($C_1$-$C_8$) cycloalkyl, ($C_1$-$C_8$) alkyl, —$NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^{13}$ or —$OR^{13}$, and wherein S is unsubstituted or forms sulfonyl, wherein said substituted phenyl or 4-, 5-, or 6-membered heteroaryl has at least one substituent being halogen, mono-, di- or trihalo($C_1$-$C_4$)alkyl, —$SO_2R^{14}$ or —$OR^{14}$ where $R^{14}$ is lower alkyl, cyano, lower alkyl, or —$SO_2NR^{15}R^{16}$, where $R^{15}$ and $R^{16}$ are independently selected from H and lower alkyl;

including a tautomer, stereoisomer or racemic mixture thereof.

In some embodiments, X is selected from —O—, —$SO_2$—, and —C(═O)—. In preferred embodiments, X is —$SO_2$—.

In embodiments, Y is selected from —$OR^2$, —$SO_2R^2$, and —C(═O)$R^2$. In preferred embodiments, Y is —$SO_2R^2$ where $R^2$ is lower alkyl, but preferably methyl, or —$NR^6R^7$, where $R^6$ and $R^7$ are independently selected from H and lower alkyl. In some embodiments, Y is —C(═O)$R^2$ where $R^2$ is lower alkyl or $NR^6R^7$ where $R^6$ and $R^7$ are independently selected from H and lower alkyl. In other embodiments, Y is —C(═O)$R^2$ or —$SO_2R^2$ where $R^2$ is $NR^6R^7$ where $R^6$ and $R^7$ form a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^8$ or —$OR^8$ where $R^8$ is lower alkyl, and wherein S is unsubstituted or forms sulfonyl. In preferred embodiments, $R^6$ and $R^7$ form together a ($C_3$-$C_6$) hetero-cycloalkyl, wherein the ($C_3$-$C_6$) hetero-cycloalkyl is piperidin-1-yl, piperazin-1-yl, 4-methylpiperazin-1-yl, 4-(methylsulfonyl) piperazin-1-yl, 4-morpholinyl, 1,1-dioxidothiomorpholinyl In some embodiments, $R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, wherein said substituted phenyl, benzyl, or 4, 5, or 6-membered heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl. In a preferred embodiment, Y is —$SO_2R^2$ where $R^2$ is In some embodiments, Z is selected from —$R^3$, —$SO_2R^3$, and —$OR^3$. In some embodiments, $R^3$ is unsubstituted or substituted phenyl or unsubstituted or substituted 4, 5, or 6-membered heteroaryl containing 1 to 2 heteroatom(s) each independently selected from N, O, and S, wherein said substituted phenyl or 4-, 5-, or 6-membered heteroaryl has at least one substituent being halogen, mono-, di- or trihalo ($C_1$-$C_4$)alkyl, —$SO_2R^{14}$ or —$OR^{14}$ where $R^{14}$ is lower alkyl, cyano, lower alkyl, or $—SO_2NR^{15}R^{16}$, where $R^{15}$ and $R^{16}$ are independently selected from H and lower alkyl. In preferred embodiments, Z is phenyl. In some embodiments, $R^3$ is mono-, di-, or trihalo($C_1$-$C_4$)alkyl, ($C_1$-$C_8$) cycloalkyl, ($C_1$-$C_8$) alkyl, or $—NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or $—SO_2R^{13}$ or $—OR^{13}$, and wherein S is unsubstituted or forms sulfonyl. In some embodiments, $R^{11}$ and $R^{12}$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In preferred embodiments, $R^3$ is substituted or unsubstituted phenyl, substituted or unsubstituted pyrimindin-2-yl, substituted or unsubstituted pyridin-4-yl, methoxy, halogen, cyclohexyl, methylsulfonyl, dimethylaminosulfonyl, or trifluoromethyl, wherein said phenyl, pyrimindin-2-yl, or pyridin-4-yl is substituted with halogen, cyano, lower alkyl, or methylsulfonyl.

Yet other embodiments include compounds of Formula If and methods of inhibiting one or more LOX enzymes in a subject by administering such Formula If compound. These methods comprise administering to a subject in need thereof an effective amount of a LOX enzyme-inhibiting compound in accordance with Formula If or a pharmaceutically acceptable salt or hydrate thereof. Formula If is as follows:

If

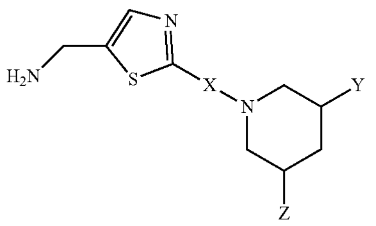

wherein:

X is independently selected from —O—, $—SO_2—$, and —C(═O)—.

Y is independently selected from $—OR^2$, $—SO_2R^2$, and $—C(═O)R^2$

Z is independently selected from $—R^3$, $—CH_2—R^3$, $—SO_2R^3$, $—C(═O)R^3$, and $—OR^3$ $R^2$ is substituted or unsubstituted phenyl, substituted or unsubstituted benzyl, substituted or unsubstituted 4-, 5-, or 6-membered heteroaryl containing 1 to 2 heteroatom(s) each independently selected from N, O, and S, ($C_1$-$C_8$) alkyl, ($C_1$-$C_8$) cycloalkyl, mono-, di-, or trihalo($C_1$-$C_4$)alkyl, $—NR^6R^7$, where $R^6$ and $R^7$ are independently selected from H and lower alkyl or where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or $—SO_2R^8$ or $—OR^8$, and wherein S is unsubstituted or forms sulfonyl, wherein said substituted phenyl, benzyl, or 4, 5, or 6-membered heteroaryl has at least one substituent being halogen, mono-, di- or trihalo($C_1$-$C_4$)alkyl, $—SO_2R^8$ or $—OR^8$ where $R^8$ is lower alkyl, cyano, lower alkyl, or $—SO_2NR^9R^{10}$, where $R^9$ and $R^{10}$ are independently selected from H and lower alkyl.

$R^3$ is unsubstituted or substituted phenyl or unsubstituted or substituted 4-, 5-, or 6-membered heteroaryl containing 1 to 2 heteroatom(s) each independently selected from N, O, and S, mono-, di-, or trihalo($C_1$-$C_4$)alkyl, ($C_1$-$C_8$) cycloalkyl, ($C_1$-$C_8$) alkyl, $—NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or $—SO_2R^{13}$ or $—OR^{13}$, and wherein S is unsubstituted or forms sulfonyl, wherein said substituted phenyl or 4-, 5-, or 6-membered heteroaryl has at least one substituent being halogen, mono-, di- or trihalo($C_1$-$C_4$)alkyl, $—SO_2R^{14}$ or $—OR^{14}$ where $R^{14}$ is lower alkyl, cyano, lower alkyl, or $—SO_2NR^{15}R^{16}$, where $R^{15}$ and $R^{16}$ are independently selected from H and lower alkyl;

including a tautomer, stereoisomer or racemic mixture thereof.

In some embodiments, X is selected from —O—, $—SO_2—$, and —C(═O)—. In preferred embodiments, X is $—SO_2—$.

In embodiments, Y is selected from $—OR^2$, $—SO_2R^2$, and $—C(═O)R^2$. In preferred embodiments, Y is $—SO_2R^2$ where $R^2$ is lower alkyl, but preferably methyl, or $—NR^6R^7$, where $R^6$ and $R^7$ are independently selected from H and lower alkyl. In some embodiments, Y is $—C(═O)R^2$ where $R^2$ is lower alkyl or $NR^6R^7$ where $R^6$ and $R^7$ are independently selected from H and lower alkyl. In other embodiments, Y is $—C(═O)R^2$ or $—SO_2R^2$ where $R^2$ is $NR^6R^7$ where $R^6$ and $R^7$ form a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or $—SO_2R^8$ or $—OR^8$ where $R^8$ is lower alkyl, and wherein S is unsubstituted or forms sulfonyl. In preferred embodiments, $R^6$ and $R^7$ form together a ($C_3$-$C_6$) hetero-cycloalkyl, wherein the ($C_3$-$C_6$) hetero-cycloalkyl is piperidin-1-yl, piperazin-1-yl, 4-methylpiperazin-1-yl, 4-(methylsulfonyl) piperazin-1-yl, 4-morpholinyl, 1,1-dioxidothiomorpholinyl In some embodiments, $R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, wherein said substituted phenyl, benzyl, or 4, 5, or 6-membered heteroaryl has at least one substituent being halogen, mono-, di- or trihalo($C_1$-$C_4$)alkyl, $—SO_2R^8$ or $—OR^8$ where $R^8$ is lower alkyl, cyano, lower alkyl, or $—SO_2NR^9R^{10}$, where $R^9$ and $R^{10}$ are independently selected from H and lower alkyl. In a preferred embodiment, Y is $—SO_2R^2$ where $R^2$ is In some embodiments, Z is selected from $—R^3$, $—SO_2R^3$, and $—OR^3$. In some embodiments, $R^3$ is unsubstituted or substituted phenyl or substituted or unsubstituted 4, 5, or 6-membered heteroaryl containing 1 to 2 heteroatom(s) each independently selected from N, O, and S, wherein said substituted phenyl or 4-, 5-, or 6-membered heteroaryl has at least one substituent being halogen, mono-, di- or trihalo ($C_1$-$C_4$)alkyl, $—SO_2R^{14}$ or $—OR^{14}$ where $R^{14}$ is lower alkyl, cyano, lower alkyl, or $—SO_2NR^{15}R^{16}$, where $R^{15}$ and $R^{16}$ are independently selected from H and lower alkyl. In preferred embodiments, Z is phenyl. In some embodiments, $R^3$ is mono-, di-, or trihalo($C_1$-$C_4$)alkyl, ($C_1$-$C_8$) cycloalkyl, $(C_1-C_8)$ alkyl, or —$NR^{11}R^{12}$, where $R^{11}$ and $R^{12}$ are independently selected from H and lower alkyl or where $R^{11}$ and $R^{12}$ form together a $(C_3-C_6)$ hetero-cycloalkyl, wherein the $(C_3-C_6)$ hetero-cycloalkyl optionally contains besides the nitrogen one additional heteroatom selected from N, O, and S, wherein N is optionally substituted with lower alkyl or —$SO_2R^{13}$ or —$OR^{13}$, and wherein S is unsubstituted or forms sulfonyl. In some embodiments, $R^{11}$ and $R^{12}$ form together a $(C_3-C_6)$ hetero-cycloalkyl, wherein the $(C_3-C_6)$ hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In preferred embodiments, $R^3$ is substituted or unsubstituted phenyl, substituted or unsubstituted pyrimindin-2-yl, substituted or unsubstituted pyridin-4-yl, methoxy, halogen, cyclohexyl, methylsulfonyl, dimethylaminosulfonyl, or trifluoromethyl, wherein said phenyl, pyrimindin-2-yl, or pyridin-4-yl is substituted with halogen, cyano, lower alkyl, or methylsulfonyl.

Some embodiments include compounds of Formula Ig and methods of inhibiting one or more LOX enzymes in a subject in need thereof by administering to said subject an effective amount of a LOX enzyme-inhibiting compound in accordance with Formula Ig or a pharmaceutically acceptable salt or hydrate thereof. Formula Ig is as follows:

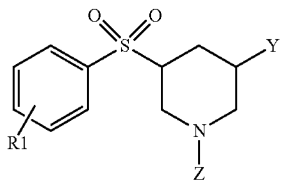

Ig wherein:

Y is independently selected from —$OR^2$, —$SO_2R^2$, and —$C(=O)R^2$

Z is independently selected from —$R^3$, —$CH_2$—$R^3$, —$SO_2R^3$, —$C(=O)R^3$, and —$OR^3$ $R^1$ is —$CR^4R^5NH_2$ and optionally halogen or lower alkyl, where $R^4$ and $R^5$ are independently H or lower alkyl or $R^4$ and $R^5$ form a $(C_1-C_8)$ cycloalkyl or $(C_1-C_8)$ hetero-cycloalkyl.

$R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, $(C_1-C_8)$ alkyl, $(C_1-C_8)$ cycloalkyl, mono-, di-, or trihalo$(C_1-C_4)$alkyl, —$NR^6R^7$, where $R^6$ and $R^7$ are independently selected from H and lower alkyl or where $R^6$ and $R^7$ form together a $(C_3-C_6)$ hetero-cycloalkyl, wherein the $(C_3-C_6)$ hetero-cycloalkyl optionally contains besides the nitrogen one additional heteroatom selected from N, O, and S, wherein N is optionally substituted with lower alkyl or —$SO_2R^8$ or —$OR^8$, and wherein S is unsubstituted or forms sulfonyl, wherein said substituted phenyl, benzyl, or 4, 5, or 6-membered heteroaryl has at least one substituent being halogen, mono-, di- or trihalo$(C_1-C_4)$alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl.

$R^3$ is unsubstituted or substituted phenyl or substituted or unsubstituted 4-, 5-, or 6-membered heteroaryl containing 1 to 2 heteroatom(s) each independently selected from N, O, and S, mono-, di-, or trihalo$(C_1-C_4)$alkyl, $(C_1-C_8)$ cycloalkyl, $(C_1-C_8)$ alkyl, —$NR^{11}R^{12}$, where $R^{11}$ and $R^{12}$ are independently selected from H and lower alkyl or where $R^{11}$ and $R^{12}$ form together a $(C_3-C_6)$ hetero-cycloalkyl, wherein the $(C_3-C_6)$ hetero-cycloalkyl optionally contains besides the nitrogen one additional heteroatom selected from N, O, and S, wherein N is optionally substituted with lower alkyl or —$SO_2R^{13}$ or —$OR^{13}$, and wherein S is unsubstituted or forms sulfonyl, wherein said substituted phenyl or 4-, 5-, or 6-membered heteroaryl has at least one substituent being halogen, mono-, di- or trihalo$(C_1-C_4)$alkyl, —$SO_2R^{14}$ or —$OR^{14}$ where $R^{14}$ is lower alkyl, cyano, lower alkyl, or —$SO_2NR^{15}R^{16}$, where $R^{15}$ and $R^{16}$ are independently selected from H and lower alkyl;

including a tautomer, stereoisomer or racemic mixture thereof.

In embodiments, $R^1$ is —$CR^4R^5NH_2$ where $R^4$ and $R^5$ are independently H or lower alkyl or $R^4$ and $R^5$ form a $(C_1-C_8)$ cycloalkyl or $(C_1-C_8)$ hetero-cycloalkyl. In preferred embodiments, $R^4$ and $R^5$ are both hydrogen. In some embodiments, $R^4$ and $R^5$ are independently H or methyl or $R^4$ and $R^5$ form cyclohexyl, 1,1-dioxidotetrahydro-2H-thiopyran-4-yl, or tetrahydropyran-4-yl. In particular embodiments, X is —$SO_2$— or —O— and $R^1$ is —$CR^4R^5NH_2$ where $R^4$ and $R^5$ are both hydrogen.

In embodiments, Y is selected from —$OR^2$, —$SO_2R^2$, and —$C(=O)R^2$.

In preferred embodiments, Y is —$SO_2R^2$ where $R^2$ is lower alkyl, but preferably methyl, or —$NR^6R^7$, where $R^6$ and $R^7$ are independently selected from H and lower alkyl. In some embodiments, Y is —$C(=O)R^2$ where $R^2$ is lower alkyl or $NR^6R^7$ where $R^6$ and $R^7$ are independently selected from H and lower alkyl. In other embodiments, Y is —$C(=O)R^2$ or —$SO_2R^2$ where $R^2$ is $NR^6R^7$ where $R^6$ and $R^7$ form a $(C_3-C_6)$ hetero-cycloalkyl, wherein the $(C_3-C_6)$ hetero-cycloalkyl optionally contains besides the nitrogen one additional heteroatom selected from N, O, and S, wherein N is optionally substituted with lower alkyl or —$SO_2R^8$ or —$OR^8$ where $R^8$ is lower alkyl, and wherein S is unsubstituted or forms sulfonyl. In preferred embodiments, $R^6$ and $R^7$ form together a $(C_3-C_6)$ hetero-cycloalkyl, wherein the $(C_3-C_6)$ hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In some embodiments, $R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, wherein said substituted phenyl, benzyl, or 4, 5, or 6-membered heteroaryl has at least one substituent being halogen, mono-, di- or trihalo$(C_1-C_4)$alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl.

In some embodiments, Z is selected from —$R^3$, —$SO_2R^3$, and —$OR^3$. In some embodiments, $R^3$ is unsubstituted or substituted phenyl or substituted or unsubstituted 4, 5, or 6-membered heteroaryl containing 1 to 2 heteroatom(s) each independently selected from N, O, and S, wherein said substituted phenyl or 4-, 5-, or 6-membered heteroaryl has at least one substituent being halogen, mono-, di- or trihalo $(C_1-C_4)$alkyl, —$SO_2R^{14}$ or —$OR^{14}$ where $R^{14}$ is lower alkyl, cyano, lower alkyl, or —$SO_2NR^{15}R^{16}$, where $R^{15}$ and $R^{16}$ are independently selected from H and lower alkyl. In preferred embodiments, Z is phenyl. In some embodiments, $R^3$ is mono-, di-, or trihalo$(C_1-C_4)$alkyl, $(C_1-C_8)$ cycloalkyl, $(C_1-C_8)$ alkyl, or —$NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^{13}$ or —$OR^{13}$, and wherein S is unsubstituted or forms sulfonyl. In some embodiments, $R^{11}$ and $R^{12}$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In preferred embodiments, $R^3$ is substituted or unsubstituted phenyl, substituted or unsubstituted pyrimindin-2-yl, substituted or unsubstituted pyridin-4-yl, methoxy, halogen, cyclohexyl, methylsulfonyl, dimethylaminosulfonyl, or trifluoromethyl, wherein said phenyl, pyrmindin-2-yl, or pyridin-4-yl is substituted with halogen, cyano, lower alkyl, or methylsulfonyl.

Yet other embodiments include compounds of Formula Ih and methods of inhibiting one or more LOX enzymes in a subject by administering such Formula Ih compound. These methods comprise administering to a subject in need thereof an effective amount of a LOX enzyme-inhibiting compound in accordance with Formula Ih or a pharmaceutically acceptable salt or hydrate thereof. Formula Ih is as follows:

Ih

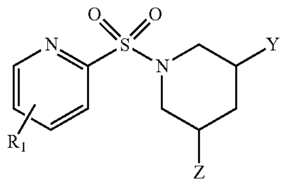

wherein:

Y is independently selected from —$OR^2$, —$SO_2R^2$, and —C(═O)$R^2$

Z is independently selected from —$R^3$, —$CH_2$—$R^3$, —$SO_2R^3$, —C(═O)$R^3$, and —$OR^3$ $R^2$ is substituted or unsubstituted phenyl, substituted or unsubstituted benzyl, substituted or unsubstituted 4-, 5-, or 6-membered heteroaryl containing 1 to 2 heteroatom(s) each independently selected from N, O, and S, ($C_1$-$C_8$) alkyl, ($C_1$-$C_8$) cycloalkyl, mono-, di-, or trihalo($C_1$-$C_4$)alkyl, —$NR^6R^7$, where $R^6$ and $R^7$ are independently selected from H and lower alkyl or where $R^6$ and $R^7$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^8$ or —$OR^8$, and wherein S is unsubstituted or forms sulfonyl, wherein said substituted phenyl, benzyl, or 4, 5, or 6-membered heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl.

$R^3$ is unsubstituted or substituted phenyl or unsubstituted or substituted 4-, 5-, or 6-membered heteroaryl containing 1 to 2 heteroatom(s) each independently selected from N, O, and S, mono-, di-, or trihalo($C_1$-$C_4$)alkyl, ($C_1$-$C_8$) cycloalkyl, ($C_1$-$C_8$) alkyl, —$NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^{13}$ or —$OR^{13}$, and wherein S is unsubstituted or forms sulfonyl, wherein said substituted phenyl or 4-, 5-, or 6-membered heteroaryl has at least one substituent being halogen, mono-, di- or trihalo($C_1$-$C_4$)alkyl, —$SO_2R^{14}$ or —$OR^{14}$ where $R^{14}$ is lower alkyl, cyano, lower alkyl, or —$SO_2NR^{15}R^{16}$, where $R^{15}$ and $R^{16}$ are independently selected from H and lower alkyl;

including a tautomer, stereoisomer or racemic mixture thereof.

In embodiments, Y is selected from —$OR^2$, —$SO_2R^2$, and —C(═O)$R^2$. In some embodiments, Y is —C(═O)$R^2$ where $R^2$ is lower alkyl, but preferably methyl, or —$NR^6R^7$, where $R^6$ and $R^7$ are independently selected from H and lower alkyl. In some embodiments, Y is —C(═O)$R^2$ where $R^2$ is lower alkyl or $NR^6R^7$ where $R^6$ and $R^7$ are independently selected from H and lower alkyl. In preferred embodiments, Y is —C(═O)$R^2$ where $R^2$ is $NR^6R^7$ where $R^6$ and $R^7$ form a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^8$ or —$OR^8$ where $R^8$ is lower alkyl, and wherein S is unsubstituted or forms sulfonyl. In preferred embodiments, $R^6$ and $R^7$ form together a ($C_3$-$C_6$) hetero-cycloalkyl, wherein the ($C_3$-$C_6$) hetero-cycloalkyl is piperidin-1-yl, piperazin-1-yl, 4-methylpiperazin-1-yl, 4-(methylsulfonyl)piperazin-1-yl, 4-morpholinyl, 1,1-dioxidothiomorpholinyl. In some embodiments, $R^2$ is substituted or unsubstituted phenyl, substituted or unsubstituted benzyl, or substituted or unsubstituted 4-, 5-, or 6-membered heteroaryl containing 1 to 2 heteroatom(s) each independently selected from N, O, and S, wherein said substituted phenyl, benzyl, or 4, 5, or 6-membered heteroaryl has at least one substituent being halogen, mono-, di- or trihalo($C_1$-$C_4$)alkyl, —$SO_2R^8$ or —$OR^8$ where $R^8$ is lower alkyl, cyano, lower alkyl, or —$SO_2NR^9R^{10}$, where $R^9$ and $R^{10}$ are independently selected from H and lower alkyl. In a preferred embodiment, Y is —C(═O)$R^2$ where $R^2$ is 4-morpholinyl.

In some embodiments, Z is selected from —$R^3$, —$SO_2R^3$, and —$OR^3$. In some embodiments, $R^3$ is unsubstituted or substituted phenyl or substituted or unsubstituted 4, 5, or 6-membered heteroaryl containing 1 to 2 heteroatom(s) each independently selected from N, O, and S, wherein said substituted phenyl or 4-, 5-, or 6-membered heteroaryl has at least one substituent being halogen, mono-, di- or trihalo ($C_1$-$C_4$)alkyl, —$SO_2R^{14}$ or —$OR^{14}$ where $R^{14}$ is lower alkyl, cyano, lower alkyl, or —$SO_2NR^{15}R^{16}$, where $R^{15}$ and $R^{16}$ are independently selected from H and lower alkyl. In preferred embodiments, Z is phenyl. In some embodiments, $R^3$ is mono-, di-, or trihalo($C_1$-$C_4$)alkyl, ($C_1$-$C_8$) cycloalkyl, ($C_1$-$C_8$) alkyl, or —$NR^{11}R^{12}$, where $R^{11}$ and $R^{12}$ are independently selected from H and lower alkyl or where $R^{11}$ and $R^{12}$ form together a ($C_3$-$C_6$) hetero-cycloalkyl, wherein the ($C_3$-$C_6$) hetero-cycloalkyl optionally contains besides the nitrogen one additional heteroatom selected from N, O, and S, wherein N is optionally substituted with lower alkyl or —$SO_2R^{13}$ or —$OR^{13}$, and wherein S is unsubstituted or forms sulfonyl. In some embodiments, $R^{11}$ and $R^{12}$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl. In preferred embodiments, $R^3$ is substituted or unsubstituted phenyl, substituted or unsubstituted pyrimindin-2-yl, substituted or unsubstituted pyridin-4-yl, methoxy, halogen, cyclohexyl, methylsulfonyl, dimethylaminosulfonyl, or trifluoromethyl, wherein said phenyl, pyrimindin-2-yl, or pyridin-4-yl is substituted with halogen, cyano, lower alkyl, or methylsulfonyl.

Specific compounds within the scope of Formula I are provided below in Table 1. Provided are the compounds listed in the table, as well as pharmaceutically acceptable salts and hydrates thereof, and also provided are stereoisomers of the depicted compounds and racemic mixtures of the stereoisomers, and pharmaceutically acceptable salts and hydrates thereof. Also provided are methods of treatment or prevention of a disease or disorder associated with LOX enzymes in a subject in need thereof comprising administering one or more of the following compounds, including pharmaceutically acceptable salts, hydrates, stereoisomers, and racemic mixtures thereof, to the subject in need thereof.

TABLE 1

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| cis-1-((5-(Aminomethyl)thiophen-2-yl)sulfonyl)-N,N-dimethyl-5-phenylpiperidine-3-carboxamide 2,2,2-trifluoroacetate | 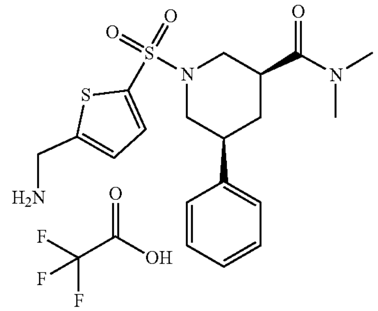<br>racemic |
| cis-(4-Fluoro-3-((1-(methylsulfonyl)-5-phenylpiperidin-3-yl)oxy)phenyl)methanamine 2,2,2-trifluoroacetate | 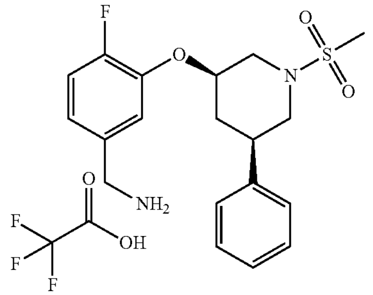<br>racemic |
| cis-(1-((5-(Aminomethyl)thiophen-2-yl)sulfonyl)-5-phenylpiperidin-3-yl)(piperidin-1-yl)methanone 2,2,2-trifluoroacetate | 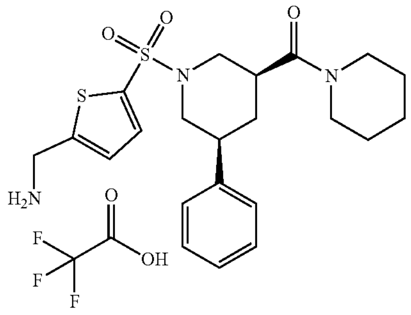<br>racemic |

TABLE 1-continued

Exemplary Compounds of Formula I, Formula Ia, Formula Ib, Formula Ic, Formula Id, Formula Ie, Formula If, Formula Ig, or Formula Ih

| IUPAC Name | Structure |
| --- | --- |
| cis-(3-((1-Mmethylsulfonyl)-5-phenylpiperidin-3-yl)sulfonyl)phenyl) methanamine 2,2,2-trifluoroacetate | 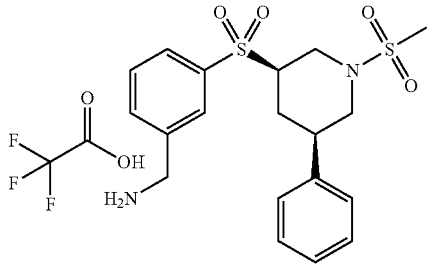<br>racemic |
| ((3S,5S)-1-((5-(aminomethyl) thiophen-2-yl)sulfonyl)-5-phenylpiperidin-3-yl)(morpholino) methanone | 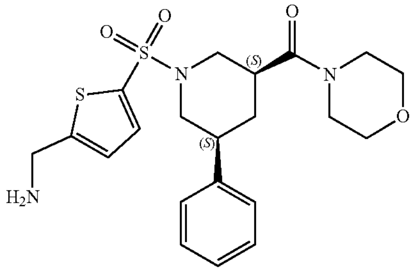<br>unconfirmed |
| cis-(3-((5-(2-Fluorophenyl)-1-(methylsulfonyl) piperidin-3-yl)oxy)phenyl) methanamine 2,2,2-trifluoroacetate | 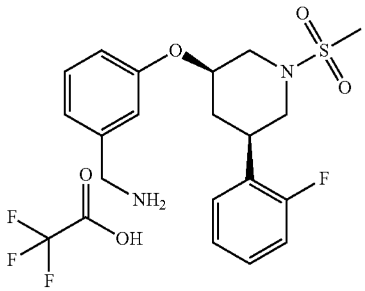<br>racemic |
| ((3R,5R)-1-((5-(aminomethyl) thiophen-2-yl)sulfonyl)-5-phenylpiperidin-3-yl)(morpholino) methanone | 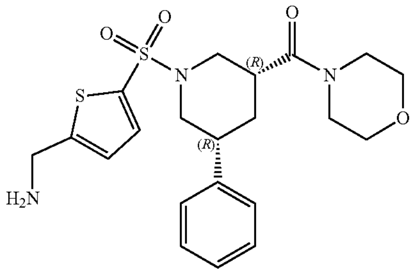<br>unconfirmed |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| cis-(4-Fluoro-3-((5-(2-fluorophenyl)-1-(methylsulfonyl) piperidin-3-yl)oxy)phenyl) methanamine 2,2,2-trifluoroacetate | 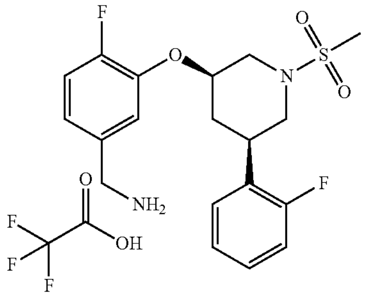 racemic |
| cis-(1-((5-(Aminomethyl) thiophen-2-yl)sulfonyl)-5-phenylpiperidin-3-yl)(piperazin-1-yl)methanone 2,2,2-trifluoroacetate | 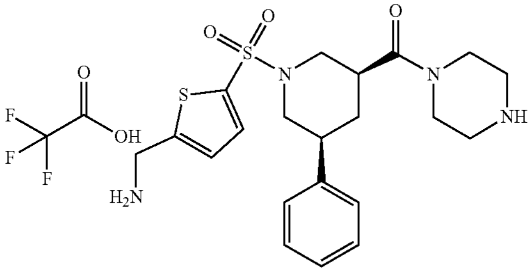 racemic |
| cis-(3-(3-(Aminomethyl) phenoxy)-5-phenylpiperidin-1-yl)(1,1-dioxidothio-morpholino) methanone | 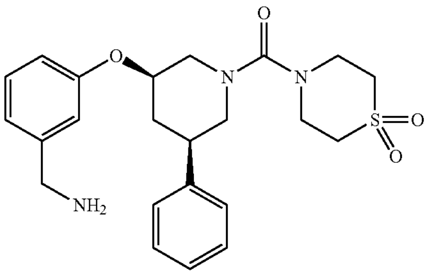 racemic |
| cis-(1-((5-(Aminomethyl) thiophen-2-yl)sulfonyl)-5-phenylpiperidin-3-yl)(4-methylpiperazin-1-yl)methanone 2,2,2-trifluoroacetate | 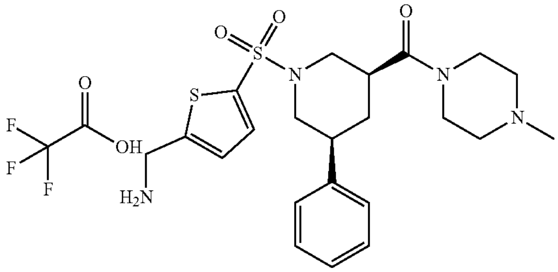 racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| cis-(3-(3-(Aminomethyl)phenoxy)-5-phenylpiperidin-1-yl)(morpholino)methanone | 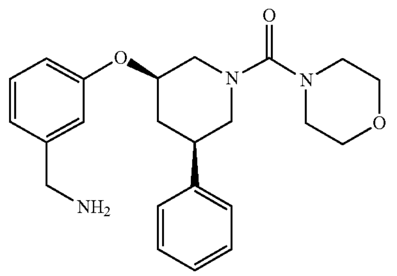 racemic |
| cis-(4-((-5-(Methylsulfonyl)-1-phenylpiperidin-3-yl)oxy)phenyl)methanamine 2,2,2-trifluoroacetate | 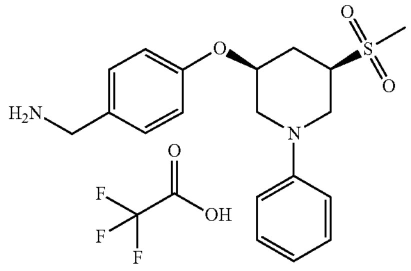 racemic |
| cis-3-((3-(Aminomethyl)phenyl)sulfonyl)-N,N-dimethyl-5-phenylpiperidine-1-carboxamide 2,2,2-trifluoroacetate | 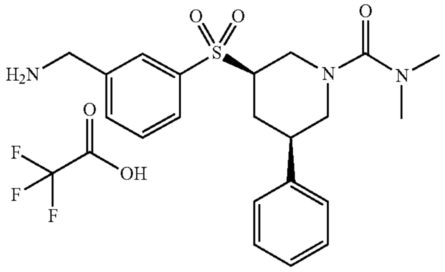 racemic |
| cis-(3-((5-(Methylsulfonyl)-1-phenylpiperidin-3-yl)oxy)phenyl)methanamine 2,2,2-trifluoroacetate | 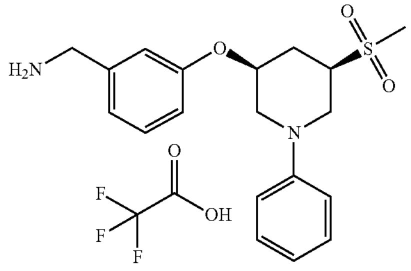 racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| cis-(1-((5-(Aminomethyl)thiophen-2-yl)sulfonyl)-5-phenylpiperidin-3-yl)(1,1-dioxidothiomorpholino)methanone 2,2,2-trifluoroacetate | 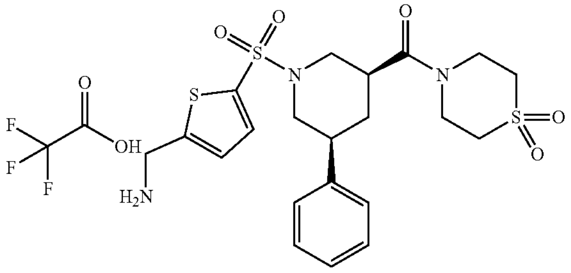 racemic |
| cis-(4-((5-(Methylsulfonyl)-1-phenylpiperidin-3-yl)sulfonyl)phenyl)methanamine 2,2,2-trifluoroacetate | 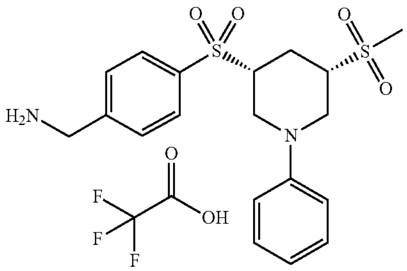 racemic |
| trans-(1-((5-(Aminomethyl)thiophen-2-yl)sulfonyl)-5-phenylpiperidin-3-yl)(1,1-dioxidothiomorpholino)methanone 2,2,2-trifluoroacetate | 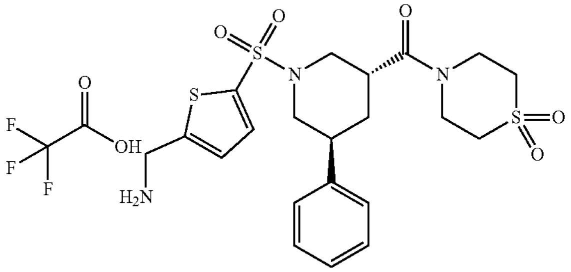 racemic |
| cis-(3-((5-(Methylsulfonyl)-1-phenylpiperidin-3-yl)sulfonyl)phenyl)methanamine | 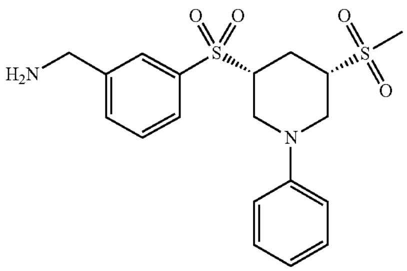 racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| cis-(1-((5-(Aminomethyl)thiophen-2-yl)sulfonyl)-5-phenylpiperidin-3-yl)(4-(methylsulfonyl)piperazin-1-yl)methanone 2,2,2-trifluoroacetate | 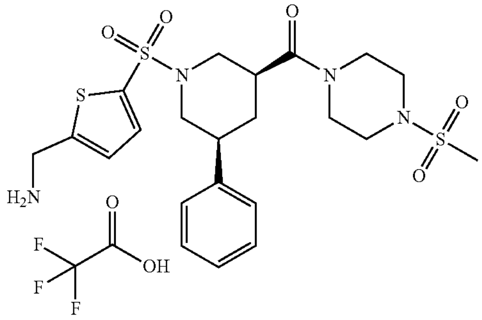 racemic |
| cis-(4-((1-(Methylsulfonyl)-5-phenylpiperidin-3-yl)oxy)phenyl)methanamine 2,2,2-trifluoroacetate | 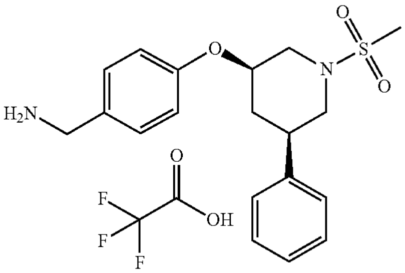 racemic |
| cis-(1-((3-(Aminomethyl)phenyl)sulfonyl)-5-phenylpiperidin-3-yl)(1,1-dioxidothiomorpholino)methanone 2,2,2-trifluoroacetate | 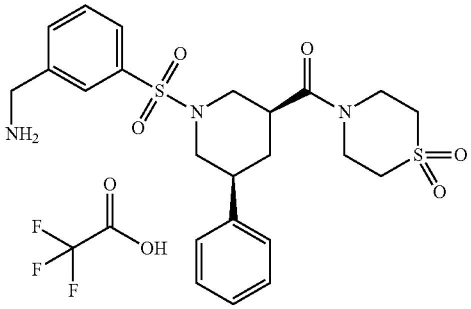 racemic |
| cis-(3-((1-(Methylsulfonyl)-5-phenylpiperidin-3-yl)oxy)phenyl)methanamine 2,2,2-trifluoroacetate | 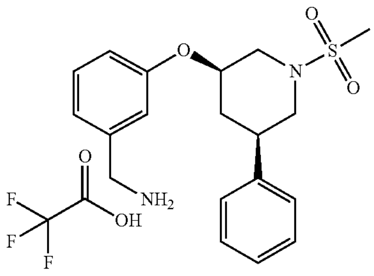 racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| cis-(1-((3-(Aminomethyl)phenyl)sulfonyl)-5-phenylpiperidin-3-yl)(4-(methylsulfonyl)piperazin-1-yl)methanone 2,2,2-trifluoroacetate | 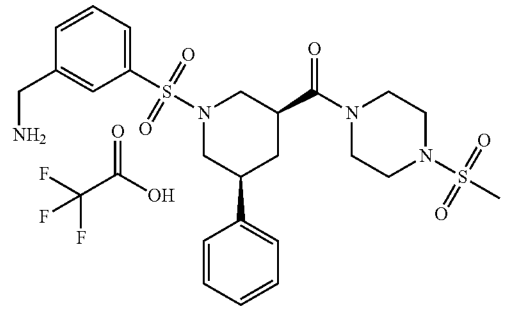 racemic |
| cis-(4-((1-(Methylsulfonyl)-5-phenylpiperidin-3-yl)sulfonyl)phenyl)methanamine 2,2,2-trifluoroacetate | 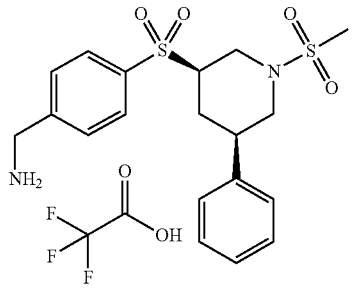 racemic |
| trans-(1-((3-(Aminomethyl)phenyl)sulfonyl)-5-phenylpiperidin-3-yl)(4-(methylsulfonyl)piperazin-1-yl)methanone 2,2,2-trifluoroacetate | 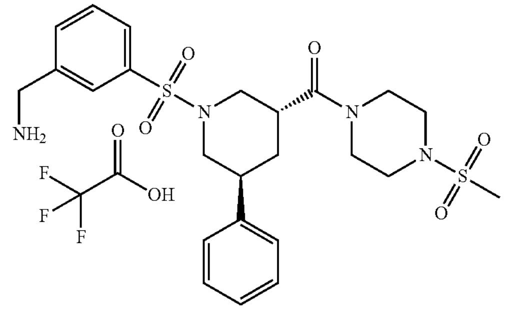 racemic |
| trans-(3-((5-(Methylsulfonyl)-1-phenylpiperidin-3-yl)sulfonyl)phenyl)methanamine | 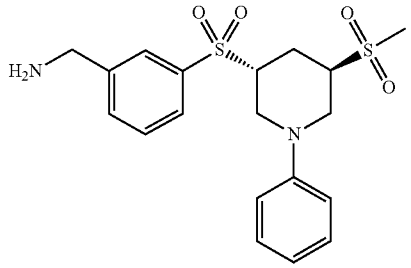 racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| trans-(1-((3-(Aminomethyl)phenyl)sulfonyl)-5-phenylpiperidin-3-yl)(1,1-dioxidothiomorpholino)methanone 2,2,2-trifluoroacetate | 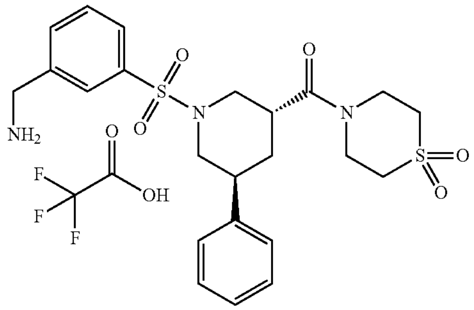 racemic |
| trans-(3-(3-(Aminomethyl)phenoxy)-5-phenylpiperidin-1-yl)(1,1-dioxidothio-morpholino)methanone | 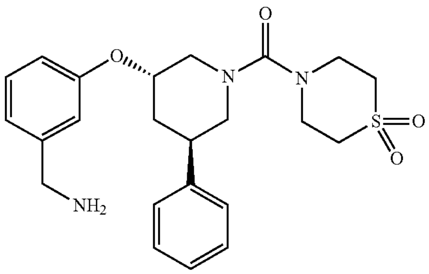 racemic |
| trans-(4-Fluoro-3-((-1-(methylsulfonyl)-5-phenylpiperidin-3-yl)oxy)phenyl)methanamine 2,2,2-trifluoroacetate | 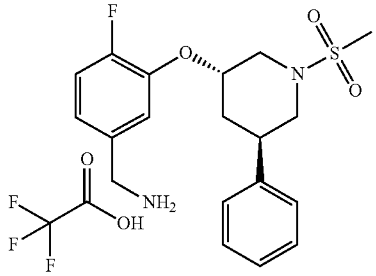 racemic |
| cis-(1-((5-(Aminomethyl)thiophen-2-yl)sulfonyl)-5-(2-fluorophenyl)piperidin-3-yl)(4-(methylsulfonyl)piperazin-1-yl)methanone 2,2,2-trifluoroacetate | 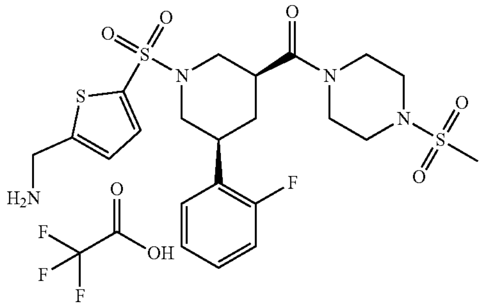 racemic |

TABLE 1-continued

Exemplary Compounds of Formula I, Formula Ia, Formula Ib, Formula Ic, Formula Id, Formula Ie, Formula If, Formula Ig, or Formula Ih

| IUPAC Name | Structure |
|---|---|
| trans-(4-Fluoro-3-((5-(2-fluorophenyl)-1-(methylsulfonyl) piperidin-3-yl)oxy)phenyl) methanamine 2,2,2-trifluoroacetate | 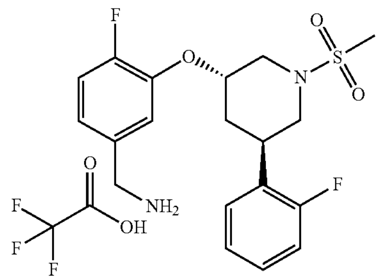 racemic |
| cis-(3-((1-(2-Fluorophenyl)-5-(methylsulfonyl) piperidin-3-yl)sulfonyl)phenyl) methanamine 2,2,2-trifluoroacetate | 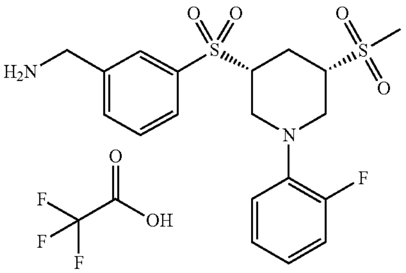 racemic |
| trans-3-((3-(Aminomethyl) phenyl)sulfonyl)-N,N-dimethyl-5-phenylpiperidine-1-carboxamide 2,2,2-trifluoroacetate | 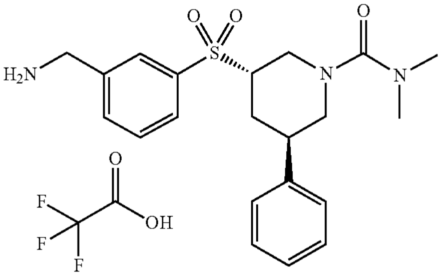 racemic |
| cis-(1-((3-(Aminomethyl) phenyl)sulfonyl)-5-(trifluoromethyl) piperidin-3-yl)(morpholino) methanone 2,2,2-trifluoroacetate | 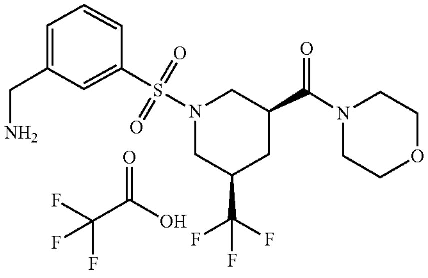 racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| cis-(1-((5-(Aminomethyl)thiazol-2-yl)sulfonyl)-5-phenylpiperidin-3-yl)(morpholino) methanone 2,2,2-trifluoroacetate | 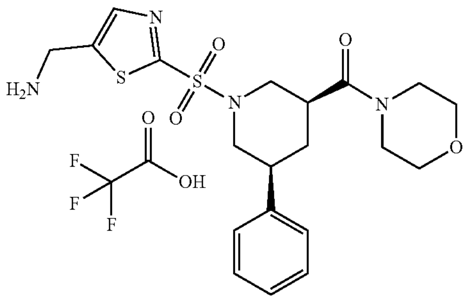<br>racemic |
| cis-(1-((3-(Aminomethyl) phenyl)sulfonyl)-5-(trifluoromethyl) piperidin-3-yl)(1,1-dioxidothio-morpholino) methanone 2,2,2-trifluoroacetate | 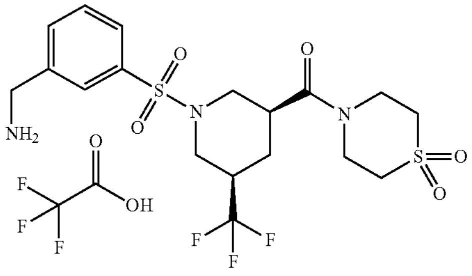<br>racemic |
| cis-(1-((3-(1-Aminoethyl)phenyl) sulfonyl)-5-phenylpiperidin-3-yl)(morpholino) methanone 2,2,2-trifluoroacetate | 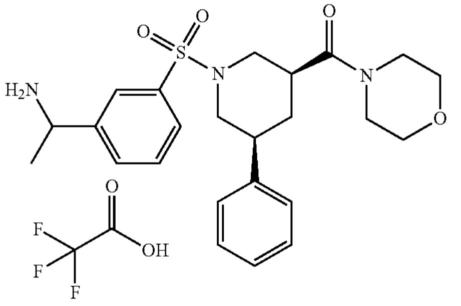<br>racemic |
| trans-(1-((3-(1-Aminoethyl)phenyl) sulfonyl)-5-phenylpiperidin-3-yl)(1,1-dioxidothio-morpholino) methanone 2,2,2-trifluoroacetate | 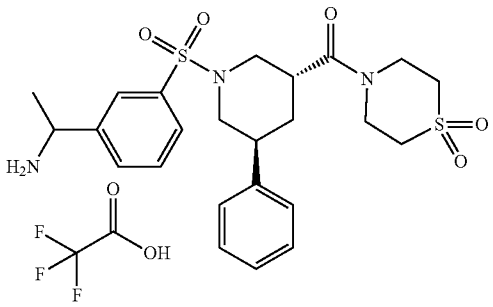<br>racemic |

TABLE 1-continued

Exemplary Compounds of Formula I, Formula Ia, Formula Ib, Formula Ic, Formula Id, Formula Ie, Formula If, Formula Ig, or Formula Ih

| IUPAC Name | Structure |
|---|---|
| cis-(1-((3-(Aminomethyl)phenyl) sulfonyl)-5-(tert-butyl)piperidin-3-yl)(morpholino) methanone 2,2,2-trifluoroacetate | 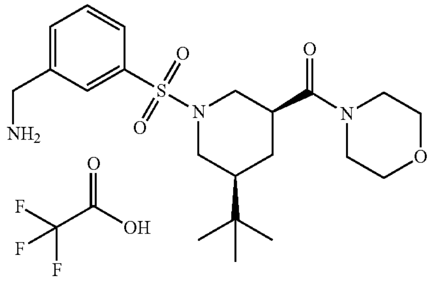 racemic |
| trans-(1-((3-(1-Aminoethyl)phenyl) sulfonyl)-5-phenylpiperidin-3-yl)(morpholino) methanone 2,2,2-trifluoroacetate | 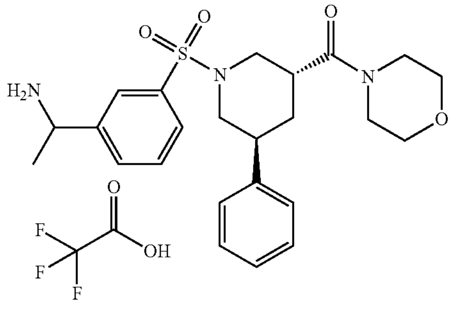 racemic |
| cis-(1-((5-(Aminomethyl)thiazol-2-yl)sulfonyl)-5-phenylpiperidin-3-yl)(4-(methylsulfonyl) piperazin-1-yl)methanone 2,2,2-trifluoroacetate | 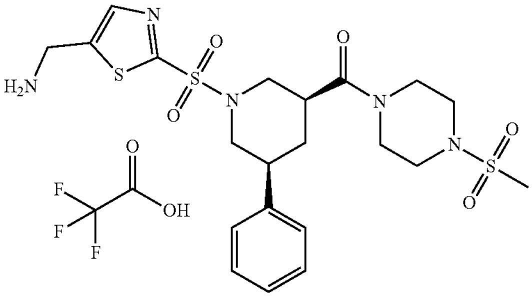 racemic |
| trans-(1-((3-(Aminomethyl) phenyl)sulfonyl)-5-(trifluoromethyl) piperidin-3-yl)(morpholino) methanone 2,2,2-trifluoroacetate | 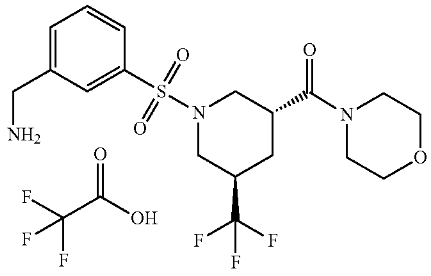 racemic |

TABLE 1-continued

Exemplary Compounds of Formula I, Formula Ia, Formula Ib, Formula Ic, Formula Id, Formula Ie, Formula If, Formula Ig, or Formula Ih

| IUPAC Name | Structure |
| --- | --- |
| cis-(1-((5-(Aminomethyl)thiazol-2-yl)sulfonyl)-5-phenylpiperidin-3-yl)(1,1-dioxidothiomorpholino) methanone 2,2,2-trifluoroacetate | 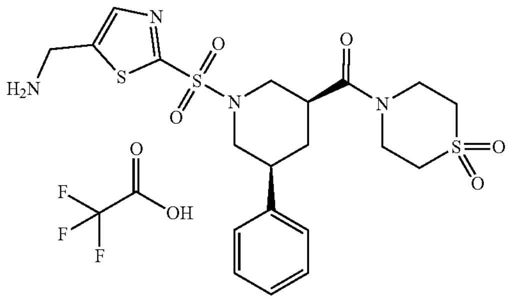 racemic |
| trans-(1-((5-(Aminomethyl) thiazol-2-yl)sulfonyl)-5-phenylpiperidin-3-yl)(morpholino) methanone 2,2,2-trifluoroacetate | 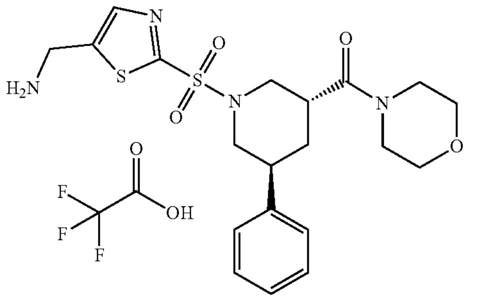 racemic |
| cis-(1-((6-(Aminomethyl)pyrid-2-yl)sulfonyl)-5-phenylpiperidin-3-yl)(morpholino) methanone | 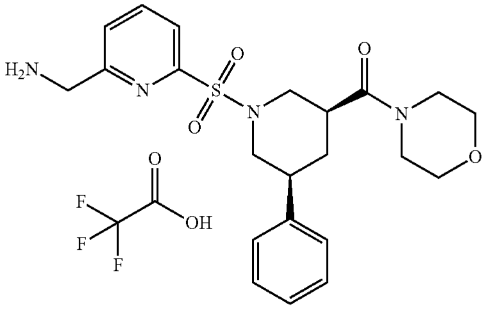 racemic |
| cis-(1-((6-(Aminomethyl) pyridin-2-yl)sulfonyl)-5-phenylpiperidin-3-yl)(1,1-dioxidothiomorpholino) methanone 2,2,2-trifluoroacetate | 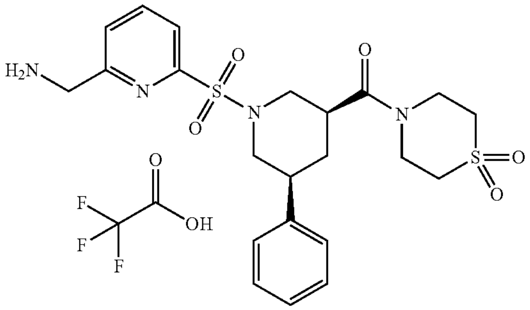 racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| trans-(1-((2-(Aminomethyl) pyridin-4-yl)sulfonyl)-5-phenylpiperidin-3-yl)(1,1-dioxidothio-morpholino) methanone 2,2,2-trifluoroacetate | 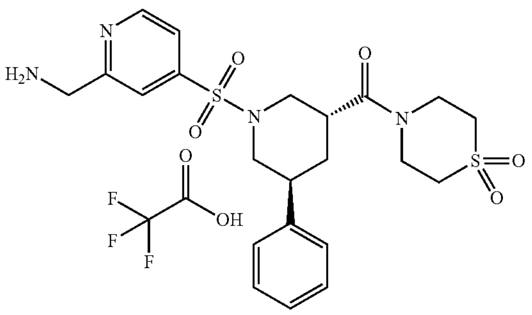 racemic |
| cis-(1-((2-(Aminomethyl) pyridin-4-yl)sulfonyl)-5-phenylpiperidin-3-yl)(1,1-dioxidothio-morpholino) methanone 2,2,2-trifluoroacetate | 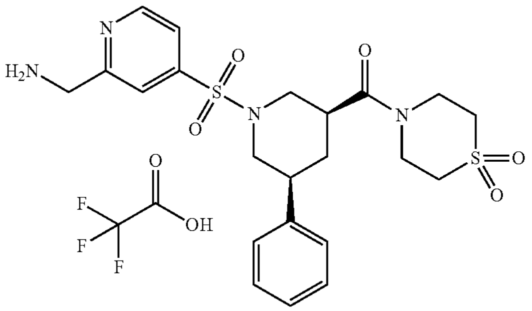 racemic |
| cis-(1-((5-(Aminomethyl) pyridin-3-yl)sulfonyl)-5-phenylpiperidin-3-yl)(1,1-dioxidothio-morpholino) methanone 2,2,2-trifluoroacetate | 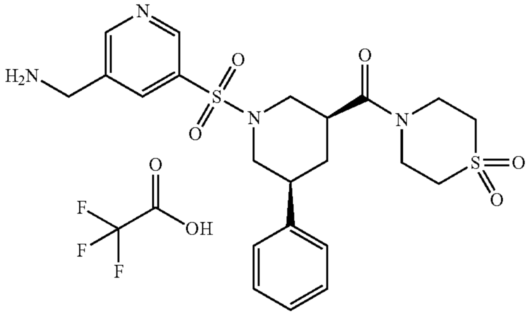 racemic |
| cis-(1-((5-(Aminomethyl) pyridin-3-yl)sulfonyl)-5-phenylpiperidin-3-yl)(morpholino) methanone 2,2,2-trifluoroacetate | 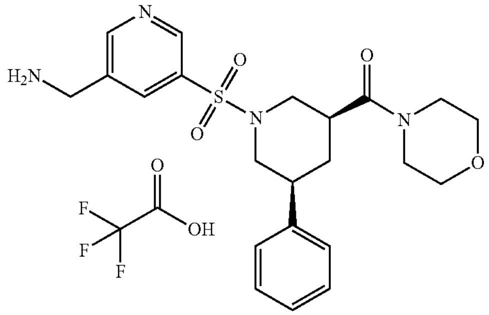 racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| cis-1-((4-(Aminomethyl) pyridin-2-yl)sulfonyl)-5-cyclohexyl-N,N-dimethylpiperidine-3-carboxamide 2,2,2-trifluoroacetate | 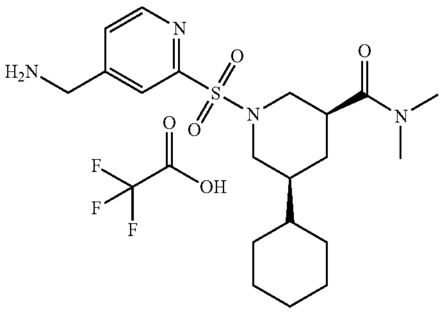 racemic |
| cis-(1-((4-(Aminomethyl) pyridin-2-yl)sulfonyl)-5-phenylpiperidin-3-yl)(1,1-dioxidothio-morpholino) methanone 2,2,2-trifluoroacetate | 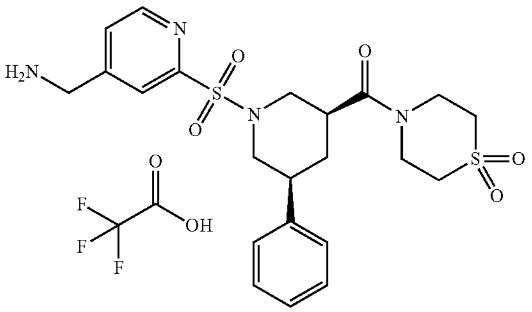 racemic |
| cis-(1-((4-(Aminomethyl) pyridin-2-yl)sulfonyl)-5-cyclohexylpiperidin-3-yl)(1,1-dioxidothio-morpholino) methanone 2,2,2-trifluoroacetate | 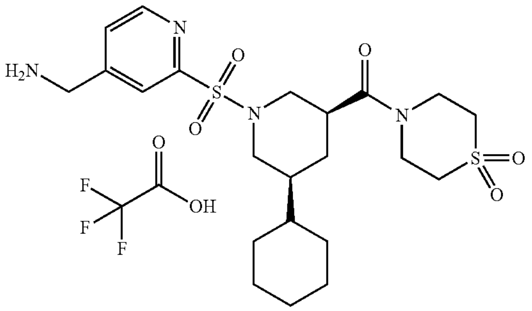 racemic |
| cis-(1-((4-(Aminomethyl) pyridin-2-yl)sulfonyl)-5-cyclohexylpiperidin-3-yl)(morpholino) methanone 2,2,2-trifluoroacetate | 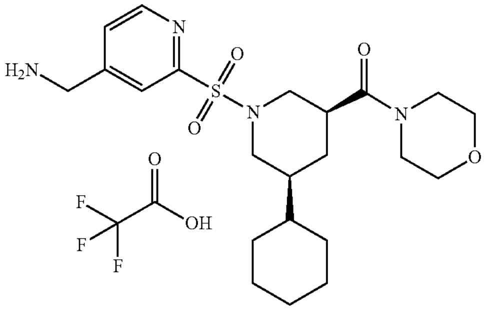 racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| trans-(1-((6-(Aminomethyl)pyridin-2-yl)sulfonyl)-5-phenylpiperidin-3-yl)(1,1-dioxidothio-morpholino)methanone 2,2,2-trifluoroacetate | 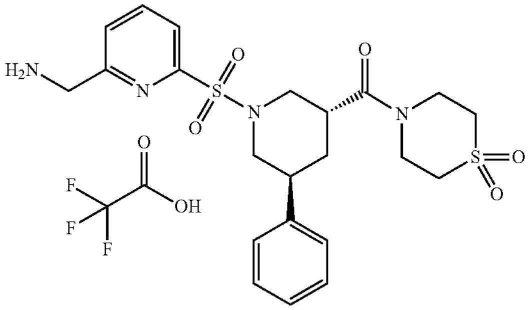 racemic |
| trans-(1-((6-(Aminomethyl)pyridin-2-yl)sulfonyl)-5-phenylpiperidin-3-yl)(morpholino)methanone 2,2,2-trifluoroacetate | 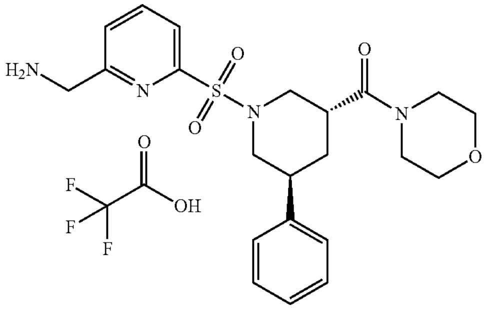 racemic |
| trans-(1-((5-(Aminomethyl)thiazol-2-yl)sulfonyl)-5-phenylpiperidin-3-yl)(1,1-dioxidothio-morpholino)methanone 2,2,2-trifluoroacetate | 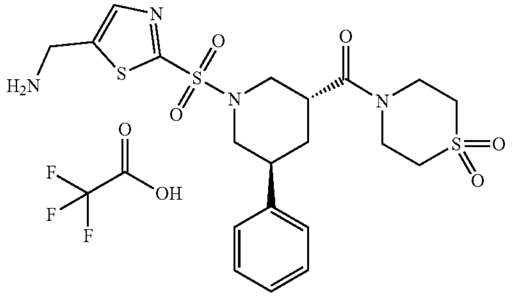 racemic |
| trans-(1-((6-(Aminomethyl)pyridin-2-yl)sulfonyl)-5-phenylpiperidin-3-yl)(4-(methylsulfonyl)piperazin-1-yl)methanone 2,2,2-trifluoroacetate | 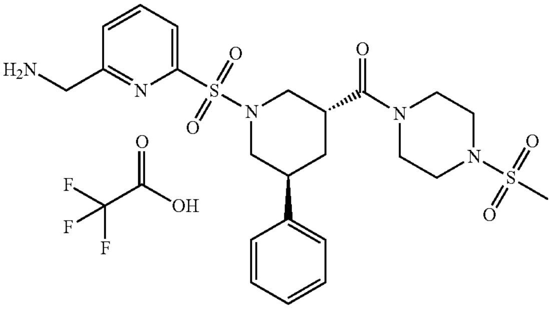 racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| cis-5-((3-(Aminomethyl)phenyl)sulfonyl)-1-cyclohexyl-N,N-dimethylpiperidine-3-carboxamide | 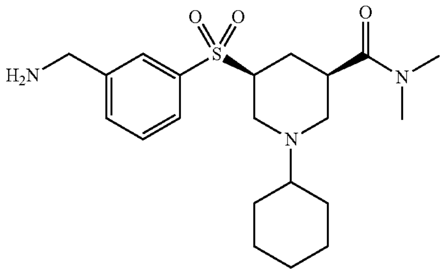 racemic |
| trans-(1-((5-(Aminomethyl)thiazol-2-yl)sulfonyl)-5-phenylpiperidin-3-yl)(4-(methylsulfonyl)piperazin-1-yl)methanone 2,2,2-trifluoroacetate | 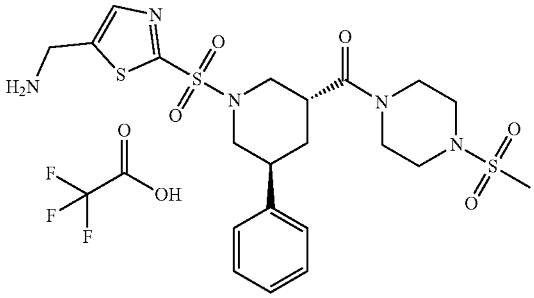 racemic |
| trans-(5-((3-(Aminomethyl)phenyl)sulfonyl)-1-cyclohexylpiperidin-3-yl)(morpholino)methanone 2,2,2-trifluoroacetate | 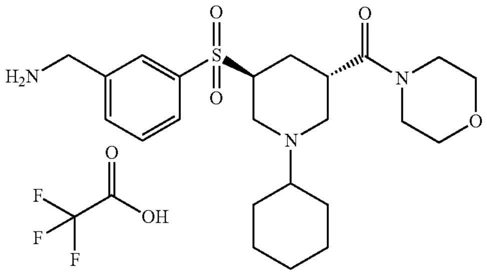 racemic |
| trans-5-((3-(Aminomethyl)phenyl)sulfonyl)-1-cyclohexyl-N,N-dimethylpiperidine-3-carboxamide | 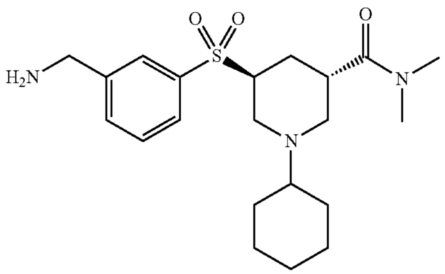 racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| cis-(5-((3-(Aminomethyl)phenyl) sulfonyl)-1-cyclohexylpiperidin-3-yl)(morpholino) methanone 2,2,2-trifluoroacetate | 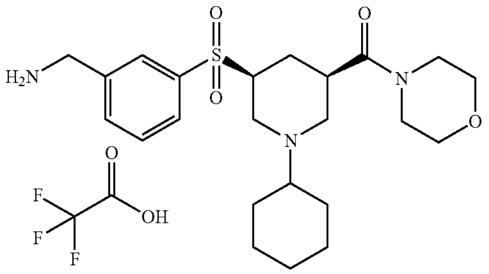<br>racemic |
| cis-(5-((3-(Aminomethyl) phenyl)sulfonyl)-1-cyclohexylpiperidin-3-yl)(1,1-dioxidothio-morpholino) methanone 2,2,2-trifluoroacetate | 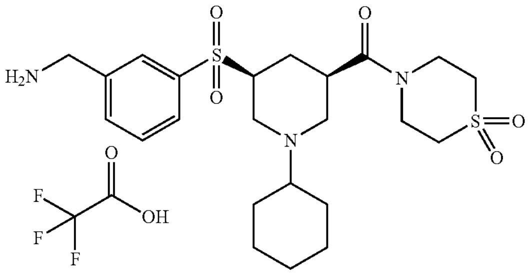<br>racemic |
| cis-(1-((3-(Aminomethyl)phenyl) sulfonyl)-5-(1,3-dioxan-2-yl)piperidin-3-yl)(1,1-dioxidothio-morpholino) methanone | 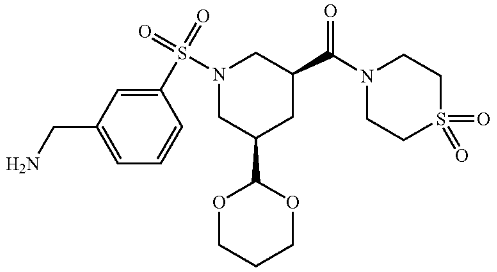<br>racemic |
| cis-(5-((3-(Aminomethyl) phenyl)sulfonyl)-1-cyclohexylpiperidin-3-yl)(1,1-dioxidothio-morpholino) methanone 2,2,2-trifluoroacetate | 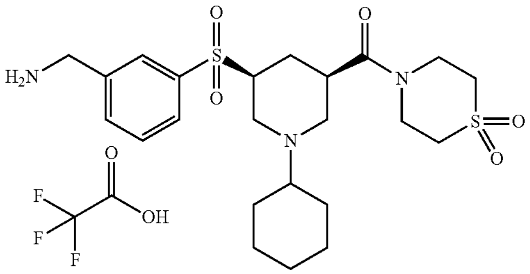<br>racemic |

TABLE 1-continued

Exemplary Compounds of Formula I, Formula Ia, Formula Ib, Formula Ic, Formula Id, Formula Ie, Formula If, Formula Ig, or Formula Ih

| IUPAC Name | Structure |
| --- | --- |
| cis-(3-((3-(Aminomethyl)phenyl)sulfonyl)-5-cyclohexylpiperidin-1-yl)(1,1-dioxidothiomorpholino)methanone | 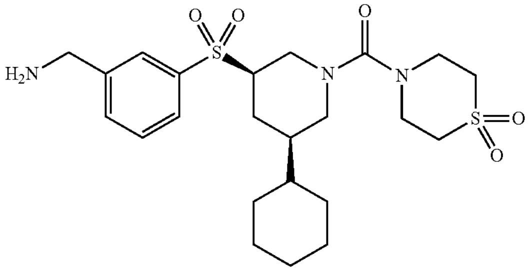 racemic |
| cis-3-((3-(Aminomethyl)phenyl)sulfonyl)-5-cyclohexyl-N,N-dimethylpiperidine-1-carboxamide | 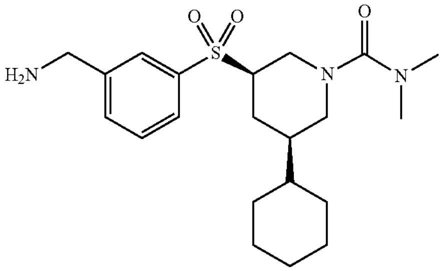 racemic |
| cis-(1'-((4-(Aminomethyl)pyridin-2-yl)sulfonyl)-[1,3'-bipiperidin]-5'-yl)(4-(methylsulfonyl)piperazin-1-yl)methanone 2,2,2-trifluoroacetate | 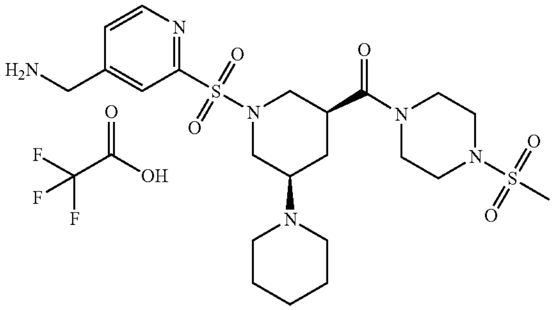 racemic |
| trans-(3-((3-(Aminomethyl)phenyl)sulfonyl)-5-cyclohexylpiperidin-1-yl)(1,1-dioxidothiomorpholino)methanone | 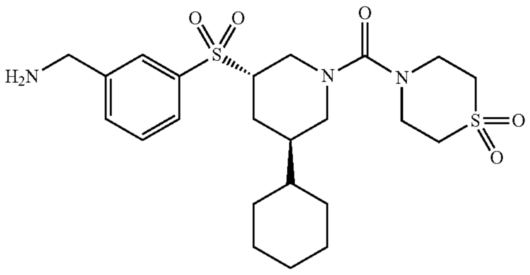 racemic |

TABLE 1-continued

Exemplary Compounds of Formula I, Formula Ia, Formula Ib, Formula Ic, Formula Id, Formula Ie, Formula If, Formula Ig, or Formula Ih

| IUPAC Name | Structure |
| --- | --- |
| cis-(1'-((4-(Aminomethyl) pyridin-2-yl)sulfonyl)-[1,3'-bipiperidin]-5'-yl)(morpholino) methanone 2,2,2-trifluoroacetate | 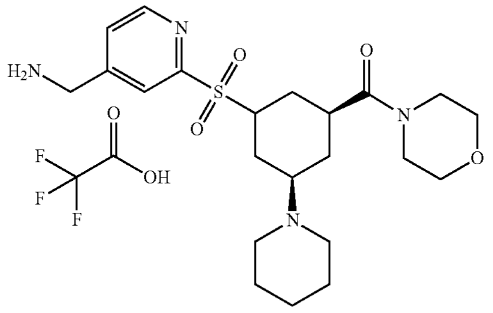<br>cis racemic |
| cis-(1'-((4-(Aminomethyl) pyridin-2-yl)sulfonyl)-[1,3'-bipiperidin]-5'-yl)(1,1-dioxidothio-morpholino) methanone 2,2,2-trifluoroacetate | 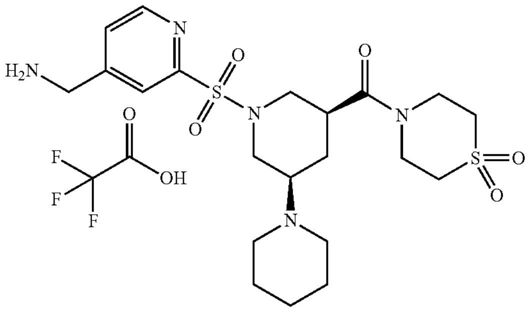<br>cis racemic |
| cis-(1'-((4-(Aminomethyl) pyridin-2-yl)sulfonyl)-[1,3'-bipiperidin]-5'-yl)(4-methylpiperazin-1-yl)methanone 2,2,2-trifluoroacetate | 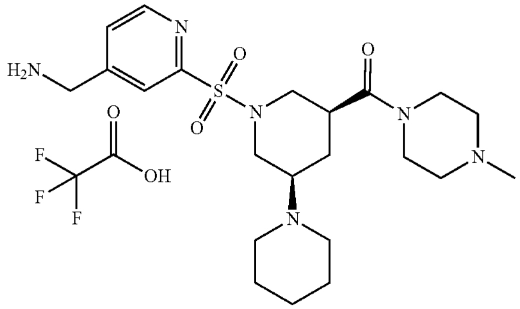<br>cis racemic |
| cis-(1-((4-(Aminomethyl) pyridin-2-yl)sulfonyl)-5-morpholino-piperidin-3-yl)(morpholino) methanone 2,2,2-trifluoroacetate | 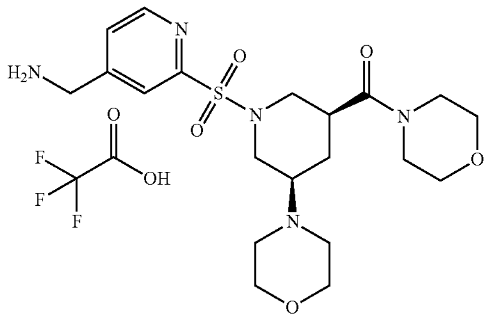<br>cis racemic |

TABLE 1-continued

Exemplary Compounds of Formula I, Formula Ia, Formula Ib, Formula Ic, Formula Id, Formula Ie, Formula If, Formula Ig, or Formula Ih

| IUPAC Name | Structure |
| --- | --- |
| cis-(1-((4-(Aminomethyl) pyridin-2-yl)sulfonyl)-5-morpholino-piperidin-3-yl)(1,1-dioxidothio-morpholino) methanone 2,2,2-trifluoroacetate | 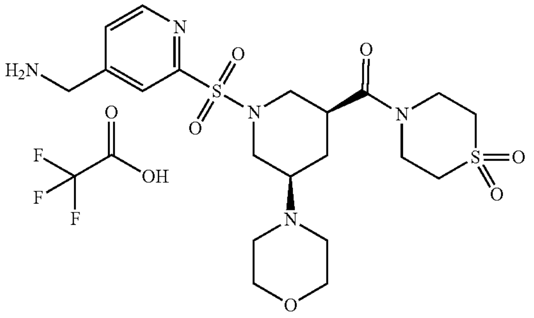 cis racemic |
| cis-(1-((4-(Aminomethyl) pyridin-2-yl)sulfonyl)-5-morpholino-piperidin-3-yl)(4-(methylsulfonyl) piperazin-1-yl)methanone 2,2,2-trifluoroacetate | 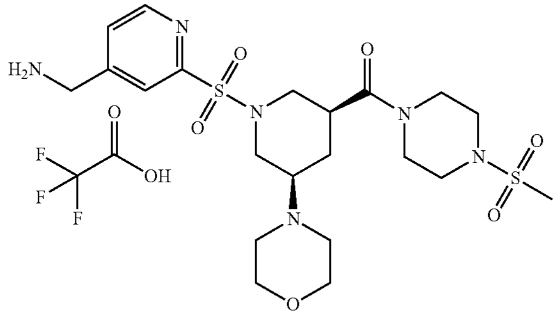 cis racemic |
| cis-1'-((4-(Aminomethyl)pyridin-2-yl)sulfonyl)-5'-(morpholine-4-carbonyl)-[1,3'-bipiperidin]-2-one 2,2,2-trifluoroacetate | 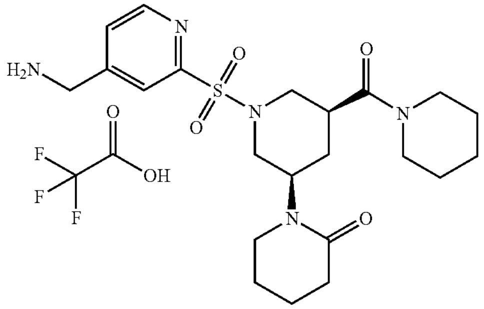 cis racemic |
| cis-1'-((4-(Aminomethyl) pyridin-2-yl)sulfonyl)-5'-(1,1-dioxidothio-morpholine-4-carbonyl)-[1,3'-bipiperidin]-2-one 2,2,2-trifluoroacetate | 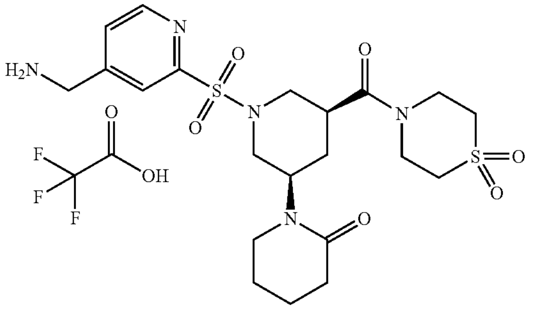 cis racemic |

TABLE 1-continued

| Exemplary Compounds of Formula I, Formula Ia, Formula Ib, Formula Ic, Formula Id, Formula Ie, Formula If, Formula Ig, or Formula Ih | |
|---|---|
| IUPAC Name | Structure |
| cis-1'-((4-(Aminomethyl)pyridin-2-yl)sulfonyl)-5'-(4-(methylsulfonyl)piperazine-1-carbonyl)-[1,3'-bipiperidin]-2-one 2,2,2-trifluoroacetate | 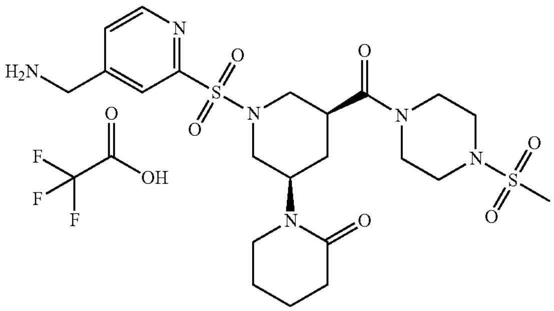 cis racemic |

While the above compound structures refer to racemic, the present disclosure is not limited to such. The present disclosure covers compounds of any form, including racemic mixtures or enantiomerically pure or substantially pure forms of any stereoisomer.

Also provided are methods of synthesizing compounds of Formula I, Formula Ia, Formula Ib, Formula Ic, Formula Id, Formula Ie, Formula If, Formula Ig, Formula Ih, or Table 1 or intermediates 1 to 25 according to the synthetic methods described in Examples 1 to 25, including synthetic schemes 1 to 35 or synthetic methods A-T.

A compound or compounds (including pharmaceutical salts and hydrates thereof, stereoisomers and racemic mixtures thereof, of Formula I, Formula Ia, Formula Ib, Formula Ic, Formula Id, Formula Ie, Formula If, Formula Ig, Formula Ih, or Table 1 can be provided in a pharmaceutical composition. The composition can further comprise a pharmaceutically acceptable carrier as described herein. Pharmaceutical compositions can comprise one or more compounds described herein in combination with a second therapeutic agent that is effective for the treatment of the indication. Such pharmaceutical compositions can be administered in methods described herein.

Methods can also comprise administration of a compound (s) of the invention in combination with an additional therapeutic agent.

Methods comprise the use of LOX enzyme-inhibiting compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, for treating, managing, ameliorating the symptoms of or preventing fibrotic disorders, proliferative disorders, inflammatory disorders, cardiovascular diseases, ocular diseases, primary or metastatic cancers, neurological and neuropsychiatric conditions, pulmonary conditions, or other diseases or medical conditions for which inhibiting any one of LOX, LOXL1, LOXL2, LOXL3, or LOXL4 provides a therapeutic benefit.

In some embodiments, the method comprises administering an effective amount of LOX-inhibiting compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, to a subject suffering from any of the conditions listed in Tables 2, 3, and 4.

In one embodiment, the method of the invention comprises administering an effective amount of LOX-inhibiting compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, in combination with one or more of the agents described below to a subject in need thereof.

In particular, exemplary embodiments of the invention include methods of treating, managing, ameliorating the symptoms of or preventing fibrotic disorders, which include, but are not limited to, fibrotic conditions affecting the liver (e.g. NASH, cirrhosis), lung (e.g. idiopathic pulmonary fibrosis), kidney (e.g. chronic kidney disease), heart (e.g. myocardial infarction, sarcoidosis, myocarditis, cardiomyopathy), bone marrow (e.g. myeloproliferative neoplasms, MDS, AML), skin (e.g. scleroderma), and gut (e.g. IBD, Crohn's) by administering compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, to a subject in need thereof.

LOX family enzymes may have distinct roles in diseases as described herein. Accordingly the selective inhibition of any of the LOX enzymes or selective inhibition of a specific combination of any of the LOX enzymes (e.g. LOXL2/LOX or LOXL2/LOXL3) may be advantageous. In one embodiment, the compounds disclosed herein including, pharmaceutically acceptable salts or hydrates thereof, or stereoisomers or racemic mixtures thereof, may be used in the selective or specific inhibition of LOX, LOXL1, LOXL2, LOXL3 or LOXL4. In other embodiments, it may be advantageous to inhibit two or more enzymes of the LOX family. Accordingly in another embodiment, the compounds disclosed herein, including pharmaceutically acceptable salts or hydrates thereof, or stereoisomers or racemic mixtures thereof, may be used in the selective inhibition of two or more members of the LOX family selected from LOX, LOXL1, LOXL2, LOXL3 or LOXL4.

Targeting cardiac tissue fibrosis is orthogonal to existing therapeutic strategies. Given the social and economic impact of HF, there remains an urgent need for novel, complementary medical therapies to improve HF clinical outcomes. Such therapeutic gap can be filled by using LOXL2-selective or LOXL2-specific inhibitors to reduce cardiac tissue fibrosis and relieve the constraint of fibrosis on heart pump function. LOXL2-targeting therapy is expected to provide clinical benefits on top of the standard of care.

Consequently, a particular method comprises the use of LOXL2-selective or LOXL2-specific inhibitor of Formula I, and preferably Formula Id, Formula Ig, or Formula Ih, including pharmaceutically acceptable salts or hydrates thereof, or stereoisomers or racemic mixtures thereof, for treating, managing, ameliorating the symptoms of or preventing cardiovascular diseases or fibrotic disorders affecting the heart or other diseases or medical conditions for which selectively or specifically inhibiting LOXL2 provides a therapeutic benefit. In a preferred embodiment, the fibrotic disorder of the heart or cardiovascular diseases is heart failure (HF). In one embodiment, the method comprises administering an effective amount of LOXL2-selective or LOXL2-specific inhibitor of Formula I, and preferably Formula Id, Formula Ig, or Formula Ih, including pharmaceutically acceptable salts or hydrates thereof, or stereoisomers or racemic mixtures thereof, in combination with guideline-directed medical therapy for HF including but not limited to one or more of the agents selected from angiotensin-converting-enzyme inhibitors, p-blocker, angiotensin receptor blocker, digoxins, diuretics, nitrates, hydralazines, or mineralcorticoid receptor antagonists (Virani et al., 2020) to a subject suffering from HF.

A particular method comprises also the use of a compound of Formula I which selectively or specifically inhibits LOX for treating, managing, ameliorating the symptoms of or preventing fibrotic disorders affecting the bone marrow or other diseases or medical conditions for which selectively or specifically inhibiting LOX provides a therapeutic benefit. In a preferred embodiment, the fibrotic disorder of the bone marrow is primary myelofibrosis (MF), polycythemia vera (PV), essential thrombocythemia (ET), post-PV MF, or post-ET MF. In one embodiment, the method comprises administering an effective amount of a compound of Formula I, including pharmaceutically acceptable salts or hydrates thereof, or stereoisomers or racemic mixtures thereof, which selectively or specifically inhibits LOX in combination with one or more of the agents selected from Janus kinase inhibitors (e.g. ruxolitinib, fedratinib), hydroxyurea, aspirin, anagrelide, and interferon therapy to a subject suffering from primary MF, PV, ET, post-PV MF, or post-ET MF or other bone marrow disorders presenting with bone marrow fibrosis.

A particular method comprises also the use of LOX enzyme-inhibiting compounds of Formula I, and preferably Formula Ia, Formula Ie, or Formula, If, including pharmaceutically acceptable salts or hydrates thereof, or stereoisomers or racemic mixtures thereof, for treating, managing, ameliorating the symptoms of or preventing primary or metastatic cancer or other diseases or medical conditions for which dual inhibition of LOX and LOXL2 (and optionally LOXL3 and/or LOXL4) provides a therapeutic benefit. In a preferred embodiment, the cancer is primary or metastatic breast cancer. In one embodiment, the breast cancer is estrogen-receptor negative breast cancer or inflammatory breast cancer. In one embodiment, the method comprises administering an effective amount of LOX enzyme-inhibiting compounds of Formula I, and preferably Formula Ia, Formula Ie, or Formula If, including pharmaceutically acceptable salts or hydrates thereof, or stereoisomers or racemic mixtures thereof, in combination with one or more of chemotherapeutic agents described below and/or radiation therapy to a subject suffering from primary or metastatic cancer.

As discussed above, the LOX enzyme-inhibiting compounds of the invention can be used for treating, managing, ameliorating the symptoms of or preventing fibrotic disorders, proliferative disorders, acute or chronic inflammatory disorders, cardiovascular diseases, ocular diseases, primary or metastatic cancers, neurological and neuropsychiatric conditions, pulmonary conditions, or other diseases or medical conditions for which inhibiting any one of LOX, LOXL1, LOXL2, LOXL3, or LOXL4 provides a therapeutic benefit.

The disease of medical condition mediated by LOX, LOXL1, LOXL2, LOXL3, and/or LOXL4 may be any of the diseases or medical conditions listed hereon (Tables 2, 3, and 4).

Fibrotic Indications

LOX family enzymes are implicated in fibrotic diseases. In some embodiments, the compounds of the invention or a pharmaceutically acceptable salt or hydrate thereof are used in the treatment of a fibrotic disorder. In some embodiments, the fibrotic disorder is characterized by excess fibrosis, for example an excess of fibrous connective tissue in a tissue or organ. In some embodiments, the excess of fibrous connective tissue is triggered by a reparative or reactive process or in response to injury (e.g. scarring or healing) or excess fibrotic tissue arising from a single cell line (e.g., fibroma). In some embodiments, compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, are used in the treatment of a fibrotic disorder selected from any one of the diseases listed in Tables 2, 3 and 4 infra. In preferred embodiments, the fibrotic disorder is a fibrotic condition affecting the lungs, liver, kidney, heart, vascular system, mediastinum, bone, brain, nervous system, retroperitoneum, skin, GI tract, connective tissue, and eye.

TABLE 2

Diseases and Medical Conditions Mediated by any of the LOX Family Enzymes

| Organ | Disorders |
|---|---|
| Lung | Idiopathic pulmonary fibrosis, cystic fibrosis, pulmonary fibrosis secondary to cystic fibrosis, chronic obstructive pulmonary disease, diffuse parenchymal lung disease, pulmonary hypertension, emphysema, thromboembolic disease, coal worker's progressive massive fibrosis, cryptogenic fibrosing alveolitis, chronic fibrosing interstitial pneumonia, interstitial lung disease, chronic asthma |

TABLE 2-continued

Diseases and Medical Conditions Mediated by any of the LOX Family Enzymes

| Organ | Disorders |
|---|---|
| Liver | Liver fibrosis, cirrhosis, Wilson's disease, portal hypertension, liver fibrosis/cirrhosis due to non-alcoholic steatohepatitis (NASH), HIV and/or Hepatitis B or C- infection or primary sclerosing cholangitis, compensated liver cirrhosis due to NASH, non-alcoholic fatty liver disease, primary biliary cirrhosis, biliary cirrhosis or autoimmune hepatitis |
| Eye | Subretinal fibrosis, epiretinal fibrosis, ocular fibrosis following surgery or pseudoexfoliation syndrome glaucoma |
| Retroperitoneum | Retroperitoneal fibrosis |
| Mediastinum | Mediastinal fibrosis |
| Heart | Endomyocardial fibrosis, old myocardial infarction, atrial fibrosis hypertensive heart disease, hypertension and fibrosis associated with hypertension, pressure overload, myocardial ischemia, (congestive) heart failure, myocarditis, sarcoidosis, cardiomyopathy (e.g. hypertrophic cardiomyopathy), valvular disease, arrhythmia, cardiac hypertrophy, and atherosclerosis, restenosis (e.g. coronary, carotid, and cerebral lesions) |
| Skin | Scleroderma, hypertrophic scar, systemic sclerosis, nephrogenic systemic fibrosis, keloid formation and scarring |
| Kidney | Chronic kidney disease, cystic fibrosis, nephrogenic systemic fibrosis, renal anemia, diabetic nephropathy, vesicoureteral reflux, tubulointerstitial renal fibrosis; glomerulonephritis or glomerular nephritis, including focal segmental glomerulosclerosis and membranous glomerulonephritis or mesangiocapillary glomerular nephritis |
| Brain, Nervous System | Glial scar, amyloid-beta related diseases (e.g. Alzheimers) |
| Bone marrow | (Primary) myelofibrosis, polycythemia vera (PV), essential thrombocythemia (ET), post-PV MF, post-ET MF, myelodysplastic syndrome (MDS), chronic myelogenous leukemia, acute megakaryocytic leukemia |
| Breast | Fibrocystic breast disease |
| Gut | Inflammatory bowel disease, ulcerative colitis, Crohn's disease, intestinal fibrosis, enteropathies |
| Joint | Arthrofibrosis, capsuliti |
| Pancreas | Pancreatic fibrosis, cystic fibrosis, chronic pancreatitis, duct obstruction |
| Female/ Reproductive Organs | Endometriosis, uterine fibroids |

In some embodiments, the fibrotic indication is bone marrow fibrosis, for example primary myelofibrosis (MF), polycythemia vera (PV), or essential thrombocythemia (ET). Among the preferred fibrotic indications is treating, managing, ameliorating the symptoms of or preventing progression of blood disorders associated with myeloproliferative neoplasms, for example progression of PV and/or ET to post-PV/ET-MF myelofibrosis, preferably when co-administered with JAK inhibitor Jakafi® or fedratinib. In some embodiments, a LOX-specific or LOX-selective inhibitor is used in the treatment of are primary myelofibrosis (MF), polycythemia vera (PV), essential thrombocythemia (ET), post-ET MF, or post-PV MF. In another embodiment, a pan-LOX inhibitor is used in the treatment of bone marrow fibrosis, for example primary myelofibrosis (MF), polycythemia vera (PV), essential thrombocythemia (ET), post-ET MF, or post-PV MF.

Among the preferred indications are fibrotic conditions affecting the heart, in particular, cardiac interstitial fibrosis and heart failure (HF). In some embodiments, a LOXL2-selective or LOXL2-specific inhibitor of Formula I, and preferably Formula Id, Formula Ig, or Formula Ih, is used for treating, managing, ameliorating the symptoms of or preventing cardiovascular diseases or fibrotic disorders affecting the heart, in particular HF, or other diseases or medical conditions for which selectively or specifically inhibiting LOXL2 provides a therapeutic benefit.

Cancer

LOX enzymes play a critical role in primary cancer and metastasis [reviewed by Barker, Cox, et al. 2012].

As such, in some embodiments, the method of use of compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, is the treatment of a cancer, which may be metastatic or non-metastatic cancer, and which may further be a solid tumor or a hematological cancer selected from Table 3 infra. For example, in some embodiments, the primary or metastatic cancer includes, but is not limited to, head and neck cancer, breast cancer, colorectal cancer, lung cancer, liver cancer, prostate cancer, brain cancer, renal cancer, esophageal and laryngeal cancer, or skin cancer.

In some embodiments, the cancer is a carcinoma, including for example tumors derived from stratified squamous epithelia (squamous cell carcinomas), tumors arising within organs or glands (adenocarcinomas), and tumors developing in the basal cell (basal cell carcinomas). In other embodiments, the cancer is a sarcoma, including for example tumors arising within fat, muscle, blood vessels, deep skin tissues, nerves, bones, and cartilage. In other embodiments, the cancer is has mixed histology, including for example adenosquamous carcinoma, mixed mesodermal tumor, carcinosarcoma or teratocarcinoma.

TABLE 3

| Primary and Metastatic Cancer Indications for LOX-inhibiting Compounds of this Invention | |
|---|---|
| Organ | Disorders |
| Lung | Non-small cell lung cancer (e.g. adenocarcinoma, squamous cell carcinoma, and large cell carcinoma), small cell lung carcinoma, bronchogenic carcinoma, and bronchioloalveolar carcinoma |
| Liver | Hepatocellular carcinoma (HCC), cirrhotic HCC, liver and bile duct carcinoma (for example cholangiocarcinoma and hemangioma) |
| Skin, glandular structures | Melanoma, uveal melanoma, retinoblastoma, basal cell carcinoma, eccrine carcinoma, sebaceous gland carcinoma, papillary carcinoma, papillary adenocarcinoma, cystadenocarcinoma, |
| Brain/Nervous System | Glioblastoma, astrocytoma, glioma, and medulloblastoma, craniopharyngioma, ependymoma, pinealoma, hemangioblastoma, acoustic neuroma, oligodendroglioma, meningioma, neuroblastoma and schwannoma; |
| Head/neck, thyroid | Oral and oropharyngeal carcinoma (e.g. squamous cell carcinomas), esophageal carcinoma (e.g. esophageal adenocarcinoma and squamous cell carcinoma), laryngeal carcinoma (e.g. larynx squamous cell carcinoma), nasopharyngeal carcinoma, head and neck cancer (e.g. squamous cell carcinomas), thyroid cancer (e.g. anaplastic thyroid cancer), |
| Bone/Blood | Myelogenous and granulocytic leukemia, lymphatic, lymphocytic, and lymphoblastic leukemia; myeloproliferative neoplasm (e.g. polycythemia vera and erythremia; myelofibrosis, and essential thrombocythemia), myelodysplastic syndrome, myeloma, multiple myeloma, lymphomas (e.g. hodgkin and non-hodgkin lymphomas), osteosarcoma and osteogenic sarcoma, |
| Breast | ER-negative breast cancer, basal-like breast carcinoma, ductal carcinoma (in situ), lobular carcinoma, inflammatory breast cancer, clear cell carcinoma, mucinous carcinoma, medullary carcinoma |
| GI tract | Colorectal cancer (e.g. colon carcinoma and rectal carcinoma), anal carcinoma, stomach carcinoma (e.g. stomach adenocarcinoma, gastrointestinal stromal tumor), gastric carcinoma |
| Pancreas | Pancreatic ductal adenocarcinoma, pancreatic adenocarcinoma, acinar cell carcinoma, intraductal papillary mucinous neoplasm with invasive carcinoma, mucinous cystic neoplasm with invasive carcinoma, islet cell carcinoma and neuroendocrine tumors |
| Ovary, Uterus | Ovarian epithelial carcinoma or surface epithelial-stromal tumor (e.g. serous tumor, endometrioid tumor and mucinous cystadenocarcinoma, sex-cord-stromal tumor), cervical carcinoma, uterine carcinoma (e.g. endometrial adenocarcinoma, uterine papillary serous carcinoma, uterine clear-cell carcinoma, uterine sarcomas and leiomyosarcomas, mixed mullerian tumors), germ cell tumors, choriocarcinoma |
| Prostate, Testicles | Prostate carcinoma, germ cell tumors, ductal carcinoma in situ, choriocarcinoma, seminoma, embryonal carcinoma, testicular carcinoma, germ cell tumor of the testicles (e.g. seminoma, teratoma, embryonal carcinoma) |
| Bladder, Kidneys | Bladder carcinoma (e.g. transitional cell carcinoma), kidney carcinoma (e.g. renal cell carcinoma, clear cell carcinoma and Wilm's tumor), |
| Connective tissue (fat, muscle, blood vessels, deep skin tissues, nerves, bones, and cartilage) | Mesothelial sarcoma and mesothelioma, fibrosarcoma, angiosarcoma and hemangioendothelioma, liposarcoma, myxosarcoma, chordoma, endotheliosarcoma, lymphangiosarcoma, lymphangioendotheliosarcoma, synovioma, chondrosarcoma, leiomyosarcoma, rhabdomyosarcoma, Ewing's sarcoma, mesenchymous and mixed mesodermal tumor and other soft tissue sarcomas |
| Other | Signet ring cell carcinoma, neuroendocrine tumors, adrenocortical carcinoma, medullary carcinoma, epithelial carcinoma, sarcomatoid carcinoma |

In some embodiments, the method of use of the compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, is to improve the delivery of chemotherapeutic drugs and/or the therapeutic efficacy of chemotherapeutics in a subject with primary or metastatic cancer. In other embodiments, the method of use of the compounds disclosed herein is to prevent or reduce metastatic spread of the primary tumor to distant sites. In specific embodiments, the method of use of the compounds of this invention is to prevent or reduce the metastatic spread of primary breast cancer, for example ER-negative breast cancer, to the bone. In specific embodiments, the method of use of the compounds disclosed herein is to prevent or reduce the metastatic spread of primary cancers upon surgical resection of the tumor. In some embodiments, the method of use of the compounds disclosed herein is to inhibit or treat the growth of fibrous or connective tissue which may occur around a neoplasm, causing dense fibrosis around the tumor, or scar tissue (adhesions), for example within the abdomen after abdominal surgery.

Other Indications

Other indications include, but are not limited to, ocular diseases, pulmonary diseases, acute and chronic inflammatory diseases, autoimmune disorders, cardiovascular diseases, obesity, viral, bacterial, and parasitic infections, genetic skin disorders, and neurological and neuropsychiatric disorders. In some embodiments, compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, are used to treat any of the diseases listed in Table 4 infra.

TABLE 4

| Other Indications | |
|---|---|
| Organ | Disorders |
| Ocular | |
| Pulmonary (including inflammatory conditions) | Acute respiratory distress syndrome (ARDS), acute lung injury, endotoxin-induced lung injury, pulmonary inflammation, chronic obstructive pulmonary disease and systemic cachexia, primary alveolar proteinosis, bronchopulmonary dysplasia. |
| Acute and chronic inflammatory conditions | Inflammatory bowel disease, Crohn's disease, ulcerative colitis, psoriasis, eczema, allergic rhinitis, allergic conjunctivitis, sarcoidosis, rheumatoid arthritis, osteoarthritis, psoriatic arthritis, Reiter's syndrome, traumatic arthritis, rubella arthritis, acute synovitis, gouty arthritis and spondylitis, diabetes, systemic cachexia, gout, endotoxemia, toxic shock syndrome, a bone resorption disease, osteoporosis, reperfusion injury, graft versus host reaction, allograft rejection, sepsis, septic shock, endotoxic shock, Gram negative sepsis, glomerulonephritis, restenosis, vasculitis, thrombosis, polymyositis, systemic lupus or interstitial nephritis. |
| Neurological, Neuropsychiatric | Alzheimer's disease, hereditary cerebral hemorrhage with amyloidosis of the Dutch type (HCHWA-D), non-Alzheimer's dementia, bipolar disorder, nerve damage and spinal cord injury |
| Cardiovascular | Atherosclerosis, prevention of fibrotic atrial remodelling, old myocardial infarction; congestive heart failure, cardiomyopathy, hypertensive heart disease, (pulmonary) hypertension, restenosis (e.g. coronary, carotid, and cerebral lesions), and heart disease associated with cardiac ischemic events. |
| Skin (genetic) | Keratinization disorder is selected from among Darier's disease, Hailey-Hailey disease, erythrodermic autosomal recessive lamellar ichthyosis, nonerythrodermic autosomal recessive lamellar ichthyosis, autosomal dominant lamellar ichthyosis, bullous congenital ichthyosiform erythroderma, palmoplantar keratoderma, erythrokeratodermia variabilis, verrucous epidermal nevi, pityriasis rubra pilaris, Netherton syndrome, idiopathic vulgaris, ichthyosis vulgaris, monilethrix, keratosis piliaris, bullous ichthyosiform erythroderma, nonbullous congenital ichthyosis, Sjogren-Larsson syndrome, erythrokeratodermica variabilis, hyperkeratosis lenticularis perstans, eythrokeratodermia figurate variabilis, mutilating keratoderma of Vohwinkel, Harlequin ichthyosis and Tay's syndrome. |
| Viral Infections | Rhinovirus, influenza virus, parainfluenza virus, coronavirus, adenovirus, respiratory syncytial virus, picornavirus, metapneumovirus, hantavirus, measles virus, Epstein-Barr virus, herpes simplex virus or cytomegalovirus. |
| Other | Obesity, parasitic infection (e.g. schistosomiasis), Chlamydia infection |

In particularly desirable embodiments, the LOX enzyme-inhibiting compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, are useful for treating any of the cardiovascular diseases listed in Tables 2 and 4. Accordingly, a method for treating cardiovascular diseases comprises administering to a patient in need thereof a LOX-enzyme inhibiting compound described hereinabove.

The compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, are useful in methods for the prevention, treatment, control, amelioration, or reduction of risk of the diseases, disorders and conditions noted herein.

IV. Combination Therapy

The compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, are further useful in a method for treating, managing, ameliorating the symptoms of or preventing aforementioned diseases, disorders and conditions in combination with other agents. In many instances, the combination of the drugs together is safer or more effective than either drug alone; the compounds of the present invention and the other active ingredients may often be used in lower doses than when each is used singly. The drug(s) in the combination may be administered contemporaneously or sequentially (i.e. one preceding or following the other, at any appropriate time interval). When administered contemporaneously, the drugs may be administered separately, or a single dosage form may contain both active agents.

Accordingly, the subject compounds may be used in combination with other agents, which are known to be beneficial in the subject indications, or other drugs that affect receptors or enzymes that either increase the efficacy, safety, convenience, or reduce unwanted side effects or toxicity of the compounds of the present invention. It will be appreciated that any of the drugs listed herein may be in the form of a pharmaceutically acceptable salt.

The compounds are useful in combination with standard cancer therapies. Standard cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Chemotherapeutic agents are non-peptidic (i.e., non-proteinaceous) compounds and encompass anti-neoplastic/anti-proliferative agents, cytotoxic agents, cytostatic agents, anti-invasion agents, anti-angiogenic agents, and inhibitors of growth factor functions. Non-limiting examples of chemotherapeutic agents include alkylating agents, nitrosoureas, antimetabolites, antitumor antibiotics, plant (*vinca*) alkaloids, and steroid hormones. In addition, the compounds disclosed herein are useful in combination with gene therapy approaches, immunotherapy approaches, targeted therapies, and chimeric antigen receptors, anticancer vaccines and arginase inhibitors.

The compounds of Formula I, Formula Ia, Formula Ib, Formula Ic, Formula Id, Formula Ie, Formula If, Formula Ig, Formula Ih, or Table 1 are useful in combination with one or more additional chemotherapeutics selected from the group of alkylating agents, antimetabolites, natural products and their derivatives, microtubule affecting agents, hormone modulators and steroids, metal complexes, urea compounds and hydrazines, immunosuppressants, proteasome inhibitors, kinase inhibitors, anti-apoptotic inhibitors, DNA repair inhibitors, HDAC inhibitors, DNA demethylating agents, anti-angiogenic agents, interferon therapy, growth factor antibodies and growth factor receptor antibodies, immunotherapies, gene therapy, and/or radiotherapy:

In a particularly preferred embodiment, the subject compound is employed in combination with Janus kinase inhibitors ruxolitinib or fedratinib. In other embodiments, the LOX-enzyme inhibiting compound is administered in combination with urea compounds, for example hydroxyurea, and hydrazines, aspirin, anagrelide, or interferon therapy to a subject suffering from primary MF, PV, ET, post-PV MF, or post-ET MF or other bone marrow disorders presenting with bone marrow fibrosis.

In another embodiment, the subject compound may be employed in combination with a neuroleptic or antipsychotic agent, or pharmaceutically acceptable salts thereof, including but not limited to anticholinergics such as biperiden and trihexyphenidyl (benzhexol) hydrochloride, other COMT inhibitors such as entacapone, MOA-B inhibitors, antioxidants, Ala adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In a particularly preferred embodiment, the LOX-inhibiting compound of the invention is administered in combination with heart medication including but not limited to anticoagulants, antiplatelet agents and dual antiplatelet therapy, angiotensin-converting enzyme inhibitors, angiotensin II receptor blockers, angiotensin receptor-neprilysin inhibitors, p-blockers, calcium channel blockers, diuretics, nitrates, and cholesterol-lowering medications.

In a particularly preferred embodiment, the LOX-inhibiting compound of the invention is administered in combination with to other anti-fibrotic drugs, for example nintedanib, pirfenidone, TGF-β inhibitors (e.g. AVID200), LSD1 inhibitors (e.g. IMG-2789), pamrevlumab (FG-3019), pentraxin 2 (PRM-151), GLPG-1690, PBI-4050, AD-214, AD-114, endothelin receptor antagonist (e.g. bosentan, ambrisentan), MMP inhibitors or antibodies (e.g. Marimastat), integrin inhibitors (PLN-74809, IDL-2965), or angiotensin receptor blocker.

V. Formulation and Administration

The invention provides a method for administering a LOX enzyme-inhibiting compound of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, to a patient suffering from a condition, or prone to a condition, that is responsive to treatment or prevention with the compound. The method comprises administering, e.g. orally, transdermally, or parenterally, a therapeutically effective amount of the compound, preferably provided as part of a pharmaceutical preparation.

In some embodiments, a prodrug of the LOX enzyme-inhibiting compound is administered.

The invention also provides pharmaceutical preparations comprising a LOX enzyme-inhibiting compound in combination with a pharmaceutical excipient.

In addition to primates, such as humans, a variety of other mammals can be treated according to the method of the present invention. For instance, mammals including, but not limited to, cows, sheep, goats, horses, dogs, cats, guinea pigs, or other bovine, ovine, equine, canine, feline, or rodent, such as mouse, species can be treated. However, the method can also be practiced in other species, such as avian species (e.g., chickens).

The compounds disclosed herein may be administered by oral, parenteral injection or infusion (e.g., intramuscular, intraperitoneal, intravenous, intraarterial, intrathecal, ICV, or intracisternal injection or infusion), subcutaneous injection or implant, by inhalation spray, other transmucosal delivery (e.g., nasal, vaginal, rectal, or sublingual delivery) or topical routes of administration. A preferred administration is oral administration or topical routes of administration. The compounds may be formulated, alone or together, in suitable dosage unit formulations containing conventional pharmaceutically acceptable carriers, adjuvants and vehicles appropriate for each route of administration.

Suitable formulation types for parenteral administration include ready-for-injection solutions, dry powders for combination with a solvent prior to use, suspensions ready for injection, dry insoluble compositions for combination with a vehicle prior to use, emulsions and liquid concentrates for dilution prior to administration.

The pharmaceutical carrier(s) employed may be solid or liquid. Liquid carriers can be used in the preparation of solutions, emulsions, suspensions and pressurized compositions. The compounds are dissolved or suspended in a pharmaceutically acceptable liquid excipient. Suitable examples of liquid carriers for parenteral administration include, but are not limited to, water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

Exemplary excipients include, without limitation, carbohydrates, inorganic salts, antimicrobial agents, antioxidants, surfactants, buffers, acids, bases, and combinations thereof. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer including, but not limited to, citric acid, sodium chloride, potassium chloride, sodium sulfate, potassium nitrate, sodium phosphate monobasic, sodium phosphate dibasic, and combinations thereof.

A surfactant may be present as an excipient. Exemplary surfactants include, but are not limited to, polysorbates such as Tween 20 and Tween 80 and pluronics such as F68 and F88 (both available from BASF, Mount Olive, N.J.); sorbitan esters; lipids, such as phospholipids such as lecithin and other phosphatidyl cholines, phosphatidyl ethanolamines (although preferably not in liposomal form), and fatty acids and fatty esters.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof For parenteral administration, the carrier can also be an oily ester such as ethyl oleate and isopropyl myristate. Sterile carriers are useful in sterile liquid form compositions for parenteral administration. Sterile liquid pharmaceutical compositions, solutions or suspensions can be utilized by, for example, intraperitoneal injection, subcutaneous injection, intravenously, or topically. The compositions can also be administered intravascularly or via a vascular stent.

For pressurized compositions, the liquid carrier can be a halogenated hydrocarbon or other pharmaceutically acceptable propellant. Such pressurized compositions may also be lipid encapsulated for delivery via inhalation. For administration by intranasal or intrabronchial inhalation or insufflation, the compositions may be formulated into an aqueous or partially aqueous solution, which can then be utilized in the form of an aerosol.

The compositions may be administered topically, as a solution, cream, or lotion, by formulation with pharmaceutically acceptable vehicles containing the active compound. The compositions can be in a form suitable for use in transdermal devices.

The compositions of this invention may be orally administered, in formulations such as capsules, tablets, powders or granules, or as suspensions or solutions in water or non-aqueous media. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

The amount of the compound in the composition will vary depending on a number of factors but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the LOX enzyme-inhibiting compound in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then further exploring the range at which optimal performance is attained with no significant adverse effects. Generally, however, the excipient will be present in the composition in an amount of about 1% to about 99% by weight, preferably from about 5%-98% by weight, more preferably from about 15-95% by weight of the excipient, with concentrations less than 30% by weight most preferred.

The foregoing pharmaceutical excipients, along with other excipients, are described in "Remington: The Science & Practice of Pharmacy", 21st ed., Williams & Williams, (2005), the "Physician's Desk Reference", 67th ed., PDR Network, Montvale, N.J. (2013), and Kibbe, A. H., "Handbook of Pharmaceutical Excipients", 7th Edition, Pharmaceutical Press, Washington, D.C., 2012.

The dose of the compounds of Formula I, Formula Ia, Formula Ib, Formula Ic, Formula Id, Formula Ie, Formula If, Formula Ig, Formula Ih, or Table 1, including pharmaceutically acceptable salts or hydrates thereof, or stereoisomers or racemic mixtures thereof, to be administered, both unit dosage and dosing schedule, will vary depend upon the age, weight, and general condition of the subject, as well as the desired therapeutic effect, the route of administration, and the duration of the treatment. The compounds of the invention are administered to the patient in therapeutically effective amounts. Methods are known to those skilled in the art to adjust the dose to obtain maximal benefit. Generally, dosage levels of between 0.001 to 10 mg/kg of body weight daily are administered to the patient. The dosage range will generally be about 0.5 mg to 1.0 g per patient per day, which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. The compounds may be administered on a regimen of 1 to 4 times per day, such as once or twice per day.

EXAMPLES

The present compounds can be prepared and evaluated according to procedures provided in the following Examples. The following Examples further describe, but do not limit, the scope of the invention.

Example 1—LOXL2/LOXL3 Inhibition Assay Procedures

The ability of compounds to inhibit one or more of the lysyl oxidases LOXL2 and/or LOXL3 was determined using a fluorometric assay. This assay measures the activity of lysyl oxidases by coupling the reaction with horseradish peroxidase-catalyzed oxidation of cadaverine. The activity assay protocol uses cadaverine as substrate that releases hydrogen peroxide upon transformation by the specific LOX family enzyme present in the sample. Hydrogen peroxide is in turn detected using a red fluorescence substrate for HRP-coupled reactions (Amplex Red Enzyme Assays, Thermo Scientific Fisher). This leads to increase in fluorescence that can be easily detected at Ex/Em=540/590 nm in a fluorescence microplate reader.

Enzymes: Recombinant human LOXL2 (lysyl oxidase like 2) and recombinant human LOXL3 (lysyl oxidase like 3) were purchased from R&D systems and assays were performed in 1.2 M urea, 50 mM sodium borate buffer pH 8.0, and 10 mM CaCl.

Reaction: Final concentration in the LOXL2 and LOXL3 assays were as following and performed in a total volume of 15d:

TABLE 5

| LOXL2/LOXL3 Reaction mix | | |
|---|---|---|
| | LOXL3 | LOXL2 |
| Protein (nM) | 150 | 130 |
| Cadaverine (mM) | 1 | 2.5 |
| Amplex Red (μM) | 20 | 20 |
| HPR U/mL | 1 | 1 |

Experimental procedure: 5 μl of freshly prepared reaction buffer were delivered to reaction wells. Compounds were resuspended in 100% DMSO at 10 mM and delivered into buffer using acoustic technology (Echo550; nanoliter range). A 3× solution of LOXL2 or LOXL3 in reaction buffer was prepared ("enzyme solution") and 5 μL of enzyme solution was added into the reaction wells. Buffer only was added to column 1 for no protein control. Reactions were incubated for 30 minutes at 37° C. A 3×mixture of cadaverine, Amplex Red, and HRP ("Substrate/Detection Mix) was prepared and subsequently 5 μL of the mixture added to each reaction well. Progress of reactions was monitored for 60 minutes at 37° C. using Clariostar plate reader (ex 530-12, ems 600-40). For all activity assays, pan-LOX inhibitor CCT365623 (Tang et al, 2017) and LOXL2/LOXL3 inhibitor PAT-1251 (PharmaKea) were included as standards.

Data analysis: Slope of the linear portion of the progress curve was calculated using Clariostar software. Typical analysis interval was between 8-30 min, but varied between experiments. The background subtracted signals (No protein wells are considered as background) were converted to % activity relative to DMSO controls. Data was analyzed using GraphPad Prism 4 with "sigmoidal dose-response (variable slope)"; 4 parameters with Hill Slope. Constraints: Bottom=Constant equal to 0. Top=Must be less than 120.

For all activity assays, pan-LOX inhibitor CCT365623 (Tang et al, 2017) and LOXL2/LOXL3 inhibitor PAT-1251 (PharmaKea) were included as standards.

Activity data are shown in Table 8.

Example 2—LOX Inhibition Assay Procedures

The ability of compounds to inhibit prototypic LOX was determined using a fluorometric assay. This assay measures the activity of lysyl oxidases by coupling the reaction with horseradish peroxidase-catalyzed oxidation of cadaverine. The activity assay protocol uses cadaverine as substrate that releases hydrogen peroxide upon transformation by prototypic LOX enzyme present in the sample. Hydrogen peroxide is in turn detected using a red fluorescence substrate for HRP-coupled reactions (Amplex Red Enzyme Assays, Thermo Scientific Fisher). This leads to increase in fluorescence that can be easily detected at Ex/Em=540/590 nm in a fluorescence microplate reader.

Enzyme: Bovine lysyl oxidase (LOX) was extracted by adapting the methodology from [Kagan et al. 1979 and Borel et al. 2001.] from bovine tendon: Frozen adult bovine tendon was placed in room temperature water to defrost, and then membranes were removed and the remaining tissue cut into 1 cm pieces. The material was first passed through a course mesh meat grinder, and this mince was passed through a fine mesh grinder. The mince was homogenized in 10 v/w of buffer (16 mM sodium phosphate buffer pH 7.8, 400 mM NaCl) using a Waring blender. The homogenate was centrifuged at 15,000×g for 15 min at 4° C. After centrifugation, the supernatant was discarded and the pellets resuspended in 10 volumes of the same buffer. The mixture was blended again and centrifuged with the same settings. This time the pellets were blended in 3 volumes of extraction buffer (16 mM sodium phosphate buffer pH 7.8) and left to incubate at 4° C. for 2 h. After this time, the slurry was centrifuged with the same settings as described above. The supernatant was used in an ultrafiltration step to remove large proteins by size exclusion through a 30 kDalton filter (EMD Millipore). The filtrate was mixed with DEAE Sephadex (GE Healthcare), or passed over a MonoQ FPLC column. After two washes, one in 16 mM sodium phosphate buffer pH 7.8, 380 mM NaCl, and another in 16 mM sodium phosphate buffer pH 7.8, the proteins were eluted with 16 mM sodium phosphate pH 7.8, 10 μM $CuSO_4$, and 4 M urea. Fractions containing Lox activity were collected and stored frozen at −70° C.

Reaction: Final concentration in the LOX assay was as following and performed in a total volume of 15 μl:

TABLE 6

| LOX reaction mix | |
|---|---|
| | LOX |
| Protein (μl) | 1 |
| Cadaverine (mM) | 5 |
| Amplex Red (μM) | 20 |
| HPR U/mL | 10 |

Experimental procedure: 7 μl of freshly prepared reaction buffer were delivered to reaction wells. Compounds were resuspended in 100% DMSO at 10 mM and delivered into buffer using acoustic technology (Echo550; nanoliter range). A 2.85× solution of LOX protein in reaction buffer was prepared ("LOX solution") and 7 μl of LOX solution was added into the reaction wells. Buffer only was added to column 1 for no protein control. Reactions were incubated for 30 minutes at 37° C. A 3.33× mixture of cadaverine, Amplex Red, and HRP ("Substrate/Detection Mix) was prepared and subsequently 6 μL of the mixture was added to each reaction well. Progress of reactions was monitored for 120 minutes at 37° C. using Clariostar plate reader (ex530-12, ems 600-40). For all activity assays, pan-LOX inhibitor CCT365623 (Tang et al, 2017) and LOXL2/LOXL3 inhibitor PAT-1251 (PharmaKea) were included as standards.

Data analysis: Slope of the linear portion of the progress curve was calculated using Clariostar software. Typical analysis interval was between 20-50 min, but varied between experiments. The background subtracted signals (No protein wells were considered as background) were converted to % activity relative to DMSO controls. Data was analyzed using GraphPad Prism 4 with "sigmoidal dose-response (variable slope)"; 4 parameters with Hill Slope. Constraints: Bottom=Constant equal to 0. Top=Must be less than 120.

For all activity assays, pan-LOX inhibitor CCT365623 (Tang et al, 2017) and LOXL2/LOXL3 inhibitor PAT-1251 (PharmaKea) were included as standards.

Activity data are shown in Table 8.

Example 3—LOXL1/4 Inhibition Assay Procedures

The ability of compounds to inhibit human LOX, LOXL1 and/or LOXL4 is determined using a fluorometric assay. This assay measures the activity of lysyl oxidases by coupling the reaction with horseradish peroxidase-catalyzed oxidation of cadaverine. The activity assay protocol uses cadaverine as substrate that releases hydrogen peroxide upon transformation by the lysyl oxidase enzyme present in the sample. Hydrogen peroxide is in turn detected using a red fluorescence substrate for HRP-coupled reactions (Amplex Red Enzyme Assays, Thermo Scientific Fisher). This leads to increase in fluorescence that can be easily detected at Ex/Em=540/590 nm in a fluorescence microplate reader.

Recombinant human LOX, recombinant human and/or bovine LOXL1 (lysyl oxidase like 1), and recombinant human and/or bovine LOXL4 (lysyl oxidase like 4) are used for activity assays and assays are performed in 1.2 M urea, 50 mM sodium borate buffer pH 8.0, and 10 mM CaCl.

Final concentration in the LOX, LOXL1, and LOXL4 assays can be as following and are performed in a total volume of 15 μl:

TABLE 7

LOX/LOXL1/LOXL4 Reaction Mix

| | LOX | LOXL1 | LOXL4 |
|---|---|---|---|
| Protein (μl) | 1-5 | 1-5 | 1-5 |
| Cadaverine (mM) | 1-10 | 1-10 | 1-10 |
| Amplex Red (μM) | 5-20 | 5-20 | 5-20 |
| HPR U/mL | 5-10 | 5-10 | 5-10 |

Experimental procedure: 1-5 μl of freshly prepared reaction buffer is delivered to reaction wells. Compounds are resuspended in 100% DMSO at 10 mM and delivered into buffer using acoustic technology (Echo550; nanoliter range). A 3× solution of LOX, LOXL1, or LOXL4 in reaction buffer is prepared ("enzyme solution") and 1-5 μL of enzyme solution is added into the reaction wells. Buffer only is added to column 1 for no protein control. Reactions are incubated for 30 minutes at 37° C. A 3× mixture of cadaverine, Amplex Red, and HRP ("Substrate/Detection Mix) is prepared and subsequently 5 μL of the mixture is added to each reaction well. Progress of reactions is monitored for 120 minutes at 37° C. using Clariostar plate reader (ex 530-12, ems 600-40).

Data analysis: Slope of the linear portion of the progress curve is calculated using Clariostar software. Typical analysis interval is between 8-30 min, but may vary between experiments. The background subtracted signals (No protein wells are considered as background) are converted to % activity relative to DMSO controls. Data is analyzed using GraphPad Prism 4 with "sigmoidal dose-response (variable slope)"; 4 parameters with Hill Slope. Constraints: Bottom=Constant equal to 0. Top=Must be less than 120.

For all activity assays, pan-LOX inhibitor CCT365623 (Tang et al, 2017) and LOXL2/LOXL3 inhibitor PAT-1251 (PharmaKea) are included as standards.

Example 4—Activity Data of Selected Compounds

As the data herein indicate, a broad variety of compounds of formula I were found effective as LOX enzyme inhibitors at low concentrations. IC50 values for exemplary compounds of Formula I, Formula Ia, Formula Ib, Formula Ic, Formula Id, Formula Ie, Formula If, Formula Ig, Formula Ih, or Table 1, are provided in Table 8 below. Any compound with an IC50 below or equal to 500 nM in all LOX, LOXL2, and LOXL3 assays, as described above, is deemed a pan-LOX inhibitor. Any compound with an IC50 below or equal to 500 nM in the LOXL2 assay and greater than 30 μM in both the LOX and LOXL3 assay, as described above, is deemed a LOXL2 inhibitor. Any compound with an IC50 below or equal to 500 nM in the LOX assay and greater than 30 μM in the LOXL2/LOXL3 assays, as described above, is deemed a LOX inhibitor. Any compound with an IC50 below or equal to 500 nM in both the LOXL2 and LOXL3 assay and greater than 30 μM in the LOX assay, as described above, is deemed a dual LOXL2/LOXL3 inhibitor. Any compound with an IC50 below or equal to 500 nM in the LOXL3 assay and greater than 30 μM in the LOX and LOXL2 assay, as described above, is deemed a LOXL3 inhibitor. Any compound with an IC50 below or equal to 500 nM in the LOXL2 assay and greater than 30 μM □M in LOX and an IC50 which is 10-fold greater in the LOXL3 assay than the LOXL2 assay, as described above, is deemed a LOXL2-selective inhibitor.

As the data herein indicate, a broad variety of compounds of Formula I were found effective as LOX enzyme inhibitors at low concentrations. IC50 values for exemplary compounds of formula I (see below for compound names and structures) are provided in Table 8 infra. Any compound with an IC50 superior or equal to 10 μM in this assay, as described above, is deemed a LOX enzyme-inhibiting compound. In the table below, a three plus signs (+++) are associated with an IC50 of less than or equal to 500 nM; two plus signs (++) is associated with an IC50 of from 500 nM to less than 1□M; and a single plus sign (+) is associated with an IC50 of equal or greater than 1 μM and less than or equal to 30 μM.

TABLE 8

Activity Data of Exemplary LOX-inhibiting Compounds

| Example | Activity Range LOX | Activity Range LOXL2 | Activity Range LOXL3 |
|---|---|---|---|
| 9 | ++ | +++ | |
| 11 | +++ | +++ | |
| 13A | +++ | +++ | |
| 13B | +++ | +++ | |
| 15 | ++ | +++ | |
| 17 | ++ | +++ | |
| 20 | + | + | |
| 21 | − | ++ | |
| 22 | + | +++ | |
| 23 | − | +++ | + |
| 24 | − | + | |
| 25 | + | ++ | |
| 26 | + | +++ | |
| 27 | + | +++ | |
| 69 | − | +++ | |
| 70 | − | +++ | + |
| 71 | − | ++ | |
| 72 | − | + | |
| 73 | − | + | |
| 74 | − | +++ | + |
| 75 | +++ | +++ | |

TABLE 8-continued

| Activity Data of Exemplary LOX-inhibiting Compounds | | | |
|---|---|---|---|
| Example | Activity Range LOX | Activity Range LOXL2 | Activity Range LOXL3 |
| 75B | +++ | +++ | |
| 76 | +++ | +++ | |
| 77 | – | + | |
| 78 | – | ++ | |
| 79 | – | +++ | + |
| 82 | – | + | |
| 84 | + | +++ | |
| 85 | – | +++ | + |
| 90 | – | ++ | |
| 91 | +++ | +++ | |
| 92 | – | +++ | + |
| 93 | – | +++ | |
| 94 | – | ++ | |
| 98 | – | + | |
| 99 | – | + | |
| 100 | – | ++ | |
| 102RAC | – | – | |
| 102TR | – | – | |
| 106 | – | – | |
| 110 | – | + | |
| 111 | – | ++ | |
| 112 | + | +++ | |
| 112T | + | ++ | |
| 113 | + | +++ | |
| 113T | + | +++ | |
| 114 | | – | |
| 114T | | + | – |
| 115 | | – | – |
| 115T | – | + | – |
| 116 | – | + | |
| 116T | – | + | |
| 120 | +++ | +++ | |
| 120T | +++ | +++ | |
| 121 | +++ | +++ | |
| 122 | +++ | +++ | +++ |
| 124 | – | + | |
| 126 | – | + | |
| 130 | + | ++ | |
| 130T | + | +++ | |
| 131 | – | + | |
| 132 | – | + | |
| 133 | + | +++ | +++ |
| 133A | + | +++ | ++ |
| 133B | + | +++ | +++ |
| 134 | + | +++ | +++ |
| 135 | – | +++ | |
| 136 | – | +++ | + |
| 137 | – | +++ | |
| 137T | – | +++ | |
| 138 | – | +++ | + |
| 139 | – | ++ | + |
| 140 | – | ++ | + |
| 141 | – | +++ | |
| 141T | – | +++ | |
| 142 | – | +++ | |
| 142T | – | +++ | |
| 143 | – | +++ | |
| 144 | + | +++ | +++ |
| 145 | + | +++ | ++ |
| 146 | + | +++ | +++ |
| 147 | – | +++ | |
| 148 | + | +++ | |
| 149 | – | ++ | |
| 150 | + | ++ | |
| 155 | + | ++ | |
| 186 | + | +++ | |
| 187 | + | +++ | |

Synthetic Procedures

Exemplary compounds were prepared via several general synthetic routes set forth in the Examples below. Any of the disclosed compounds of the present invention can be prepared according to one or more of these synthetic routes or specific examples, or via modifications thereof accessible to the person of ordinary skill in the art.

Example 5: Preparation of Common Intermediates

Intermediate 1: Methyl 5-phenylpiperidine-3-carboxylate

Scheme 1

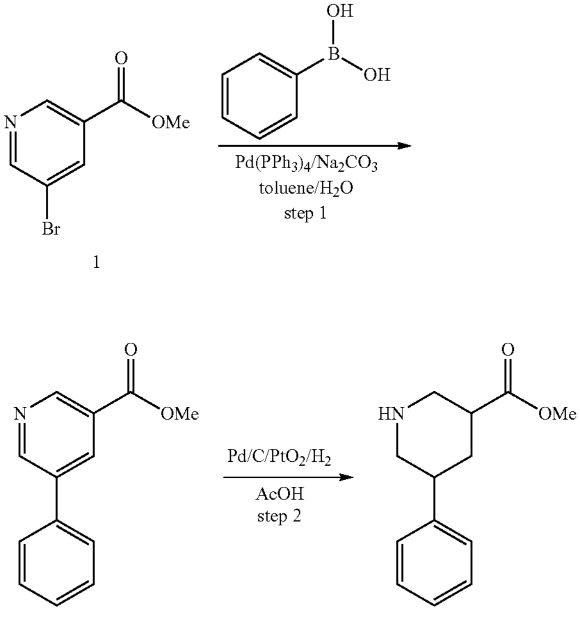

1

2

Intermediate 1

Step 1: Methyl 5-phenylnicotinate

To a stirred solution of methyl 5-bromonicotinate (10 g, 46.3 mmol, 1.00 equiv) in toluene (90 mL) and $H_2O$ (10 mL) were added phenylboronic acid (6.21 g, 50.9 mmol, 1.10 equiv), $Pd(PPh_3)_4$ (5.35 g, 4.63 mmol, 0.10 equiv) and $Na_2CO_3$ (14.7 g, 139 mmol, 3.00 equiv) in portions under nitrogen. The reaction mixture was stirred overnight at 110° C. The mixture was quenched with $H_2O$ (100 mL) and extracted with EtOAc (3×100 mL). The organic layers were combined and dried over anhydrous $Na_2SO_4$ and concentrated under vacuum. The residue was eluted from silica gel with EtOAc/PE (1:3). This resulted in 9.0 g (91%) of the title compound as yellow oil. MS-ESI: 214 (M+1).

Step 2: Methyl 5-phenylpiperidine-3-carboxylate

To a stirred solution of methyl 5-phenylpyridine-3-carboxylate (9.0 g, 42.2 mmol, 1.00 equiv) in AcOH (60 mL) was added Pd/C (10% wt., 898 mg) and $PtO_2$ (1.34 g, 5.9 mmol, 0.14 equiv) under nitrogen in portions. The flask was evacuated and refilled three times with hydrogen. The mixture was stirred for 72 h at rt under hydrogen atmosphere with a hydrogen balloon. The mixture filtered through a celite pad and the filtrate was concentrated under vacuum. This resulted in 9.0 g (crude) of the title compound as dark brown oil. MS-ESI: 220 (M+1).

Intermediate 2: Morpholino(5-phenylpiperidin-3-yl)methanone

Scheme 2

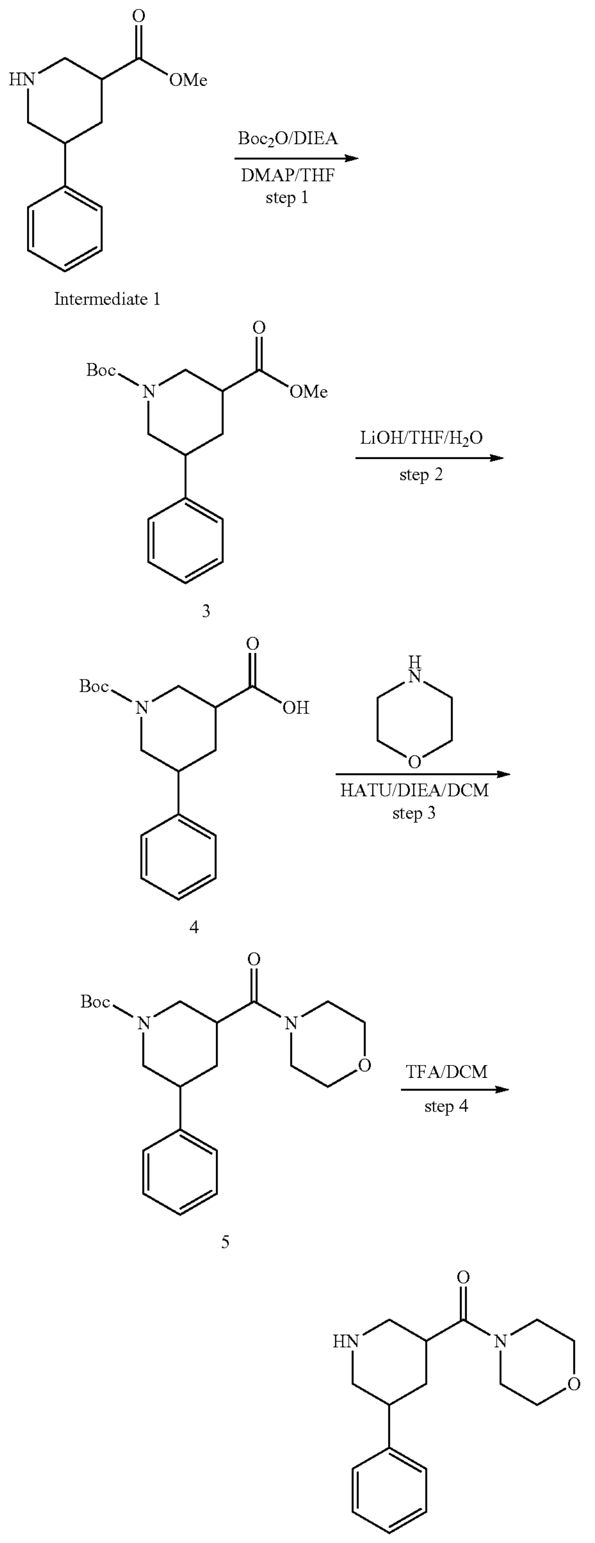

Intermediate 1

3

4

5

Intermediate 2

Step 1: 1-(tert-butyl) 3-methyl 5-phenylpiperidine-1,3-dicarboxylate

To a stirred solution of methyl 5-phenylpiperidine-3-carboxylate (9.0 g, crude) in THF (6 mL) were added DIEA (10.6 g, 82.1 mmol, 2.00 equiv), DMAP (502 mg, 4.10 mmol, 0.10 equiv) and $Boc_2O$ (10.8 g, 49.3 mmol, 1.20 equiv) in portions. The reaction mixture was stirred for 2 h at rt. The mixture was quenched with $H_2O$ (150 mL) and extracted with EtOAc (3×200 mL). The combined organic layers were dried over anhydrous $Na_2SO_4$. After filtration, the filtrate was concentrated under vacuum. The residue was eluted from silica gel with PE/EtOAc (10:1). This resulted in 7.0 g (53.4%) of the title compound as light yellow oil. MS-ESI: 320 (M+1).

Step 2: 1-(tert-butoxycarbonyl)-5-phenylpiperidine-3-carboxylic acid

To a stirred solution of 1-tert-butyl 3-methyl 5-phenylpiperidine-1,3-dicarboxylate (7.0 g, 21.9 mmol, 1.00 equiv) in THF (15 mL) and $H_2O$ (10 mL) was added LiOH (2.63 g, 110 mmol, 5.0 equiv) in portions. The reaction mixture was stirred for 12 h at rt. The mixture was adjusted to pH 4 with HCl (1 M). The mixture was diluted with $H_2O$ (10 mL) and extracted with EtOAc (3×100 mL). The combined organic layers were dried over anhydrous $Na_2SO_4$. After filtration, the filtrate was concentrated under vacuum. This resulted in 6.0 g (crude) of the title compound as light yellow oil. MS-ESI: 304 (M−1).

Step 3: tert-butyl 3-(morpholine-4-carbonyl)-5-phenylpiperidine-1-carboxylate To a stirred solution of 1-(tert-butoxycarbonyl)-5-phenylpiperidine-3-carboxylic acid (900 mg, 2.95 mmol, 1.00 equiv) in DMF (12 mL) were added HATU (1.34 g, 3.52 mmol, 1.20 equiv), DIEA (1.33 g, 10.3 mmol, 3.49 equiv) and morpholine (257 mg, 2.95 mmol, 1.00 equiv) in portions. The reaction mixture was stirred for 2 h at rt. The mixture was diluted with $H_2O$ (10 mL) and extracted with EtOAc (3×50 mL). The combined organic layers were dried over anhydrous $Na_2SO_4$. After filtration, the filtrate was concentrated under vacuum. The residue was eluted from silica gel with EtOAc/PE (1:3). This resulted in 640 mg (57.9%) of the title compound as a light yellow solid. MS-ESI: 375 (M+1).

Step 4: Morpholino(5-phenylpiperidin-3-yl)methanone

A solution of tert-butyl 3-(morpholine-4-carbonyl)-5-phenylpiperidine-1-carboxylate (640 mg, 1.71 mmol, 1.00 equiv) in DCM (5 mL) and TFA (2 mL) was stirred for 30 min at rt. The reaction mixture was concentrated under vacuum. This resulted in 1.0 g (crude) of the title compound as light yellow oil. MS-ESI: 275 (M+1).

The intermediate in the following table were prepared using the similar procedures for converting intermediate 1 to intermediate 2 shown in Scheme 2 from appropriated starting materials:

| Intermediate # | Structure | IUPAC Name | Exact mass [M + H]+ |
|---|---|---|---|
| Intermediate 3 | 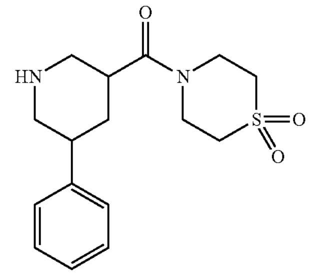 [SMILES: O=C(C1CNCC(c2ccccc2)C1)N1CCS(=O)(=O)CC1] | (1,1-Dioxidothiomorpholino)(5-phenylpiperidin-3-yl)methanone | 323 |
| Intermediate 4 | 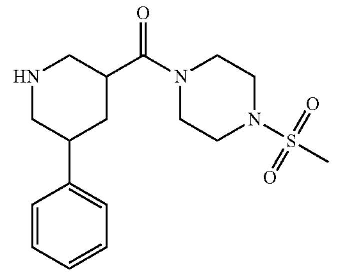 [SMILES: CS(=O)(=O)N1CCN(C(=O)C2CNCC(c3ccccc3)C2)CC1] | (4-(Methylsulfonyl)piperazin-1-yl)(5-phenylpiperidin-3-yl)methanone | 352 |

Intermediate 5: Methyl 4-((5-(methylsulfonyl)piperidin-3-yl)sulfonyl)benzoate

Scheme 3

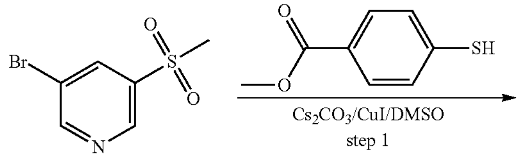

6

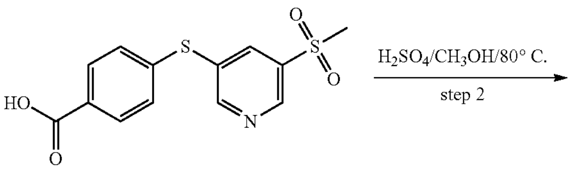

7

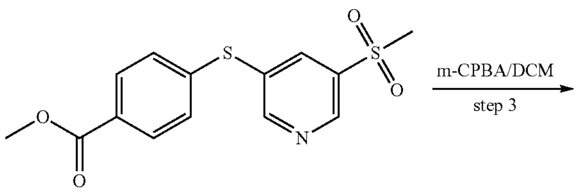

8

-continued

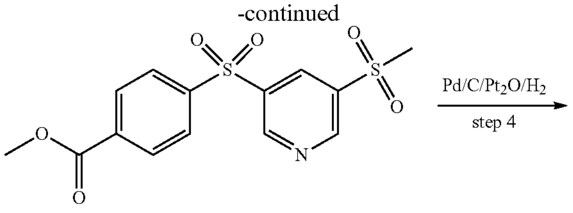

9

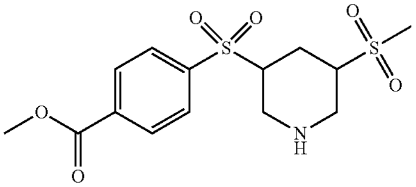

Intermediate 5

Step 1: 4-((5-(Methylsulfonyl)pyridin-3-yl)thio)benzoic acid

To a stirred solution of 3-bromo-5-(methylsulfonyl)pyridine (4.5 g, 19.1 mmol, 1.00 equiv) in DMSO (60 mL) under nitrogen were added methyl 4-mercaptobenzoate (3.84 g, 22.9 mmol, 1.20 equiv) and 2,2,6,6-tetramethylheptane-3,5-dione (1.05 g, 5.73 mmol, 0.30 equiv), then followed by the addition of $Cs_2CO_3$ (18.6 g, 57.2 mmol, 3.00 equiv) and CuI (726 mg, 3.81 mmol, 0.20 equiv) in portions. The reaction mixture was stirred for 5 h at 130° C. The reaction was quenched with $H_2O$ (60 mL). The pH value of the mixture was adjusted to 2 with HCl (1 M). The mixture was extracted with EtOAc (3×60 mL). The organic layers were combined and dried over anhydrous $Na_2SO_4$ and concentrated under vacuum. This resulted in 3.0 g (crude) of the title compound as brown oil. MS-ESI: 308 (M−1).

Step 2: Methyl 4-((5-(methylsulfonyl)pyridin-3-yl)thio)benzoate

To a stirred solution of 4-((5-(methylsulfonyl)pyridin-3-yl)thio)benzoic acid (2.5 g, crude) in MeOH (15 mL) was added cc·$H_2SO_4$ (1 mL) dropwise at 0° C. The resulting solution was stirred for 3 h at 80° C. The reaction was quenched with $H_2O$ (50 mL). The mixture was extracted with EtOAc (2×30 mL). The organic layers were combined and concentrated under vacuum. The residue was eluted from silica gel with EtOAc/PE (1:1). This resulted in 1.2 g (crude) of the title compound as a yellow solid. MS-ESI: 324 (M+1).

Step 3: Methyl 4-((5-(methylsulfonyl)pyridin-3-yl) sulfonyl)benzoate

To a stirred solution of methyl 4-((5-(methylsulfonyl) pyridin-3-yl)thio)benzoate (1.1 g, crude) in DCM (2.1 mL) was added m-CPBA (1.76 g, 10.2 mmol, 3.00 equiv) in portions at 0° C. The reaction mixture was stirred for 3 h at rt. The reaction was quenched with sat. $Na_2S_2O_3$ aq. (20 mL). The mixture was extracted with DCM (3×60 mL). The combined organic layers were dried over anhydrous $Na_2SO_4$ and concentrated under vacuum. The residue was eluted from silica gel with EtOAc/PE (1:1). This resulted in 720 mg (60%) of the title compound as a yellow solid. MS-ESI: 356 (M+1).

Step 4: Methyl 4-((5-(methylsulfonyl)piperidin-3-yl)sulfonyl)benzoate

To a stirred solution of methyl 4-((5-(methylsulfonyl) pyridin-3-yl)sulfonyl)benzoate (720 mg, 2.04 mmol, 1.00 equiv) in AcOH (15 mL) under nitrogen were added $PtO_2$ (720 mg, 3.18 mmol) and Pd/C (10% wt., 720 mg). The mixture solution was evacuated and refilled three times with hydrogen. The mixture was stirred for 3 h at 85° C. under an atmosphere of hydrogen with 60 atm. The solids were filtered out. The mixture was concentrated under vacuum. The residue was eluted from silica gel with DCM/MeOH (10:1). This resulted in 250 mg (33.9%) of the title compound as a yellow solid. MS-ESI: 362 (M+1).

The intermediate in the following table were prepared using the similar procedures for converting compound 6 to intermediate 5 shown in Scheme 3 from appropriated starting materials:

| Intermediate # | Structure | IUPAC Name | Exact Mass $[M + H]^+$ |
|---|---|---|---|
| Intermediate 6 | 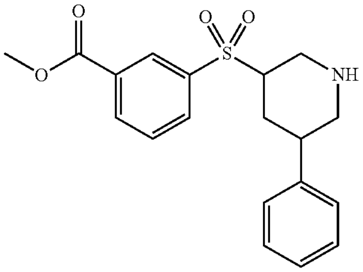 [SMILES: COC(=O)c1cccc(S(=O)(=O)C2CNCC(c3ccccc3)C2)c1] | Methyl 3-((5-phenylpiperidin-3-yl)sulfonyl)benzoate | 360 |

Intermediate 7: cis-Methyl 4-fluoro-3-((1-(methylsulfonyl)-5-phenylpiperidin-3-yl)oxy)benzoate Scheme 4

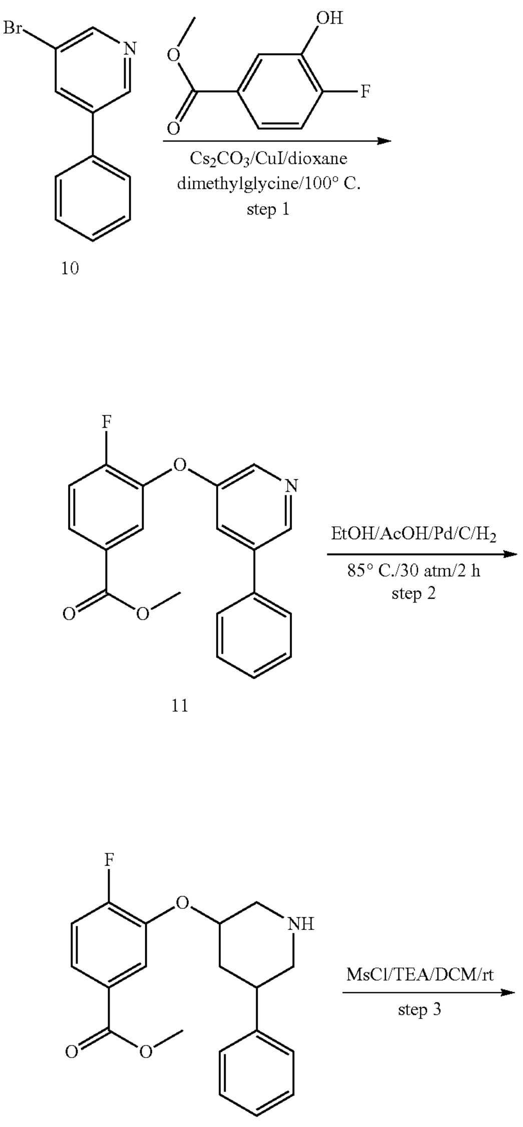

10

11

12

-continued

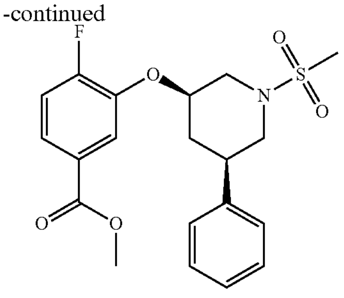

racemic
Intermedite 7

Step 1: Methyl 4-fluoro-3-((5-phenylpyridin-3-yl)oxy)benzoate

To a stirred solution of 3-bromo-5-phenylpyridine (2.0 g, 8.54 mmol, 1.00 equiv) in dioxane (40 mL) under nitrogen were added methyl 4-fluoro-3-hydroxybenzoate (2.91 g, 17.1 mmol, 2.00 equiv) and dimethylglycine (441 mg, 4.27 mmol, 0.50 equiv). To the above solution were added $Cs_2CO_3$ (8.35 g, 25.6 mmol, 3.00 equiv) and CuI (814 mg, 4.27 mmol, 0.50 equiv). The reaction mixture was stirred for 24 h at 100° C. The reaction was quenched with $H_2O$ (200 mL). The mixture was extracted with EtOAc (3×200 mL) and the combined organic layers dried over anhydrous $Na_2SO_4$ and concentrated under vacuum. The residue was eluted from silica gel with EtOAc/PE (1:10). This resulted in 800 mg (28.9%) of the title compound as yellow oil. MS-ESI: 324 (M+1).

Step 2: Methyl 4-fluoro-3-((5-phenylpiperidin-3-yl)oxy)benzoate

To a stirred solution of methyl 4-fluoro-3-((5-phenylpyridin-3-yl)oxy)benzoate (800 mg, 2.47 mmol, 1.00 equiv) in AcOH (10 mL) and EtOH (10 mL) was added Pd/C (10% wt., 800 mg) under nitrogen in portions. The mixture was evacuated and refilled three times with hydrogen. The mixture was stirred for 1 h at 85° C. under an atmosphere of hydrogen with 30 atm. The mixture filtered through a celite pad and the filtrate was concentrated under vacuum. The residue was eluted from silica gel with DCM/MeOH (15:1). This resulted in 200 mg (40.5%) of the title compound as yellow oil. MS-ESI: 330 (M+1).

Step 3: cis-methyl 4-fluoro-3-((1-(methylsulfonyl)-5-phenylpiperidin-3-yl)oxy)benzoate To a stirred solution of methyl 4-fluoro-3-((5-phenylpiperidin-3-yl)oxy)benzoate (200 mg, 0.61 mmol, 1.00 equiv) in DCM (10 mL) was added methanesulfonyl chloride (104 mg, 0.91 mmol, 1.50 equiv) dropwise at 0° C. To the above solution was added TEA (184 mg, 1.82 mmol, 3.00 equiv). The reaction mixture was stirred for 2 h at rt. The reaction was quenched with sat. $NH_4Cl$ aq. (10 mL). The mixture was extracted with DCM (3×10 mL). The combined organic layers were dried over anhydrous $Na_2SO_4$ and concentrated under vacuum. The residue was eluted from silica gel with EtOAc/PE (1:1). This resulted in 85 mg (34%) of the title compound as a yellow solid. MS-ESI 408 (M+1).

Intermediate 8: Methyl 4-fluoro-3-((5-(2-fluorophenyl)-1-(methylsulfonyl)piperidin-3-yl)oxy)benzoate Scheme 5

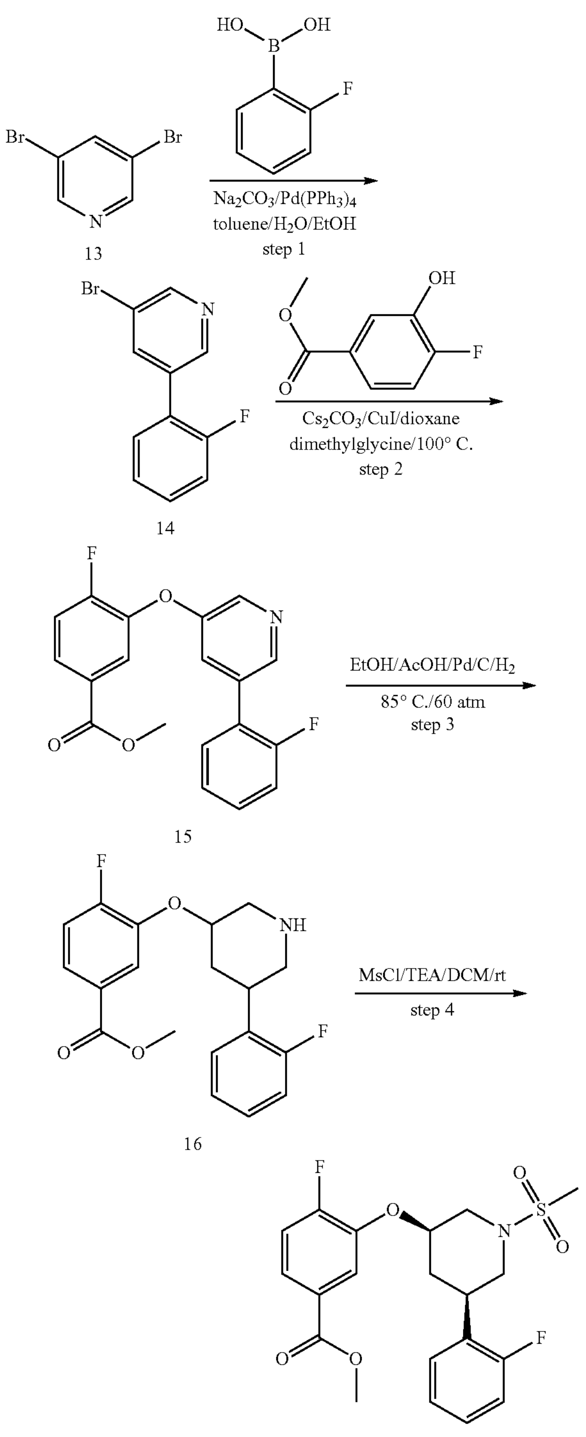

Intermediate 8

Step 1: 3-Bromo-5-(2-fluorophenyl)pyridine

To a stirred solution of 3,5-dibromopyridine (11 g, 46.4 mmol, 1.30 equiv) in toluene (100 mL) and EtOH (25 mL)

and $H_2O$ (25 mL) under nitrogen were added 2-fluorophenyl)boronic acid (5.0 g, 35.7 mmol, 1.00 equiv), $Na_2CO_3$ (11.4 g, 107 mmol, 3.00 equiv) and $Pd(PPh_3)_4$ (1.85 g, 1.79 mmol, 0.05 equiv). The reaction mixture was stirred overnight at 90° C. The reaction was diluted with $H_2O$ (50 mL). The mixture was extracted with EtOAc (3×100 mL) and the organic layers was combined. The combined organic layers were washed with sat. NaCl aq. (2×100 mL) and dried over anhydrous $Na_2SO_4$ and concentrated under vacuum. The residue was eluted from silica gel with EtOAc/PE (1:5). This resulted in 10.6 g (crude) of the title compound as a white solid. MS-ESI: 252 (M+1).

Steps 2-4: used similar procedures for converting compound 10 to intermediate 7 shown in Scheme 4 to afford intermediate 8 from compound 14. MS-ESI: 426 (M+1).

Intermediate 9: tert-butyl (3-((5-(2-fluorophenyl)piperidin-3-yl)oxy)benzyl)carbamate Scheme 6

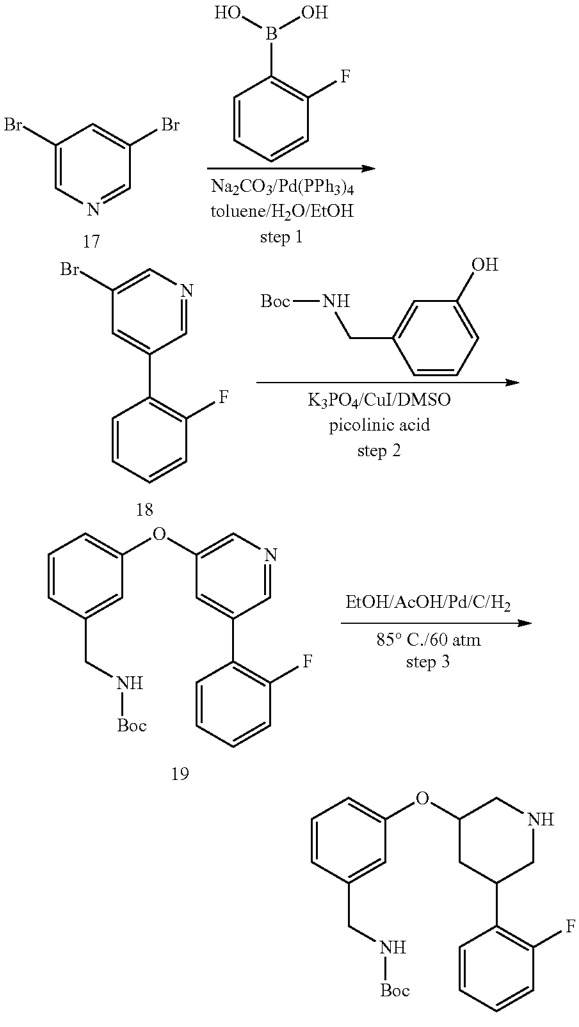

17

18

19

Intermediate 9

Step 1 used similar procedures for converting compound 13 to compound 14 shown in Scheme 5 to afford compound 18 from compound 17. MS-ESI: 252/254 (M+1).

Step 2: tert-butyl (3-((5-(2-fluorophenyl)pyridin-3-yl)oxy)benzyl)carbamate

To a stirred solution of 3-bromo-5-(2-fluorophenyl)pyridine (200 mg, 0.79 mmol, 1.00 equiv) in DMSO (6 mL) under nitrogen were added tert-butyl (3-hydroxybenzyl) carbamate (177 mg, 0.79 mmol, 1.00 equiv) and $K_3PO_4$ (505 mg, 2.38 mmol, 3.00 equiv). To the above solution were added CuI (15.1 mg, 0.08 mmol, 0.10 equiv) and picolinic acid (19.5 mg, 0.159 mmol, 0.20 equiv). The reaction mixture was stirred for 5 h at 90° C. The reaction was diluted with $H_2O$ (5 mL). The mixture was extracted with EtOAc (3×80 mL) and the combined organic layers were washed with sat. NaCl aq. (3×80 mL). The organic layer was dried over anhydrous $Na_2SO_4$ and concentrated under vacuum. The residue was eluted from silica gel with EtOAc/PE (3:10). This resulted in 68 mg (21.7%) of the title compound as white oil. MS-ESI: 395 (M+1).

Step 3 used similar procedures for converting compound 11 to compound 12 shown in Scheme 4 to afford intermediate 9 from compound 19. MS-ESI: 401 (M+1).

Intermediate 10: tert-butyl (3-((5-phenylpiperidin-3-yl)oxy)benzyl)carbamate

Scheme 7

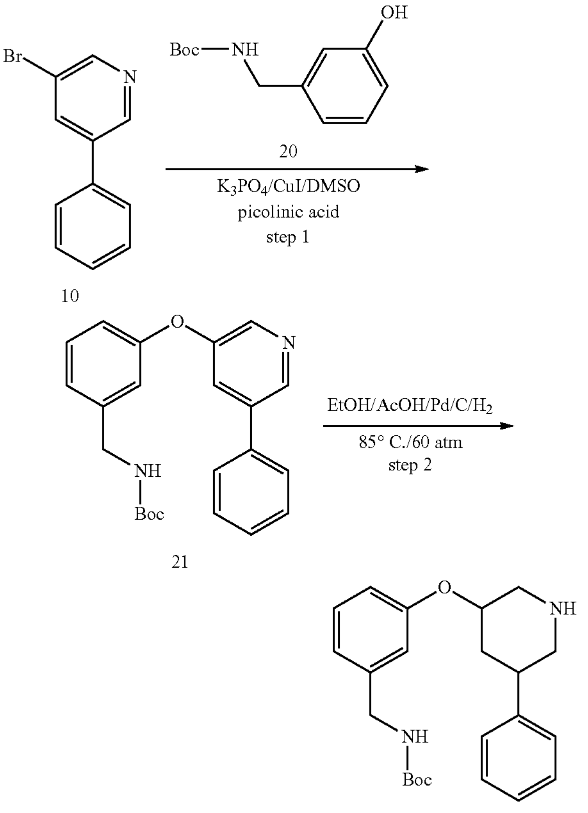

10

20

21

Intermediate 10

Steps 1-2 used similar procedures for converting compound 18 to intermediate 9 shown in Scheme 6 to afford intermediate 10 from compound 20. MS-ESI: 383 (M+1).

The intermediate in the following table were prepared using the similar procedures for converting compound 20 to intermediate 8 shown in Scheme 7 from appropriated starting materials.

| Intermediate # | Structure | IUPAC Name | Exact Mass $[M + H]^+$ |
|---|---|---|---|
| Intermediate 11 | 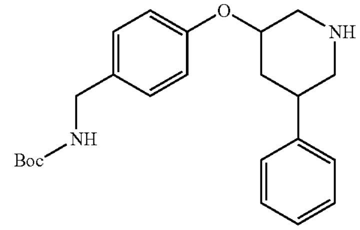 [SMILES: CC(C)(C)OC(=O)NCc1ccc(OC2CNCC(c3ccccc3)C2)cc1] | tert-butyl (4-((5-phenylpiperidin-3-yl)oxy)benzyl)carbamate | 383 |

Intermediate 12: 3-Bromo-1-(methylsulfonyl)-5-phenylpiperidine

Scheme 8

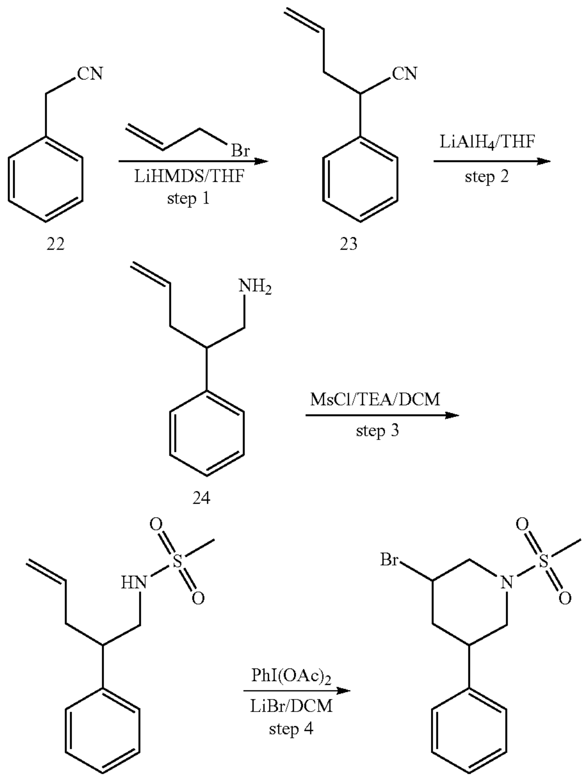

22
23
24
25
Intermediate 12

Step 1: 2-Phenylpent-4-enenitrile

To a stirred solution of 2-phenylacetonitrile (10 g, 86.6 mmol, 1.00 equiv) in THF (100 mL) under nitrogen was added LiHMDS in THF (1 M, 16.3 mL, 86.6 mmol, 1.00 equiv) dropwise at −78° C. The reaction solution was stirred for 20 min at −78° C. Then 3-bromoprop-1-ene (11.5 g, 95.3 mmol, 1.10 equiv) was added to the reaction solution slowly at −78° C. Then the reaction solution was stirred overnight at rt. The reaction was quenched with $H_2O$ (100 mL). The mixture was extracted with EtOAc (3×200 mL). The combined organic layers were dried over anhydrous $Na_2SO_4$ and concentrated under vacuum. This resulted in 9.0 g (crude) of the title compound as brown oil. MS-ESI: 156 (M−1).

Step 2: 2-Phenylpent-4-en-1-amine

To a stirred solution of 2-phenylpent-4-enenitrile (9.0 g, crude) in $Et_2O$ (150 mL) under nitrogen was added $LiAlH_4$ (4.59 g, 121 mmol, 2.00 equiv) in portions at 0° C. The reaction mixture was stirred for 30 min at 0° C. The mixture was stirred overnight at rt. The reaction was quenched with MeOH (50 mL) and concentrated under vacuum. The residue was eluted from silica gel with EtOAc/PE (1:1). This resulted in 7.0 g (50%, over two steps) of the title compound as brown oil. MS-ESI: 162 (M+1).

Step 3: N-(2-phenylpent-4-en-1-yl)methanesulfonamide

To a stirred solution of 2-phenylpent-4-en-1-amine (3.0 g, 18.6 mmol, 1.00 equiv) in DCM (50 mL) under nitrogen were added methanesulfonyl chloride (2.56 g, 22.3 mmol, 1.2 equiv) and TEA (3.77 g, 37.2 mmol, 2.00 equiv) dropwise at 0° C. The reaction solution was stirred for 3 h at rt. The reaction was quenched with $H_2O$ (50 mL). The mixture was extracted with DCM (3×100 mL). The combined organic layers were dried over anhydrous $Na_2SO_4$ and concentrated under vacuum. The residue was eluted from silica gel with EtOAc/PE (1:1). This resulted in 3.6 g (40.4%) of the title compound as yellow oil. MS-ESI: 240 (M+1).

Step 4: 3-Bromo-1-(methylsulfonyl)-5-phenylpiperidine

To a stirred solution of N-(2-phenylpent-4-en-1-yl)methanesulfonamide (3.0 g, 12.5 mmol, 1.00 equiv) in DCM (40 mL) were added (acetyloxy)(phenyl)-lambda3-iodanyl acetate (4.44 g, 13.8 mmol, 1.10 equiv) and LiBr (2.18 g, 25.1 mmol, 2.00 equiv). The reaction mixture was stirred for 16 h at rt. The reaction was quenched with $H_2O$ (40 mL). The mixture was extracted with DCM (3×40 mL). The organic layers were combined and dried over anhydrous $Na_2SO_4$ and concentrated under vacuum. The residue was eluted from silica gel with EtOAc/PE (1:3). This resulted in 2.5 g (62.7%) of the title compound as a yellow solid. MS-ESI: 318/320 (M+1).

Intermediate 13: Methyl 5-(trifluoromethyl)piperidine-3-carboxylate

Scheme 9

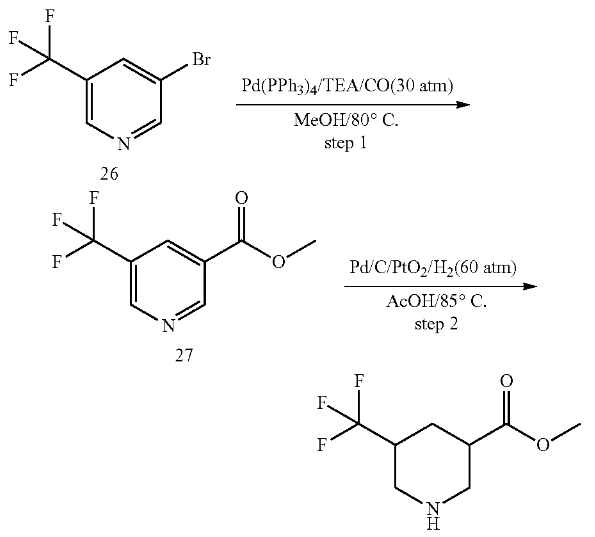

Intermediate 13

Step 1: Methyl 5-(trifluoromethyl)nicotinate

To a stirred solution of 3-bromo-5-(trifluoromethyl)pyridine (2.0 g, 8.85 mmol, 1.00 equiv) in MeOH (20 mL) under nitrogen were added $Pd(PPh_3)_4$ (1.02 g, 0.89 mmol, 0.10 equiv) and TEA (1.79 g, 17.7 mmol, 2.00 equiv), The reaction mixture was evacuated and refilled three times with CO(g). The mixture was stirred overnight at 80° C. The mixture was diluted with $H_2O$ (50 mL) and extracted with EtOAc (3×100 mL). The combined organic layers were washed with sat. NaCl aq. (3×100 mL) and dried over anhydrous $Na_2SO_4$ The organic layer was concentrated under vacuum. The residue was eluted from silica gel with EtOAc/PE (1:1). This resulted in 950 mg (52.3%) of the title compound as a white solid. MS-ESI: 206 (M+1).

Step 2 used similar procedures for converting compound 11 to compound 12 shown in Scheme 4 to afford intermediate 13 from compound 27. MS-ESI: 212 (M+1).

Intermediate 14: Perfluorophenyl 4-(((tert-butyldimethylsilyl)oxy)methyl)pyridine-2-sulfonate Scheme 10

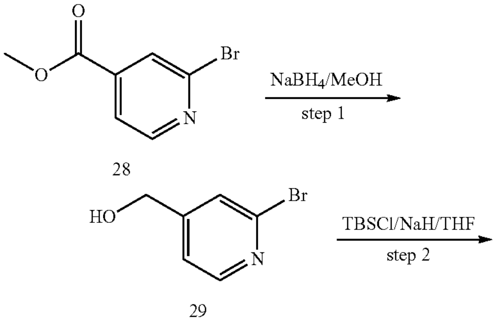

-continued

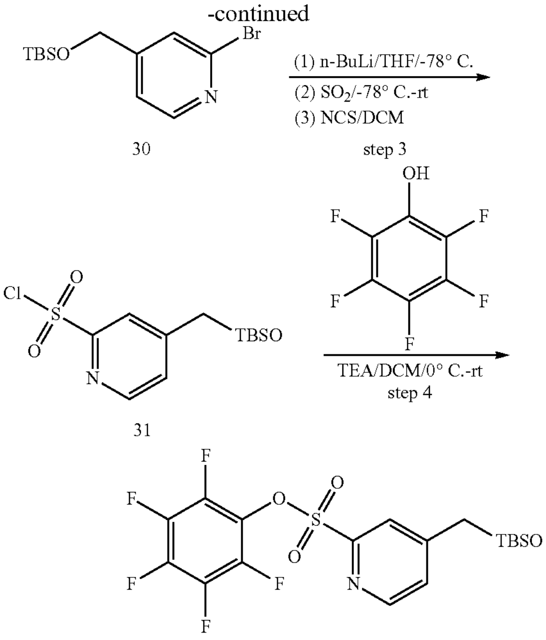

Intermediate 14

Step 1: (2-Bromopyridin-4-yl)methanol

To a stirred solution of methyl 2-bromoisonicotinate (10 g, 46.3 mmol, 1.00 equiv) in MeOH (300 mL) was added $NaBH_4$ (8.8 g, 232 mmol, 5.00 equiv) in portions at 0° C. under nitrogen. The resulting mixture was stirred for 30 min at rt. The reaction was quenched with ice/water (500 mL). The mixture was extracted with EtOAc (3×500 mL). The combined organic layers were dried with anhydrous $Na_2SO_4$ and concentrated under vacuum. This resulted in 8.6 g (crude) of the title compound as yellow solid. MS-ESI: 188/200 (M+1).

Step 2: 2-Bromo-4-(((tert-butyldimethylsilyl)oxy)methyl)pyridine

To a stirred solution of (2-bromopyridin-4-yl)methanol (8.6 g, crude) in THF (400 mL) was added NaH (60% wt. dispersion in mineral oil, 3.65 g, 91.3 mmol, 2.00 equiv) in portions at 0° C. under nitrogen. The mixture was stirred for 10 min at 0° C. To above mixture was added TBSCl (7.23 g, 48 mmol, 1.05 equiv) in portions at 0° C. The resulting mixture was stirred for 1 h at rt. The reaction was quenched with $H_2O$ (200 mL) and extracted with EtOAc (3×200 mL). The combined organic layers were dried with anhydrous $Na_2SO_4$ and concentrated under vacuum. The residue was eluted from silica gel with EtOAc/PE (1:10). This resulted in 13.7 g (over two steps, 98%) of the title compound as yellow oil. MS-ESI: 302/304 (M+1).

Step 3: 4-(((tert-butyldimethylsilyl)oxy)methyl)pyridine-2-sulfonyl chloride

To a stirred solution of 2-bromo-4-(((tert-butyldimethylsilyl)oxy)methyl)pyridine (3.0 g, 9.92 mmol, 1.00 equiv) in THF (50 mL) was added n-BuLi in hexanes (2.5 M, 7.94 mL, 19.8 mmol, 2.00 equiv) dropwise at −78° C. The reaction solution was stirred for 40 min at −78° C. Then to the solution was introduced $SO_2$ (g) bubble for 20 min. Then the mixture was stirred and warmed slowly to rt for 2 h. The mixture was concentrated under vacuum at low temperature. The obtained solid was dissolved into DCM (70 mL) at 0° C. and NCS (2.65 g, 19.8 mmol, 2.00 equiv) was added to the above mixture at 0° C. The resulting mixture was stirred for an additional 2 h at 0° C. The reaction mixture was used for next step directly without any workup.

Step 4: Perfluorophenyl 4-(((tert-butyldimethylsilyl)oxy)methyl)pyridine-2-sulfonate To a stirred mixture of 4-(((tert-butyldimethylsilyl)oxy)methyl)pyridine-2-sulfonyl chloride (from last step) were added TEA (4.72 g, 46.6 mmol, 3.00 equiv) and pentafluorophenol (3.64 g, 19.8 mmol, 2.00 equiv) in portions at 0° C. The resulting mixture was stirred for 16 h at rt. The mixture was then quenched with water/ice (100 mL) and extracted with 3×100 mL of DCM. The combined organic layers were dried over anhydrous $Na_2SO_4$ and concentrated under vacuum. The residue was eluted from silica gel with EtOAc/PE (1:5). This resulted in 800 mg (17.2%, over two steps) of the title compound as yellow oil. MS-ESI: 470 (M+1).

The intermediate in the following table were prepared using the similar procedures for converting compound 28 to intermediate 14 shown in Scheme 10 from appropriated starting materials:

-continued

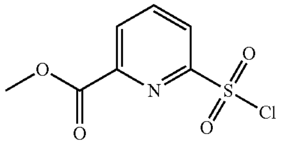

Intermediate 17

Step 1: Methyl 6-(benzylthio)picolinate

To a stirred solution of methyl 6-bromopicolinate (5.0 g, 23.1 mmol, 1.00 equiv) in dioxane (100 mL) under nitrogen were added phenylmethanethiol (5.75 g, 46.3 mmol, 2.00 equiv) and $Pd_2(dba)_3$ (4.24 g, 4.63 mmol, 0.20 equiv). To above mixture were added Xantphos (2.68 g, 4.63 mmol, 0.20 equiv) and DIEA (8.97 g, 69.4 mmol, 3.00 equiv). The resulting solution was stirred for 16 h at 100° C. The reaction was quenched with $H_2O$ (100 mL) and extracted with EtOAc (3×200 mL). The combined organic layers were dried with anhydrous $Na_2SO_4$ and concentrated under vacuum. The residue was eluted from silica gel with EtOAc/PE (1:3). This resulted in 5.0 g (83.3%) of the title combined as brown oil. MS-ESI: 260 (M+1).

| Intermediate # | Structure | IUPAC Name | Exact Mass $[M + H]^+$ |
|---|---|---|---|
| Intermediate 15 | 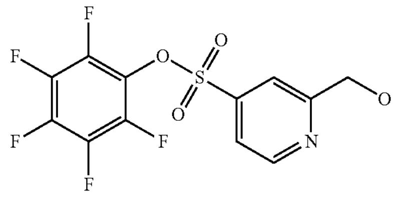 [SMILES: O=S(=O)(Oc1c(F)c(F)c(F)c(F)c1F)c1ccnc(CO)c1] | Perfluorophenyl 2-(((tert-butyldimethylsilyl)oxy)methyl)pyridine-4-sulfonate | 470 |
| Intermediate 16 | 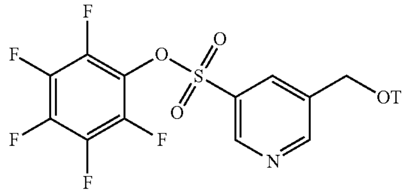 | Perfluorophenyl 5-(((tert-butyldimethylsilyl)oxy)methyl)pyridine-3-sulfonate | 470 |

Intermediate 17: Methyl 6-(chlorosulfonyl)picolinate

Scheme 11

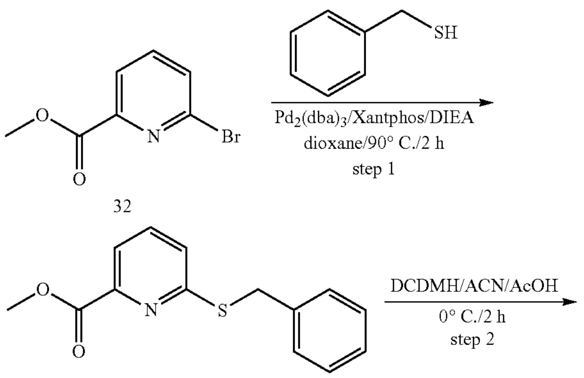

32

33

Step 2: Methyl 6-(chlorosulfonyl)picolinate

To a stirred solution of methyl 6-(benzylthio)picolinate (5.0 g, 19.3 mmol, 1.00 equiv) in MeCN (50 mL) and AcOH (50 mL) was added DCDMH (7.6 g, 38.6 mmol, 2.00 equiv) at 0° C. The resulting solution was stirred for 30 min at 0° C. The reaction was quenched with water/ice (200 mL) and extracted with DCM (3×200 mL). The combined organic layers were dried over anhydrous $Na_2SO_4$ and concentrated under vacuum. The residue was eluted from silica gel with EtOAc/PE (1:4). This resulted in 2.0 g (22%) of the title compound as a yellow solid. MS-ESI: 236/238 (M+1).

Intermediate 18: Methyl 2-(chlorosulfonyl)thiazole-5-carboxylate

Scheme 12

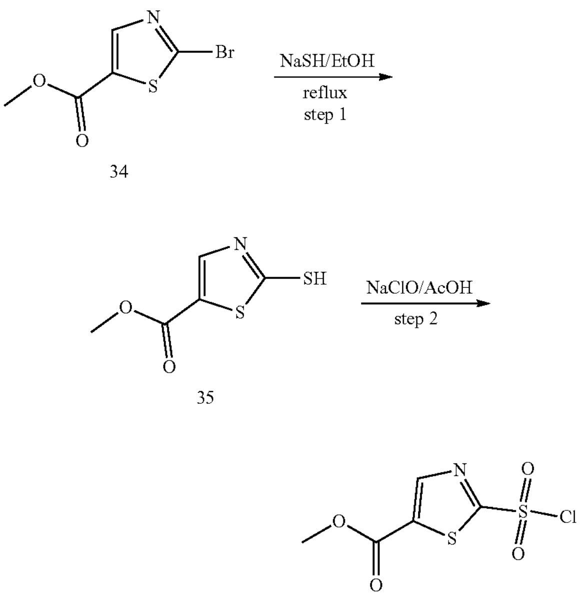

34

35

Intermediate 18

Step 1: Methyl 2-mercaptothiazole-5-carboxylate

To a stirred solution of methyl 2-bromothiazole-5-carboxylate (1.0 g, 4.5 mmol, 1.00 equiv) in EtOH (13 mL) was added NaSH (505 mg, 9.01 mmol, 2.00 equiv) at rt. The resulting mixture was stirred for 2 h at 80° C. The resulting mixture was diluted with $H_2O$ (3 mL). The mixture was adjusted to pH 4 with 1 M HCl (aq.). The precipitated solids were collected by filtration and washed with $H_2O$ (2×5 mL). This resulted in 600 mg (76%) of the title compound as a light yellow solid. MS-ESI: 176 (M+1).

Step 2: Methyl 2-(chlorosulfonyl)thiazole-5-carboxylate

To a stirred solution of methyl 2-mercaptothiazole-5-carboxylate (600 mg, 3.42 mmol, 1.00 equiv) were added NaClO (14.5% wt., 12 mL) and AcOH (18 mL) dropwise slowly at 0° C. The resulting mixture was stirred for 20 min at 0° C. The reaction was quenched with $H_2O$ (6 mL) at rt. The resulting mixture was extracted with DCM (3×30 mL). The combined organic layers were washed with water (2×20 mL) and dried with anhydrous $Na_2SO_4$. After filtration, the filtrate was concentrated under vacuum. This resulted in 700 mg (crude) of the title compound as light yellow oil.

Intermediate 19: 1-((5-Bromothiophen-2-yl)sulfonyl)-5-cyclohexylpiperidine-3-carboxylic acid Scheme 13

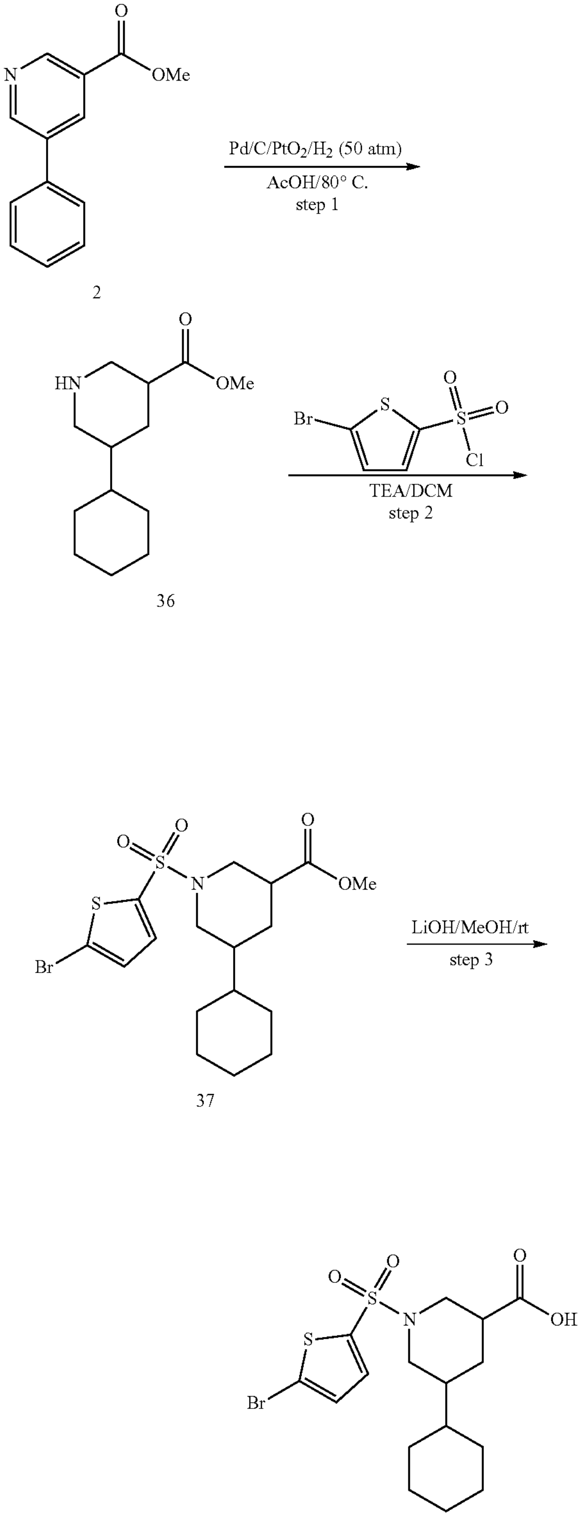

2

36

37

Intermediate 19

Step 1: Methyl 5-cyclohexylpiperidine-3-carboxylate

To a stirred solution of methyl 5-phenylnicotinate (10 g, 46.9 mmol, 1.00 equiv) in AcOH (300 mL) were added Pd/C (10% wt., 5.0 g) and $PtO_2$ (5.0 g, 22 mmol, 0.47 equiv) under nitrogen. The pressure tank reactor was evacuated and refilled three times with hydrogen. The reaction was stirred for 2 h at 80° C. under an atmosphere of hydrogen with 60 atm. The solids were filtered out. The filtrate was concentrated under vacuum. This resulted in 10 g (crude) as yellow oil. MS-ESI: 226 (M+1).

Step 2: Methyl 1-((5-bromothiophen-2-yl)sulfonyl)-5-cyclohexylpiperidine-3-carboxylate To a stirred solution of methyl 5-cyclohexylpiperidine-3-carboxylate (10 g, crude) in DCM (200 mL) was added TEA (17.9 g, 177 mmol, 4.00 equiv). The mixture was stirred for 10 min. Then to above mixture was added 5-bromothiophene-2-sulfonyl chloride (15 g, 57.5 mmol, 1.30 equiv) in portions at 0° C. The reaction was stirred overnight at rt. The reaction was quenched with $H_2O$ (200 mL) and extracted with DCM (3×300 mL). The combined organic layers were dried with anhydrous $Na_2SO_4$ and concentrated under vacuum. The residue was eluted from silica gel with EtOAc/PE (1:2). This resulted in 12.5 g (62.8%, over two steps) of the title compound as a yellow oil. MS-ESI 450/452 (M+1).

Step 3: 1-((5-Bromothiophen-2-yl)sulfonyl)-5-cyclohexylpiperidine-3-carboxylic acid To a stirred mixture of methyl 1-((5-bromothiophen-2-yl) sulfonyl)-5-cyclohexylpiperidine-3-carboxylate (7.00 g, 15.6 mmol, 1.00 equiv) in THF (80 mL) and $H_2O$ (80 mL) was added LiOH (1.87 g, 77.8 mmol, 5.00 equiv). The resulting mixture was stirred for 10 h at rt. The mixture was adjusted to pH 4 with HCl (1 M, aq.) and extracted with EtOAc (3×100 mL). The combined organic layers were concentrated under vacuum. This resulted in 7.0 g (crude) of the title compound as a white solid. MS-ESI: 436/438 (M+1).

The intermediate in the following table were prepared using the similar procedures for converting compound 2 to intermediate 19 shown in Scheme 13 from appropriated starting materials:

| Intermediate # | Structure | IUPAC Name | Exact Mass $[M + H]^+$ |
|---|---|---|---|
| Intermediate 20 | 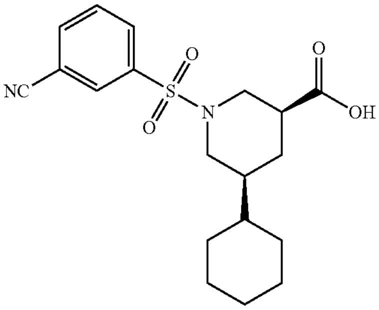 [SMILES: N#Cc1cccc(S(=O)(=O)N2C[C@@H](C(=O)O)C[C@@H](C3CCCCC3)C2)c1] | cis-1-((3-Cyanophenyl)sulfonyl)-5-cyclohexylpiperidine-3-carboxylic acid | 377 |

Intermediate 21: 1-Cyclohexyl-5-((3-(methoxycarbonyl)phenyl)sulfonyl)piperidine-3-carboxylic acid Scheme 14

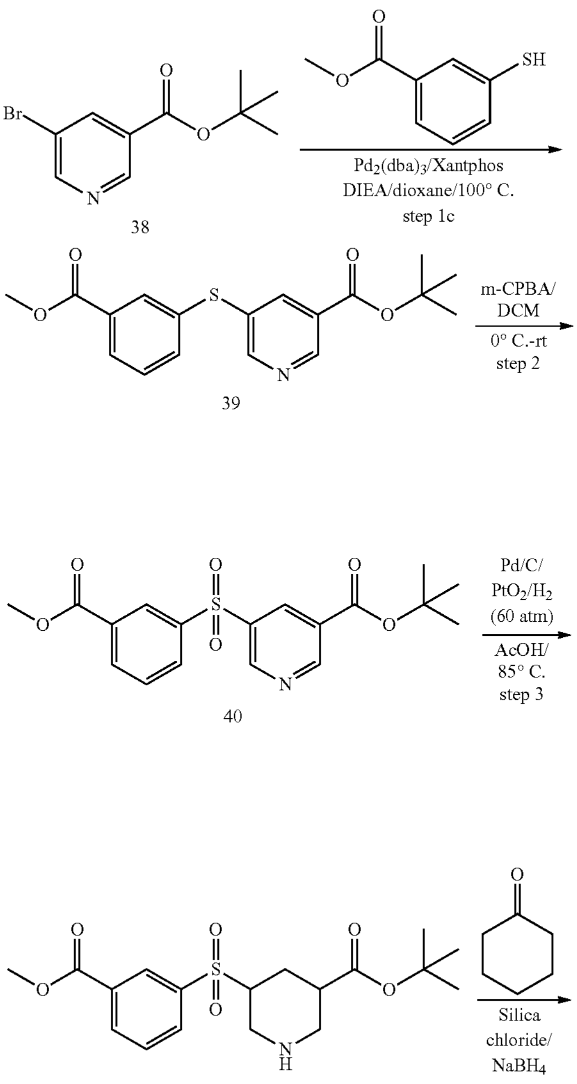

38

39

40

41

-continued

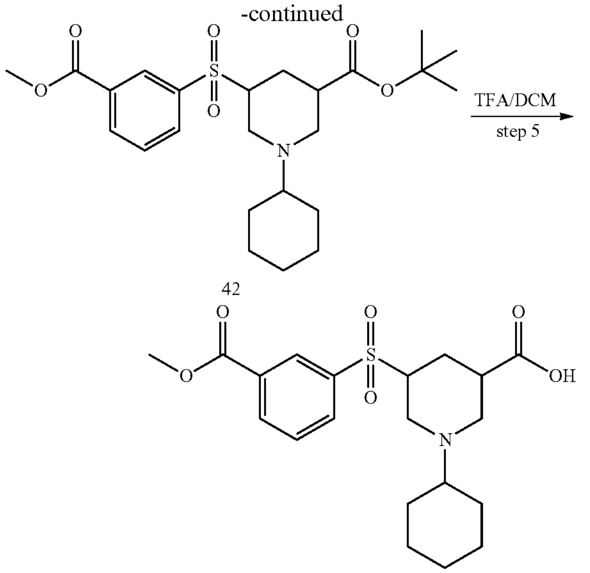

42

Intermediate 21

Step 1: tert-butyl 5-((3-(methoxycarbonyl)phenyl)thio)nicotinate

To a stirred solution of tert-butyl 5-bromonicotinate (5.5 g, 21.3 mmol, 1.00 equiv) in dioxane (200 mL) were added methyl 3-mercaptobenzoate (4.66 g, 27.7 mmol, 1.30 equiv), $Pd_2(dba)_3$ (1.95 g, 2.13 mmol, 0.10 equiv), Xantphos (2.47 g, 4.26 mmol, 0.20 equiv) and DIEA (8.26 g, 63.9 mmol, 3.00 equiv) under nitrogen. The resulting solution was stirred for 2 h at 100° C. under nitrogen. The reaction was diluted with $H_2O$ (500 mL) and extracted with EtOAc (3×300 mL). The combined organic layers were dried over anhydrous $Na_2SO_4$ and concentrated under vacuum. The residue was eluted from silica gel with EtOAc/PE (1:3). This resulted in 4.5 g (61.1%) of the title compound as yellow oil. MS-ESI: 346 (M+1).

Step 2: tert-butyl 5-((3-(methoxycarbonyl)phenyl)sulfonyl)nicotinate

To a stirred solution of tert-butyl 5-((3-(methoxycarbonyl)phenyl)thio)nicotinate (4.5 g, 13 mmol, 1.00 equiv) in DCM (9 mL) was added m-CPBA (6.74 g, 39 mmol, 3.00 equiv) in portions at 0° C. The resulting solution was stirred for 10 min at rt. The reaction was quenched with sat. $Na_2S_2O_3$ aq. and extracted with DCM (3×100 mL). The combined organic layers were dried over anhydrous $Na_2SO_4$ and concentrated under vacuum. The residue was eluted from silica gel with EtOAc/PE (1:5). This resulted in 3.8 g (77.3%) of the title compound as a yellow solid. MS-ESI: 378 (M+1).

Step 3: tert-butyl 5-((3-(methoxycarbonyl)phenyl)sulfonyl)piperidine-3-carboxylate To a stirred solution of tert-butyl 5-((3-(methoxycarbonyl)phenyl)sulfonyl)nicotinate (3.0 g, 7.95 mmol, 1.00 equiv) in AcOH (100 mL) was added Pd/C (10% wt., 3.00 g) and $PtO_2$ (3.00 g) in portions. The pressure tank reactor was evacuated and refilled three times with hydrogen. The resulting mixture was stirred for 5 h at 85° C. under an atmosphere of hydrogen with 60 atm. The solids were filtered out. The filtrate was concentrated under vacuum. The residue was eluted from silica gel with DCM/MeOH (10:1). This resulted in 2.05 g (67.3%) of the title compound as yellow oil. MS-ESI: 384 (M+1).

Step 4: tert-butyl 1-cyclohexyl-5-((3-(methoxycarbonyl)phenyl)sulfonyl)piperidine-3-carboxylate To a stirred solution of tert-butyl 5-((3-(methoxycarbonyl)phenyl)sulfonyl)piperidine-3-carboxylate (1.8 g, 4.69 mmol, 1.00 equiv) in cyclohexanone (3 mL) were added $NaBH_4$ (188 mg, 4.96 mmol, 1.00 equiv) and Silica chloride (1.00 g). The resulting solution was stirred for 16 h at rt. The reaction was quenched with $H_2O$ (10 mL). The resulting mixture was concentrated under vacuum. The residue was eluted from silica gel column with EtOAc/PE (5:1). This resulted in 600 mg (27.5%) of the title compound as yellow oil. MS-ESI: 466 (M+1).

Step 5: 1-Cyclohexyl-5-((3-(methoxycarbonyl)phenyl)sulfonyl)piperidine-3-carboxylic acid A solution of tert-butyl 1-cyclohexyl-5-((3-(methoxycarbonyl)phenyl)sulfonyl)piperidine-3-carboxylate (600 mg, 1.29 mmol, 1.00 equiv) in DCM (10 mL) was added TFA (10 mL). The reaction was stirred overnight at rt. The mixture was concentrated under vacuum. This resulted in 700 mg (crude) of the title compound as yellow oil. MS-ESI: 410 (M+1).

Intermediate 22: Methyl 3-((5-cyclohexylpiperidin-3-yl)sulfonyl)benzoate

Scheme 15

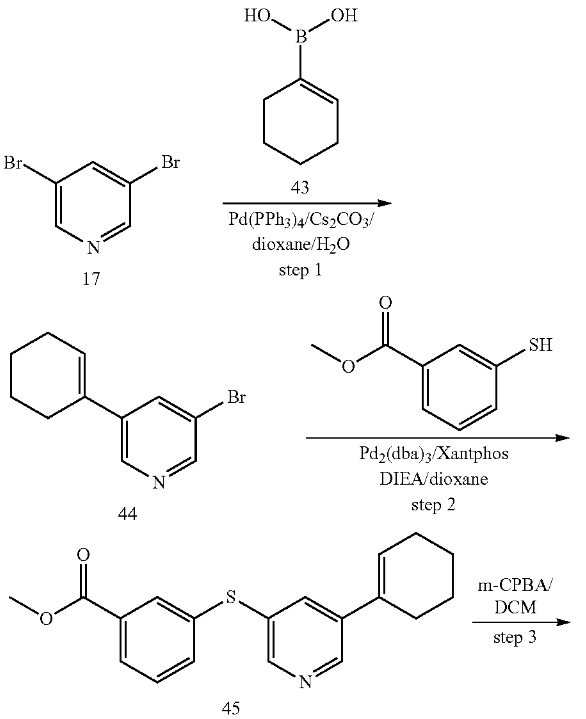

43

17

44

45

-continued

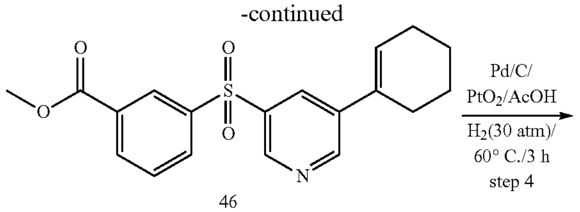

46

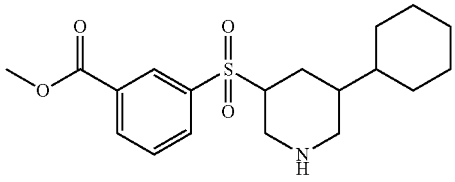

Intermediate 22

Step 1 used similar procedures for converting compound 1 to compound 2 shown in Scheme 1 to afford compound 44 from compound 43. MS-ESI: 238/240 (M+1).

Steps 2-4 used similar procedures for converting compound 38 to compound 41 shown in Scheme 14 to afford intermediate 22 from compound 44. MS-ESI: 366 (M+1).

Example 6: Synthesis of PH-AOV-0013A/B (Method A)

Scheme 16

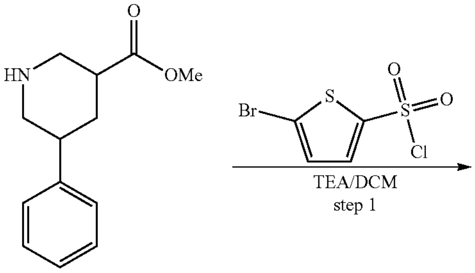

Intermediate 1

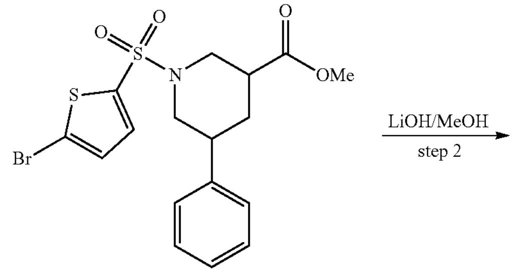

AOV-0013-1

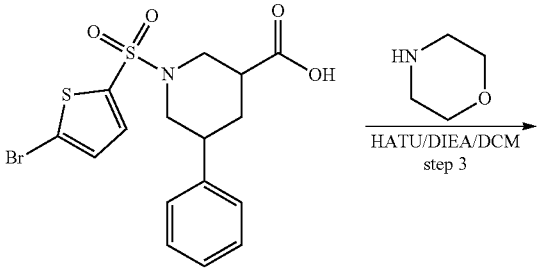

AOV-0013-2

-continued

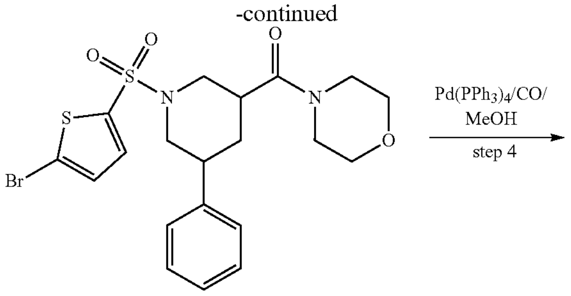

AOV-0013-3

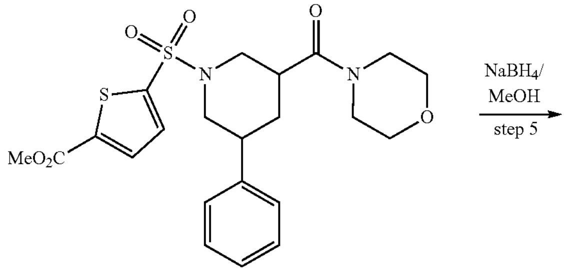

AOV-0013-4

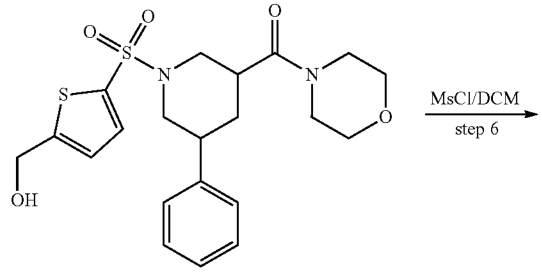

AOV-0013-5

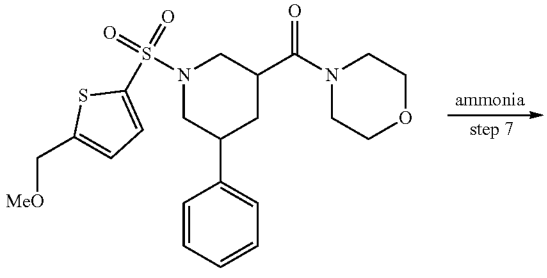

AOV-0013-6

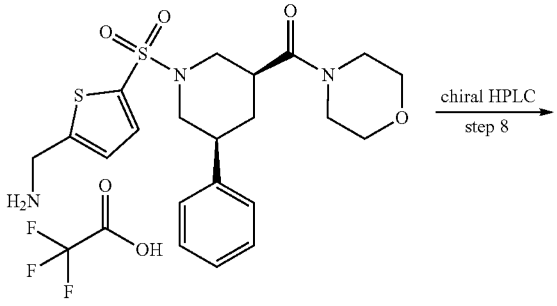

PH-AOV-0013

-continued

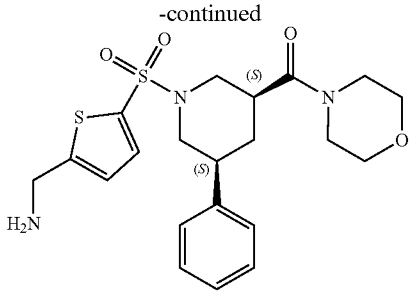

PH-AOV-0013A

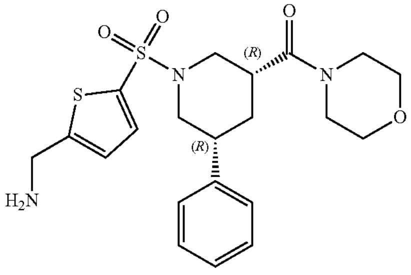

PH-AOV-0013B

Step 1: Methyl-1-((5-bromothiophen-2-yl)sulfonyl)-5-phenylpiperidine-3-carboxylate To a stirred solution of methyl-5-phenylpiperidine-3-carboxylate (5.0 g, 22.8 mmol, 1.00 equiv) in DCM (25 mL) were added 5-bromothiophene-2-sulfonyl chloride (8.94 g, 34.2 mmol, 1.50 equiv) and TEA (9.51 mL, 68.4 mmol, 3.00 equiv). The reaction solution was stirred for 2 h at rt. The reaction was quenched with $H_2O$ (30 mL) and the mixture was extracted with EtOAc (3×20 mL). The combined organic layers were dried over anhydrous $Na_2SO_4$ and concentrated under vacuum. The residue was eluted from silica gel with EtOAc/PE (1/1). This resulted in 6.0 g (59.2%) of the title compound as a white solid. MS-ESI: 444/446 (M+1).

Step 2: 1-((5-Bromothiophen-2-yl)sulfonyl)-5-phenylpiperidine-3-carboxylic acid

To a stirred solution of methyl 1-((5-bromothiophen-2-yl)sulfonyl)-5-phenylpiperidine-3-carboxylate (6.0 g, 13.5 mmol, 1.00 equiv) in MeOH (20 mL) was added LiOH (970 mg, 40.5 mmol, 3 equiv). The reaction mixture was stirred overnight at 40° C. The pH value of the solution was adjusted to 4 with HCl aq. (1 M). The mixture was diluted with $H_2O$ (50 mL) and extracted with EtOAc (3×100 mL). The combined organic layers were dried over anhydrous $Na_2SO_4$ and concentrated under vacuum. This resulted in 5.0 g (crude) of the title compound as a white solid. MS-ESI: 428 (M−1).

Step 3: (1-((5-Bromothiophen-2-yl)sulfonyl)-5-phenylpiperidin-3-yl)(morpholino)methanone To a stirred solution of 1-((5-bromothiophen-2-yl)sulfonyl)-5-phenylpiperidine-3-carboxylic acid (1.5 g, crude) in DCM (50 mL) were added morpholine (364 mg, 4.18 mmol, 1.20 equiv), HATU (1.99 g, 5.23 mmol, 1.50 equiv) and DIEA (1.82 mL, 14.1 mmol, 3.00 equiv). The reaction solution was stirred for 3 h at rt. The reaction was quenched with $H_2O$ (50 mL) and extracted with DCM (3×50 mL). The combined organic layers were dried over anhydrous $Na_2SO_4$ and concentrated under vacuum. The crude product was eluted from silica gel with EtOAc/PE (1:1). This resulted in 1.0 g, (57.4%) of the title compound as a white solid. MS-ESI: 499/501 (M+1).

Step 4: Methyl 5-((3-(morpholine-4-carbonyl)-5-phenylpiperidin-1-yl)sulfonyl)thiophene-2-carboxylate To a stirred solution of (1-((5-bromothiophen-2-yl)sulfonyl)-5-phenylpiperidin-3-yl)(morpholino)methanone (800 mg, 1.6 mmol, 1.00 equiv) in MeOH (25 mL) under nitrogen were added $Pd(PPh_3)_4$ (185 mg, 0.16 mmol, 0.10 equiv) and TEA (324 mg, 3.2 mmol, 2.0 equiv). The above mixture was evacuated and refilled three times with CO(g). The mixture was stirred overnight at 80° C. under atmosphere of CO (g) with 10 atm. The solids were filtered out. The mixture was concentrated under vacuum. The crude product was eluted from silica gel with EtOAc/PE (1:1). This resulted in 280 mg (36.5%) of the title compound as a yellow solid. MS-ESI: 479 (M+1).

Step 5: (1-((5-(Hydroxymethyl)thiophen-2-yl)sulfonyl)-5-phenylpiperidin-3-yl)(morpholino)methanone To a stirred solution of methyl 5-((3-(morpholine-4-carbonyl)-5-phenylpiperidin-1-yl)sulfonyl) thiophene-2-carboxylate (280 mg, 0.59 mmol, 1.00 equiv) in MeOH (10 mL) was added $NaBH_4$ (44 mg, 1.17 mmol, 2.00 equiv) under nitrogen. The reaction mixture was stirred overnight at rt. The reaction was quenched with $H_2O$ (10 mL). The mixture was extracted with EtOAc (3×15 mL). The combined organic layers were dried over anhydrous $Na_2SO_4$ and concentrated under vacuum. The crude product was eluted from silica gel with DCM/MeOH (10:1). This resulted in 160 mg (60.7%) of the title compound as an off-white solid. MS-ESI: 451 (M+1).

Step 6: (5-((3-(Morpholine-4-carbonyl)-5-phenylpiperidin-1-yl)sulfonyl)thiophen-2-yl)methyl methanesulfonate To a stirred solution of (1-((5-(hydroxymethyl)thiophen-2-yl)sulfonyl)-5-phenylpiperidin-3-yl)(morpholino) methanone (160 mg, 0.36 mmol, 1.00 equiv) in DCM (10 mL) were added TEA (0.11 mL, 0.72 mmol, 2.00 equiv) and methanesulfonyl chloride (48.8 mg, 0.43 mmol, 1.20 equiv) dropwise at 0° C. The reaction solution was stirred for 2 h at rt. The reaction solution was quenched with sat. $NH_4Cl$ aq. (10 mL). The mixture was extracted with DCM (3×10 mL). The combined organic layer was concentrated under vacuum. This resulted in 100 mg (crude) of the title compound as a yellow solid. MS-ESI: 529 (M+1).

Step 7: cis-(1-((5-(aminomethyl)thiophen-2-yl)sulfonyl)-5-phenylpiperidin-3-yl)(morpholino)methanone 2,2,2-trifluoroacetate A solution of (5-((3-(morpholine-4-carbonyl)-5-phenylpiperidin-1-yl)sulfonyl)thiophen-2-yl)methyl methanesulfonate (100 mg, crude) in $NH_3 \cdot H_2O$ (25% wt., 2 mL) was stirred overnight at rt. The mixture was concentrated under vacuum. The crude product was purified by Prep-HPLC with the following conditions: Sunfire prep C18 Column, 30*150, 5 um; Mobile Phase A: water (0.05% TFA), Mobile Phase B: ACN; Flow rate: 60 mL/min; Gradient:10% B to 38% B over 7 min; Detector, UV 254/210 nm; RT1:6.90 min. This resulted in 30 mg (15%, over two steps) of the title compound as a white solid. MS-ESI 450 (M+1).

$^{1}$H NMR (400 MHz, MeOH-$d_4$) δ 7.56 (d, J=3.6 Hz, 1H), 7.35-7.28 (m, 3H), 7.27-7.20 (m, 3H), 4.40 (s, 2H), 3.90-3.80 (m, 2H), 3.74-3.50 (m, 8H), 3.29-3.16 (m, 1H), 3.15-2.99 (m, 1H), 2.60 (t, J=11.4 Hz, 1H), 2.33 (t, J=11.5 Hz, 1H), 2.04 (d, J=13.0 Hz, 1H), 1.65 (q, J=12.5 Hz, 1H).

Step 8: ((3S,5S)-1-((5-(aminomethyl)thiophen-2-yl)sulfonyl)-5-phenylpiperidin-3-yl)(morpholino)methanone and ((3R,5R)-1-((5-(aminomethyl)thiophen-2-yl)sulfonyl)-5-phenylpiperidin-3-yl) (morpholino)methanone cis-(1-((5-(Aminomethyl)thiophen-2-yl)sulfonyl)-5-phenylpiperidin-3-yl)(morpholino)methanone 2,2,2-trifluoroacetate (30 mg) was separated by Chiral-Prep-HPLC with the following conditions: CHIRALPAK IE, 2*25 cm, 5 um; Mobile Phase A: Hex:DCM=3:1 (10 mMNH$_3$-MeOH), Mobile Phase B: EtOH; Flow rate: 18 mL/min; Gradient:

50% B to 50% B in 17 min; Detector, UV 254/220 nm; RT1:8.986; RT2:13.782. This resulted of ((3S,5S)-1-((5-(aminomethyl)thiophen-2-yl)sulfonyl)-5-phenylpiperidin-3-yl)(morpholino)methanone (12.5 mg) and ((3R,5R)-1-((5-(aminomethyl)thiophen-2-yl) sulfonyl)-5-phenylpiperidin-3-yl)(morpholino)methanone (13.7 mg) as a white solid. MS-ESI: 451 (M+1).

PH-AOV-0013 A: $^{1}$H-NMR (400 MHz, MeOD-$d_4$) δ 7.56 (d, J=4.0 Hz, 1H), 7.38-7.28 (m, 3H), 7.27-7.20 (m, 3H), 4.63 (s, 1H), 4.41 (s, 2H), 3.93-3.79 (m, 2H), 3.77-3.54 (m, 7H), 3.26-3.16 (m, 1H), 3.14-3.02 (m, 1H), 2.59 (t, J=11.4 Hz, 1H), 2.35 (t, J=11.5 Hz, 1H), 2.06 (d, J=13.0 Hz, 1H), 1.67 (q, J=12.5 Hz, 1H).

PH-AOV-0013 B: $^{1}$H-NMR (400 MHz, MeOD-$d_4$) δ 7.48 (d, J=3.8 Hz, 1H), 7.38-7.30 (m, 2H), 7.30-7.21 (m, 3H), 7.12 (d, J=4.0 Hz, 1H), 4.05 (s, 2H), 3.91-3.79 (m, 2H), 3.78-3.53 (m, 8H), 3.24-3.14 (m, 1H), 3.07-2.97 (m, 1H), 2.62 (t, J=11.4 Hz, 1H), 2.39 (t, J=11.6 Hz, 1H), 2.00 (d, J=13.3 Hz, 1H), 1.70 (q, J=12.6 Hz, 1H).

Example in the following table were prepared using similar conditions as described in Method A/PH-AOV-0013A/B from appropriate starting materials:

| Ex | Structure | Name | Data | Prep Info |
|---|---|---|---|---|
| AOV-0009 | 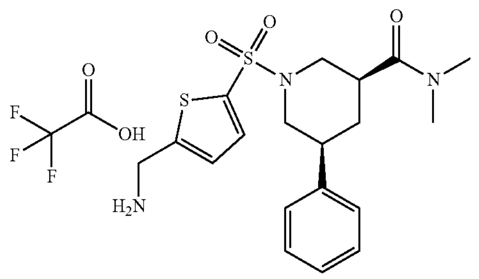 racemic | cis-1-((5-(Aminomethyl)thiophen-2-yl)sulfonyl)-N,N-dimethyl-5-phenylpiperidine-3-carboxamide 2,2,2-trifluoroacetate | MS-ESI: 408 (M + 1) | XSelect CSH Prep C18 OBD; 19*250 mm, 5 um; Water (0.05% TFA)/ ACN: Gradient: 20% ACN to 43% ACN over 7 min |
| AOV-0011 | 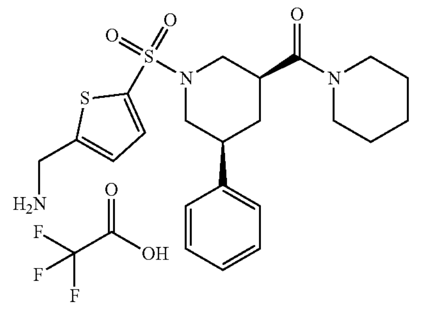 racemic | cis-(1-((5-(Aminomethyl)thiophen-2-yl)sulfonyl)-5-phenylpiperidin-3-yl)(piperidin-1-yl)methanone 2,2,2-trifluoroacetate | MS-ESI: 448 (M + 1) | Sunfire prep C18, 30*150, 5 um; Water (0.05% TFA)/ ACN, Gradient: 15% ACN to 45% ACN over 7 min |
| AOV-0015 | 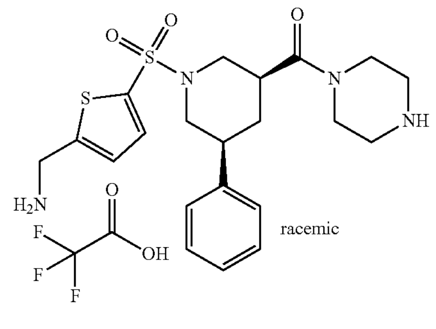 racemic | cis-(1-((5-(Aminomethyl)thiophen-2-yl)sulfonyl)-5-phenylpiperidin-3-yl)(piperazin-1-yl)methanone 2,2,2-trifluoroacetate | MS-ESI: 449 (M + 1) | Sunfire prep C18, 30*150, 5 um; Water(0.05% TFA)/ACN; Gradient: 5% ACN to 25% ACN over 7 min |

-continued

| Ex | Structure | Name | Data | Prep Info |
|---|---|---|---|---|
| AOV-0017 | 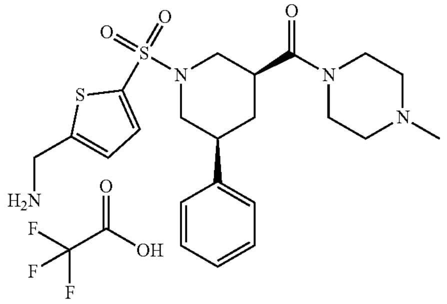 racemic | cis-(1-((5-(Aminomethyl)thiophen-2-yl)sulfonyl)-5-phenylpiperidin-3-yl)(4-methylpiperazin-1-yl)methanone 2,2,2-trifluoroacetate | MS-ESI: 463 (M + 1) | Sunfire prep C18, 30*150, 5 um; Water(0.05% TFA)/ACN; Gradient: 20% ACN to 29% ACN over 7 min |
| AOV-0075 | 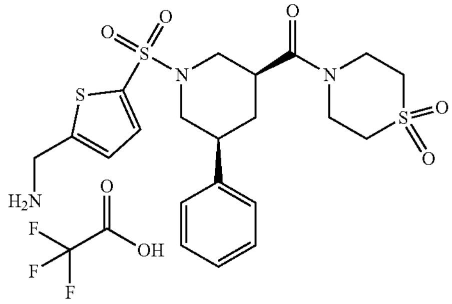 racemic | cis-(1-((5-(Aminomethyl)thiophen-2-yl)sulfonyl)-5-phenylpiperidin-3-yl)(1,1-dioxidothiomorpholino) methanone 2,2,2-trifluoroacetate | MS-ESI: 498 (M + 1) | Sunfire prep C18 column, 30*150, 5 um; Water(0.05% TFA)/ACN, Gradient: 18% ACN to 40% ACN over 7 min |
| AOV-0075 B | 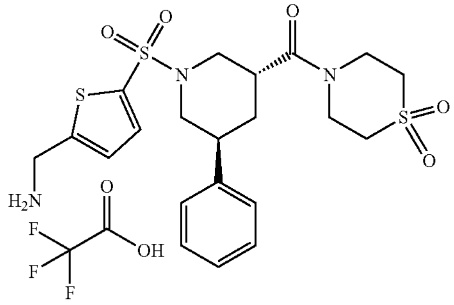 racemic | trans-(1-((5-(Aminomethyl)thiophen-2-yl)sulfonyl)-5-phenylpiperidin-3-yl)(1,1-dioxidothiomorpholino) methanone 2,2,2-trifluoroacetate | MS-ESI: 498 (M + 1) | Sunfire prep C18 column, 30*150, 5 um; Water(0.05% TFA)/ACN, Gradient: 18% ACN to 40% ACN over 7 min |
| AOV-0076 | 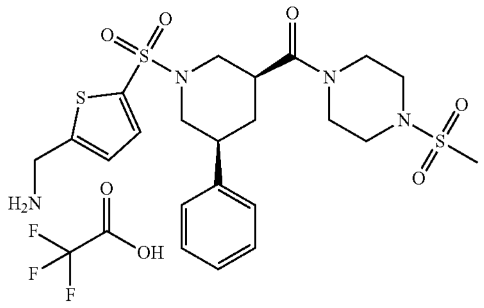 racemic | cis-(1-((5-Aminomethyl)thiophen-2-yl)sulfonyl)-5-phenylpiperidin-3-yl)(4-(methylsulfonyl)piperazin-1-yl)methanone 2,2,2-trifluoroacetate | MS-ESI: 527 (M + 1) | XSelect CSH Prep C18 OBD, 5 um, 19*150 mm; Water(0.05% TFA)/ACN; Gradient: 30% ACN to 42% ACN over 10 min |

-continued

| Ex | Structure | Name | Data | Prep Info |
|---|---|---|---|---|
| AOV-0091 | 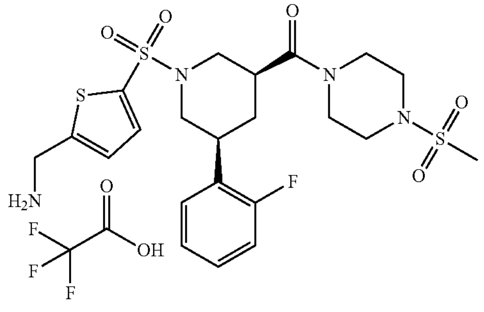 racemic | cis-(1-((5-(Aminomethyl)thiophen-2-yl)sulfonyl)-5-(2-fluorophenyl)piperidin-3-yl)(4-(methylsulfonyl)piperazin-1-yl)methanone 2,2,2-trifluoroacetate | MS-ESI: 545 (M + 1) | Xselect CSH OBD 30*150 mm 5 um; Water(0.05% TFA)/ACN; Gradient: 21% ACN to 27% ACN over 10 min |

Example 7: Synthesis of PH-AOV-0020 (Method B)

Scheme 17

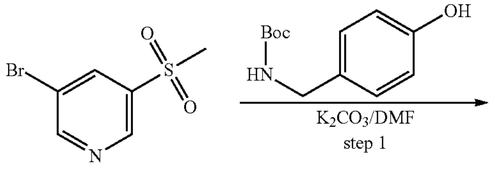

SM1

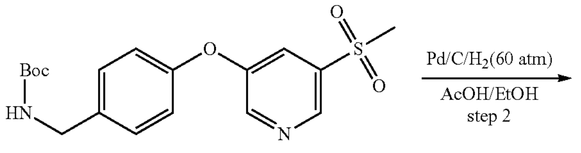

AOV-0020-1

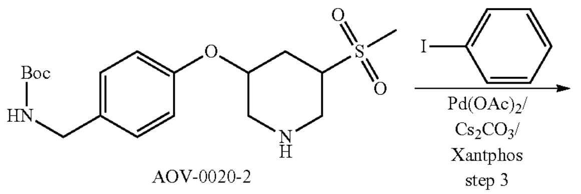

AOV-0020-2

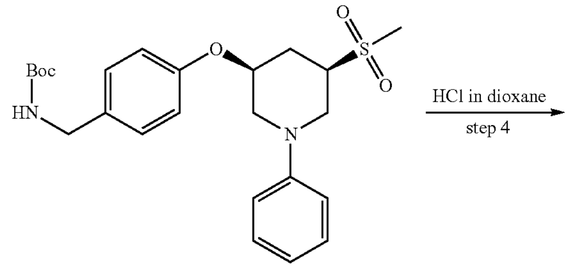

racemic
AOV-0020-3

-continued

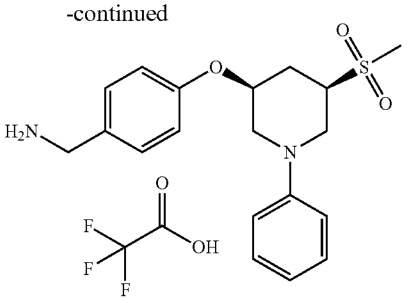

racemic
PH-AOV-0020

Step 1: tert-butyl (4-((5-(methylsulfonyl)pyridin-3-yl)oxy)benzyl)carbamate

To a stirred solution of 3-bromo-5-(methylsulfonyl)pyridine (4.0 g, 17.0 mmol, 1.00 equiv) in DMF (30 mL) were added tert-butyl (4-hydroxybenzyl)carbamate (3.8 g, 17.0 mmol, 1.00 equiv) and $K_2CO_3$ (4.68 g, 33.9 mmol, 2.00 equiv). The reaction mixture was stirred overnight at 90° C. The mixture was quenched with $H_2O$ (80 mL) and extracted with EtOAc (3×100 mL). The combined organic layers were washed with sat. NaCl aq. (3×100 mL). The organic layer was concentrated under vacuum. The residue was eluted from silica gel with EtOAc/PE (3:10). This resulted in 1.68 g (26.3%) of the title compound as a white solid. MS-ESI: 379(M+1).

Step 2: tert-butyl (4-((-5-(methylsulfonyl)piperidin-3-yl)oxy)benzyl)carbamate To a stirred solution of tert-butyl (4-((5-(methylsulfonyl)pyridin-3-yl)oxy)benzyl)carbamate (1.5 g, 3.95 mmol, 1.00 equiv) in EtOH (15 mL) and AcOH (15 mL) was added Pd/C (10% wt., 1.5 g) under nitrogen in a 100-mL pressure tank reactor. The 100-mL pressure tank reactor was evacuated and filled three times with hydrogen. The reaction mixture was stirred for 1 h at 85° C. under an atmosphere of hydrogen with 60 atm. The solids were filtered out. The filtrate was concentrated under vacuum. The residue was eluted from a silica gel with DCM/MeOH (10:1). This resulted in 280 mg (18.4%) of the title compound as a white solid. MS-ESI: 385(M+1).

Step 3: cis-tert-butyl (4-((5-(methylsulfonyl)-1-phenylpiperidin-3-yl)oxy)benzyl)carbamate To a stirred solution of tert-butyl (4-((5-(methylsulfonyl) piperidin-3-yl)oxy)benzyl)carbamate (230 mg, 0.6 mmol, 1.00 equiv) in toluene (10 mL) were added $Pd(OAc)_2$ (26.9 mg, 0.12 mmol, 0.20 equiv) and Xantphos (69.2 mg, 0.12 mmol, 0.20 equiv). To the above mixture were added $Cs_2CO_3$ (390 mg, 1.2 mmol, 2.00 equiv) and iodophenyl (122 mg, 0.6 mmol, 1.00 equiv). The mixture was stirred for 2 h at 110° C. The mixture was quenched with $H_2O$ (10 mL) and extracted with EtOAc (3×20 mL). The organic layers were combined and concentrated under vacuum. The residue was eluted from silica gel with EtOAc/PE (1:1). This resulted in 96 mg (34.8%) of the title compound as a white solid. MS-ESI: 461(M+1).

Step 4: cis-(4-((-5-(Methylsulfonyl)-1-phenylpiperidin-3-yl)oxy)phenyl)methanamine2,2,2-trifluoroacetate A solution of cis-tert-butyl (4-((5-(methylsulfonyl)-1-phenylpiperidin-3-yl)oxy)benzyl)carbamate (96 mg, 0.21 mmol, 1.00 equiv) in HCl (gas) in 1,4-dioxane (4 M, 5 mL) was stirred for 30 min at rt. The reaction was concentrated under vacuum and the crude product was purified by Prep-HPLC with the following conditions: XSelect CSH Prep C18 OBD Column, 5 um, 19*150 mm; Mobile Phase A: water (0.05% TFA), Mobile Phase B: ACN; Flow rate: 25 mL/min; Gradient: 15% B to 31% B over 7 min; Detector, UV 254/210 nm; RT1:5.93. This resulted in 42 mg (43%) of the title compound a light yellow solid. MS-ESI: 361(M+1).

$^1$H-NMR (400 MHz, MeOD-$d_4$) δ 7.40 (d, J=8.4 Hz, 2H), 7.33-7.22 (m, 2H), 7.09 (m, J=8.8 Hz, 2H), 7.01 (d, J=8.0 Hz, 2H), 6.91 (t, J=7.3 Hz, 1H), 4.68-4.58 (m, 1H), 4.12-4.07 (m, 1H), 4.06 (s, 2H), 4.00-3.94 (m, 1H), 3.62-3.52 (m, 1H), 3.06-2.98 (m, 4H), 2.84-2.76 (m, 1H), 2.75-2.68 (m, 1H), 1.81 (q, J=12.4, 1H).

Example in the following table were prepared using similar conditions as described in Method B/PH-AOV-0020 from appropriate starting materials:

Example 8: Synthesis of PH-AOV-0022 (Method C)

Scheme 18

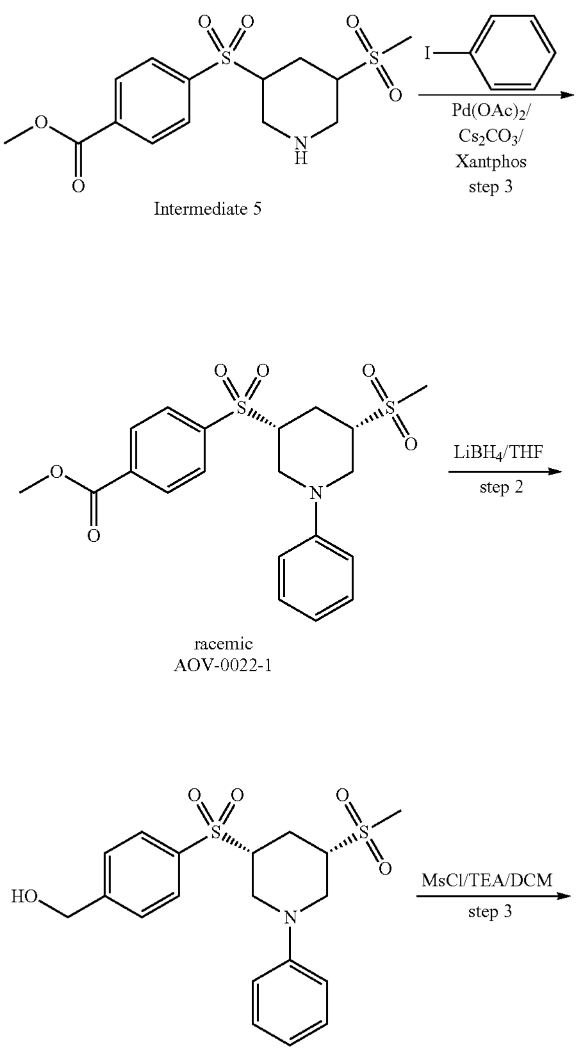

Intermediate 5 racemic
AOV-0022-1 racemic
AOV-0022-2

| Ex | Structure | Name | Data | Prep Info |
|---|---|---|---|---|
| AOV-0021 | 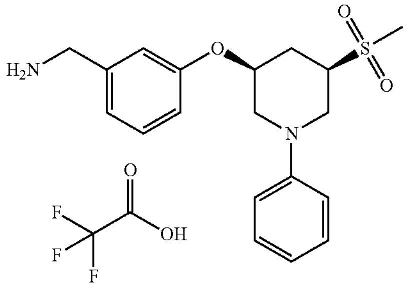 racemic | cis-(3-((-5-(Methylsulfonyl)-1-phenylpiperidin-3-yl)oxy)phenyl) methanamine 2,2,2-trifluoroacetate | MS-ESI: 361(M + 1) | XSelect CSH Prep C18 OBD Column,, 5 um, 19*150 mm, Water(0.05% TFA)/ ACN, Gradient: 15% ACN to 32% ACN over 9 min |

-continued

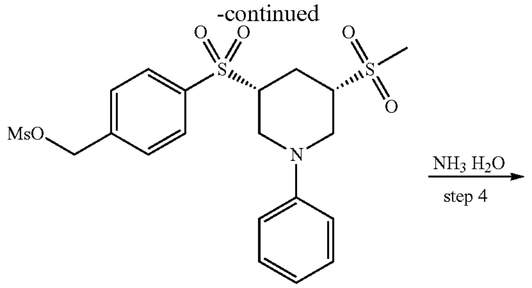

racemic
AOV-0022-3

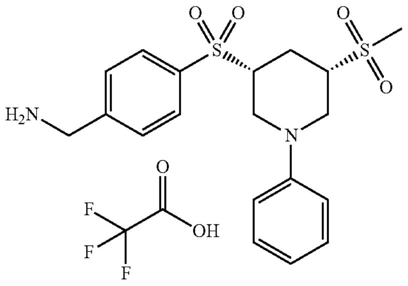

racemic
PH-AOV-0022

Step 1: cis-Methyl 4-((5-(methylsulfonyl)-1-phenylpiperidin-3-yl)sulfonyl)benzoate To a solution of methyl 4-((5-(methylsulfonyl)piperidin-3-yl)sulfonyl)benzoate (250 mg, 0.69 mmol, 1.00 equiv) in toluene (15 mL) under nitrogen were added iodobenzene (282 mg, 2.77 mmol, 2.00 equiv) and $Pd(OAc)_2$ (15.5 mg, 0.07 mmol, 0.10 equiv), followed by the addition of Xantphos (40 mg, 0.07 mmol, 0.10 equiv) and $Cs_2CO_3$ (680 mg, 2.08 mmol, 3.00 equiv). The reaction mixture was stirred for 2 h at 110° C. The reaction was quenched with $H_2O$ (20 mL). The mixture was extracted with EtOAc (3×20 mL). The combined organic layers were dried over anhydrous $Na_2SO_4$ and concentrated under vacuum. The residue was eluted from silica gel with EtOAc/PE (1:1). This resulted in 170 mg (57.8%) of the title compound as a yellow solid. MS-ESI: 438 (M+1).

Step 2: cis-(4-((5-(Methylsulfonyl)-1-phenylpiperidin-3-yl)sulfonyl)phenyl)methanol To a stirred solution of cis-methyl 4-((5-(methylsulfonyl)-1-phenylpiperidin-3-yl)sulfonyl)benzoate (170 mg, 0.4 mmol, 1.00 equiv) in THF (15 mL) under nitrogen was added $LiBH_4$ (58 mg, 2.4 mmol, 6.00 equiv). The reaction mixture was stirred for 3 h at rt. The reaction was quenched with $H_2O$ (10 mL). The mixture was concentrated under vacuum. The residue was eluted from silica gel with DCM/MeOH (15:1). This resulted in 85 mg (52%) of the title compound as a white solid. MS-ESI: 410 (M+1).

Step 3: cis-4-((5-(Methylsulfonyl)-1-phenylpiperidin-3-yl)sulfonyl)benzyl methanesulfonate To a stirred solution of cis-(4-((5-(methylsulfonyl)-1-phenylpiperidin-3-yl)sulfonyl)phenyl)methanol (85 mg, 0.21 mmol, 1.00 equiv) in DCM (10 mL) under nitrogen was added methanesulfonyl chloride (26.2 mg, 0.23 mmol, 1.1 equiv) and TEA (27.3 mg, 0.27 mmol, 1.3 equiv) at 0° C. The reaction solution was stirred for 2 h at rt. The reaction was quenched with sat. $NH_4Cl$ aq. (10 mL) and extracted with DCM (3×15 mL). The combined organic layers were dried over anhydrous $Na_2SO_4$ and concentrated under vacuum. This resulted in 109 mg (crude) of the title compound as yellow oil. MS-ESI: 488 (M+1).

Step 4: cis-(4-((5-(Methylsulfonyl)-1-phenylpiperidin-3-yl)sulfonyl)phenyl)methanamine 2,2,2-trifluoroacetate To a stirred solution of cis-4-((5-(methylsulfonyl)-1-phenylpiperidin-3-yl)sulfonyl)benzyl methanesulfonate (109 mg, crude) in THF (2 mL) was added $NH_3H_2O$ (15 mL). The reaction mixture was stirred overnight at rt. The mixture was concentrated under vacuum. The crude product was purified by Prep-HPLC with the following conditions: Column: Sunfire prep C18 column, 30*150, 5 um; Mobile Phase A: water (0.05% TFA), Mobile Phase B: ACN; Flow rate: 60 mL/min; Gradient: 10% B to 32% B over 7 min; Detector, UV 254/210 nm; RT1:7.00. This resulted in 22.5 mg (19.3%, over two steps) of the title compound as a white solid. MS-ESI: 409 (M+1).

$^1$H NMR (400 MHz, DMSO-$d_6$) δ 8.34 (br s, 2H), 8.03 (t, J=8.0 Hz, 2H), 7.81-7.73 (m, 2H), 7.30-7.24 (m, 2H), 7.00-6.82 (m, 3H), 4.21 (s, 2H), 4.11-4.01 (m, 1H), 4.00-3.88 (m, 1H), 3.77-3.60 (m, 1H), 3.49-3.44 (m, 1H), 3.10 (s, 3H), 2.91 (q, J=12.4 Hz, 2H), 2.40-2.32 (m, 1H), 1.73 (q, J=12.3 Hz, 1H). 13341 Example in the following table were prepared using similar conditions as described in Method C/PH-AOV-0022 from appropriate starting materials:

| Ex | Structure | Name | Data | Prep Info |
|---|---|---|---|---|
| AOV-0023 | 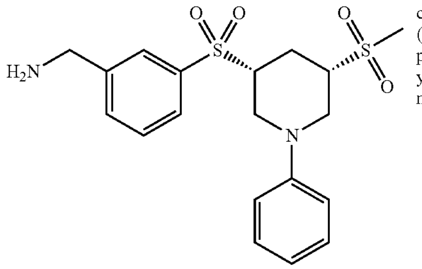 racemic | cis-(3-((-5-(Methylsulfonyl)-1-phenylpiperidin-3-yl)sulfonyl)phenyl) methanamine | MS-ESI: 409(M + 1) | Sunfire prep C18 column, 30*150, 5 um, Water(0.05% $NH_3H_2O$)/ACN, Gradient: 10% ACN to 35% ACN over 7 min |

-continued

| Ex | Structure | Name | Data | Prep Info |
|---|---|---|---|---|
| AOV-0079 | 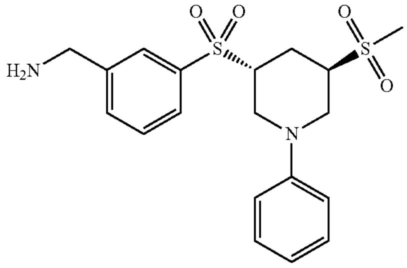 racemic | trans-(3-((-5-(Methylsulfonyl)-1-phenylpiperidin-3-yl)sulfonyl)phenyl) methanamine | MS-ESI: 409 (M + 1) | Sunfire prep C18 column, 30*150, 5 um, Water(0.05% $NH_3H_2O$)/ ACN, Gradient: 10% ACN to 35% ACN over 7 min |
| AOV-0092 | 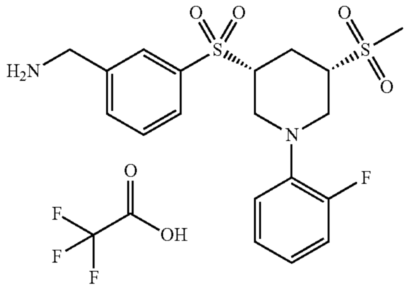 racemic | cis-(3-((-1-(2-Fluorophenyl)-5-(methylsulfonyl) piperidin-3-yl)sulfonyl)phenyl) methanamine 2,2,2-trifluoroacetate | MS-ESI: 427 (M + 1) | XSelect CSH Prep C18 OBD Column, 5 um, 19*150 mm, Water(0.05% TFA)/ ACN, Gradient: 5% ACN to 35% ACN over 10 min |

Example 9: Synthesis of PH-AOV-0024 (Method D)

Scheme 19

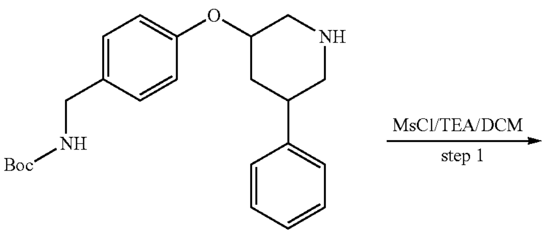

Intermediate 11

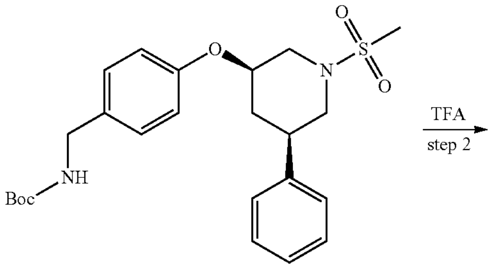

racemic
AOV-0024-1

-continued

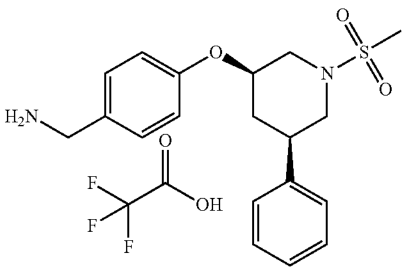

racemic
PH-AOV-0024

Step 1: cis-tert-butyl (4-((1-(methylsulfonyl)-5-phenylpiperidin-3-yl)oxy)benzyl)carbamate To a stirred solution of tert-butyl (4-((5-phenylpiperidin-3-yl)oxy)benzyl)carbamate (220 mg, 0.6 mmol, 1.00 equiv) in DCM (10 mL) were added TEA (242 mg, 2.4 mmol, 4.00 equiv) and methanesulfonyl chloride (103 mg, 0.9 mmol, 1.50 equiv). The reaction solution was stirred for 1 h at rt. The reaction was quenched with sat. $NH_4Cl$ aq. (10 mL). The mixture was extracted with DCM (2×10 mL). The combined organic layers were washed with brine (2×10 mL). The organic layer was dried over $Na_2SO_4$ and concentrated under vacuum. This resulted in 200 mg (crude) of the title compound as a brown oil solid. MS-ESI: 461 (M+1).

Step 2: cis-(4-((1-(Methylsulfonyl)-5-phenylpiperidin-3-yl)oxy)phenyl)methanamine 2,2,2-trifluoroacetate A solution of cis-tert-butyl (4-((1-(methylsulfonyl)-5-phenylpiperidin-3-yl)oxy)benzyl)carbamate (50 mg, crude) in HCl (gas) in 1,4-dioxane (4 M, 10 mL). The reaction solution was stirred for 1 h at rt. The reaction solution was concentrated under vacuum. The crude product was purified by Prep-HPLC with the following conditions: XSelect CSH Prep C18 OBD Column, 5 um, 19*150 mm; Mobile phase: water (0.05% TFA) and ACN (22% ACN up to 32% ACN over 7 min); Detector, UV 254/220 nm; RT1:6.37. This resulted in 10.4 mg (20.2%) of the title compound as an off-white solid. MS-ESI: 361 (M+1).

$^1$H NMR (400 MHz, MeOD-$d_4$): δ 7.39 (d, J=8.8 Hz, 2H), 7.36-7.30 (m, 4H), 7.29-7.22 (m, 1H), 7.08 (d, J=8.4 Hz, 2H), 4.70-4.55 (m, 1H), 4.07 (dd, J=11.4 Hz, 4.3 Hz, 1H), 4.04 (s, 2H), 3.78 (dd, J=11.8 Hz, 4.2 Hz, 1H), 3.15-3.00 (m, 1H), 2.89 (s, 3H), 2.86 (t, J=11.6 Hz, 1H), 2.76 (t, J=10.8 Hz, 1H), 2.41 (d, J=12.4 Hz, 1H), 1.83 (q, J=12.8 Hz, 1H).

Example in the following table were prepared using similar conditions as described in Method D/PH-AOV-0024 from appropriate starting materials:

| Ex | Structure | Name | Data | Prep Info |
|---|---|---|---|---|
| AOV-0025 | 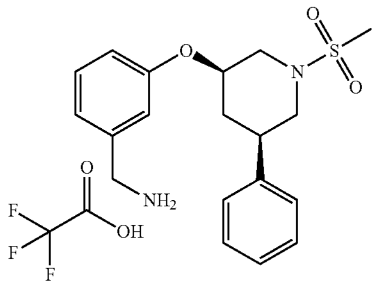 racemic | cis-(3-((-1-(Methylsulfonyl)-5-phenylpiperidin-3-yl)oxy)phenyl) methanamine 2,2,2-trifluoroacetate | MS-ESI: 361(M + 1) | Sunfire prep C18 column, 30*150, 5 um, Water (0.05% TFA)/ ACN,Gradient: 18% ACN to 38% ACN over 7 min; |
| AOV-0070 | 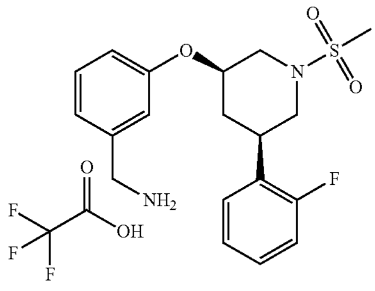 racemic | cis-(3-((5-(2-Fluorophenyl)-1-(methylsulfonyl) piperidin-3-yl)oxy)phenyl) methanamine 2,2,2-trifluoroacetate | MS-ESI: 379(M + 1) | XSelect CSH Prep C18 OBD, 5 um, 19*150 mm; Water (0.05% TFA)/ ACN,Gradient: 12% ACN to 42% ACN over 7 min; |

Example 10: Synthesis of PH-AOV-0069 (Method E)

Scheme 20

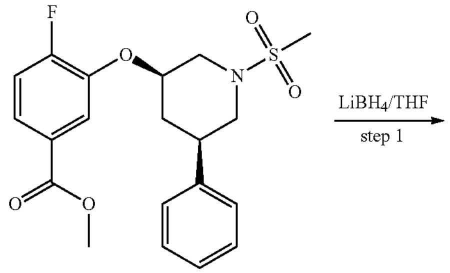

racemic
Intermediate 7

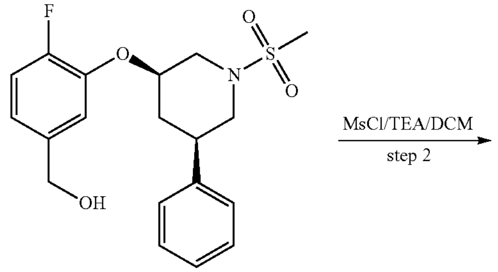

racemic
AOV-0069-1

-continued

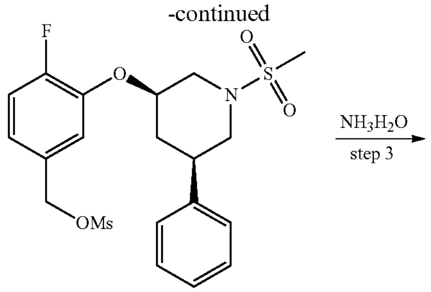

racemic
AOV-0069-2

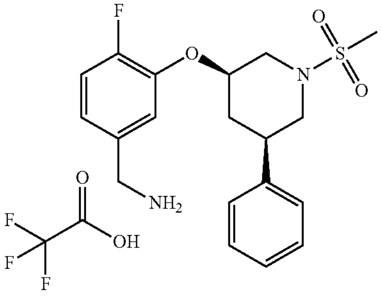

racemic
PH-AOV-0069

Steps 1-3 used similar procedures for converting compound AOV-0022-1 to PH-AOV-0022 shown in Method C to afford PH-AOV-0069 from intermediate 7. MS-ESI: 379 (M+1).

$^1$H NMR (400 MHz, MeOD-$d_4$) δ 7.40-7.33 (m, 5H), 7.33-7.20 (m, 2H), 7.13-7.08 (m, 1H), 4.65-4.55 (m, 1H), 4.18-4.10 (m, 3H), 3.85-3.77 (m, 1H), 3.12-3.02 (m, 1H), 2.93 (s, 3H), 2.92-2.83 (m, 2H), 2.49 (d, J=12.5 Hz, 1H), 2.08-1.88 (m, 1H).

Example in the following table were prepared using similar conditions as described in Method E/PH-AOV-0069 from appropriate starting materials:

| Ex | Structure | Name | Data | Prep Info |
| --- | --- | --- | --- | --- |
| AOV-0090 | 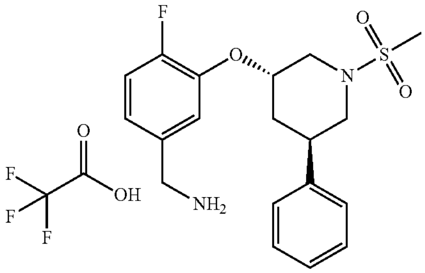 racemic | trans-(4-Fluoro-3-((1-(methylsulfonyl)-5-phenylpiperidin-3-yl)oxy)phenyl) Methanamine 2,2,2-trifluoroacetate | MS-ESI: 379(M + 1) | Sunfire prep C18 column, 30*150, 5 um; Water(0.05% TFA)/ ACN, Gradient: 17% ACN to 37% ACN over 7 min |
| AOV-0071 | 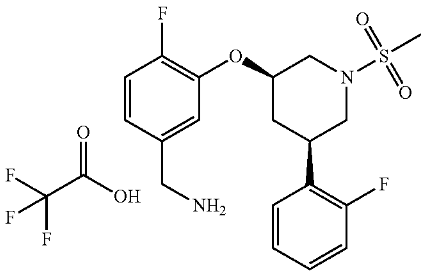 racemic | cis-(4-Fluoro-3-((-5-(2-fluorophenyl)-1-(methylsulfonyl) piperidin-3-yl)oxy)phenyl) methanamine 2,2,2-trifluoroacetate | MS-ESI: 397(M + 1) | Sunfire prep C18 column, 30*150, 5 um, Water(0.05% TFA)/ACN, Gradient: 25% ACN to 55% ACN over 7 min. |

-continued

| Ex | Structure | Name | Data | Prep Info |
|---|---|---|---|---|
| AOV-0093 | 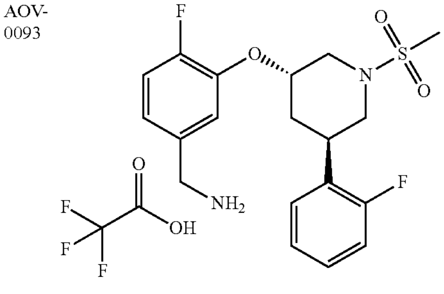 racemic | trans-(4-Fluoro-3-((-5-(2-fluorophenyl)-1-(methylsulfonyl)piperidin-3-yl)oxy)phenyl)methanamine 2,2,2-trifluoroacetate | MS-ESI: 397(M + 1) | Sunfire prep C18 column, 30*150, 5 um, Water(0.05% TFA)/ACN, Gradient: 25% ACN to 55% ACN over 7 min. |

Example 11: Synthesis of PH-AOV-0072 (Method F)

Scheme 21

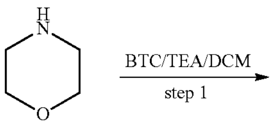

SM

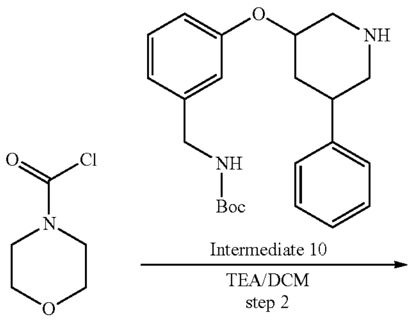

AOV-0072-1

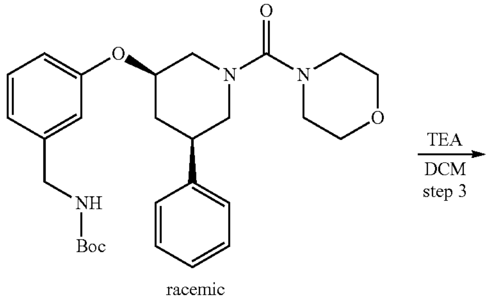

racemic
AOV-0072-2

-continued

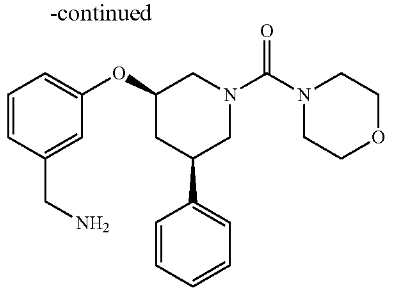

racemic
PH-AOV-0072

Step 1: Morpholine-4-carbonyl chloride

To a stirred solution of morpholine (400 mg, 4.59 mmol, 1.00 equiv) in DCM (15 mL) was added TEA (929 mg, 9.18 mmol, 2.00 equiv) and BTC (1.36 g, 4.59 mmol, 1.00 equiv) in portions at 0° C. The reaction mixture was stirred for 2 h at rt. The mixture was concentrated under vacuum. This resulted in 600 mg (crude) of morpholine-4-carbonyl chloride as a white solid.

Step 2: cis-tert-butyl (3-((-1-(morpholine-4-carbonyl)-5-phenylpiperidin-3-yl)oxy)benzyl)carbamate To a stirred solution of tert-butyl (3-((5-phenylpiperidin-3-yl)oxy)benzyl)carbamate (200 mg, 0.5 mmol, 1.00 equiv) in DCM (20 mL) were added morpholine-4-carbonyl chloride (151 mg, crude) and TEA (102 mg, 1.01 mmol, 2.00 equiv). The reaction mixture was stirred for 2 h at rt. The reaction was quenched with $H_2O$ (20 mL). The mixture was extracted with DCM (3×10 mL). The combined organic layers were dried over anhydrous $Na_2SO_4$ and concentrated under vacuum. The residue was eluted from silica gel with EtOAc/PE (1:1). This resulted in 170 mg (68%) of the title compound as a white solid. MS-ESI: 496 (M+1).

Step 3: cis-((3-(3-(Aminomethyl)phenoxy)-5-phenylpiperidin-1-yl)(morpholino)methanone To a solution of cis-tert-butyl (3-((1-(morpholine-4-carbonyl)-5-phenylpiperidin-3-yl)oxy)benzyl)carbamate (160 mg, 0.32 mmol, 1.00 equiv) in DCM (10 mL) was added TFA (2 mL). The reaction solution was stirred for 5 h at rt. The reaction mixture was concentrated under vacuum. The crude product was purified by Prep-HPLC with the following conditions: Column, YMC-Actus Triart C18, 30*250.5 um; mobile phase, water (10 mM $NH_4HCO_3$+0.1% $NH_3 \cdot H_2O$) and ACN (28% ACN up to 58% ACN over 7 min); Detector, UV 220/254 nm; RT1:6.53. This resulted in 24.5 mg (19%) of the title compound as a white solid. MS-ESI: 396 (M+1).

$^1H$ NMR (400 MHz, DMSO-$d_6$) δ 7.38-7.31 (m, 4H), 7.29-7.21 (m, 3H), 7.02 (s, 1H), 6.96-6.82 (m, 3H), 4.54-4.45 (m, 1H), 4.11 (d, J=6.0 Hz, 1H), 3.98-3.93 (m, 1H), 3.68 (s, 2H), 3.56 (t, J=4.8 Hz, 4H), 3.25-3.13 (m, 4H), 2.99-2.86 (m, 2H), 2.77 (t, J=10.4 Hz, 1H), 2.32 (d, J=13.2 Hz, 1H), 1.82 (q, J=11.6 Hz, 1H).

Examples in the following table were prepared using similar conditions as described in Method F/PH-AOV-0072 from appropriate starting materials:

| Ex | Structure | Name | Data | Prep Info |
|---|---|---|---|---|
| AOV-0073 | 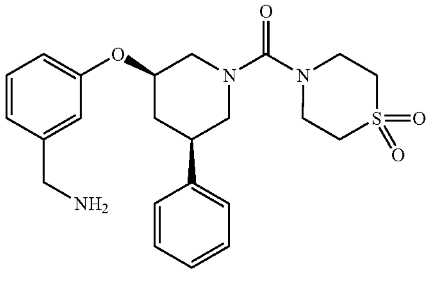 racemic | cis-(3-(3-(Aminomethyl) phenoxy)-5-phenylpiperidin-1-yl)(1,1-dioxidothiomorpholino) methanone | MS-ESI: 444(M + 1) | YMC-Actus Triart C18, 30*250, 5 um; Water(10 Mm $NH_4HCO_3$ + 0.1% $NH_3$•$H_2O$)/ACN, Gradient: 30% ACN to 46% ACN over 13 min |
| AOV-0082 | 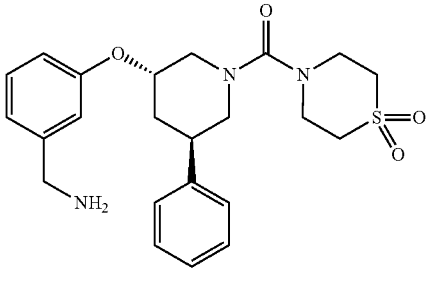 racemic | trans-(3-(3-(Aminomethyl) phenoxy)-5-phenylpiperidin-1-yl)(1,1-dioxidothiomorpholino) methanone | MS-ESI: 444(M + 1) | YMC-Actus Triart C18, 30*250, 5 um; Water(10 Mm $NH_4HCO_3$ + 0.1% $NH_3$•$H_2O$)/ACN, Gradient: 30% ACN to 46% ACN over 13 min |

Example 12: Synthesis of PH-AOV-0026 (Method G)

Scheme 22

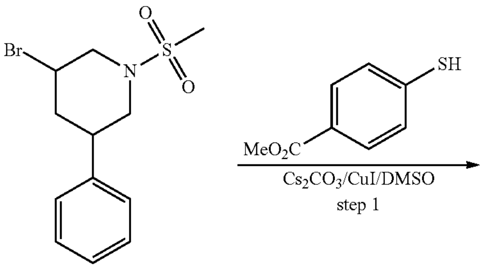

Intermediate 12

-continued

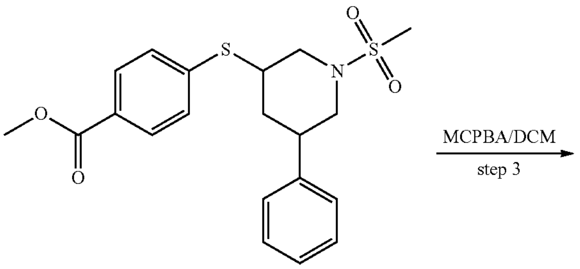

AOV-0026-2

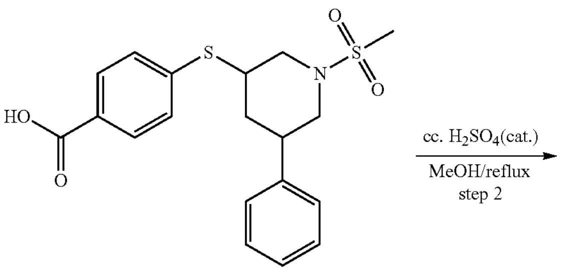

AOV-0026-1

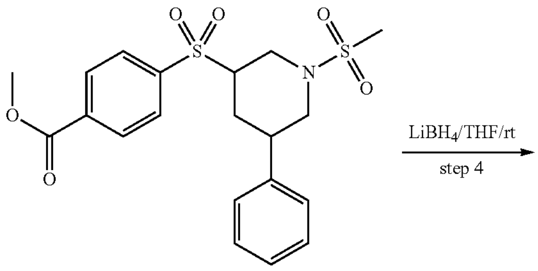

AOV-0026-3

-continued

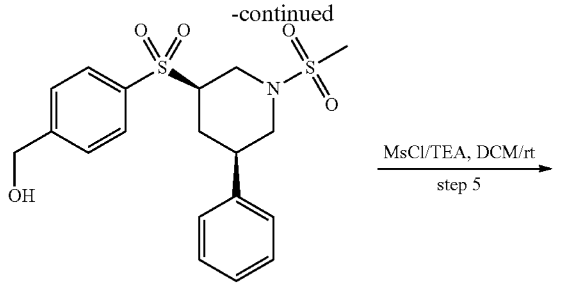

racemic
AOV-0026-4

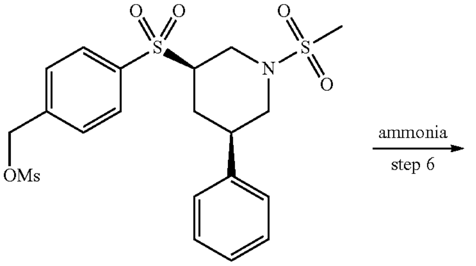

racemic
AOV-0026-5

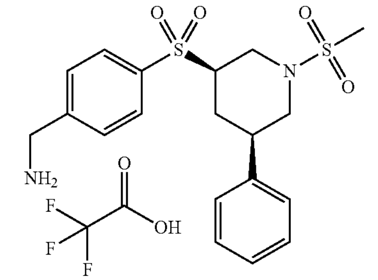

racemic
PH-AOV-0026

Step 1: 4-((1-(Methylsulfonyl)-5-phenylpiperidin-3-yl)thio)benzoic acid

To a solution of 3-bromo-1-(methylsulfonyl)-5-phenylpiperidine (2.5 g, 7.86 mmol, 1.00 equiv) in DMSO (30 mL) under nitrogen were added methyl 4-mercaptobenzoate (1.59 g, 9.43 mmol, 1.20 equiv), 2,2,6,6-tetramethylheptane-3,5-dione (434 mg, 2.36 mmol, 0.30 equiv), $Cs_2CO_3$ (7.68 g, 23.6 mmol, 3.00 equiv) and CuI (299 mg, 1.57 mmol, 0.20 equiv). The reaction mixture was stirred for 5 h at 130° C. The reaction was quenched with $H_2O$ (50 mL). The mixture was extracted with EtOAc (3x50 mL). The combined organic layers were dried over anhydrous $Na_2SO_4$ and concentrated under vacuum. This resulted in 3.0 g (crude) of the title compound as dark brown oil. MS-ESI: 392 (M+1).

Step 2: Methyl 4-((1-(methylsulfonyl)-5-phenylpiperidin-3-yl)thio)benzoate

To a stirred solution of 4-((1-(methylsulfonyl)-5-phenylpiperidin-3-yl)thio)benzoic acid (3.0 g, crude) in MeOH (40 mL) was added $H_2SO_4$ (98% wt., 1 mL). The reaction solution was stirred for 5 h at 80° C. The reaction was quenched with $H_2O$ (40 mL). The mixture was extracted with EtOAc (3x30 mL). The combined organic layers were dried over anhydrous $Na_2SO_4$ and concentrated under vacuum. The residue was eluted from silica gel with EtOAc/PE (1:1). This resulted in 2.6 g (81.5%, over two steps) of the title compound as yellow oil. MS-ESI: 406 (M+1).

Step 3: Methyl 4-((1-(methylsulfonyl)-5-phenylpiperidin-3-yl)sulfonyl)benzoate

To a stirred solution of methyl 4-((1-(methylsulfonyl)-5-phenylpiperidin-3-yl)thio)benzoate (2.6 g, 6.41 mmol, 1.00 equiv) in DCM (4.3 mL) was added m-CPBA (3.32 g, 19.2 mmol, 3.00 equiv) in portions at 0° C. The reaction mixture was stirred for 2 h at 0° C. The reaction was quenched with sat. $Na_2S_2O_3$ aq. (10 mL). The mixture was extracted with DCM (3x20 mL). The combined organic layers were dried over anhydrous $Na_2SO_4$ and concentrated under vacuum. The residue was eluted from silica gel with EtOAc/PE (1:1). This resulted in 2.2 g (78.4%) of the title compound as a yellow solid. MS-ESI: 438 (M+1).

Steps 4-6 used similar procedures for converting compound AOV-0022-1 to PH-AOV-0022 shown in Method C to afford PH-AOV-0026 from compound AOV-0026-3. MS-ESI: 409 (M+1)

$^1H$ NMR (400 MHz, DMSO-$d_6$) δ 8.34 (br s, 2H), 8.00 (d, J=8.0 Hz, 2H), 7.74 (d, J=8.0 Hz, 2H), 7.39-7.30 (m, 4H), 7.29-7.23 (m, 1H), 4.21 (s, 2H), 4.16-4.06 (m, 1H), 3.98-3.67 (m, 3H), 3.36-3.26 (m, 1H), 3.25-3.11 (m, 1H), 3.01 (s, 3H), 2.67-2.56 (m, 1H), 2.15-2.05 (m, 1H).

Example 13: Synthesis of PH-AOV-0027 (Method H)

Scheme 23

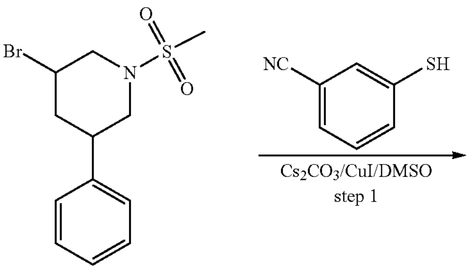

Intermediate 12

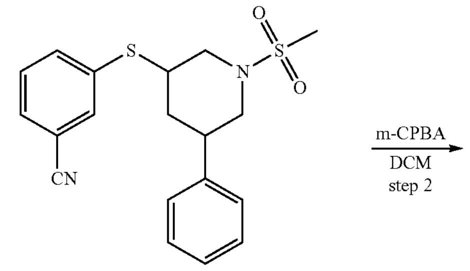

AOV-0027-1

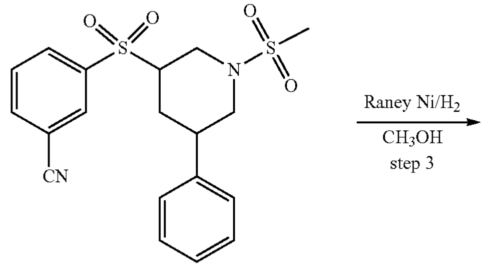

AOV-0027-2

-continued

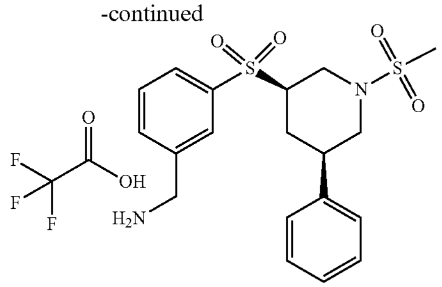

racemic
PH-AOV-0027

Step 1: 3-((1-(Methylsulfonyl)-5-phenylpiperidin-3-yl)thio)benzonitrile

To a stirred solution of 3-bromo-1-(methylsulfonyl)-5-phenylpiperidine (1.5 g, 4.71 mmol, 1.00 equiv) in DMSO (20 mL) under nitrogen were added 3-mercaptobenzonitrile (765 mg, 5.66 mmol, 1.20 equiv), 2,2,6,6-tetramethylheptane-3,5-dione (261 mg, 1.41 mmol, 0.30 equiv), CuI (180 mg, 0.94 mmol, 0.20 equiv) and $Cs_2CO_3$ (4.61 g, 14.1 mmol, 3.00 equiv). The reaction mixture was stirred for 5 h at 130° C. The reaction was quenched with $H_2O$ (20 mL). The mixture was extracted with EtOAc (3x20 mL). The combined organic layers were dried over anhydrous $Na_2SO_4$ and concentrated under vacuum. The residue was eluted from silica gel with EtOAc/PE (1:1). This resulted in 800 mg (45.6%) of the title compound as a yellow solid. MS-ESI: 373 (M+1).

Step 2: 3-((1-(Methylsulfonyl)-5-phenylpiperidin-3-yl)sulfonyl)benzonitrile

To a stirred solution of 3-((1-(methylsulfonyl)-5-phenylpiperidin-3-yl)thio)benzonitrile (300 mg, 0.81 mmol, 1.00 equiv) in DCM (0.54 mL) was added m-CPBA (417 mg, 2.42 mmol, 3.00 equiv) in portions at 0° C. The reaction mixture was stirred for 2 h at rt. The reaction was quenched with sat. $Na_2S_2O_3$ aq. (10 mL). The mixture was extracted with DCM (3x10 mL). The combined organic layers were dried over anhydrous $Na_2SO_4$ and concentrated under vacuum. The residue was eluted from silica gel with EtOAc/PE (1:1). This resulted in 200 mg (61.4%) of the title compound as a yellow solid. MS-ESI: 405 (M+1).

Step 3: cis-(3-((1-(Methylsulfonyl)-5-phenylpiperidin-3-yl)sulfonyl)phenyl)methanamine 2,2,2-trifluoroacetate To a stirred solution of 3-((1-(methylsulfonyl)-5-phenylpiperidin-3-yl)sulfonyl)benzonitrile (200 mg, 0.49 mmol, 1.00 equiv) in MeOH (10 mL) under nitrogen was added Raney Ni (30 mg, 0.35 mmol, 0.71 equiv). The mixture was evacuated and refilled three times with hydrogen. The mixture was stirred for 16 h at rt. The solids were filtered out. The filtrate was concentrated under vacuum. The crude product was purified by Prep-HPLC with the following conditions: Column: Sunfire prep C18, 30*150, 5 um; Mobile Phase A: water (0.05% TFA), Mobile Phase B: ACN; Flow rate: 60 mL/min; Gradient: 16% B to 28% B over 10 min; Detector, UV 254/210 nm; RT1:9.62. This resulted in 36.8 mg (14.2%) of the title compound a white solid. MS-ESI: 409 (M+1).

$^1H$ NMR (400 MHz, DMSO-$d_6$) δ 8.24 (br s, 2H), 8.09 (t, J=1.8 Hz, 1H), 7.96 (dt, J=8.0 Hz, 1.4 Hz, 1H), 7.84 (dt, J=8.0 Hz, 1.4 Hz, 1H), 7.75 (t, J=7.7 Hz, 1H), 7.38-7.30 (m, 4H), 7.29-7.24 (m, 1H), 4.24-4.16 (m, 2H), 4.15-4.08 (m, 1H), 3.91-3.82 (m, 1H), 3.86-3.79 (m, 1H), 3.75 (dd, J=13.7 Hz, 3.0 Hz, 1H), 3.73-3.26 (m, 1H), 3.21 (t, J=11.2 Hz, 1H), 3.02 (s, 3H), 2.69-2.62 (m, 1H), 2.16-2.06 (m, 1H)

Example 14: Synthesis of PH-AOV-0074 (Method I)

Scheme 24

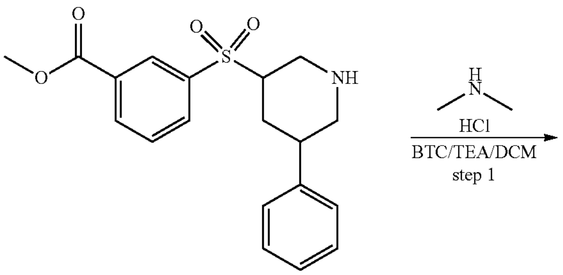

Intermediate 6

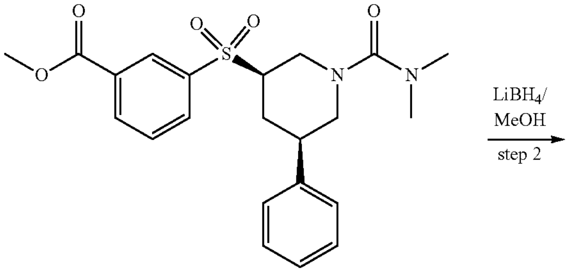

racemic
AOV-0074-1

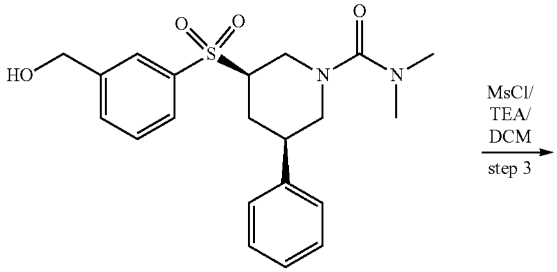

racemic
AOV-0074-2

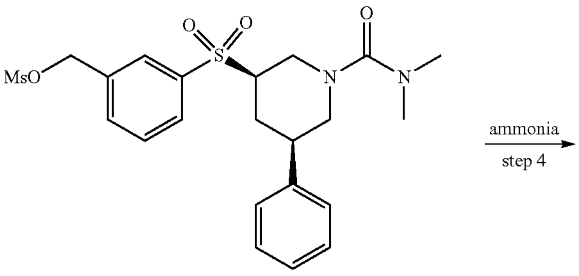

racemic
AOV-0074-3

-continued

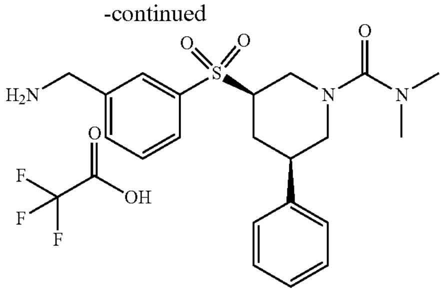

racemic
PH-AOV-0074

Step 1: cis-Methyl 3-((1-(dimethylcarbamoyl)-5-phenylpiperidin-3-yl)sulfonyl)benzoate To a stirred solution of BTC (225 mg, 0.76 mmol, 1.50 equiv) in DCM (15 mL) were added dimethylamine (33.9 mg, 0.75 mmol, 1.00 equiv) and TEA (152 mg, 1.5 mmol, 3.0 equiv) at 0° C. The reaction mixture was stirred for 3 h at 0° C. The reaction mixture was added methyl 3-((5-phenylpiperidin-3-yl)sulfonyl)benzoate (180 mg, 0.5 mmol, 1.00 equiv) in DCM (5 mL) dropwise. The reaction mixture was stirred for 2 h at rt. The reaction was quenched with $H_2O$ (10 mL). The mixture was extracted with DCM (3×20 mL). The combined organic layers were dried over anhydrous $Na_2SO_4$ and concentrated under vacuum. The residue was eluted from silica gel with EtOAc/PE (1:1). This resulted in 160 mg (74.2%) of the title compound as a white solid. MS-ESI: 431 (M+1).

Steps 2-4 used similar procedures for converting compound AOV-0022-1 to PH-AOV-0022 shown in Method C to afford PH-AOV-0074 from compound AOV-0074-1. MS-ESI: 402 (M+1).

$^1$H NMR (400 MHz, MeOD-$d_4$) δ 8.09 (t, J=1.8 Hz, 1H), 8.03 (dt, J=7.8, 1.5 Hz, 1H), 7.86 (dt, J=8.0, 1.4 Hz, 1H), 7.78 (t, J=7.7 Hz, 1H), 7.39-7.30 (m, 2H), 7.29-7.23 (m, 3H), 4.29 (s, 2H), 3.91-3.90 (m, 1H), 3.69-3.57 (m, 2H), 3.06-2.92 (m, 2H), 2.83 (s, 6H), 2.82-2.75 (m, 1H), 2.32-2.23 (m, 1H), 1.98 (q, J=12.4 Hz, 1H).

Examples in the following table were prepared using similar conditions as described in Method I/PH-AOV-0074 from appropriate starting materials.

| Ex | Structure | Name | Data | Prep Info |
|---|---|---|---|---|
| AOV-0094 | 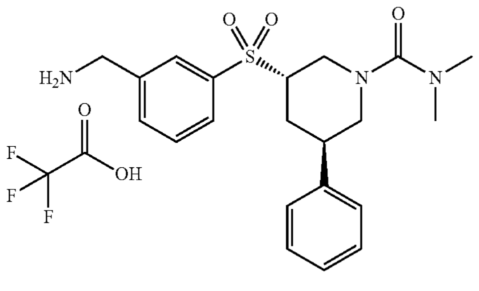 racemic | trans-3-((3-(Aminomethyl) phenyl)sulfonyl)-N,N-dimethyl-5-phenylpiperidine-1-carboxamide 2,2,2-trifluoroacetate | MS-ESI: 402 (M + 1) | XSelect CSH Prep C18 OBD Column,, 5 um, 19*150 mm, Water(0.05% TFA)/ ACN, Gradient: 18% ACN to 38% ACN over 7 min |

Example 15: Synthesis of PH-AOV-0077 (Method J)

Scheme 25

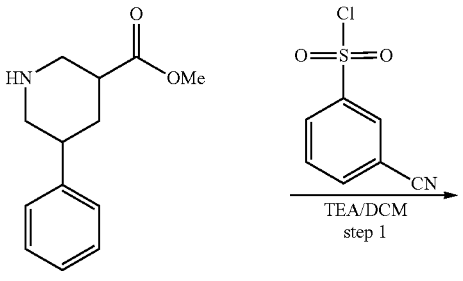

Intermediate 1

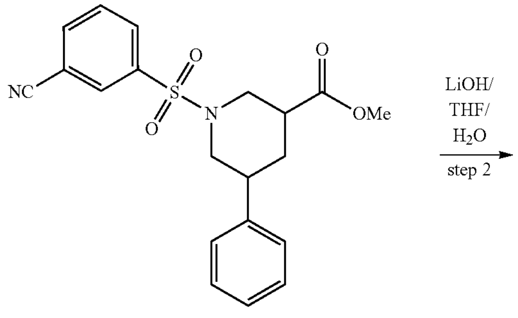

AOV-0077-1

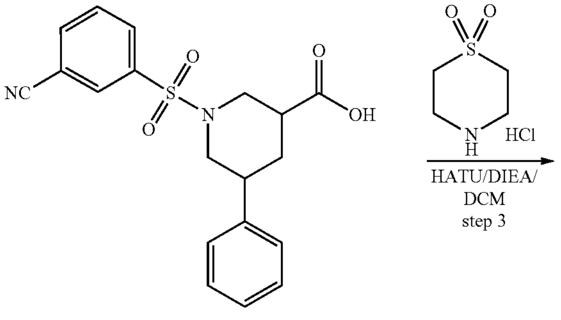

AOV-0077-2

-continued

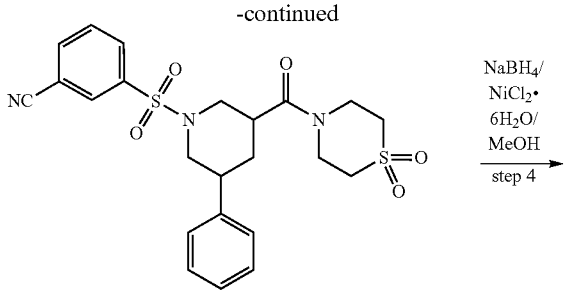

AOV-0077-3

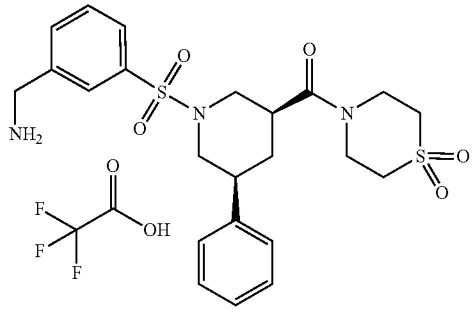

racemic
PH-AOV-0077

Step 1: Methyl 1-((3-cyanophenyl)sulfonyl)-5-phenylpiperidine-3-carboxylate

To a stirred solution of methyl 5-phenylpiperidine-3-carboxylate (4.0 g, 18.2 mmol, 1.00 equiv) in DCM (50 mL) were added 3-cyanobenzenesulfonyl chloride (5.52 g, 27.4 mmol, 1.50 equiv) and TEA (9.23 g, 91.2 mmol, 5.00 equiv) in portions. The reaction solution was stirred for 2 h at rt. The reaction solution was quenched with $H_2O$ (50 mL) and extracted with DCM (3x100 mL). The combined organic layers were washed with sat. NaCl aq. (3x200 mL). The organic layer was concentrated under vacuum. The residue was eluted from silica gel with EtOAc/PE (1:1). This resulted in 3.4 g (48.5%) of the title compound as a white solid. MS-ESI: 385 (M+1).

Step 2: 1-((3-Cyanophenyl)sulfonyl)-5-phenylpiperidine-3-carboxylic acid

To a stirred solution of methyl 1-((3-cyanophenyl)sulfonyl)-5-phenylpiperidine-3-carboxylate (1.0 g, 2.6 mmol, 1.00 equiv) in THF (20 mL) and $H_2O$ (20 mL) was LiOH (187 mg, 7.8 mmol, 3.0 equiv). The reaction mixture was stirred overnight at rt. The pH value of the solution was adjusted to 3 with HCl (2 M). The mixture was extracted with EtOAc (3x50 mL). The combined organic layers were washed with sat. NaCl aq. (3x50 mL). The organic layer was concentrated under vacuum. The residue was eluted from silica gel with DCM/MeOH (10:1). This resulted in 800 mg (83%) of the title compound as a white solid. MS-ESI: 371 (M+1).

Step 3: 3-((3-(1,1-Dioxidothiomorpholine-4-carbonyl)-5-phenylpiperidin-1-yl)sulfonyl)benzonitrile To a stirred solution of 1-((3-cyanophenyl)sulfonyl)-5-phenylpiperidine-3-carboxylic acid (450 mg, 1.22 mmol, 1.00 equiv) in DCM (20 mL) were added thiomorpholine 1,1-dioxide hydrochloride (313 mg, 1.82 mmol, 1.50 equiv), HATU (693 mg, 1.82 mmol, 1.50 equiv) and DIEA (785 mg, 6.07 mmol, 5.00 equiv). The reaction mixture was stirred for 2 h at rt. The reaction mixture was quenched with $H_2O$ (20 mL) and extracted with DCM (3x80 mL). The combined organic layers were concentrated under vacuum. The residue was eluted from silica gel with DCM/MeOH (10:1). This resulted 340 mg (57.4%) of the title compound as a white solid. MS-ESI: 488 (M+1).

Step 4: cis-1-((3-(Aminomethyl)phenyl)sulfonyl)-5-phenylpiperidin-3-yl)(1,1-dioxidothiomorpholino) methanone 2,2,2-trifluoroacetate To a stirred solution of 3-((3-(1,1-dioxidothiomorpholine-4-carbonyl)-5-phenylpiperidin-1-yl)sulfonyl) benzonitrile (300 mg, 0.61 mmol, 1.00 equiv) in MeOH (10 mL) under nitrogen was added $NaBH_4$ (117 mg, 3.07 mmol, 5.00 equiv) and $NiCl_2 \cdot 6H_2O$ (290 mg, 1.22 mmol, 2.00 equiv) at 0° C. The reaction mixture was stirred for 2 h at rt. The reaction was quenched with $H_2O$ (5 mL). The mixture was concentrated under vacuum. The residue was eluted from silica gel with DCM/MeOH (10:1). The crude product was purified by Prep-HPLC with the following conditions: Column, Sunfire prep C18 column, 30*150, 5 um; Mobile phase, water (0.05% TFA) and ACN (15% ACN up to 29% ACN over 10 min); Detector, UV 220/254 nm. This resulted in 12.8 mg (2.3%) of the title compound as a white solid. MS-ESI: 493 (M+1).

$^1H$ NMR (400 MHz, MeOD-$d_4$) δ 7.94-7.85 (5, 2H), 7.82-7.70 (m, 2H), 7.37-7.29 (m, 2H), 7.28-7.20 (m, 3H), 4.26 (s, 2H), 4.25-4.11 (m, 2H), 4.10-3.36 (m, 4H), 3.30-3.23 (m, 1H), 3.22-3.03 (m, 5H), 2.56 (t, J=11.4 Hz, 1H), 2.30 (t, J=11.6 Hz, 1H), 2.14-2.01 (m, 1H), 1.68 (q, J=12.6 Hz, 1H).

Examples in the following table were prepared using similar conditions as described in PH-AOV-0077 from appropriate starting materials.

| Ex | Structure | Name | Data | Prep Info |
|---|---|---|---|---|
| AOV-0078 | 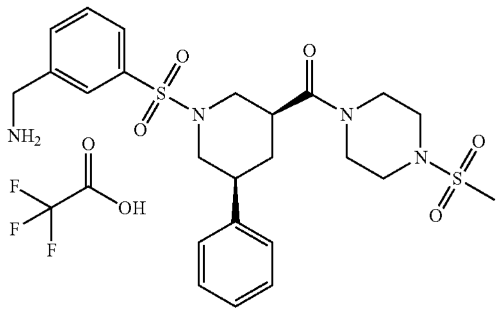 racemic | cis-(1-((3-(Aminomethyl)phenyl) sulfonyl)-5-phenylpiperidin-3-yl)(4-(methylsulfonyl) piperazin-1-yl)methanone 2,2,2-trifluoroacetate | MS-ESI: 521(M + 1) | Sunfire prep C18 column, 30*150, 5 um, Water(0.05% TFA)/ ACN, Gradient: 15% ACN to 29% ACN over 10 min |

-continued

| Ex | Structure | Name | Data | Prep Info |
|---|---|---|---|---|
| AOV-0084 | 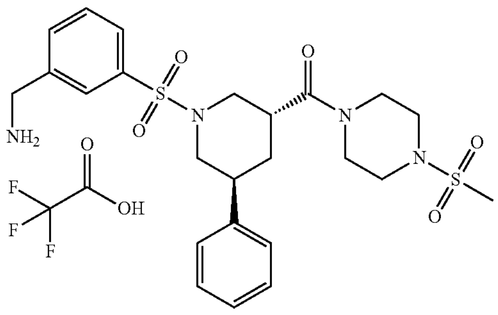 racemic | trans-(1-((3-(Aminomethyl)phenyl) sulfonyl)-5-phenylpiperidin-3-yl)(4-(methylsulfonyl) piperazin-1-yl)methanone 2,2,2-trifluoroacetate | MS-ESI: 521(M + 1) | Sunfire prep C18 column, 30*150, 5 um, Water (0.05% TFA)/ ACN, Gradient: 15% ACN to 29% ACN over 10 min |
| AOV-0085 | 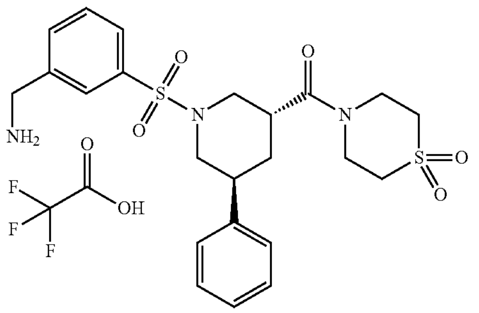 racemic | trans-(1-((3-(Aminomethyl)phenyl) sulfonyl)-5-phenylpiperidin-3-yl)(1,1-dioxidothiomorpholino) methanone 2,2,2-trifluoroacetate | MS-ESI: 492(M + 1) | XSelect CSH Prep C18 OBD Column,, 5 um, 19*150 mm, Water(0.05% TFA)/ ACN, Gradient: 23% ACN to 35% ACN over 10 min |
| AOV-0098 | 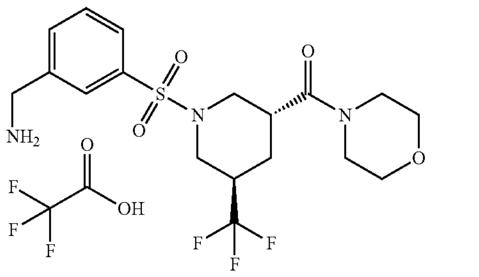 racemic | cis-(1-((3-(Aminomethyl)phenyl) sulfonyl)-5-(trifluoromethyl) piperidin-3-yl)(morpholino) methanone 2,2,2-trifluoroacetate | MS-ESI: 436(M + 1) | XSelect CSH Prep C18 OBD Column,, 5 um, 19*150 mm, Water(0.05% TFA)/ ACN; Gradient: 37% ACN to 51% ACN over 10 min |
| AOV-0099 | 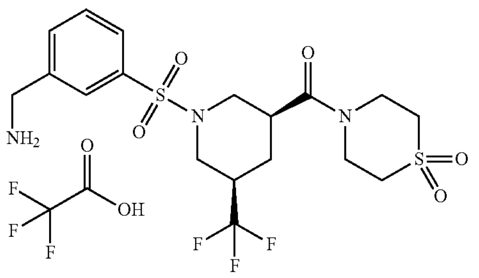 racemic | cis-(1-((3-(Aminomethyl)phenyl) sulfonyl)-5-(trifluoromethyl) piperidin-3-yl)(1,1-dioxidothiomorpholino) methanone 2,2,2-trifluoroacetate | MS-ESI: 484(M + 1) | XSelect CSH Prep C18 OBD Column,, 5 um, 19*150 mm, Water(0.05% TFA)/ ACN; Gradient: 30% ACN to 45% ACN over 10 min |

-continued
| Ex | Structure | Name | Data | Prep Info |
|---|---|---|---|---|
| AOV-0110 | 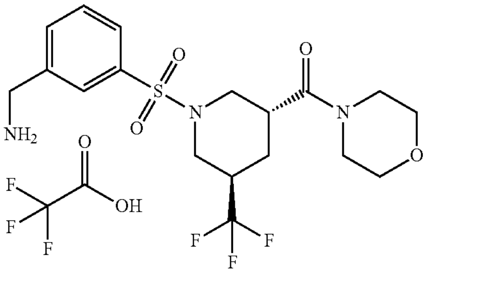 racemic | (trans-(1-((3-(Aminomethyl)phenyl) sulfonyl)-5-(trifluoromethyl) piperidin-3-yl)(morpholino) methanone 2,2,2-trifluoroacetate | MS-ESI: 436(M + 1) | XSelect CSH Prep C18 OBD Column,, 5 um, 19*150 mm, Water(0.05% TFA)/ ACN; Gradient: 37% ACN to 51% ACN over 10 min |
Example 16: Synthesis of PH-AOV-0106 (Method K)
Scheme 26
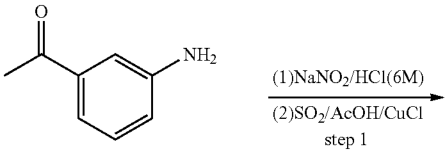
SM
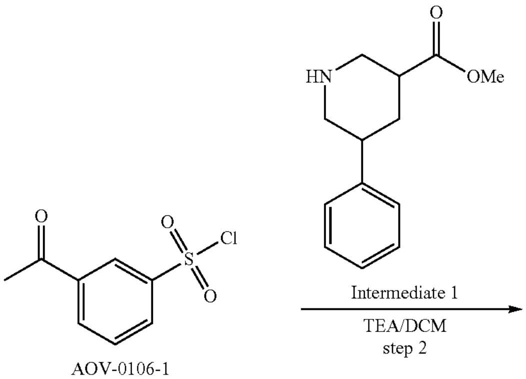
AOV-0106-1
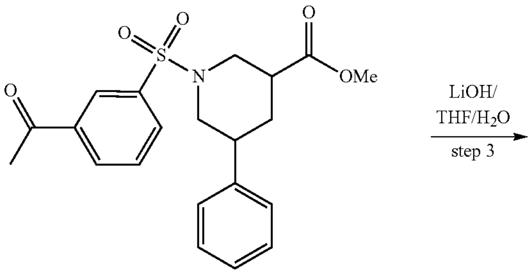
AOV-0106-2
-continued
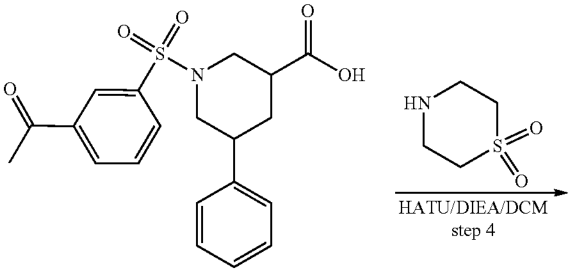
AOV-0106-3
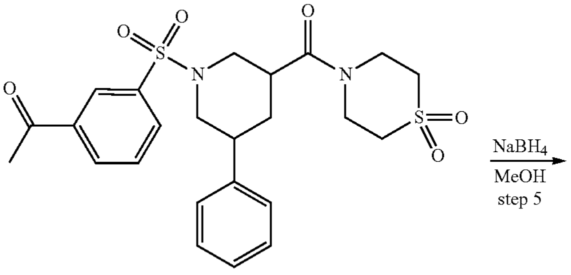
AOV-0106-4
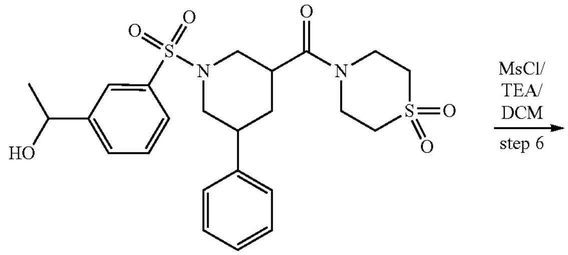
AOV-0106-5
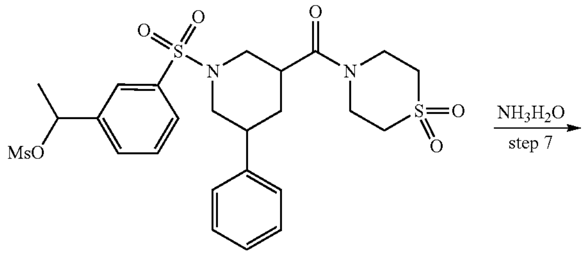
AOV-0106-6

-continued

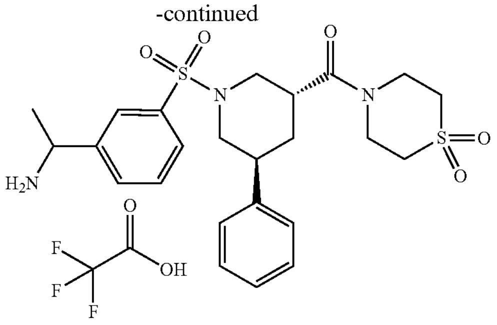

trans racemic
PH-AOV-0106

Step 1: 3-Acetylbenzenesulfonyl chloride

To a stirred solution of 1-(3-aminophenyl)ethan-1-one (5.0 g, 37 mmol, 1.00 equiv) in HCl aq. (6M, 30 mL) was added $NaNO_2$ (3.83 g, 55.5 mmol, 1.50 equiv) in $H_2O$ (3 mL) dropwise at −5° C. The reaction solution was stirred for 30 min at −5° C. This solution was assigned solution A. Then CuCl (5.49 g, 55.5 mmol, 1.50 equiv) was added to a 250-mL single necked round-bottom flask with AcOH (30 mL) as the solvent, $SO_2$ (g) was bubbled to the solution with stirring at 0° C. for 20 min, this solution was assigned as solution B. To the solution B was added solution A dropwise with stirring at −5° C. The reaction solution was stirred for additional 1 h at rt. The mixture was added ice/$H_2O$ (50 mL) and extracted with DCM (3×200 mL). The combined organic layers were washed with water (3×200 mL) and dried over anhydrous $Na_2SO_4$. After filtration, the filtrate was concentrated under vacuum. This resulted in 3.0 g (crude) of the title compound as yellow oil.

Step 2: Methyl 1-((3-acetylphenyl)sulfonyl)-5-phenylpiperidine-3-carboxylate

To a stirred solution of methyl 5-phenylpiperidine-3-carboxylate (2.0 g, 9.12 mmol, 1.00 equiv) in DCM (30 mL) were added 3-acetylbenzenesulfonyl chloride (3.0 g, crude) and TEA (4.61 g, 45.6 mmol, 5.00 equiv) at rt. The reaction solution was stirred for 12 h at rt. The reaction mixture was quenched with $H_2O$ (30 mL) and extracted with DCM (3×50 mL). The combined organic layers were dried over anhydrous $Na_2SO_4$. After filtration, the filtrate was concentrated under vacuum. The residue was eluted from silica gel with PE/EtOAc (3:1). This resulted in 1.0 g (crude) of the title compound as a brown oil. MS-ESI: 402 (M+1).

Step 3: 1-((3-Acetylphenyl)sulfonyl)-5-phenylpiperidine-3-carboxylic acid

To a stirred solution of methyl 1-((3-acetylphenyl)sulfonyl)-5-phenylpiperidine-3-carboxylate (1.0 g, crude) in THF (5 mL) and $H_2O$ (4 mL) was added LiOH (416 mg, 45.6 mmol, 5.00 equiv) at rt. The reaction mixture was stirred for 12 h at rt. The mixture was adjusted to pH 4 with HCl aq. (1 M). The mixture was extracted with EtOAc (3×40 mL). The combined organic layers were dried over anhydrous $Na_2SO_4$. After filtration, the filtrate was concentrated under vacuum. This resulted in 500 mg (crude) of the title compound as light brown oil. MS-ESI: 386 (M−1).

Step 4: 1-(3-((3-(1,1-Dioxidothiomorpholine-4-carbonyl)-5-phenylpiperidin-1-yl)sulfonyl)phenyl)ethan-1-one To a stirred solution of 1-((3-acetylphenyl)sulfonyl)-5-phenylpiperidine-3-carboxylic acid (500 mg, crude) in DMF (10 mL) were added HATU (553 mg, 1.46 mmol, 1.20 equiv), DIEA (549 mg, 4.25 mmol, 3.50 equiv) at rt. The reaction solution was stirred for 10 min at rt. This was followed by the addition of a solution of thiomorpholine 1,1-dioxide (164 mg, 1.21 mmol, 1.00 equiv) in DMF (2 mL) dropwise with stirring at rt. The reaction solution was stirred for 2 h at rt. The reaction solution was diluted with $H_2O$ (10 mL) and extracted with EtOAc (3×50 mL). The combined organic layers were dried over anhydrous $Na_2SO_4$ and concentrated under vacuum. The residue was eluted from silica gel with EtOAc/PE (3:1). This resulted in 550 mg (crude) of the title compound as a light yellow solid. MS-ESI: 505 (M+1).

Step 5: (1,1-Dioxidothiomorpholino)(1-((3-(1-hydroxyethyl)phenyl)sulfonyl)-5-phenylpiperidin-3-yl)methanone To a stirred solution of 1-(3-((3-(1,1-dioxidothiomorpholine-4-carbonyl)-5-phenylpiperidin-1-yl)sulfonyl) phenyl) ethan-1-one (550 mg, crude) in MeOH (10 mL) under nitrogen was added $NaBH_4$ (500 mg, 13.2 mmol, 13.3 equiv) in portions at 0° C. The reaction solution was stirred for 12 h at rt. The reaction was diluted with MeOH (4 mL). The mixture was concentrated under vacuum. The residue was eluted from silica gel with EtOAc. This resulted in 520 mg (crude) of the title compound as a light yellow solid. MS-ESI: 507 (M+1).

Step 6: 1-(3-((3-(1,1-Dioxidothiomorpholine-4-carbonyl)-5-phenylpiperidin-1-yl)sulfonyl)phenyl)ethyl methanesulfonate To a stirred solution of (1,1-dioxidothiomorpholino)(1-((3-(1-hydroxyethyl)phenyl)sulfonyl)-5-phenylpiperidin-3-yl)methanone (520 mg, crude) in DCM (10 mL) were added methanesulfonyl chloride (0.30 mL, 2.62 mmol) and TEA (0.5 mL, 2.97 mmol) at 0° C. The reaction solution was stirred for 2 h at rt. The reaction solution was quenched with ice/$H_2O$ (10 mL) and extracted with DCM (3×20 mL). The combined organic layers were washed with brine (3×25 mL) and dried over anhydrous $Na_2SO_4$. After filtration, the filtrate was concentrated under vacuum. This resulted in 350 mg (crude) of the title compound as a light yellow solid. MS-ESI: 585 (M+1).

Step 7: trans-(1-((3-(1-Aminoethyl)phenyl)sulfonyl)-5-phenylpiperidin-3-yl) (1,1-dioxidothiomorpholino)methanone 2,2,2-trifluoroacetate A solution of 1-(3-((3-(1,1-dioxidothiomorpholine-4-carbonyl)-5-phenylpiperidin-1-yl)sulfonyl)phenyl)ethyl methanesulfonate (350 mg, crude) in THF (4 mL) and $NH_3 \cdot H_2O$ (20 mL) was stirred for 12 h at rt. The reaction mixture was concentrated under vacuum. The residue was eluted from silica gel with DCM/MeOH (10:1). The crude product was purified by Prep-HPLC with the following conditions: Column, YMC-Actus Triart C18, 30*250.5 um; Mobile Phase A: water (10 mL $NH_4HCO_3$+0.1% $NH_3 \cdot H_2O$), Mobile Phase B: ACN; Flow rate: 60 mL/min; Gradient: 35% B to 45% B over 7 min; Detector UV, 254/210 nm; RT1: 6.42. After concentrated under vacuum, the crude product was for second purification by Prep-HPLC with the following conditions: Column, Xselect CSH OBD, 30*150 mm 5 um; Mobile Phase A: water (0.05% TFA), Mobile Phase B: ACN; Flow rate: 60 mL/min; Gradient: 18% B to 30% B over 7 min; Detector, UV 210/254 nm; RT1:6.5. This resulted in 13 mg (6.63%) of the title compound as a white solid. MS-ESI: 506 (M+1).

$^1H$ NMR (400 MHz, MeOH-$d_4$) δ 7.94 (s, 1H), 7.90 (dd, J=7.6, 2.0 Hz, 1H), 7.84-7.73 (m, 2H), 7.47 (dd, J=7.5, 1.9 Hz, 2H), 7.36 (dd, J=8.4, 6.9 Hz, 2H), 7.30-7.22 (m, 1H), 4.64 (q, J=6.9 Hz, 1H), 4.20 (s, 1H), 3.84 (s, 3H), 3.50-3.42 (m, 2H), 3.25-3.07 (m, 7H), 2.06-1.97 (m, 2H), 1.69 (dd, J=6.9, 1.9 Hz, 3H), 1.31 (s, 1H).

Examples in the following table were prepared using similar conditions as described in PH-AOV-0106 from appropriate starting materials.

| Ex | Structure | Name | Data | Prep Info |
| --- | --- | --- | --- | --- |
| AOV-0102 RAC | 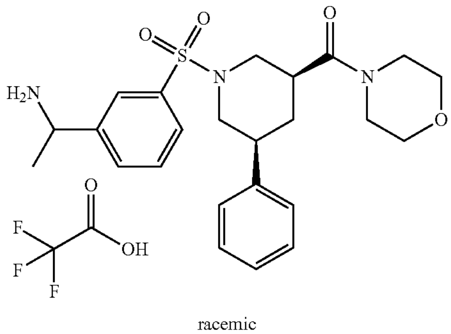 racemic | cis-(1-((3-(1-Aminoethyl)phenyl) sulfonyl)-5-phenylpiperidin-3-yl)(morpholino) methanone 2,2,2-trifluoroacetate | MS-ESI: 458(M + 1) | Xselect CSH OBD Column 30*150 mm 5 um; Water(0.05% TFA)/ACN, Gradient: 15% ACN to 28% ACN over 10 min |
| AOV-0102 TR | 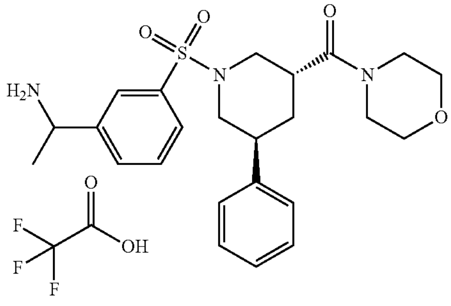 racemic | trans-(1-((3-(1-Aminoethyl)phenyl) sulfonyl)-5-phenylpiperidin-3-yl)(morpholino) methanone 2,2,2-trifluoroacetate | MS-ESI: 458(M + 1) | Xselect CSH OBD Column 30*150 mm 5 um; Water(0.05% TFA)/ACN, Gradient: 15% ACN to 28% ACN over 10 min |

Example 17: Synthesis of PH-AOV-0111 (Method L)

Scheme 27

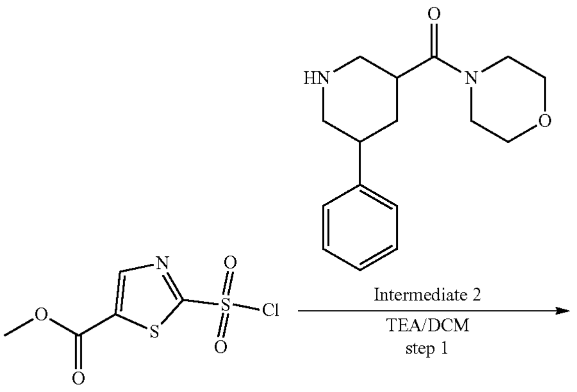

Intermediate 18

-continued

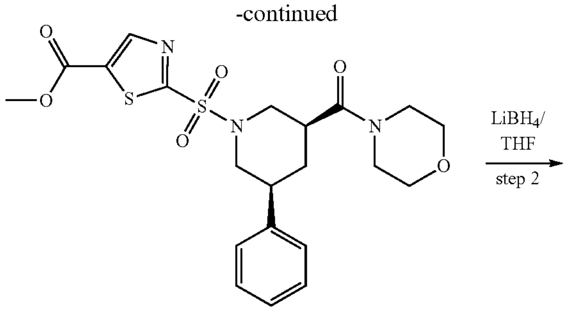

racemic
AOV-0111-1

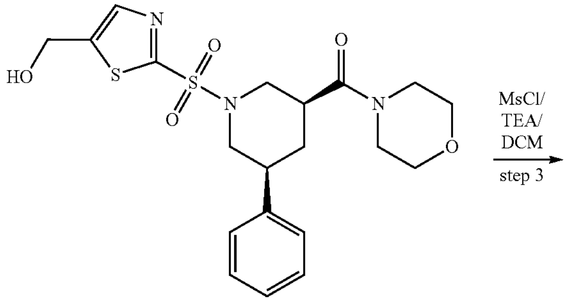

racemic
AOV-0111-2

-continued

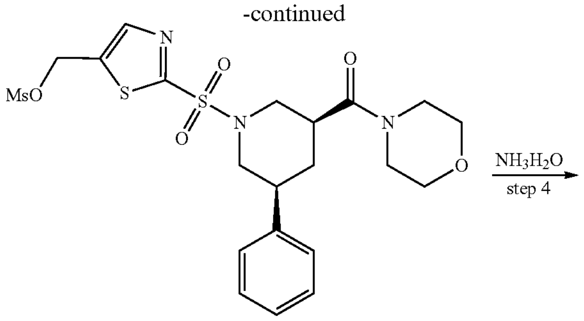

racemic
AOV-0111-3

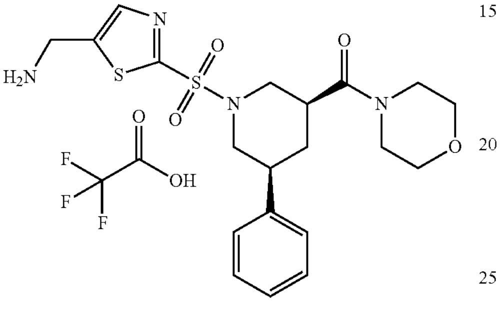

racemic
PH-AOV-0111

Step 1: cis-Methyl 2-((-3-(morpholine-4-carbonyl)-5-phenylpiperidin-1-yl)sulfonyl)thiazole-5-carboxylate To a stirred solution of morpholino(5-phenylpiperidin-3-yl)methanone (1.0 g, crude) in DCM (10 m) were added methyl 2-(chlorosulfonyl)thiazole-5-carboxylate (700 mg, crude) and TEA (2.5 g, 24.7 mmol). The reaction mixture was stirred for 5 h at rt. The mixture was diluted with $H_2O$ (10 mL). The mixture was extracted with DCM (3×35 mL). The combined organic layers were dried over anhydrous $Na_2SO_4$. After filtration, the filtrate was concentrated under vacuum. The residue was eluted from silica gel with PE/EtOAc (1:2). This resulted in 640 mg (51.8%) of the title compound as a light yellow solid. MS-ESI: 480 (M+1).

Steps 2-4 used similar procedures for converting compound AOV-0022-1 to PH-AOV-0022 shown in Method C to afford PH-AOV-0111 from compound AOV-0111-3. MS-ESI: 451 (M+1).

$^1$H NMR (400 MHz, MeOH-$d_4$) δ 8.15 (s, 1H), 7.38-7.31 (m, 2H), 7.30-7.23 (m, 3H), 4.53 (m, 2H), 4.07-3.91 (N, 2H), 3.78-3.54 (m, 8H), 3.28-3.17 (M, 1H), 3.06-2.92 (m, 2H), 2.76 (t, J=12 Hz, 1H), 2.11-2.03 (m, 1H), 1.79 (q, J=12.8 Hz, 1H).

Examples in the following table were prepared using similar conditions as described in PH-AOV-0111 from appropriate starting materials.

| Ex | Structure | Name | Data | Prep Info |
|---|---|---|---|---|
| AOV-0111T | 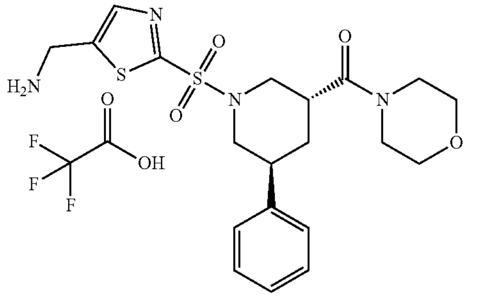 racemic | trans-(1-((5-(Aminomethyl)thiazol-2-yl)sulfonyl)-5-phenylpiperidin-3-yl)(morpholino) methanone 2,2,2-trifluoroacetate | MS-ESI: 451(M + 1) | Xselect CSH OBD Column 30*150 mm 5 um; Water (0.05% TFA)/ACN; Gradient: 26% ACN to 40% ACN over 10 min |
| AOV-0112 | 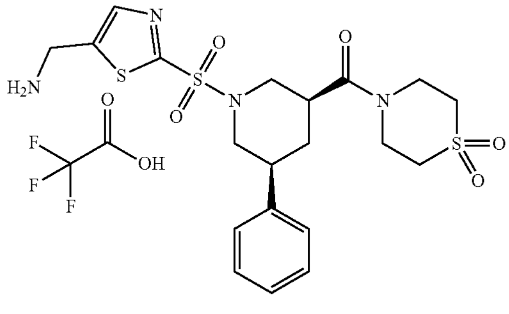 racemic | cis-(1-((5-(Aminomethyl)thiazol-2-yl)sulfonyl)-5-phenylpiperidin-3-yl)(1,1-dioxidothiomorpholino) methanone 2,2,2-trifluoroacetate | MS-ESI: 499(M + 1) | Xselect CSH OBD Column 30*150 mm 5 um, Water (0.05% TFA)/ACN; Gradient: 12% ACN to 36% ACN over 7 min |

-continued

| Ex | Structure | Name | Data | Prep Info |
|---|---|---|---|---|
| AOV-0113 | 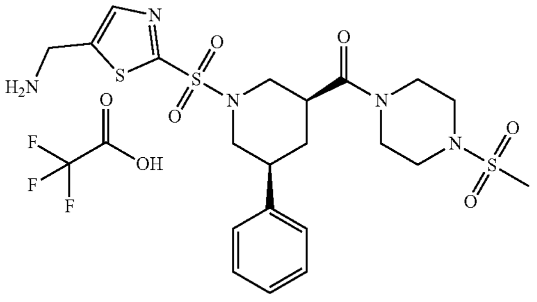 racemic | cis-(1-((5-(Aminomethyl)thiazol-2-yl)sulfonyl)-5-phenylpiperidin-3-yl)(4-(methylsulfonyl) piperazin-1-yl)methanone 2,2,2-trifluoroacetate | MS-ESI: 528(M + 1) | Xselect CSH OBD Column 30*150 mm 5 um, Water (0.05% TFA)/ACN; Gradient: 15% ACN to 45% ACN over 7 min |
| AOV-0116 | 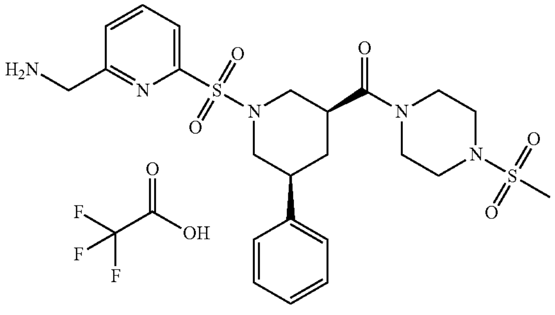 racemic | cis-(1-((6-(Aminomethyl)pyridin-2-yl)sulfonyl)-5-phenylpiperidin-3-yl)(4-(methylsulfony]) piperazin-1-yl)methanone 2,2,2-trifluoroacetate | MS-ESI: 522(M + 1) | Xselect CSH OBD Column 30*150 mm 5 um, Water(0.05% TFA)/ ACN; Gradient: 15% ACN to 25% ACN over 10 min; |
| AOV-0114T | 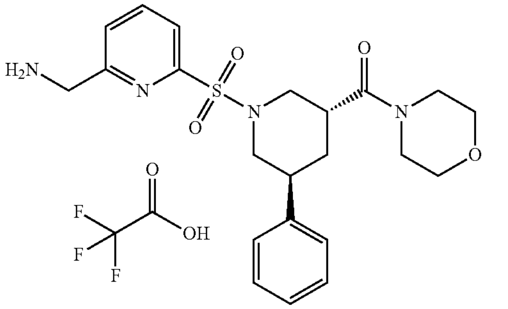 racemic | trans-(1-((6-(Aminomethyl)pyridin-2-yl)sulfonyl)-5-phenylpiperidin-3-yl)(morpholino) methanone 2,2,2-trifluoroacetate | MS-ESI: 445(M + 1) | Xselect CSH OBD 30*150 mm 5 um, water(0.05% TFA) and ACN (11% ACN to 23% ACN over 10 min); |
| AOV-0115T | 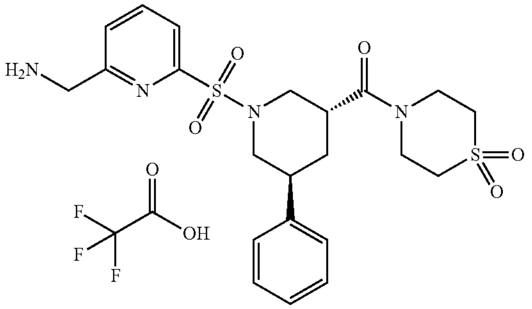 racemic | trans-(1-((6-(Aminomethyl)pyridin-2-yl)sulfonyl)-5-phenylpiperidin-3-yl)(1,1-dioxidothiomorpholino) methanone 2,2,2-trifluoroacetate | MS-ESI: 493(M + 1) | Xselect CSH OBD 30*150 mm 5 um, water(0.05% TFA) and ACN (11% ACN to 23% ACN over 10 min) |

-continued

| Ex | Structure | Name | Data | Prep Info |
|---|---|---|---|---|
| AOV-0116T | 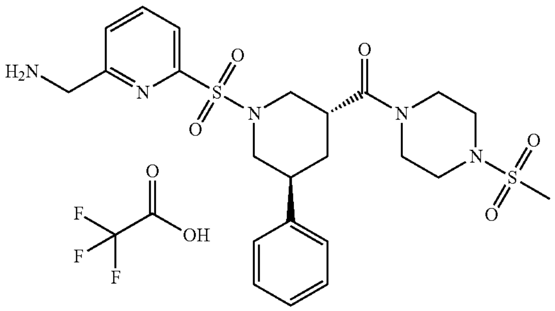 racemic | trans-(1-((6-(Aminomethyl)pyridin-2-yl)sulfonyl)-5-phenylpiperidin-3-yl)(4-(methylsulfonyl) piperazin-1-yl)methanone 2,2,2-trifluoroacetate | MS-ESI: 522(M + 1) | Xselect CSH OBD 30*150 mm 5 um, water(0.05% TFA) and ACN (11% ACN to 23% ACN over 10 min) |
| AOV-0112T | 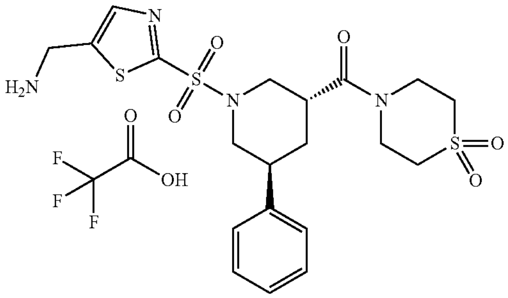 racemic | trans-(1-((5-(Aminomethyl)thiazol-2-yl)sulfonyl)-5-phenylpiperidin-3-yl)(1,1-dioxidothiomorpholino) methanone 2,2,2-trifluoroacetate | MS-ESI: 499(M + 1) | Xselect CSH OBD 30*150 mm 5 um, water(0.05% TFA) and ACN (12% ACN to 36% ACN over 7 min) |
| AOV-0113T | 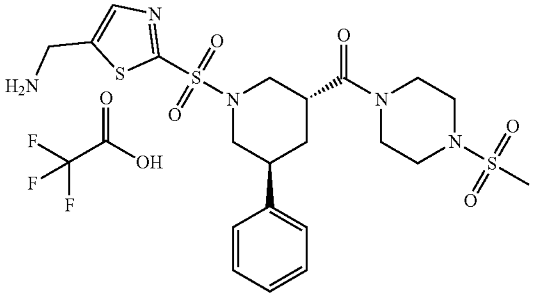 racemic | trans-(1-((5-(Aminomethyl)thiazol-2-yl)sulfonyl)-5-phenylpiperidin-3-yl)(4-(methylsulfonyl) piperazin-1-yl)methanone 2,2,2-trifluoroacetate | MS-ESI: 528 (M + 1) | Xselect CSH OBD 30*150 mm 5 um, water(0.05% TFA) and ACN (10% ACN to 40% ACN over 7 min) |

Example 18: Synthesis of PH-AOV-0133A and 0133B (Method M)

Scheme 28

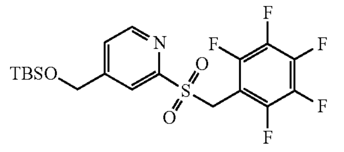

Intermediate 14

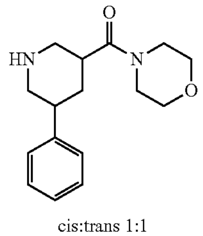

cis:trans 1:1
Intermediat 2

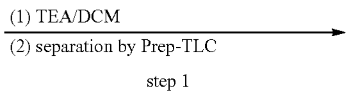

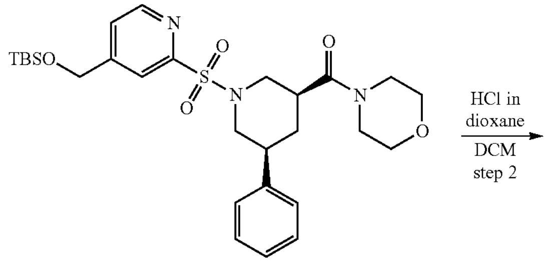

racemic
PH-AOV-0133-1

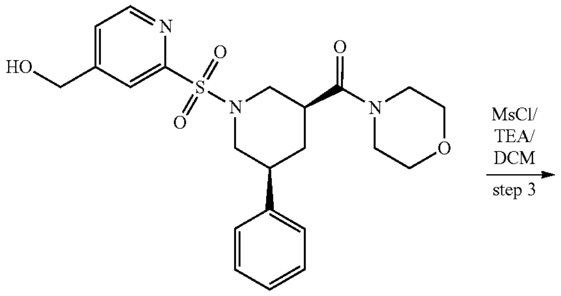

racemic
PH-AOV-0133-2

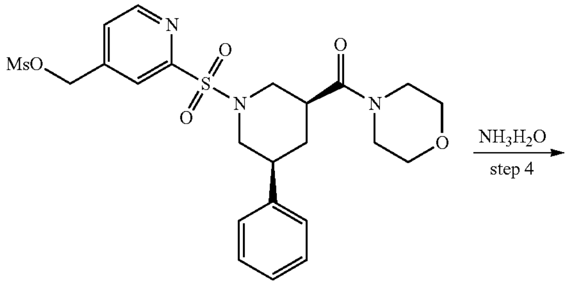

racemic
PH-AOV-0133-3

-continued

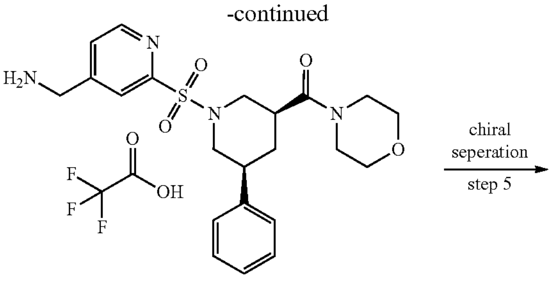

racemic
PH-AOV-0133

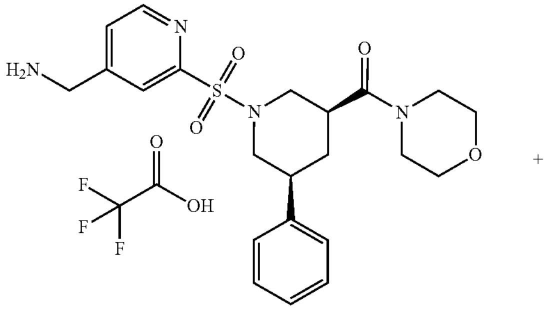

unconfirmed
PH-AOV-0133A

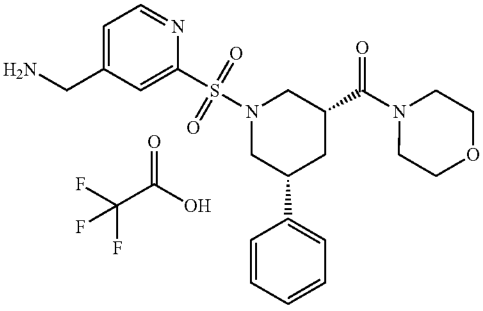

unconfirmed
PH-AOV-0133B

Step 1: cis-(1-((4-(((tert-butyldimethylsilyl)oxy) methyl)pyridin-2-yl)sulfonyl)-5-phenylpiperidin-3-yl) (morpholino)methanone To a stirred solution of morpholino(5-phenylpiperidin-3-yl)methanone (116 mg, 0.423 mmol, 1.00 equiv) in DCM (10 mL) were added perfluorophenyl 4-(((tert-butyldimethylsilyl)oxy)methyl)pyridine-2-sulfonate (397 mg, 0.85 mmol, 2.00 equiv) and TEA (128 mg, 1.27 mmol, 3.00 equiv) at 0° C. The resulting solution was stirred for 48 h at rt. The reaction was quenched with $H_2O$ (20 mL) and extracted with DCM (3×30 mL). The combined organic layers were dried over anhydrous $Na_2SO_4$ and concentrated under vacuum. The residue was eluted from silica gel with EtOAc/PE (1:1). This resulted in 188 mg (79%) of the title compound as a white solid. MS-ESI: 560 (M+1).

Step 2: cis-(1-((4-(Hydroxymethyl)pyridin-2-yl) sulfonyl)-5-phenylpiperidin-3-yl)(morpholino) methanone To a stirred solution of cis-(1-((4-(((tert-butyldimethylsilyl)oxy)methyl)pyridin-2-yl)sulfonyl)-5-phenylpiperidin-3-yl)(morpholino)methanone (188 mg, 0.336 mmol, 1.00 equiv) in DCM (4 mL) was added HCl(gas) in 1,4-dioxane (4 M, 4.00 mL). The resulting solution was stirred for 2 h at rt. The resulting mixture was concentrated under vacuum. The residue was eluted from silica gel with DCM/MeOH (10:1). This resulted in 120 mg (80.2%) of the title compound as yellow oil. MS-ESI 446 (M+1).

Step 3: cis-(2-((3-(Morpholine-4-carbonyl)-5-phenylpiperidin-1-yl)sulfonyl)pyridin-4-yl)methyl methanesulfonate To a stirred solution of cis-(1-((4-(hydroxymethyl)pyridin-2-yl)sulfonyl)-5-phenylpiperidin-3-yl)(morpholino) methanone (120 mg, 0.27 mmol, 1.00 equiv) in DCM (10 mL) were added MsCl (61.6 mg, 0.54 mmol, 2.00 equiv) and TEA (109 mg, 1.08 mmol, 4.00 equiv) dropwise slowly at 0° C. under nitrogen. The resulting solution was stirred for 2 h at rt. The reaction was quenched with water/ice (10 mL) and extracted with DCM (2×10 mL). The combined organic layers were dried over anhydrous $Na_2SO_4$ and concentrated under vacuum. This resulted in 130 mg (crude) of the title compound as yellow oil. MS-ESI: 524 (M+1).

Step 4: cis-(1-((4-(Aminomethyl)pyridin-2-yl)sulfonyl)-5-phenylpiperidin-3-yl)(morpholino)methanone 2,2,2-trifluoroacetate To a stirred solution of cis-(2-((3-(morpholine-4-carbonyl)-5-phenylpiperidin-1-yl)sulfonyl)pyridin-4-yl) methyl methanesulfonate (130 mg, crude) in THF (2 mL) was added $NH_3H_2O$ (25% wt., 10 mL) dropwise slowly at 0° C. The resulting solution was stirred for 16 h at rt. The resulting mixture was concentrated under vacuum. The residue was eluted from silica gel with DCM/MeOH (10:1). The crude product was purified by Prep-HPLC with the following conditions: Xselect CSH OBD Column 30*150 mm 5 um; Mobile Phase, water (0.05% TFA), Mobile Phase B: ACN (12% up to 34% over 7 min); Detector, UV 254 nm. This resulted in 49.1 mg (over two steps, 30.7%) of the title compound as a white solid. MS-ESI: 445 (M+1).

$^1H$ NMR (400 MHz, MeOH-$d_4$) δ 8.82 (d, J=4.8 Hz, 1H), 8.10 (d, J=0.8 Hz, 1H), 7.72-7.70 (m, 1H), 7.35-7.23 (m, 5H), 4.32 (s, 2H), 4.07-3.95 (m, 2H), 3.74-3.58 (m, 8H), 3.23-3.27 (m, 1H), 3.00-2.91 (m, 2H), 2.80-2.70 (m, 1H), 2.09-2.03 (m, 1H), 1.68 (q, J=12.4 Hz, 1H).

Step 5: ((3S,5S)-1-((4-(aminomethyl)pyridin-2-yl) sulfonyl)-5-phenylpiperidin-3-yl)(morpholino) methanone 2,2,2-trifluoroacetate and ((3R,5R)-1-((4-(aminomethyl)pyridin-2-yl)sulfonyl)-5-phenylpiperidin-3-yl)(morpholino)methanone 2,2,2-trifluoroacetate cis-(1-((4-(Aminomethyl)pyridin-2-yl)sulfonyl)-5-phenylpiperidin-3-yl)(morpholino)methanone 2,2,2-trifluoroacetate (47 mg) was separated by Chiral-Prep-HPLC with the following conditions: Column: CHIRALPAK IE, 2*25 cm, 5 μm; Mobile Phase A: MTBE (0.5% 2 M $NH_3$-MeOH), Mobile Phase B: EtOH; Flow rate: 18 m/min; Gradient: 50% B to 50% B over 13 min; Wave Length: 220/254 nm; $RT_1$(min): 6.39; RT2(min): 9.686; Injection Volume: 0.7 mL; Number Of Runs: 2. This resulted in 15.6 mg of ((3S,5S)-1-((4-(aminomethyl)pyridin-2-yl)sulfonyl)-5-phenylpiperidin-3-yl)(morpholino)methanone 2,2,2-trifluoroacetate and 14.2 mg of ((3R,5R)-1-((4-(aminomethyl)pyridin-2-yl)sulfonyl)-5-phenylpiperidin-3-yl)(morpholino) methanone 2,2,2-trifluoroacetate as a white solid. MS-ESI: 445 (M+1).

PH-AOV-0133 A: $^1H$ NMR (400 MHz, MeOH-$d_4$) δ 8.80 (d, J=5.2 Hz, 1H), 8.07 (s, 1H), 7.68 (d, J=5.2 Hz, 1H), 7.35-7.30 (m, 2H), 7.29-7.20 (m, 3H), 4.30 (s, 2H), 4.05-3.92 (m, 2H), 3.75-3.56 (m, 8H), 3.23-3.13 (m, 1H), 2.98-2.90 (m, 2H), 2.73 (t, J=12 Hz, 1H), 2.10-2.01 (m, 1H), 1.77 (q, J=12.6 Hz, 1H).

PH-AOV-0133 B: H-NMR (400 MHz, MeOD-$d_4$) δ 8.80 (d, J=4.8 Hz, 1H), 8.07 (s, 1H), 7.68 (d, J=5.2 Hz, 1H), 7.33-7.30 (m, 2H), 7.29-7.20 (m, 3H), 4.30 (s, 2H), 4.04-3.91 (m, 2H), 3.73-3.57 (m, 8H), 3.22-3.11 (m, 1H), 2.01-2.90 (m, 2H), 2.73 (t, J=12 Hz, 1H), 2.07-1.92 (i, 1H), 1.77 (q, J=12.6 Hz, 1H).

Examples in the following table were prepared using similar conditions as described in PH-AOV-0133 from appropriate starting materials.

| Ex | Structure | Name | Data | Prep Info |
|---|---|---|---|---|
| AOV-0130 | 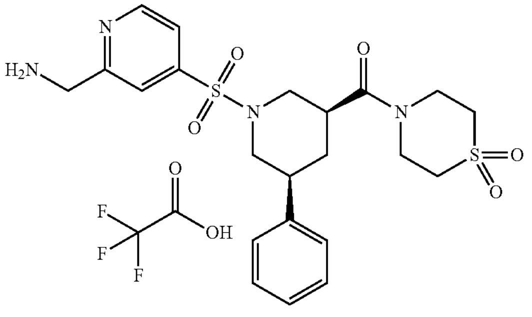 racemic | cis-(1-((2-(Aminomethyl) pyridin-4-yl)sulfonyl)-5-phenylpiperidin-3-yl)(1,1-dioxidothiomorpholino) methanone 2,2,2-trifluoroacetate | MS-ESI: 493(M + 1) | Xselect CSH OBD Column 30*150 mm, 5 um, water(0.05% TFA) and ACN (12% ACN up to 34% ACN over 7 min) |

-continued

| Ex | Structure | Name | Data | Prep Info |
|---|---|---|---|---|
| AOV-0130T | 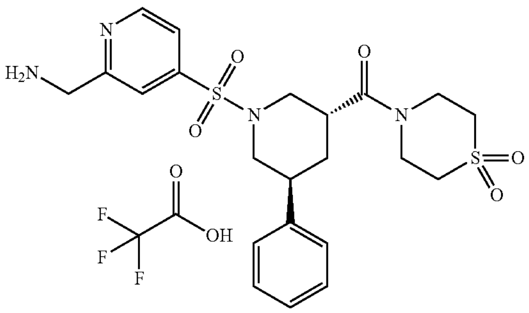 racemic | trans-(1-((2-(Aminomethyl) pyridin-4-yl)sulfonyl)-5-phenylpiperidin-3-yl)(1,1-dioxidothiomorpholino) methanone 2,2,2-trifluoroacetate | MS-ESI: 493(M + 1) | Xselect CSH OBD Column 30*150 mm 5 um, water(0.05% TFA) and ACN (12% ACN up to 34% ACN over 7 min) |
| AOV-0131 | 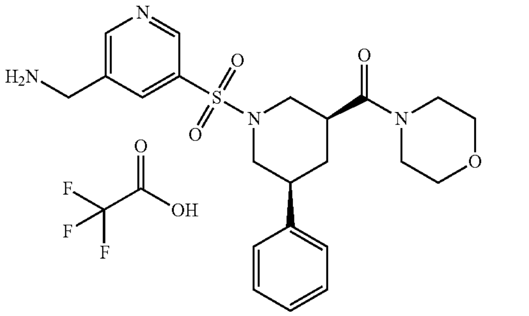 racemic | cis-(1-((5-(Aminomethyl)pyridin-3-yl)sulfonyl)-5-phenylpiperidin-3-yl)(morpholino) methanone 2,2,2-trifluoroacetate | MS-ESI: 445(M + 1) | XSelect CSH Prep C18 OBD, 5 um, 19*150 mm; water (0.05% TFA) and ACN (12% ACN up to 35% ACN over 7 min) |
| AOV-0132 | 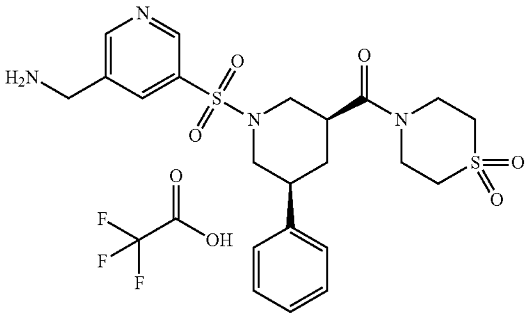 racemic | cis-(1-((5-(Aminomethyl)pyridin-3-yl)sulfonyl)-5-phenylpiperidin-3-yl)(1,1-dioxidothiomorpholino) methanone 2,2,2-trifluoroacetate | MS-ESI: 493(M + 1) | XSelect CSH Prep C18 OBD, 5 um, 19*150 mm; water (0.05% TFA) and ACN (12% ACN up to 34% ACN over 7 min) |
| AOV-0134 | 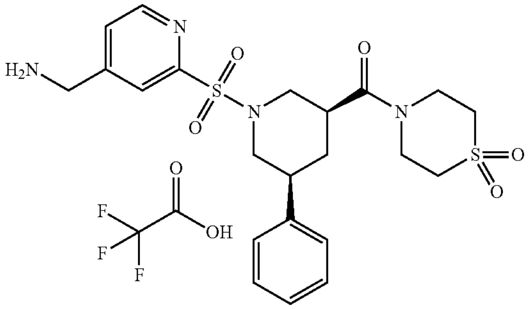 racemic | cis-(1-((4-(Aminomethyl) pyridin-2-yl)sulfonyl)-5-phenylpiperidin-3-yl)(1,1-dioxidothiomorpholino) methanone 2,2,2-trifluoroacetate | MS-ESI: 493(M + 1) | Xselect CSH OBD 30*150 mm, 5 um, water(0.05% TFA) and ACN (12% ACN up to 34% ACN over 7 min) |

-continued

| Ex | Structure | Name | Data | Prep Info |
|---|---|---|---|---|
| AOV-0144 | 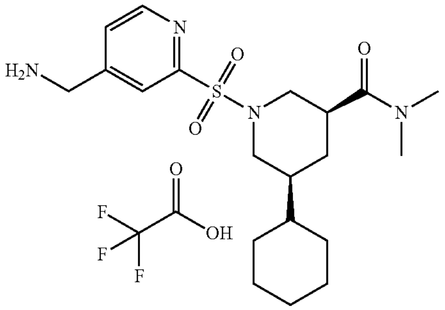 racemic | cis-1-((4-(Aminomethyl) pyridin-2-yl)sulfonyl)-5-cyclohexyl-N,N-dimethylpiperidine-3-carboxamide 2,2,2-trifluoroacetate | MS-ESI: 409(M + 1) | Xselect CSH OBD, 30*150 mm 5 um, water(0.05% TFA) and ACN (15% ACN up to 40% ACN over 7 min); |
| AOV-0145 | 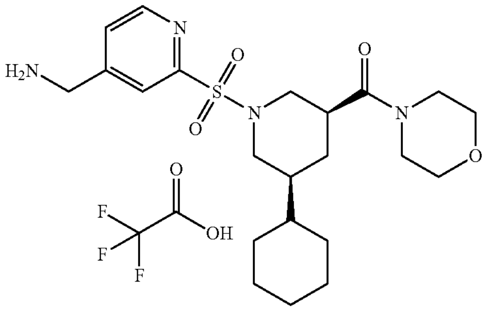 racemic | cis-(1-((4-(Aminomethyl) pyridin-2-yl)sulfonyl)-5-cyclohexylpiperidin-3-yl)(morpholino) methanone 2,2,2-trifluoroacetate | MS-ESI: 451 (M + 1) | Xselect CSH OBD 30*150 mm 5 um, water(0.05% TFA) and ACN (12% ACN up to 42% ACN over 7 min); |
| AOV-0146 | 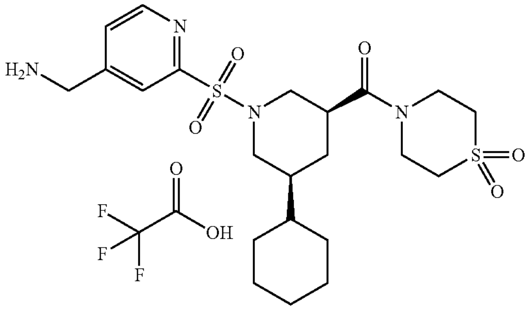 racemic | cis-(1-((4-(Aminomethyl) pyridin-2-yl)sulfonyl)-5-cyclohexylpiperidin-3-yl)(1,1-dioxidothiomorpholino) methanone 2,2,2-trifluoroacetate | MS-ESI: 499 (M + 1) | XSelect CSH Prep C18 OBD; 19*250 mm, 5 um; water(0.05% TFA) and ACN (20% ACN to 43% ACN over 7 min) |

Example 19: Synthesis of PH-AOV-0122 (Method N)

Scheme 29

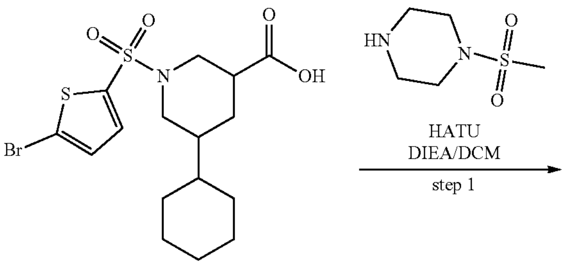

Intermediate 19

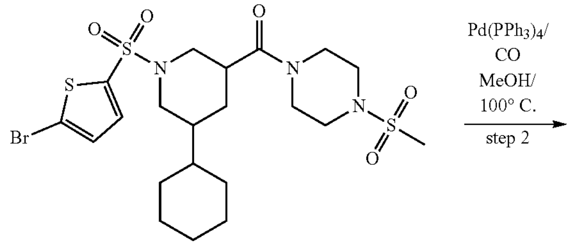

PH-AOV-0122-1

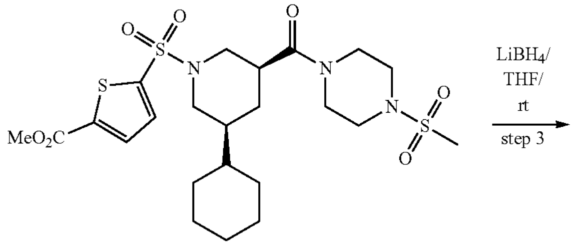

racemic
PH-AOV-0122-2

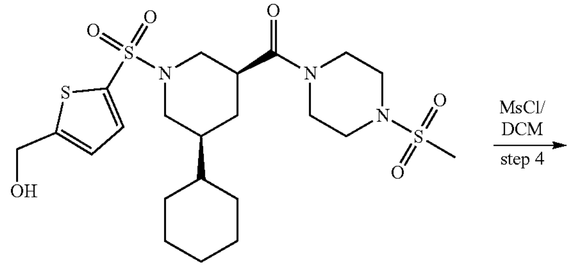

racemic
PH-AOV-0122-3

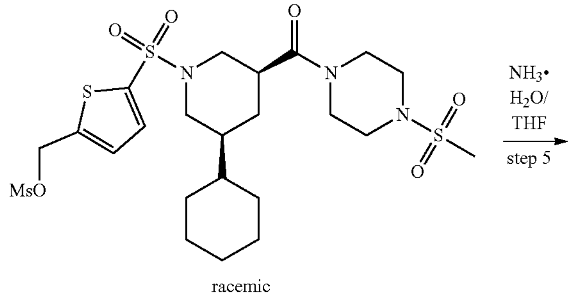

racemic
PH-AOV-0122-4

-continued

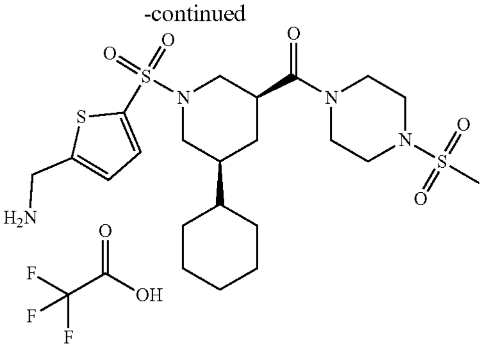

racemic
PH-AOV-0122

Step 1: (1-((5-Bromothiophen-2-yl)sulfonyl)-5-cyclohexylpiperidin-3-yl)(4-(methylsulfonyl) piperazin-1-yl)methanone To a stirred solution of 1-((5-bromothiophen-2-yl)sulfonyl)-5-cyclohexylpiperidine-3-carboxylic acid (1.5 g, 3.44 mmol, 1.00 equiv) in DCM (30 mL) was added HATU (1.57 g, 4.13 mmol, 1.20 equiv). To the above mixture were added DIEA (1.55 g, 12 mmol, 3.50 equiv) and 1-(methylsulfonyl) piperazine (677 mg, 4.13 mmol, 1.20 equiv) in portions. The resulting mixture was stirred for 3 h at rt. The resulting mixture was diluted with $H_2O$ (30 mL) and extracted with DCM (3×40 mL). The combined organic layers were dried over anhydrous $Na_2SO_4$ and concentrated under vacuum. The residue was eluted from silica gel from PE/EtOAc (1:1). This resulted in 2.0 g (99.9%) of the title compound as a white solid. MS-ESI: 582/584 (M+1).

Step 2: cis-Methyl 5-((3-cyclohexyl-5-(4-(methylsulfonyl)piperazine-1-carbonyl)piperidin-1-yl)sulfonyl) thiophene-2-carboxylate To a stirred solution of (1-((5-bromothiophen-2-yl)sulfonyl)-5-cyclohexylpiperidin-3-yl)(4-(methylsulfonyl) piperazin-1-yl)methanone (500 mg, 0.86 mmol, 1.00 equiv) in MeOH (10 mL) under nitrogen were added TEA (174 mg, 1.72 mmol, 2.00 equiv) and $Pd(PPh_3)_4$ (99.2 mg, 0.086 mmol, 0.10 equiv). The pressure tank reactor was evacuated and refilled three times with CO. The reaction mixture was stirred for 16 h at 80° C. under an atmosphere of CO with 10 atm. The reaction mixture was cooled to rt and filtered to remove insoluble solids and the filtrate was concentrated under vacuum. The residue was eluted from silica gel with PE/EtOAc (1:1.5). This resulted in 350 mg (72.6%) of the title compound as a white solid. MS-ESI: 562 (M+1).

Steps 3-5 used similar procedures for converting compound AOV-0022-1 to PH-AOV-0022 shown in Method C to afford PH-AOV-0122 from PH-AOV-0122-2. MS-ESI: 533 (M+1).

$^1$H NMR (400 MHz, DMSO-$d_6$) δ 8.41 (br s, 1H), 7.65 (d, J=3.8 Hz, 1H), 7.39 (d, J=3.9 Hz, 1H), 4.35 (s, 2H), 3.75-3.67 (m, 1H), 3.65-3.53 (m, 4H), 3.15 (s, 2H), 3.08-3.00 (m, 2H), 2.97-2.95 (m, 1H), 2.91 (d, J=7.9 Hz, 1H), 2.90 (s, 3H), 2.74 (s, 1H), 2.00 (t, J=11.4 Hz, 1H), 1.83 (d, J=12.9 Hz, 1H), 1.73-1.60 (m, 6H), 1.26-1.07 (m, 4H), 1.01-0.89 (m, 2H).

Examples in the following table were prepared using similar conditions as described in PH-AOV-0122 from appropriate starting materials.

| Ex | Structure | Name | Data | Prep Info |
|---|---|---|---|---|
| AOV-0120 | 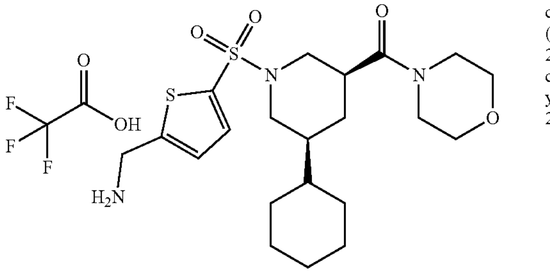 racemic | cis-(1-((5-(Aminomethyl)thiophen-2-yl)sulfonyl)-5-cyclohexylpiperidin-3-yl)(morpholino)methanone 2,2,2-trifluoroacetate | MS-ESI: 456(M + 1) | Xselect CSH OBD 30*150 mm 5 um, water (0.05% TFA) and ACN (11% ACN to 23% ACN over 10 min) |
| AOV-0121 | 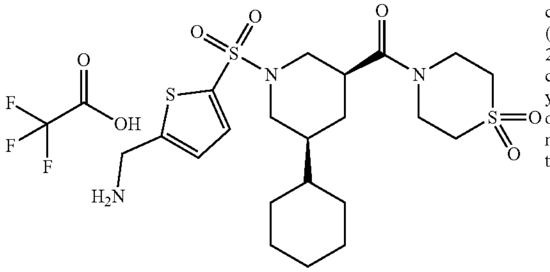 racemic | cis-(1-((5-(Aminomethyl)thiophen-2-yl)sulfonyl)-5-cyclohexylpiperidin-3-yl)(1,1-dioxidothiomorpholino) methanone 2,2,2-trifluoroacetate | MS-ESI: 504(M + 1) | Sunfire prep C18, 30*150, 5 um, water (0.05% TFA) and ACN (10% ACN to 35% ACN over 7 min) |
| AOV-0121T | 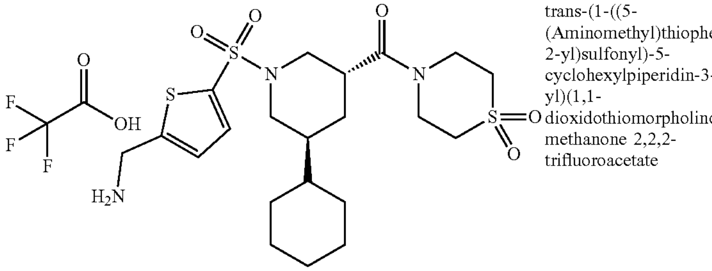 racemic | trans-(1-((5-(Aminomethyl)thiophen-2-yl)sulfonyl)-5-cyclohexylpiperidin-3-yl)(1,1-dioxidothiomorpholino) methanone 2,2,2-trifluoroacetate | MS-ESI: 504(M + 1) | Sunfire prep C18, 30*150, 5 um, water (0.05% TFA) and ACN (10% ACN to 35% ACN over 7 min) |

Example 20: Synthesis of PH-AOV-0142 (Method O)

Scheme 30

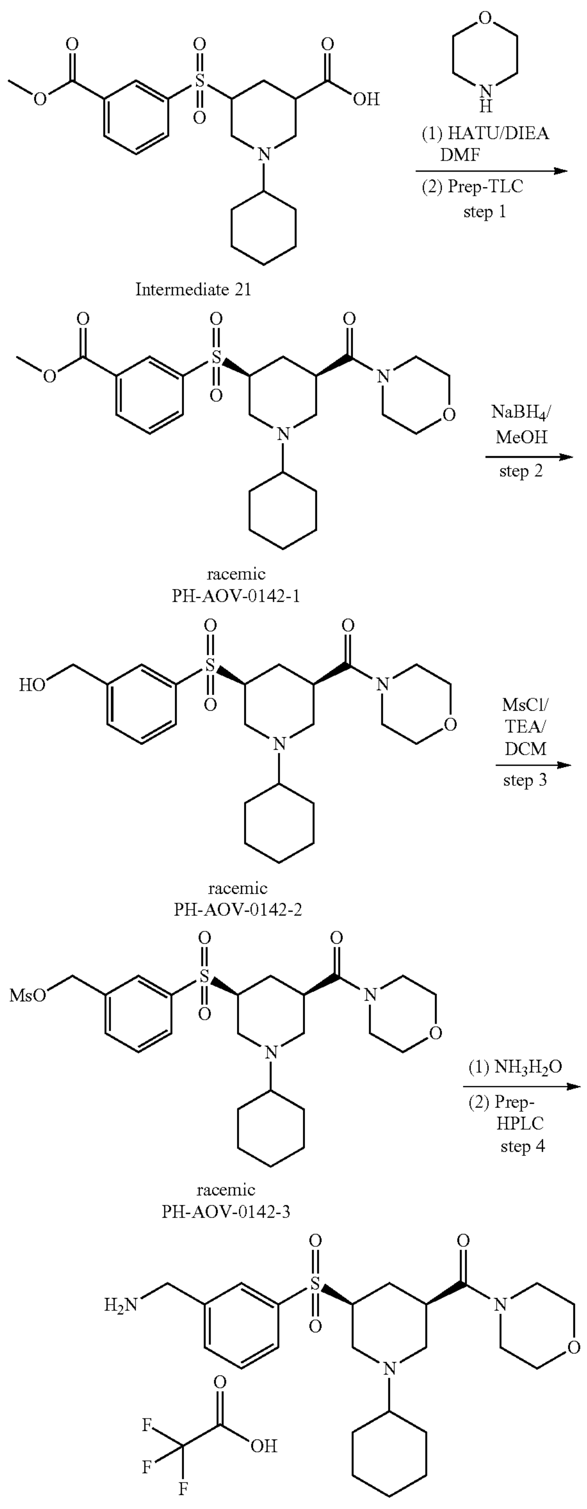

Intermediate 21 racemic PH-AOV-0142-1 racemic PH-AOV-0142-2 racemic PH-AOV-0142-3 racemic PH-AOV-0142

Step 1: cis-Methyl 3-((1-cyclohexyl-5-(morpholine-4-carbonyl)piperidin-3-yl)sulfonyl)benzoate To a stirred solution of 1-cyclohexyl-5-((3-(methoxycarbonyl)phenyl)sulfonyl)piperidine-3-carboxylic acid (350 mg, 0.86 mmol, 1.00 equiv) in DMF (10 mL) were added morpholine (112 mg, 1.28 mmol, 1.50 equiv), HATU (487 mg, 1.28 mmol, 1.50 equiv) and DIEA (331 mg, 2.57 mmol, 3.00 equiv). The resulting solution was stirred for 16 h at rt. The reaction was quenched with $H_2O$ (100 mL) and extracted with DCM (3×30 mL). The combined organic layers were dried over anhydrous $Na_2SO_4$ and concentrated under vacuum. The residue was eluted from silica gel with EtOAc/PE (1:1). This resulted in 100 mg (24.5%) of the title compound as yellow oil. MS-ESI: 479 (M+1).

Step 2: cis-(1-Cyclohexyl-5-((3-(hydroxymethyl) phenyl)sulfonyl)piperidin-3-yl)(morpholino) methanone To a stirred solution of cis-methyl 3-((1-cyclohexyl-5-(morpholine-4-carbonyl)piperidin-3-yl) sulfonyl)benzoate (100 mg, 0.21 mmol, 1.00 equiv) in MeOH (10 mL) was added $NaBH_4$ (79.1 mg, 2.09 mmol, 10.0 equiv) in portions at 0° C. The resulting solution was stirred for 16 h at rt. The reaction was quenched with water/ice (10 mL) and extracted with DCM (3×30 mL). The combined organic layers were dried with anhydrous $Na_2SO_4$ and concentrated under vacuum. The residue was eluted from silica gel column with DCM/MeOH (10:1). This resulted in 60 mg (63.7%) of the title compound as white oil. MS-ESI: 451 (M+1).

Steps 3-4 used similar procedures for converting compound PH-AOV-0022-2 to PH-AOV-0022 shown in Method C to afford PH-AOV-0142 from PH-AOV-0142-2. MS-ESI: 450 (M+4).

$^1H$ NMR (400 MHz, MeOD-$d_4$): δ 8.12 (s, 1H), 8.06 (d, J=8.0 Hz, 1H), 7.94 (d, J=8.0 Hz, 1H), 7.84 (dd, J=8.0 Hz, 7.6 Hz, 1H), 4.32 (s, 2H), 3.75-3.70 (m, 7H), 3.68-3.60 (m, 3H), 3.53-3.34 (m, 2H), 3.28-3.16 (m, 1H), 3.15-3.05 (m, 1H), 2.21-1.90 (m, 6H), 1.77-1.66 (m, 2H), 1.65-1.41 (m, 3H), 1.40-1.22 (in, 2H).

Examples in the following table were prepared using similar conditions as described in PH-AOV-0142 from appropriate starting materials.

| Ex | Structure | Name | Data | Prep Info |
|---|---|---|---|---|
| AOV-0141 | 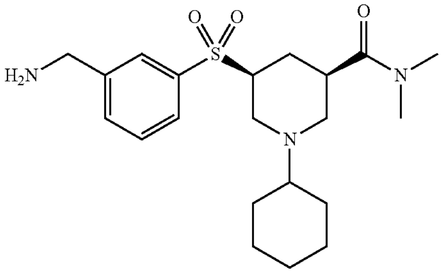 racemic | cis-5-((3-(Aminomethyl)phenyl)sulfonyl)-1-cyclohexyl-N,N-dimethylpiperidine-3-carboxamide | MS-ESI: 408(M + 1) | YMC-Actus Triart C18 ExRS, 30 mm x 150 mm, 5 um; water(10 mM $NH_4HCO_3$) and ACN (20% ACN up to 43% ACN over 7 min) |
| AOV-0141T | 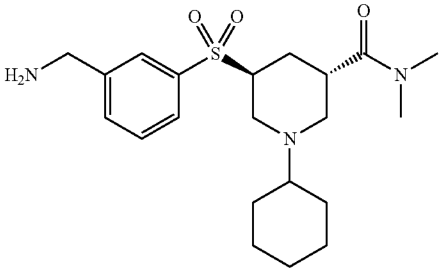 racemic | trans-5-((3-(Aminomethyl)phenyl)sulfonyl)-1-cyclohexyl-N,N-dimethylpiperidine-3-carboxamide | MS-ESI: 408(M + 1) | YMC-Actus Triart C18 ExRS, 30 mm x 150 mm, 5 um; water(10 mM $NH_4HCO_3$) and ACN (18% ACN up to 40% ACN over 7 min) |
| AOV-0142T | 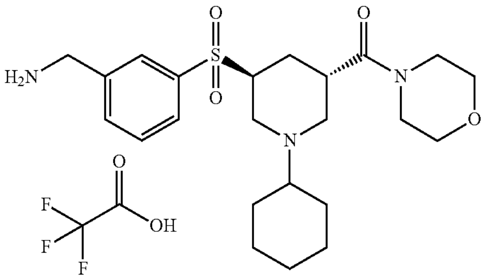 racemic | trans-(5-((3-(Aminomethyl)phenyl)sulfonyl)-1-cyclohexylpiperidin-3-yl)(morpholino)methanone 2,2,2-trifluoroacetate | MS-ESI: 450(M + 1) | Xselect CSH OBD 30*150 mm 5 um, water (0.05% TFA) and ACN (2% ACN to 22% ACN over 7 min) |
| AOV-0143 | 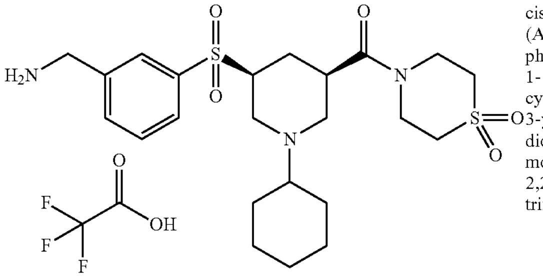 racemic | cis-(5-((3-(Aminomethyl)phenyl)sulfonyl)-1-cyclohexylpiperidin-3-yl)(1,1-dioxidothio-morpholino)methanone 2,2,2-trifluoroacetate | MS-ESI: 498(M + 1) | Sunfire prep C18, 30*150 mm, 5 μm; water(0.05% TFA) and ACN (5% ACN to 18% ACN over 8 min) |

Example 21: Synthesis of PH-AOV-0138 (Method P)

Scheme 31

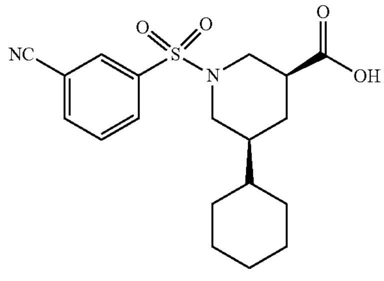

racemic
Intermediate 20

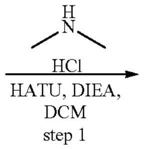

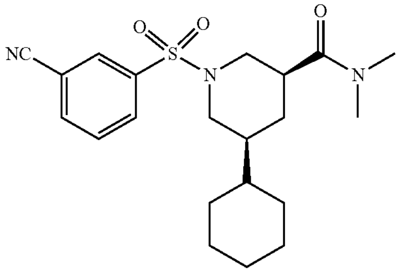

racemic
PH-AOV-0138-1

$NaBH_4$/
$NiCl_26H_2O$
MeOH
step 2

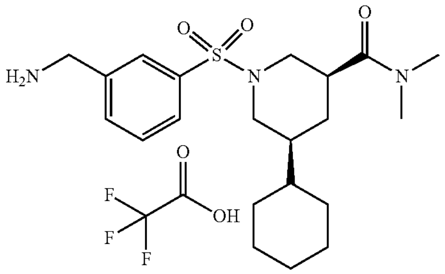

racemic
PH-AOV-0138

Step 1: cis-1-((3-Cyanophenyl)sulfonyl)-5-cyclohexyl-N,N-dimethylpiperidine-3-carboxamide cis-1-((3-Cyanophenyl)sulfonyl)-5-cyclohexylpiperidine-3-carboxylic acid (150 mg, 0.398 mmol, 1.00 equiv) was dissolved in DCM (5 mL). To above solution were added dimethylamine hydrochloride (65 mg, 0.796 mmol, 2.00 equiv), HATU (227 mg, 0.597 mmol, 1.50 equiv) and DIEA (154 mg, 1.19 mmol, 3.00 equiv). The resulting solution was stirred for 2 h at rt. The reaction was quenched with $H_2O$ (10 mL) and extracted with 3×10 mL of EtOAc. The combined organic layers were dried over anhydrous $Na_2SO_4$ and concentrated under vacuum. The residue was eluted from silica gel with EtOAc/PE (2:1). This resulted in 120 mg (74.6%) of the title compound as a yellow solid. MS-ESI: 404 (M+1).

Step 2: cis-1-((3-(Aminomethyl)phenyl)sulfonyl)-5-cyclohexyl-N,N-dimethylpiperidine-3-carboxamide 2,2,2-trifluoroacetate cis-1-((3-Cyanophenyl)sulfonyl)-5-cyclohexyl-N,N-dimethylpiperidine-3-carboxamide (120 mg, 0.297 mmol, 1.00 equiv) was dissolved in MeOH (10 mL). To above solution were added $NiCl_2 \cdot 6H_2O$ (141 mg, 0.59 mmol, 2.00 equiv) and $NaBH_4$ (22.5 mg, 0.59 mmol, 2.00 equiv). The reaction mixture was stirred for 16 h at rt. The reaction was quenched with water/ice (5 mL). The resulting mixture was concentrated under vacuum. The residue was eluted from silica gel with DCM/MeOH (10:1). The crude product was purified by Prep-HPLC with the following conditions: Xselect CSH OBD Column 30*150 mm 5 um; Mobile phase, water (0.05% TFA) and ACN (18% PhaseB up to 38% over 7 min); Detector, UV 210 nm. This resulted in 56.4 mg of the title compound as a white solid. MS-ESI: 408 (M+1).

$^1H$ NMR (400 MHz, MeOD-$d_4$) δ 7.92 (s, 1H), 7.82-7.86 (m, 1H), 7.80-7.71 (m, 2H), 4.28 (s, 2H), 3.92-3.79 (m, 2H), 3.14 (s, 3H), 3.04-2.95 (m, 1H), 2.94 (s, 3H), 2.31 (t, J=11.4 Hz, 1H), 2.00-1.90 (m, 2H), 1.85-1.51 (m, 6H), 1.34-1.12 (m, 4H), 1.11-0.96 (m, 3H).

Examples in the following table were prepared using similar conditions as described in PH-AOV-0138 from appropriate starting materials.

| Ex | Structure | Name | Data | Prep Info |
|---|---|---|---|---|
| AOV-0139 | 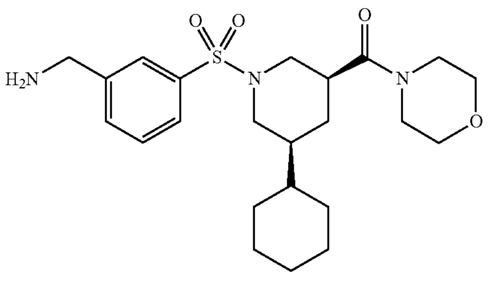 racemic | cis-(1-((3-(Aminomethyl)phenyl)sulfonyl)-5-cyclohexylpiperidin-3-yl)(morpholino)methanone | MS-ESI: 450(M + 1) | XBridge Prep Phenyl OBD, 5 um, 19*250 mm; water(10 mM $NH_4HCO_3$ + 0.1% $NH_3$•$H_2O$) and MeOH (68% MeOH up to 78% MeOH over 7 min); |

-continued

| Ex | Structure | Name | Data | Prep Info |
|---|---|---|---|---|
| AOV-0140 | 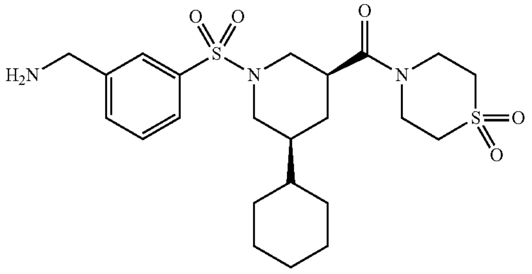 racemic | cis-(1-((3-(Aminomethyl) phenyl)sulfonyl)-5-cyclohexylpiperidin-3-yl)(1,1-dioxidothio-morpholino)methanone | MS-ESI: 498(M + 1) | XBridge Prep Phenyl OBD Column, 5 um, 19*250 mm; water(10 mM $NH_4HCO_3$ + 0.1% $NH_3$•$H_2O$) and MeOH (63% MeOH up to 78% MeOH in 10 min) |

Example 22: Synthesis of PH-AOV-0136 (Method Q)

Scheme 32

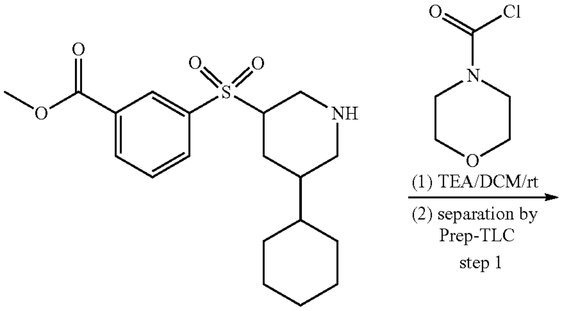

Intermediate 22

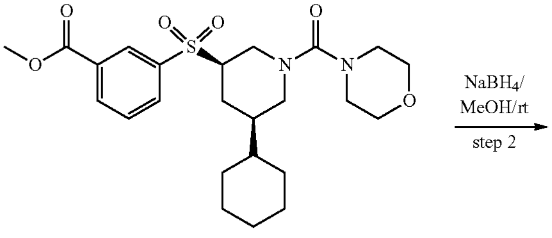

racemic
PH-AOV-0136-1

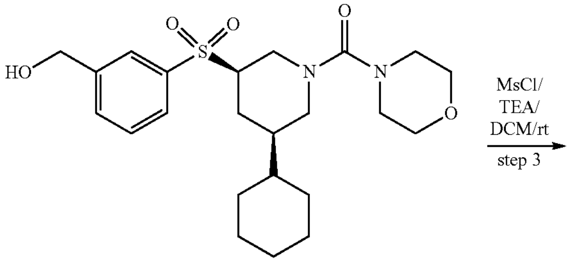

racemic
PH-AOV-0136-2

-continued

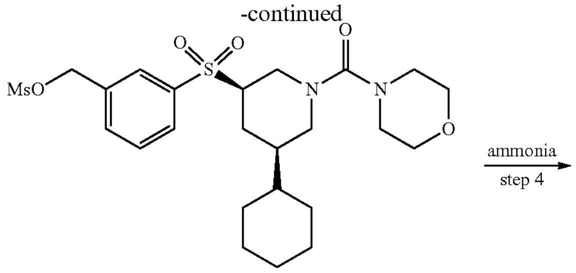

racemic
PH-AOV-0136-2

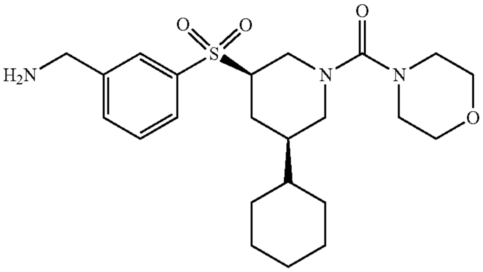

racemic
PH-AOV-0136

Step 1: cis-Methyl 3-((5-cyclohexyl-1-(morpholine-4-carbonyl)piperidin-3-yl)sulfonyl)benzoate To a stirred solution of methyl 3-((5-cyclohexylpiperidin-3-yl)sulfonyl)benzoate (200 mg, 0.55 mmol, 1.00 equiv) in DCM (10 mL) were added morpholine-4-carbonyl chloride (164 mg, 1.09 mmol, 2.00 equiv) and TEA (166 mg, 1.64 mmol, 3.00 equiv). The resulting solution was stirred for 16 h at rt. The resulting mixture was concentrated under vacuum. The residue was eluted from silica gel with EtOAc/PE (1:1). This resulted in 100 mg (38%) of the title compound as yellow oil. MS-ESI: 479 (M+1).

Steps 2-4 used similar procedures for converting compound PH-AOV-0142-1 to PH-AOV-0142 shown in Method O to afford PH-AOV-0136 from PH-AOV-0136-1. MS-ESI: 450 (M+1).

$^1H$ NMR (400 MHz, MeOD-$d_4$) δ 8.00 (s, 1H), 7.91 (d, J=8.0 Hz 1H), 7.81 (d, J=7.6 Hz, 1H), 7.19 (dd, J=7.6 Hz, 7.6 Hz, 1H), 4.10 (s, 2H), 3.85-3.77 (m, 1H), 3.71-3.62 (m, 1H), 3.61-3.54 (s, 3H), 3.45-3.36 (m, 1H), 3.23-3.15 (m,

3H), 2.83 (q, J=12.4 Hz, 1H), 2.59-2.50 (m, 1H), 2.29-2.18 (m, 1H), 1.83-1.65 (m, 5H), 1.56-1.36 (m, 2H), 1.35-1.12 (m, 6H), 1.11-0.88 (m, 3H).

Example 23: Synthesis of PH-AOV-0126 (Method R)

Scheme 33

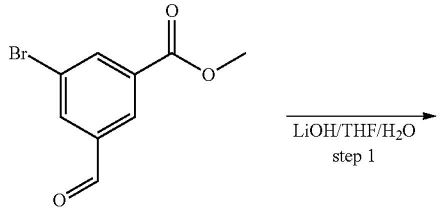

PH-AOV-0126-1

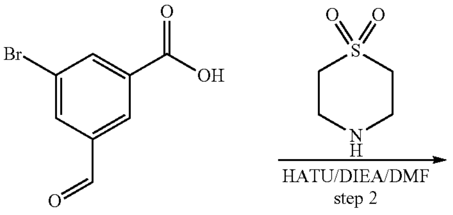

PH-AOV-0126-2

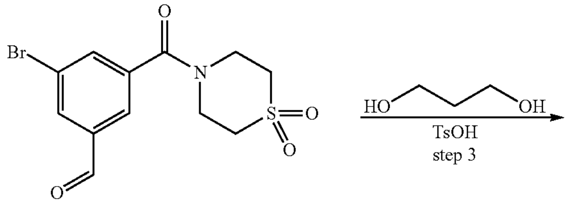

PH-AOV-0126-3

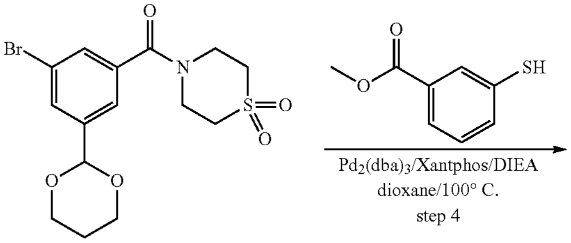

PH-AOV-0126-4

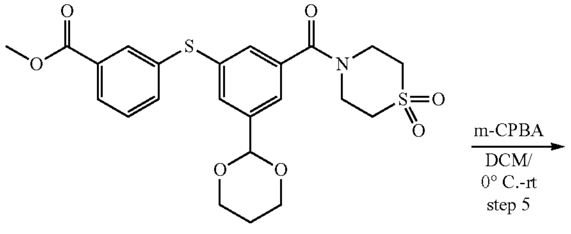

PH-AOV-0126-5

-continued

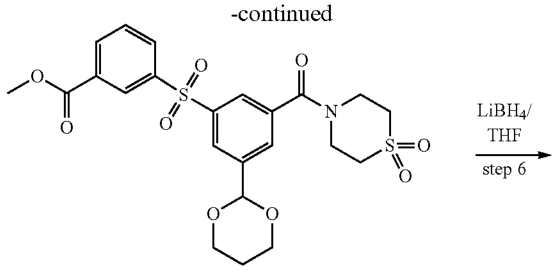

PH-AOV-0126-6

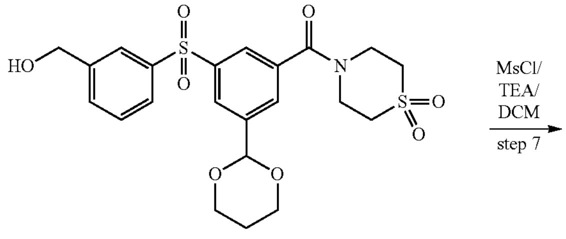

PH-AOV-0126-7

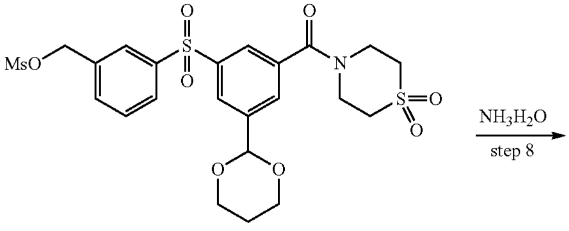

PH-AOV-0126-8

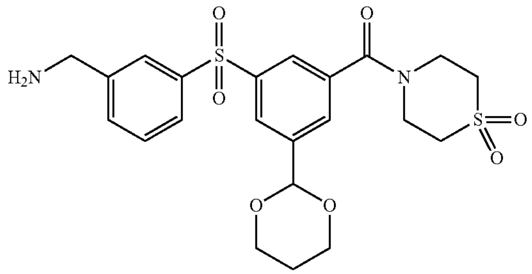

PH-AOV-0126

Step 1: 3-Bromo-5-formylbenzoic acid

To a stirred solution of methyl 3-bromo-5-formylbenzoate (2.0 g, 8.22 mmol, 1.00 equiv) in THF (20 mL) was added a solution of LiOH (592 mg, 24.6 mmol, 3.00 equiv) in $H_2O$ (20 mL). The reaction mixture was stirred for 10 min at rt. The pH value of the solution was adjusted to 3 with HCl (1 M) and extracted with EtOAc (3×60 mL). The combined organic layers were dried over anhydrous $Na_2SO_4$ and concentrated under vacuum. This resulted in 1.8 g (crude) of the title compound as yellow oil. MS-ESI: 227/229 (M−1).

Step 2: 3-Bromo-5-(1,1-dioxidothiomorpholine-4-carbonyl)benzaldehyde

To a stirred solution of 3-bromo-5-formylbenzoic acid (1.0 g, crude) in DMF (20 mL) were added thiomorpholine 1,1-dioxide (885 mg, 6.56 mmol, 1.50 equiv), HATU (2.49 g, 6.55 mmol, 1.50 equiv) and DIEA (1.69 g, 13.1 mmol, 3.00 equiv). The resulting solution was stirred for 16 h at rt. The reaction was quenched with water (50 mL) and extracted with EtOAc (3×50 mL). The combined organic layers were dried over anhydrous $Na_2SO_4$ and concentrated under vacuum. The residue was eluted from silica gel with EtOAc/PE (1:3). This resulted in 1.1 g (73%) of the title compound as a yellow solid. MS-ESI: 346/348 (M+1).

Step 3: (3-Bromo-5-(1,3-dioxan-2-yl)phenyl)(1,1-dioxidothiomorpholino)methanone

To a stirred solution of 3-bromo-5-(1,1-dioxidothiomorpholine-4-carbonyl)benzaldehyde (1.0 g, 2.89 mmol, 1.00 equiv) in 1,3-propandiol (10 mL) was added para-toluene sulfonate (49.7 mg, 0.29 mmol, 0.10 equiv). The resulting solution was stirred for 2 h at 70° C. The reaction was quenched with water (20 mL) and extracted with 3×10 mL of EtOAc. The combined organic layers were dried over anhydrous $Na_2SO_4$ and concentrated under vacuum. The residue was eluted from silica gel with EtOAc/PE (1:1). This resulted in 800 mg (68.5%) of the title compound as yellow oil. MS-ESI: 404/406 (M+1).

Step 4: Methyl 3-((3-(1,3-dioxan-2-yl)-5-(1,1-dioxidothiomorpholine-4-carbonyl)phenyl)thio)benzoate To a stirred solution of (3-bromo-5-(1,3-dioxan-2-yl)phenyl)(1,1-dioxidothiomorpholino)methanone (800 mg, 1.98 mmol, 1.00 equiv) in dioxane (10 mL) were added methyl 3-mercaptobenzoate (666 mg, 3.96 mmol, 2.00 equiv), $Pd_2(dba)_3$ (362 mg, 0.396 mmol, 0.20 equiv), Xantphos (343 mg, 0.59 mmol, 0.30 equiv) and DIEA (767 mg, 5.94 mmol, 3.00 equiv) in portions under nitrogen. The resulting solution was stirred for 3 h at 100° C. The reaction was quenched with $H_2O$ (20 mL) and extracted with EtOAc (3×10 mL). The combined organic layers were dried over anhydrous $Na_2SO_4$ and concentrated under vacuum. The residue was eluted from silica gel with EtOAc/PE (2:1). This resulted in 700 mg (72%) of the title compound as a yellow solid. MS-ESI: 492 (M+1).

Step 5: Methyl 3-((3-(1,3-dioxan-2-yl)-5-(1,1-dioxidothiomorpholine-4-carbonyl)phenyl)sulfonyl) benzoate To a stirred solution of methyl 3-((3-(1,3-dioxan-2-yl)-5-(1,1-dioxidothiomorpholine-4-carbonyl)phenyl)thio) benzoate (700 mg, 1.42 mmol, 1.00 equiv) in DCM (1 mL) was added m-CPBA (737 mg, 4.27 mmol, 3.00 equiv) in portions at 0° C. The resulting solution was stirred for 2 h at rt. The reaction was quenched with sat. $Na_2S_2O_3$ aq. (20 mL) and extracted with DCM (3×20 mL). The combined organic layers were dried with anhydrous $Na_2SO_4$ and concentrated under vacuum. The residue was eluted from silica gel column with EtOAc/PE (2:1). This resulted in 600 mg (80.5%) of the title compound as a yellow solid. MS-ESI: 524 (M+1).

Steps 6-8 used similar procedures for converting compound PH-AOV-0022-1 to PH-AOV-0022 shown in Method C to afford PH-AOV-0126 from PH-AOV-0126-6. MS-ESI: 495 (M+1).

$^1H$ NMR (400 MHz, MeOD-$d_4$) δ 8.18-8.12 (m, 2H), 8.03 (s, 1H), 7.90 (d, J=8.0 Hz, 1H), 7.86 (s, 1H), 7.67 (d, J=8.0 Hz, 1H), 7.58 (dd, J=8.0 Hz, 7.6 Hz, 1H), 5.66 (s, 1H), 4.31-4.14 (m, 3H), 4.13-4.00 (m, 3H), 3.90 (s, 2H), 3.86-3.70 (m, 2H), 3.29-3.21 (m, 3H), 3.15 (s, 1H), 2.24-2.08 (m, 1H), 1.56-1.46 (m, 1H).

Example 24: Synthesis of PH-AOV-0147 (Method S)

Scheme 34

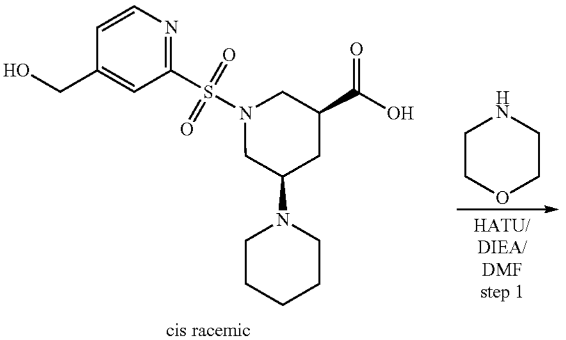

cis racemic
intermediate 23

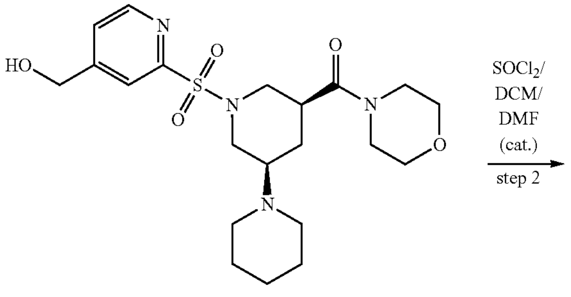

cis racemic
PH-AOV-0147-1

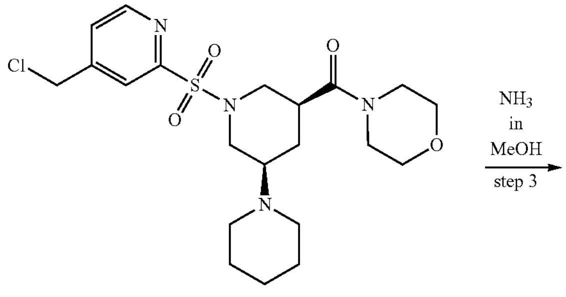

cis racemic
PH-AOV-0147-2

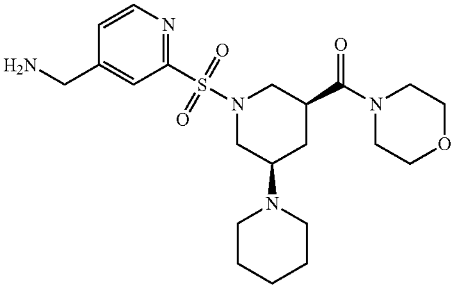

cis racemic
PH-AOV-0147

Step 1: cis-(1'-((4-(Hydroxymethyl)pyridin-2-yl) sulfonyl)-[1,3'-bipiperidin]-5'-yl)(morpholino)methanone To a stirred mixture of cis-1'-((4-(hydroxymethyl)pyridin-2-yl)sulfonyl)-[1,3'-bipiperidine]-5'-carboxylic acid (710 mg, crude) in DMF (5 mL) were added morpholine (132 mg, 1.52 mmol, 1.5 equiv), HATU (578 mg, 1.52 mmol, 1.5 equiv) and DIEA (393 mg, 3.05 mmol, 3.0 equiv) at rt. The reaction mixture was stirred overnight at rt. The residue was purified by Prep-TLC with DCM/MeOH (10:1). This resulted in 320 mg (69%, over two steps) of the title compound as yellow oil. MS-ESI: 453 (M+1).

Step 2: cis-(1'-((4-(Chloromethyl)pyridin-2-yl)sulfonyl)-[1,3'-bipiperidin]-5'-yl)(morpholino)methanone To a stirred mixture of cis-(1'-((4-(hydroxymethyl)pyridin-2-yl)sulfonyl)-[1,3'-bipiperidin]-5'-yl)(morpholino) methanone (210 mg, 0.46 mmol, 1.00 equiv) in DCM (2 mL) were added $SOCl_2$ (2 mL) and DMF (0.02 mL). The resulting mixture was stirred for 2 h at rt. The reaction mixture was concentrated under vacuum and purified by Prep-TLC with DCM/MeOH (10:1). This resulted in 180 mg (82%) of the title compound as yellow oil. MS-ESI: 471 (M+1).

Step 3: cis-(1'-((4-(Aminomethyl)pyridin-2-yl)sulfonyl)-[1,3'-bipiperidin]-5'-yl)(morpholino)methanone A solution of cis-(1'-((4-(chloromethyl)pyridin-2-yl) sulfonyl)-[1,3'-bipiperidin]-5'-yl)(morpholino)methanone (180 mg, 0.38 mmol, 1.0 equiv) in $NH_3$ in MeOH (7M, 5 mL) was stirred overnight at 60° C. The reaction mixture was concentrated under vacuum. The crude product was purified by Prep-HPLC with the following conditions: Sunfire prep C18 Column, 30*150 mm, 5 μm; Mobile Phase A: water (0.05% TFA), Mobile Phase B: ACN; Flow rate: 60 mL/min; Gradient: 5% B to 17% B over 7 min; Detector, UV 220 nm; RT1(min): 5.48. This resulted in 45.7 mg (26.6%) of the title compound as a white solid. MS-ESI: 452 (M+1).

$^1$H NMR (400 MHz, MeOD-$d_4$) δ 8.82 (d, J=4.8 Hz, 1H), 8.13 (s, 1H), 7.75 (d, J=4.8 Hz, 1H), 4.35 (s, 2H), 3.46-4.04 (m, 14H), 3.45-3.35 (m, 2H), 3.18-2.94 (m, 2H), 2.36-2.14 (m, 2H), 2.13-1.96 (m, 2H), 1.95-1.75 (m, 3H), 1.65-1.48 (m, 1H).

Examples in the following table were prepared using similar conditions as described in PH-AOV-0147 from appropriate starting materials.

| Ex | Structure | Name | Data | Prep Info |
|---|---|---|---|---|
| AOV-0148 | 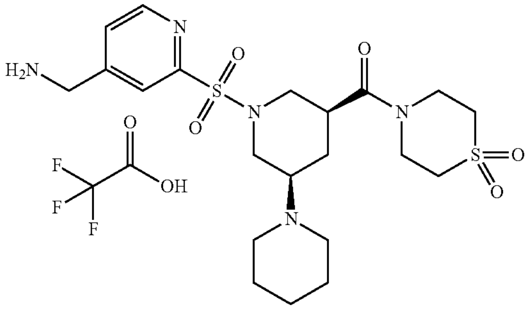 cis racemic | cis-(1'-((4-(Aminomethyl) pyridin-2-yl)sulfonyl)-[1,3'-bipiperidin]-5'-yl)(1,1-dioxidothio-morpholino) methanone 2,2,2-trifluoroacetate | MS-ESI: 500(M + 1) | Sunfire prep C18 Column, 30*150 mm, 5 μm; water(0.05% TFA) and ACN (7% ACN up to 13% ACN in 10 min) |
| AOV-0149 | 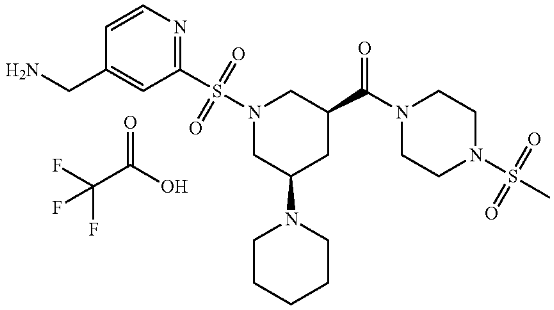 cis racemic | cis-(1'-((4-(Aminomethyl) pyridin-2-yl)sulfonyl)-[1,3'-bipiperidin]-5'-yl)(4-(methylsulfonyl) piperazin-1-yl)methanone 2,2,2-trifluoroacetate | MS-ESI: 529(M + 1) | Sunfire prep C18 Column, 30*150 mm, 5 μm; water(0.05% TFA) and ACN (7% ACN up to 13% ACN in 8 min) |

-continued

| Ex | Structure | Name | Data | Prep Info |
|---|---|---|---|---|
| AOV-0150 | 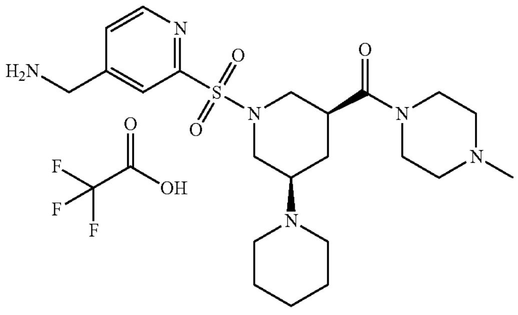 cis racemic | cis-(1'-((4-(Aminomethyl) pyridin-2-yl)sulfonyl)-[1,3'-bipiperidin]-5'-yl)(4-methylpiperazin-1-yl)methanone 2,2,2-trifluoroacetate | MS-ESI: 465(M + 1) | SunFire C18 OBD Prep Column, 19*250 mm, 5 μm; water(0.05% TFA) and ACN (2% ACN to 20% ACN in 13 min) |
| AOV-0155 | 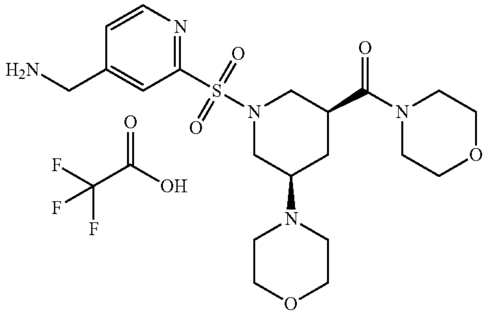 cis racemic | cis-(1-((4-(Aminomethyl) pyridin-2-yl)sulfonyl)-5-morpholino-piperidin-3-yl)(morpholino) methanone 2,2,2-trifluoroacetate | MS-ESI: 454(M + 1) | Xselect CSH C18 OBD Column 30*150 mm 5 μm, n; water(0.05% TFA) and ACN (2% ACN to 12% ACN in 7 min) |
| AOV-0156 | 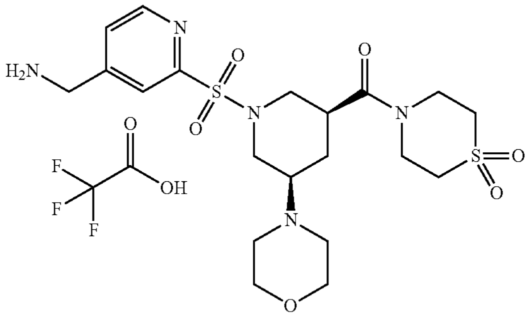 cis racemic | cis-(1-((4-(Aminomethyl) pyridin-2-yl)sulfonyl)-5-morpholino-piperidin-3-yl)(1,1-dioxidothio-morpholino) methanone 2,2,2-trifluoroacetate | MS-ESI: 502(M + 1) | SunFire C18 OBD Prep Column, 19*250 mm, 5 μm; water(0.05% TFA) and ACN (2% ACN to 13% ACN in 7 min) |
| AOV-0194 | 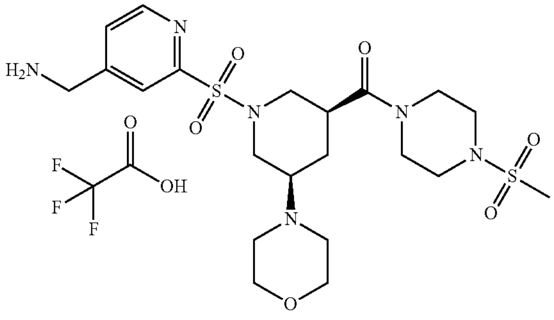 cis racemic | cis-(1-((4-(Aminomethyl) pyridin-2-yl)sulfonyl)-5-morpholino-piperidin-3-yl)(4-(methylsulfonyl) piperazin-1-yl)methanone 2,2,2-trifluoroacetate | MS-ESI: 531(M + 1) | SunFire C18 OBD Prep Column, 19*250 mm, 5 μm; water(0.05% TFA) and ACN (2% ACN to 12% ACN in 9 min) |

Example 25: Synthesis of PH-AOV-0186 (Method T)

Scheme 35

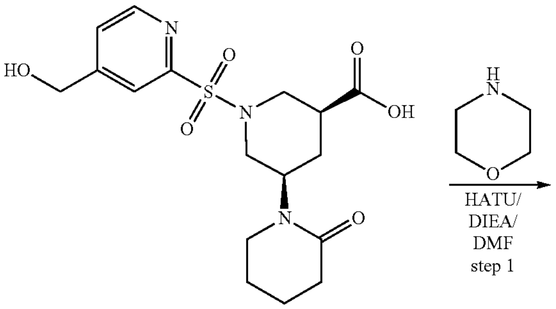

cis racemic
intermediate 25

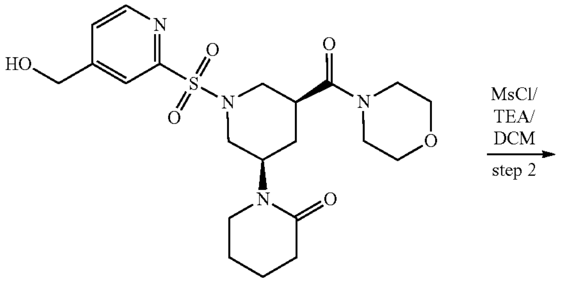

cis racemic
PH-AOV-0186-1

-continued

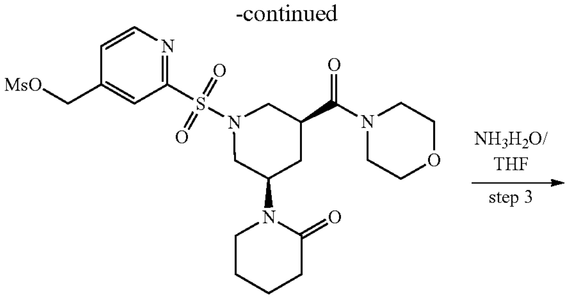

cis racemic
PH-AOV-0185-6-2

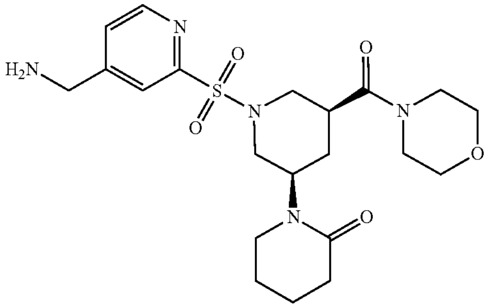

cis racemic
PH-AOV-0186

Step 1: used similar procedures for converting compound intermediate 23 to PH-AOV-0147-1 shown in Method S to afford PH-AOV-0186-1 from intermediate 25. MS-ESI: 467 (M+1).

Steps 2-3 used similar procedures for converting compound PH-AOV-0022-2 to PH-AOV-0022 shown in Method C to afford PH-AOV-0186 from PH-AOV-0186-1. MS-ESI: 466 (M+1).

$^1$H NMR (400 MHz, MeOD-$d_4$) δ 8.82 (d, J=4.8 Hz, 1H), 8.18 (s, 1H), 7.73 (d, J=3.6 Hz, 1H), 4.89 (s, 2H), 4.10-3.98 (m, 2H), 3.81-3.58 (m, 8H), 3.29-3.15 (m, 3H), 3.14-2.91 (m, 3H), 2.36 (t, J=6.0 Hz, 2H), 1.93 (q, J=12.4 Hz, 1H), 1.83-1.66 (m, 4H), 1.33 (t, J=7.2 Hz, 1H).

Examples in the following table were prepared using similar conditions as described in PH-AOV-0186 from appropriate starting materials.

| Ex | Structure | Name | Data | Prep Info |
|---|---|---|---|---|
| AOV-0187 | 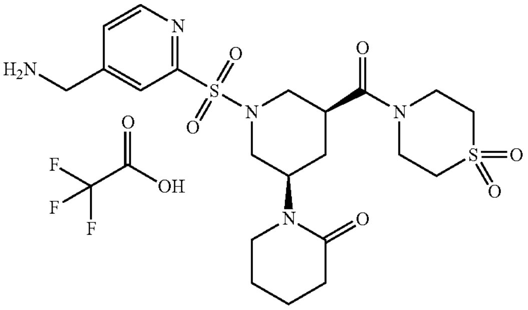 cis racemic | cis-1'-((4-(Aminomethyl) pyridin-2-yl)sulfonyl)-5'-(1,1-dioxidothio-morpholine-4-carbonyl)-[1,3'-bipiperidin]-2-one 2,2,2-trifluoroacetate | MS-ESI: 514(M + 1) | SunFire C18 OBD Prep Column, 19*250 mm, 5 μm; water(0.05% TFA) and ACN (7% ACN to 26% ACN in 7 min) |

-continued

| Ex | Structure | Name | Data | Prep Info |
|---|---|---|---|---|
| AOV-0188 | 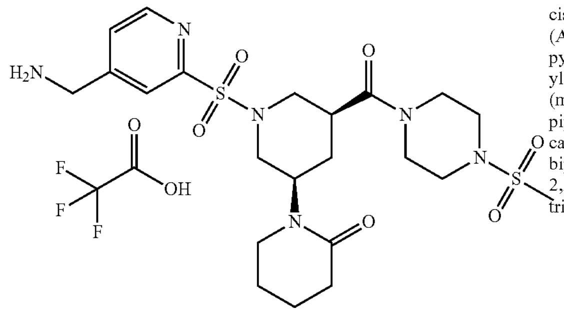 cis racemic | cis-1'-((4-(Aminomethyl) pyridin-2-yl)sulfonyl)-5'-(4-(methylsulfonyl) piperazine-1-carbonyl)-[1,3'-bipiperidin]-2-one 2,2,2-trifluoroacetate | MS-ESI: 543(M + 1) | SunFire C18 OBD Prep Column, 19*250 mm, 5 μm; water(0.05% TFA ) and ACN (10% ACN to 25% ACN in 7 min) |

Example 26: In vitro characterization of exemplary LOX enzyme-inhibiting compounds

Permeability Study

Caco-2 cell suspensions were dispensed into the inserts of the 96-well HTS Transwell plate and cultivated for 14-18 days. Transepithelial electrical resistance (TEER) across the monolayer was measured using Millicell Epithelial Volt-Ohm measuring system. The Caco-2 plate was then washed twice with pre-warmed HBSS (pH 7.4) and incubated at 37° C. for 30 minutes. To determine the rate of drug transport in the apical to basolateral direction. 5 μM test compound was added to the Transwell insert and the wells in the receiver plate were filled with HBSS (pH 7.4). To determine the rate of drug transport in the basolateral to apical direction, 5 μM test compound was added to the receiver plate wells and then the Transwell inserts were filled with HBSS (pH 7.4). The plates were incubated at 37° C. for 2 hours. 50 μL samples from donor sides and receiver sides were transferred to wells of a new 96-well plate followed by the addition of 4 volume of cold methanol containing internal standards (IS). Samples were centrifuged and the supernatant was used for LC-MS/MS analysis. After the incubation, residue solutions were removed from the Transwell plates, and Lucifer yellow (100 μM) solution was added to each Transwell insert, followed by filling the receiver wells with HBSS. The plates were incubated at 37° C. for 30 minutes. 80 μL samples were removed from the apical and basolateral wells and the fluorescence of Lucifer yellow was measured in a microplate reader with 485 nM excitation and 530 nM emission.

TABLE 9

Permeability Results of Exemplary Compounds in Caco-2 Cell Line

| Compound ID | $P_{app}$ (A-B) ($10^{-6}$, cm/s) | $P_{app}$ (B-A) ($10^{-6}$, cm/s) | Efflux Ratio | Recovery (%)AP-BL | Recovery (%)BL-AP |
|---|---|---|---|---|---|
| AOV-0013B | 1.16 | 28.49 | 24.48 | 76.77 | 78.79 |
| AOV-0075B | 0.40 | 12.08 | 30.07 | 72.13 | 83.49 |
| AOV-0091 | 0.11 | 15.60 | 137.77 | 68.63 | 78.19 |

TABLE 9-continued

Permeability Results of Exemplary Compounds in Caco-2 Cell Line

| Compound ID | $P_{app}$ (A-B) ($10^{-6}$, cm/s) | $P_{app}$ (B-A) ($10^{-6}$, cm/s) | Efflux Ratio | Recovery (%)AP-BL | Recovery (%)BL-AP |
|---|---|---|---|---|---|
| AOV-0023 | 0.38 | 23.26 | 61.38 | 86.50 | 102.95 |
| AOV-0074 | 0.71 | 33.34 | 47.15 | 77.38 | 90.82 |

Microsome Stability Study

Pooled CD-1 mouse liver microsomes at 0.5 mg/mL were pre-incubated in phosphate buffer (100 mM, pH 7.4) containing 1 mM NADPH and 3 mM $MgCl_2$ in a 96-well plate for 5 minutes at 37° C. Ultra-pure water was added instead of NADPH in the negative control group to exclude the misleading factor that resulted from instability of chemical itself. The reaction was initiated by adding test compound at the final concentration of 2 μM and incubated at 37° C. Aliquots were taken from the incubation at 0, 15, 30, 45 and 60 minutes followed by the addition of 4 volume of cold acetonitrile containing internal standards. Samples were centrifuged and supernatant was used for LC-MS/MS analysis.

TABLE 10

Metabolic Stability of Exemplary Compounds in Male Mouse Liver Microsomes

| Compound ID | Species | $T_{1/2}$ (min) | $CL_{int}$ (μL/min/mg protein) | Scaled-up $CL_{int}$ (mL/min/Kg) | Predicted hepatic CL (mL/min/kg) |
|---|---|---|---|---|---|
| AOV-0013B | Mouse | 79.65 | 17.40 | 76.13 | 41.24 |
| AOV-0075B | Mouse | 37.14 | 37.32 | 163.28 | 58.02 |
| AOV-0091 | Mouse | 24.53 | 56.50 | 247.21 | 65.98 |
| AOV-0023 | Mouse | 269.42 | 5.14 | 22.51 | 18.00 |
| AOV-0074 | Mouse | 113.21 | 12.24 | 53.56 | 33.58 |
| AOV-0120 | Mouse | 37.05 | 37.41 | 163.65 | 58.07 |
| AOV-0122 | Mouse | 21.30 | 65.08 | 284.71 | 68.38 |
| AOV-0146 | Mouse | 31.98 | 43.34 | 189.63 | 61.03 |

Example 27: In Vivo Characterization of Exemplary LOX Enzyme-Inhibiting Compounds PK/PD Study Experimental Design The objective of this study was to determine the pharmacokinetic (PK) profile of LOX enzyme inhibiting compounds following IV and PO administrations in male CD1 mice. Dosing information is shown in Table 11:

| Group | Dose Level (mg/kg) | Dose Volume (mL/kg) | Conc. (mg/Lm | Administration Route | No. of Animals |
|---|---|---|---|---|---|
| 1 | 10 | 5 | 2 | IV | 3 |
| 2 | 50 | 10 | 5 | PO | 3 |

Male CDT mice from a qualified provider were used for all studies. Mice were 6-8 weeks old at the time of the experiment (~20-30 g body weight). All animals for IV & PO administration were fasted overnight and fed after 4 hours collection. The dose formulation was kept at room temperature no more than 2 hours.

Dose formulations were prepared fresh on the day of dosing and stored at ambient temperature. Dose formulations were as following:

| Compound ID | Vehicle Composition |
|---|---|
| AOV-0074 | 5% DMSO/5% Solutol/90% Water |
| AOV-0122 | 5% DMSO/5% Solutol/90% Water |
| AOV-0146 | 5% DMSO/5% Solutol/90% Water |

Blood samples were collected from the dorsal metatarsal vein. Circa 0.03 mL were collected per time point and 0.3 mL at final time point via heart puncture. The blood samples were centrifuged at 4000 g for 5 minutes at 4° C. to obtain plasma and samples were immediately frozen in the upright position and stored at −75±15° C. prior to analysis.

Blood samples were collected at time points outlined in Table 12:

| Group | PK Time Points |
|---|---|
| IV | 5, 15, 30 min, 1, 2, 4, 8, 24 hours post dose |
| PO | 15, 30 min, 1, 2, 4, 8, 24 hours post dose |

Acceptable time ranges for blood collection were as following: 5 min and 15 min: within ±0.25 minute, 30 min, 1 hour, and 2 hours: within +2 minutes; 4 hours, 6 hours, 8 hours, and 24 hours: within ±10 minutes.

During In-Life Phase, all mice were evaluated twice daily via cage side observation. A detailed clinical observation was performed once prior to dosing on Day 1, including measuring the body weight to dosing.

Analysis

Concentrations of LOX enzyme inhibiting compounds in the plasma were analyzed using a LC-MS/MS method. WinNonlin (Phoenix™, version 8.2) software was used for pharmacokinetic calculations. The following pharmacokinetic parameters were calculated, whenever possible from the plasma concentration versus time data:

IV administration: $T_{1/2}$, $C_0$, $AUC_{last}$, $AUC_{inf}$, $MRT_{inf}$, Cl, Vss, Number of Points for Regression.

PO administration: $T_{1/2}$, $C_{max}$, $T_{max}$, $AUC_{last}$, $AUC_{inf}$ and F. Number of Points for Regression.

The pharmacokinetic data were described using descriptive statistics such as mean, standard deviation.

Results

Results are outlined in Table 13 (IV), Table 14 (PO) and FIGS. 1-3. Data represent mean values from three mice.

TABLE 13

| Pharmakokinetics Parameters - IV | | | | | | | | | |
|---|---|---|---|---|---|---|---|---|---|
| Compound ID | $T_{1/2}$ (h) | $CI_{obs}$ | $C_0$ | $AUC_{last}$ | $AUC_{inf}$ | $AUC_{_\%Extrap_}$obs | $MRT_{Inf_}$obs | $AUC_{last}$/D | $V_{ss_}$obs |
| PH-AOV-0074 | 0.89 | 85.5 | 3588 | 1962 | 1969 | 0.339 | 0.692 | 196 | 3.55 |
| PH-AOV-0122 | 1.27 | 148 | 3344 | 1143 | 1148 | 0.460 | 0.820 | 114 | 7.28 |
| PH-AOV-0146 | 4.78 | 103 | 6153 | 1638 | 1648 | 0.621 | 0.85 | 164 | 5.12 |

TABLE 14

| Pharmakokinetics Parameters - PO | | | | | | | | | |
|---|---|---|---|---|---|---|---|---|---|
| Compound ID | $T_{1/2}$ (h) | $T_{max}$ | $C_{max}$ | $AUC_{last}$ | $AUC_{inf}$ | $AUC_{_\%Extrap_}$obs | $MRT_{Inf_}$obs | $AUC_{last}$/D | F |
| PH-AOV-0074 | 0.821 | 0.417 | 5547 | 8854 | 8863 | 0.105 | 1.24 | 138 | 90 |
| PH-AOV-0122 | 1.15 | 0.5 | 1441 | 1771 | 1779 | 0.434 | 1.11 | 972 | 31 |
| PH-AOV-0146 | 5.62 | 0.250 | 503 | 563 | 590 | 4.01 | 3.68 | 11.3 | 7.2 |

EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

The discussion herein provides a better understanding of the nature of the problems confronting the art and should not be construed in any way as an admission as to prior art nor should the citation of any reference herein be construed as an admission that such reference constitutes "prior art" to the instant application.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

REFERENCES

Abbonante, V., et al. (2017). "Upregulation of lysyl oxidase and adhesion to collagen of human megakaryocytes and platelets in primary myelofibrosis." *Blood* 130(6): 829-831.

Abourbih, D. A., et al. (2010). "Lysyl oxidase expression and inhibition in uveal melanoma." *Melanoma Res* 20(2): 97-106.

Al-U'datt, D., et al. (2019). "Role of the lysyl oxidase enzyme family in cardiac function and disease." *Cardiovasc Res* 115(13): 1820-1837.

Albinger-Hegyi, A., et al. (2010). "Lysyl oxidase expression is an independent marker of prognosis and a predictor of lymph node metastasis in oral and oropharyngeal squamous cell carcinoma (OSCC)." *Int J Cancer* 126(11): 2653-2662.

Almassian, B., et al. (1991). "Induction of lung lysyl oxidase activity and lysyl oxidase protein by exposure of rats to cadmium chloride: properties of the induced enzyme." *Connect Tissue Res* 25(3-4): 197-208.

Amendola, P. G., et al. (2019). "Interplay Between LOX Enzymes and Integrins in the Tumor Microenvironment." *Cancers* (*Basel*) 11(5).

Aumiller, V., et al. (2017). "Comparative analysis of lysyl oxidase (like) family members in pulmonary fibrosis." *Sci Rep* 7(1): 149.

Baker, A. M., et al. (2013). "Lysyl oxidase enzymatic function increases stiffness to drive colorectal cancer progression through FAK." *Oncogene* 32(14): 1863-1868.

Barker, H. E., et al. (2012). "The rationale for targeting the LOX family in cancer." *Nat Rev Cancer* 12(8): 540-552.

Borel, A., et al. (2001). "Lysyl oxidase-like protein from bovine aorta. Isolation and maturation to an active form by bone morphogenetic protein-1." *J Biol Chem* 276 (52): 48944-48949.

Burke, A. A., et al. (2017). "Comparing hydrazine-derived reactive groups as inhibitors of quinone-dependent amine oxidases." *J Enzyme Inhib Med Chem* 32(1): 496-503.

Carter, E. A., et al. (1982). "Lysyl oxidase and collagenase in experimental acute and chronic liver injury." *Gastroenterology* 82(3): 526-534.

Chang, J., et al. (2017). "Pre-clinical evaluation of small molecule LOXL2 inhibitors in breast cancer." *Oncotarget* 8(16): 26066-26078.

Cheng, T., et al. (2014). "Lysyl oxidase promotes bleomycin-induced lung fibrosis through modulating inflammation." *J Mol Cell Biol* 6(6): 506-515.

Cheon, D. J., et al. (2014). "A collagen-remodeling gene signature regulated by TGF-beta signaling is associated with metastasis and poor survival in serous ovarian cancer." *Clin Cancer Res* 20(3): 711-723.

Chou, T. F., et al. (2007). "Engineered monomeric human histidine triad nucleotide-binding protein 1 hydrolyzes fluorogenic acyl-adenylate and lysyl-tRNA synthetase-generated lysyl-adenylate." *J Biol Chem* 282(20): 15137-15147.

Cosgrove, D., et al. (2018). "Lysyl oxidase like-2 contributes to renal fibrosis in Col4alpha3/Alport mice." *Kidney Int* 94(2): 303-314.

Counts, D. F., et al. (1981). "Collagen lysyl oxidase activity in the lung increases during bleomycin-induced lung fibrosis." *J Pharmacol Exp Ther* 219(3): 675-678.

de Bruyn, J. R., et al. (2018). "Fibrostenotic Phenotype of Myofibroblasts in Crohn's Disease is Dependent on Tissue Stiffness and Reversed by LOX Inhibition." *J Crohns Colitis* 12(7): 849-859.

Dentillo, D. B., et al. (2010). "Deregulation of LOXL1 and HTRA1 gene expression in endometriosis." *Reprod Sci* 17(11): 1016-1023.

Erler, J. T., et al. (2006). "Lysyl oxidase is essential for hypoxia-induced metastasis." *Nature* 440(7088): 1222-1226.

Gilad, G. M., et al. (2001). "Lysyl oxidase, the extracellular matrix-forming enzyme, in rat brain injury sites." *Neurosci Lett* 310(1): 45-48.

Gilad, G. M., et al. (2005). "Evidence for increased lysyl oxidase, the extracellular matrix-forming enzyme, in Alzheimer's disease brain." *Neurosci Lett* 376(3): 210-214.

Gorogh, T., et al. (2015). "Characterisation of seven newly established head and neck squamous cell carcinoma cell lines." *Eur Arch Otorhinolaryngol* 272(5): 1251-1258.

Goto, Y., et al. (2005). "Transforming growth factor-beta1 mediated up-regulation of lysyl oxidase in the kidneys of hereditary nephrotic mouse with chronic renal fibrosis." *Virchows Arch* 447(5): 859-868.

Hajdu, I., et al. (2018). "Inhibition of the LOX enzyme family members with old and new ligands. Selectivity analysis revisited." *Bioorg Med Chem Lett* 28(18): 3113-3118.

Halberg, N., et al. (2009). "Hypoxia-inducible factor 1alpha induces fibrosis and insulin resistance in white adipose tissue." *Mol Cell Biol* 29(16): 4467-4483.

Hase, H., et al. (2014). "LOXL2 status correlates with tumor stage and regulates integrin levels to promote tumor progression in ccRCC." *Mol Cancer Res* 12(12): 1807-1817.

Hutchinson, J. H., et al. (2017). "Small Molecule Lysyl Oxidase-like 2 (LOXL2) Inhibitors: The Identification of an Inhibitor Selective for LOXL2 over LOX." *ACS Med Chem Lett* 8(4): 423-427.

Kagan, H. M. and W. Li (2003). "Lysyl oxidase: properties, specificity, and biological roles inside and outside of the cell." *J Cell Biochem* 88(4): 660-672.

Kagan, H. M., et al. (1981). "Changes in aortic lysyl oxidase activity in diet-induced atherosclerosis in the rabbit." *Arteriosclerosis* 1(4): 287-291.

Kagan, H. M., et al. (1979). "Purification and properties of four species of lysyl oxidase from bovine aorta." *Biochem J* 177(1): 203-214.

Kim, D., et al. (2015). "Impaired osteogenesis in Menkes disease-derived induced pluripotent stem cells." *Stem Cell Res Ther* 6: 160.

Kim, Y., et al. (2009). "Differential expression of the LOX family genes in human colorectal adenocarcinomas." *Oncol Rep* 22(4): 799-804 Kirschmann, D. A., et al. (2002). "A molecular role for lysyl oxidase in breast cancer invasion." *Cancer Res* 62(15): 4478-4483.

Kumar, P., et al. (2018). "Periostin promotes liver fibrogenesis by activating lysyl oxidase in hepatic stellate cells." *J Biol Chem* 293(33): 12781-12792.

Lapointe, J., et al. (2004). "Gene expression profiling identifies clinically relevant subtypes of prostate cancer." *Proc Natl Acad Sci USA* 101(3): 811-816.

Le, Q. T., et al. (2009). "Validation of lysyl oxidase as a prognostic marker for metastasis and survival in head and neck squamous cell carcinoma: Radiation Therapy Oncology Group trial 90-03." *J Clin Oncol* 27(26): 4281-4286.

Leiva, O., et al. (2019). "Novel lysyl oxidase inhibitors attenuate hallmarks of primary myelofibrosis in mice." *Int J Hematol* 110(6): 699-708.

Li, P. A., et al. (2004). "Up-regulation and altered distribution of lysyl oxidase in the central nervous system of mutant SOD1 transgenic mouse model of amyotrophic lateral sclerosis." *Brain Res Mol Brain Res* 120(2): 115-122.

Li, W., et al. (2003). "Lysyl oxidase oxidizes basic fibroblast growth factor and inactivates its mitogenic potential." *J Cell Biochem* 88(1): 152-164.

Liu, N., et al. (2017). "Nuclear expression of lysyl oxidase enzyme is an independent prognostic factor in rectal cancer patients." *Oncotarget* 8(36): 60015-60024.

Liu, S. B., et al. (2016). "Lysyl oxidase activity contributes to collagen stabilization during liver fibrosis progression and limits spontaneous fibrosis reversal in mice." *FASEB J* 30(4): 1599-1609

Lopez, B., et al. (2009). "Impact of treatment on myocardial lysyl oxidase expression and collagen cross-linking in patients with heart failure." *Hypertension* 53(2): 236-242.

Lu, J., et al. (2018). "Hypoxia-inducible factor-1alpha regulates epithelial-to-mesenchymal transition in paraquat-induced pulmonary fibrosis by activating lysyl oxidase." *Exp Ther Med* 15(3): 2287-2294.

Lu, M., et al. (2019). "Induction of LOX by TGF-beta1/Smad/AP-1 signaling aggravates rat myocardial fibrosis and heart failure." *IUBMB Life* 71(11): 1729-1739.

Lucero, H. A. and H. M. Kagan (2006). "Lysyl oxidase: an oxidative enzyme and effector of cell function." *Cell Mol Life Sci* 63(19-20): 2304-2316.

Lucero, H. A., et al. (2008). "Lysyl oxidase oxidizes cell membrane proteins and enhances the chemotactic response of vascular smooth muscle cells." *J Biol Chem* 283(35): 24103-24117.

Mambetsariev, I., et al. (2014). "Stiffness-activated GEF-H1 expression exacerbates LPS-induced lung inflammation." *PLoS One* 9(4): e92670.

Martin, A., et al. (2015). "Lysyl oxidase-like 2 represses Notch1 expression in the skin to promote squamous cell carcinoma progression." *EMBO J* 34(8): 1090-1109.

Mesarwi, O. A., et al. (2015). "Lysyl Oxidase as a Serum Biomarker of Liver Fibrosis in Patients with Severe Obesity and Obstructive Sleep Apnea." *Sleep* 38(10): 1583-1591.

Miana, M., et al. (2015). "The lysyl oxidase inhibitor beta-aminopropionitrile reduces body weight gain and improves the metabolic profile in diet-induced obesity in rats." *Dis Model Mech* 8(6): 543-551.

Miller, B. W., et al. (2015). "Targeting the LOX/hypoxia axis reverses many of the features that make pancreatic cancer deadly: inhibition of LOX abrogates metastasis and enhances drug efficacy." *EMBO Mol Med* 7(8): 1063-1076.

Min, C., et al. (2007). "The tumor suppressor activity of the lysyl oxidase propeptide reverses the invasive phenotype of Her-2/neu-driven breast cancer." *Cancer Res* 67(3): 1105-1112.

Murawaki, Y., et al. (1991). "Serum lysyl oxidase activity in chronic liver disease in comparison with serum levels of prolyl hydroxylase and laminin." *Hepatology* 14(6): 1167-1173.

Ovchinnikova, O. A., et al. (2014). "The collagen cross-linking enzyme lysyl oxidase is associated with the healing of human atherosclerotic lesions." *J Intern Med* 276(5): 525-536.

Papadantonakis, N., et al. (2012). "Megakaryocyte pathology and bone marrow fibrosis: the lysyl oxidase connection." *Blood* 120(9): 1774-1781.

Rivera, A. D. and A. M. Butt (2019). "Astrocytes are direct cellular targets of lithium treatment: novel roles for lysyl oxidase and peroxisome-proliferator activated receptor-gamma as astroglial targets of lithium." *Transl Psychiatry* 9(1): 211.

Rowbottom, M. W., et al. (2017). "Identification of 4-(Aminomethyl)-6-(trifluoromethyl)-2-(phenoxy) pyridine Derivatives as Potent, Selective, and Orally Efficacious Inhibitors of the Copper-Dependent Amine Oxidase, Lysyl Oxidase-Like 2 (LOXL2)." *J Med Chem* 60(10): 4403-4423.

Rowbottom, M. W. et al. (2016a). "Preparation of substituted pyridinylmethylamine compounds as lysyl oxidase-like 2 inhibitors". WO2016144702

Rowbottom, M. W. et al. (2016b). "Preparation of fluorinated pyridine derivatives as lysyl oxidase-like 2 inhibitors and uses thereof." WO2016144703

Rowbottom, M. W.; Hutchinson, J. H. (2017a). "Preparation of pyrimidine derivatives as Lysyl oxidase-like 2 inhibitors useful for the treatment of fibrosis." WO2017003862

Rowbottom, M. W.; Hutchinson, J. H. (2017b). "Lysyl oxidase-like 2 inhibitors and uses thereof." WO2017015221

Ruiz, L. A., et al. (2011). "Single-nucleotide polymorphisms in the lysyl oxidase-like protein 4 and complement component 3 genes are associated with increased risk for endometriosis and endometriosis-associated infertility." *Fertil Steril* 96(2): 512-515.

Ryner, L., et al. (2015). "Upregulation of Periostin and Reactive Stroma Is Associated with Primary Chemoresistance and Predicts Clinical Outcomes in Epithelial Ovarian Cancer." *Clin Cancer Res* 21(13): 2941-2951.

Saifi, M. A. and C. Godugu (2020). "Inhibition of lysyl oxidase ameliorates renal injury by inhibiting CD44-mediated pericyte detachment and loss of peritubular capillaries." *Life Sci* 243: 117294.

Salvador, F., et al. (2017). "Lysyl Oxidase-like Protein LOXL2 Promotes Lung Metastasis of Breast Cancer." *Cancer Res* 77(21): 5846-5859.

Sasaki, T., et al. (2016). "Loss of fibulin-4 results in abnormal collagen fibril assembly in bone, caused by impaired lysyl oxidase processing and collagen cross-linking." *Matrix Biol* 50: 53-66.

Sato, S., et al. (2011). "The Ras signaling inhibitor LOX-PP interacts with Hsp70 and c-Raf to reduce Erk activation and transformed phenotype of breast cancer cells." *Mol Cell Biol* 31(13): 2683-2695.

Schilter, H., et al. (2019). "The lysyl oxidase like 2/3 enzymatic inhibitor, PXS-5153A, reduces crosslinks and ameliorates fibrosis." *J Cell Mol Med* 23(3): 1759-1770.

Siegel, R. C., et al. (1978). "Biochemical and immunochemical study of lysyl oxidase in experimental hepatic fibrosis in the rat." *Proc Natl Acad Sci USA* 75(6): 2945-2949.

Smithen, D. A., et al. (2020). "2-Aminomethylene-5-sulfonylthiazole Inhibitors of Lysyl Oxidase (LOX) and LOXL2 Show Significant Efficacy in Delaying Tumor Growth." *J Med Chem* 63(5): 2308-2324.

Springer, C et. al. (2017). "Methylamine derivatives as lysyl oxidase inhibitors for the treatment of cancer." WO2017141049

Stangenberg, S., et al. (2018). "Lysyl oxidase-like 2 inhibition ameliorates glomerulosclerosis and albuminuria in diabetic nephropathy." *Sci Rep* 8(1): 9423.

Tadmor, T., et al. (2013). "The expression of lysyl-oxidase gene family members in myeloproliferative neoplasms." *Am J Hematol* 88(5): 355-358.

Tang, H., et al. (2017). "Lysyl oxidase drives tumour progression by trapping EGF receptors at the cell surface." *Nat Commun* 8: 14909.

Tjin, G., et al. (2017). "Lysyl oxidases regulate fibrillar collagen remodelling in idiopathic pulmonary fibrosis." *Dis Model Mech* 10(11): 1301-1312.

Uzel, M. I., et al. (2001). "Multiple bone morphogenetic protein 1-related mammalian metalloproteinases process pro-lysyl oxidase at the correct physiological site and control lysyl oxidase activation in mouse embryo fibroblast cultures." *J Biol Chem* 276(25): 22537-22543.

Van Bergen, T., et al. (2015). "The Role of LOX and LOXL2 in the Pathogenesis of an Experimental Model of Choroidal Neovascularization." *Invest Ophthalmol Vis Sci* 56(9): 5280-5289.

Virani, S. S., et al. (2020). "Heart Disease and Stroke Statistics-2020 Update: A Report From the American Heart Association." Circulation 141(9): e139-e596.

Vulpe, C., et al. (1993). "Isolation of a candidate gene for Menkes disease and evidence that it encodes a copper-transporting ATPase." *Nat Genet* 3(1): 7-13.

Wakasaki, H. and A. Ooshima (1990). "Synthesis of lysyl oxidase in experimental hepatic fibrosis." *Biochem Biophys Res Commun* 166(3): 1201-1204.

Wilhelmus, M. M., et al. (2013). "Extracellular matrix modulator lysyl oxidase colocalizes with amyloid-beta pathology in Alzheimer's disease and hereditary cerebral hemorrhage with amyloidosis—Dutch type." *Exp Gerontol* 48(2): 109-114.

Yang, J., et al. (2016). "Targeting LOXL2 for cardiac interstitial fibrosis and heart failure treatment." *Nat Commun* 7: 13710.

The invention claimed is:

1. A LOX enzyme-inhibiting compound in accordance with Formula I, or a pharmaceutically acceptable salt or hydrate thereof:

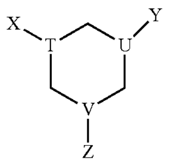

I wherein:

T, U, and V are nitrogen or carbon and only one of T, U, and Vis nitrogen;

X is independently selected from —$OR^1$, —$SO^2R^1$, and —C(═O)$R^1$;

Y is independently selected from —$OR^2$, —$SO^2R^2$, and —C(═O)$R^2$;

Z is independently selected from —$R^3$, —$CH_2$—$R^3$, —$SO^2R^3$, —C(═O)$R^3$, and —$OR^3$;

$R^1$ is phenyl or heteroaryl containing 1 to 2 heteroatom(s) each independently selected from N, O, and S, wherein said phenyl or heteroaryl is substituted with —$CR^4R^5NH_2$ and optionally substituted with halogen or lower alkyl, and wherein $R^4$ and $R^5$ are independently H or lower alkyl or $R^4$ and $R^5$ form a ($C_3$-$C_8$) cycloalkyl or ($C_1$-$C_8$) hetero-cycloalkyl or $R^4$ and $R^5$ are both H;

$R^2$ is substituted or unsubstituted phenyl, substituted or unsubstituted benzyl, substituted or unsubstituted heteroaryl containing 1 to 2 heteroatom(s) each independently selected from N, O, and S, ($C_1$-$C_8$) alkyl, ($C_3$-$C_8$) cycloalkyl, mono-, di-, or trihalo($C_1$-$C_4$)alkyl, or —$NR^6R^7$, wherein $R^6$ and $R^7$ are independently selected from H and lower alkyl or $R^6$ and $R^7$ form together a ($C_3$-$C_6$) hetero-cycloalkyl, wherein the ($C_3$-$C_6$) hetero-cycloalkyl optionally contains one additional heteroatom selected from N, O, and S, wherein N is optionally substituted with lower alkyl, —$SO^2R^8$, or —$OR^8$, wherein S is unsubstituted or forms sulfonyl, wherein said substituted phenyl, substituted benzyl, or substituted heteroaryl has at least one substituent being halogen, mono-, di-, or tri-halo($C_1$-$C_4$) alkyl, —$SO^2R^8$, or —$OR^8$, wherein $R^8$ is lower alkyl, cyano, lower alkyl, or —$SO^2NR^9R^{10}$, and wherein $R^9$ and $R^{10}$ are independently selected from H and lower alkyl;

$R^3$ is unsubstituted or substituted phenyl, substituted or unsubstituted benzyl, substituted or unsubstituted heteroaryl containing 1 to 2 heteroatom(s) each independently selected from N, O, and S, mono-, di-, or tri-halo($C_1$-$C_4$)alkyl, ($C_3$-$C_8$) cycloalkyl, ($C_1$-$C_8$) alkyl, or —$NR^{11}R^{12}$, wherein $R^{11}$ and $R^{12}$ are independently selected from H and lower alkyl or $R^{11}$ and $R^{12}$ form together a ($C_3$-$C_6$) hetero-cycloalkyl, wherein the ($C_3$-$C_6$) hetero-cycloalkyl optionally contains one additional heteroatom selected from N, O, and S, wherein N is optionally substituted with lower alkyl, —$SO^2R^{13}$, or —$OR^{13}$, wherein S is unsubstituted or forms sulfonyl, wherein said substituted phenyl, substituted benzyl, or substituted heteroaryl has at least one substituent being halogen, mono-, di- or tri-halo($C_1$-$C_4$) alkyl, —$SO^2R^{14}$, or —$OR^{14}$, wherein $R^{14}$ is lower alkyl, cyano, lower alkyl, or —$SO^2NR^{15}R^{16}$, and wherein $R^{15}$ and $R^{16}$ are independently selected from H and lower alkyl;

or a tautomer or stereoisomer thereof.

2. The compound according to claim 1, wherein T is nitrogen and U and V are carbon or wherein Vis nitrogen and U and T are carbon.

3. The compound according to claim 1, wherein $R^1$ is phenyl, thiophen-2-yl, pyridin-4-yl, pyridin-2-yl, thiazol-2-yl, or pyrimidin-2-yl, wherein said phenyl, thiophen-2-yl, pyridin-4-yl, pyridin-2-yl, thiazol-2-yl, or pyrimidin-2-yl is substituted with —$CR^4R^5NH_2$ and optionally halogen or lower alkyl, where $R^4$ and $R^5$ are independently H or lower alkyl or $R^4$ and $R^5$ form a ($C_3$-$C_8$) cycloalkyl or ($C_1$-$C_8$) hetero-cycloalkyl.

4. The compound according to claim 1, wherein when T is nitrogen, X is —$SO_2R^1$ and when Vis nitrogen, X is independently selected from —$OR^1$ or —$SO^2R^1$ and $R^1$ is phenyl where said phenyl is substituted with —$CR^4R^5NH_2$ and optionally halogen or lower alkyl, where $R^4$ and $R^5$ are independently H or lower alkyl or $R^4$ and $R^5$ form a cycloalkyl or hetero-cycloalkyl.

5. The compound according to claim 1, wherein when T is nitrogen, Z is independently selected from —$R^3$, —$CH_2$—$R^3$, and —$SO^2R^3$ or wherein V is nitrogen, Z is benzyl or benzoyl.

6. The compound according to claim 1, wherein $R^3$ is unsubstituted or substituted phenyl or unsubstituted or substituted 4-, 5-, or 6-membered heteroaryl containing 1 to 2 heteroatom(s) each independently selected from N, O, S when T is nitrogen and containing 1 to 2 nitrogen atom(s) when Vis nitrogen, wherein said substituted phenyl or 4-, 5-, or 6-membered heteroaryl has at least one substituent being halogen, cyano, methoxy, methylsulfonyl, or dimethylaminosulfonyl or wherein $R^3$ is halogen, trifluoromethyl, cyclohexyl, dimethylaminosulfonyl, methylsulfonyl, methoxy, cyano, or lower alkyl or wherein $R^3$ is —$NR^6R^7$, where $R^6$ and $R^7$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl.

7. The compound according to claim 1, wherein Y is —C(═O)$R^2$, where $R^2$ is selected from:

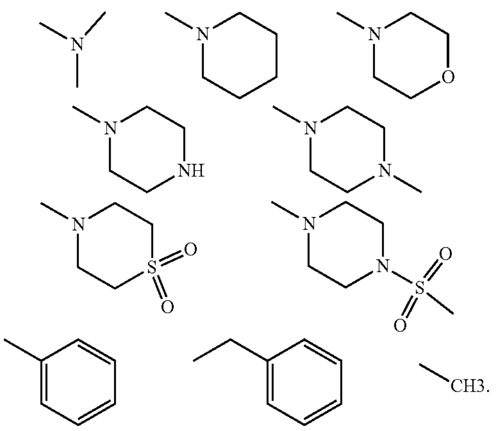

8. The compound according to claim 1, wherein U is nitrogen and T and V are carbon.

9. The compound according to claim 8, wherein X is independently selected from —$OR^1$, —$SO^2R^1$, and —C(═O)$R^1$ where $R^1$ is phenyl, thiophen-2-yl, pyridin-4-yl, pyridin-2-yl, thiazol-2-yl, or pyrimidin-2-yl, wherein said phenyl, thiophen-2-yl, pyridin-4-yl, pyridin-2-yl, thiazol-2-yl, or pyrimidin-2-yl is substituted —$CR^4R^5NH_2$ and optionally halogen or lower alkyl, where $R^4$ and $R^5$ are independently H or lower alkyl or $R^4$ and $R^5$ form a cycloalkyl or hetero-cycloalkyl; or wherein X is independently selected from —$OR^1$ or —$SO^2R^1$, where $R^1$ is phenyl where said phenyl is substituted with —$CR^4R^5NH_2$ and optionally halogen or lower alkyl, where $R^4$ and $R^5$ are independently H or lower alkyl or $R^4$ and $R^5$ form a cycloalkyl or hetero-cycloalkyl.

10. The compound according to claim 8, wherein $R^3$ is substituted or unsubstituted phenyl or unsubstituted or substituted 4-, 5-, or 6-membered heteroaryl containing 1 to 2 nitrogen atoms, wherein said substituted phenyl or 4-, 5-, or 6-membered heteroaryl containing 1 to 2 nitrogen atoms has at least one substituent being halogen, cyano, methoxy, methylsulfonyl, or dimethylaminosulfonyl; or wherein $R^3$ is halogen, trifluoromethyl, cyclohexyl, dimethylaminosulfonyl, methylsulfonyl, methoxy, cyano, or lower alkyl or, wherein $R^3$ is —$NR^6R^7$, where $R^6$ and $R^7$ form together a ($C_3$-$C_6$) hetero-cycloalkyl, wherein the ($C_3$-$C_6$) hetero-cycloalkyl is piperidinyl, piperazinyl, 4-methylpiperazin-1-yl, 4-(methylsulfonyl)piperazinyl, 4-morpholinyl, 1,1-dioxidothiomorpholinyl and optionally, wherein Z is selected from —$SO^2R^3$, —$OR^3$, and —$R^3$.

11. The compound according to claim 1, wherein $R^2$ is

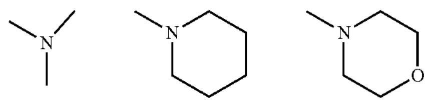

-continued

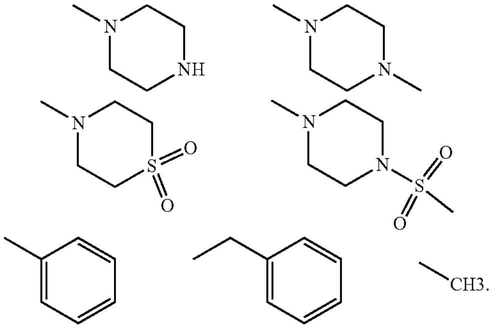

12. The compound according to claim 1, wherein the compound is one of cis-1-((5-(Aminomethyl)thiophen-2-yl)sulfonyl)-N,N-dimethyl-5-phenylpiperidine-3-carboxamide;
1-((5-(Aminomethyl)thiophen-2-yl)sulfonyl)-N,N-dimethyl-5-phenylpiperidine-3-carboxamide;
cis-(4-Fluoro-3-((-1-(methylsulfonyl)-5-phenylpiperidin-3-yl)oxy)phenyl)methanamine;
4-Fluoro-3-((-1-(methylsulfonyl)-5-phenylpiperidin-3-yl)oxy)phenylmethanamine;
1-((5-(Aminomethyl)thiophen-2-yl)sulfonyl)-5-phenylpiperidin-3-yl)(piperidin-1-yl)methanone;
cis-(1-((5-(Aminomethyl)thiophen-2-yl)sulfonyl)-5-phenylpiperidin-3-yl)(piperidin-1-yl)methanone;
(3-((-1-(Methylsulfonyl)-5-phenylpiperidin-3-yl)sulfonyl)phenyl)methanamine;
cis-(3-((1-Methylsulfonyl)-5-phenylpiperidin-3-yl)sulfonyl)phenyl)methanamine;
((3S,5S)-1-((5-(aminomethyl)thiophen-2-yl)sulfonyl)-5-phenylpiperidin-3-yl)(morpholino)methanone;
(3-((-5-(2-Fluorophenyl)-1-(methylsulfonyl)piperidin-3-yl)oxy)phenyl)methanamine;
cis-(3-((5-(2-Fluorophenyl)-1-(methylsulfonyl)piperidin-3-yl)oxy)phenyl)methanamine;
cis-(3-((5-(2-Fluorophenyl)-1-(methylsulfonyl)piperidin-3-yl)oxy)phenyl)methanamine;
((3R,5R)-1-((5-(aminomethyl)thiophen-2-yl)sulfonyl)-5-phenylpiperidin-3-yl)(morpholino)methanone;
(4-Fluoro-3-((-5-(2-fluorophenyl)-1-(methylsulfonyl)piperidin-3-yl)oxy)phenyl)methanamine;
cis-(4-Fluoro-3-((5-(2-fluorophenyl)-1-(methylsulfonyl)piperidin-3-yl)oxy)phenyl)methanamine;
1-((5-(Aminomethyl)thiophen-2-yl)sulfonyl)-5-phenylpiperidin-3-yl)(piperazin-1-yl)methanone;
cis-(1-((5-(Aminomethyl)thiophen-2-yl)sulfonyl)-5-phenylpiperidin-3-yl)(piperazin-1-yl)methanone;
(3-(3-(Aminomethyl)phenoxy)-5-phenylpiperidin-1-yl)(1,1-dioxidothiomorpholino)methanone;
cis-(3-(3-(Aminomethyl)phenoxy)-5-phenylpiperidin-1-yl)(1,1-dioxidothiomorpholino)methanone;
1-((5-(Aminomethyl)thiophen-2-yl)sulfonyl)-5-phenylpiperidin-3-yl)(4-methylpiperazin-1-yl)methanone;
cis-(1-((5-(Aminomethyl)thiophen-2-yl)sulfonyl)-5-phenylpiperidin-3-yl)(4-methylpiperazin-1-yl)methanone;
3-(3-(Aminomethyl)phenoxy)-5-phenylpiperidin-1-yl)(morpholino)methanone;
cis-3-((3-(Aminomethyl)phenyl)sulfonyl)-N,N-dimethyl-5-phenylpiperidine-1-carboxamide;
4-((-5-(Methylsulfonyl)-1-phenylpiperidin-3-yl)oxy)phenyl)methanamine;
cis-(4-((-5-(Methylsulfonyl)-1-phenylpiperidin-3-yl)oxy)phenyl)methanamine
3-((3-(Aminomethyl)phenyl)sulfonyl)-N,N-dimethyl-5-phenylpiperidine-1-carboxamide;
cis-(3-((5-(Methylsulfonyl)-1-phenylpiperidin-3-yl)oxy)phenyl)methanamine;
(3-((-5-(Methylsulfonyl)-1-phenylpiperidin-3-yl)oxy)phenyl)methanamine;
1-((5-(Aminomethyl)thiophen-2-yl)sulfonyl)-5-phenylpiperidin-3-yl)(1,1-dioxidothiomorpholino)methanone;
cis-(1-((5-(Aminomethyl)thiophen-2-yl)sulfonyl)-5-phenylpiperidin-3-yl)(1,1-dioxidothiomorpholino)methanone;
4-((-5-(Methylsulfonyl)-1-phenylpiperidin-3-yl)sulfonyl)phenyl)methanamine;
cis-(4-((5-(Methylsulfonyl)-1-phenylpiperidin-3-yl)sulfonyl)phenyl)methanamine;
trans-(1-((5-(Aminomethyl)thiophen-2-yl)sulfonyl)-5-phenylpiperidin-3-yl)(1,1-dioxidothiomorpholino)methanone;
1-((5-(aminomethyl)thiophen-2-yl)sulfonyl)-5-phenylpiperidin-3-yl)(1,1-dioxidothiomorpholino)methanone;
cis-(1-((5-(Aminomethyl)thiophen-2-yl)sulfonyl)-5-phenylpiperidin-3-yl)(4-(methylsulfonyl)piperazin-1-yl)methanone;
3-((-5-(Methylsulfonyl)-1-phenylpiperidin-3-yl)sulfonyl)phenyl)methanamine;
cis-(3-((5-(Methylsulfonyl)-1-phenylpiperidin-3-yl)sulfonyl)phenyl)methanamine;
(1-((5-(Aminomethyl)thiophen-2-yl)sulfonyl)-5-phenylpiperidin-3-yl)(4-(methylsulfonyl)piperazin-1-yl)methanone;
(4-((-1-(Methylsulfonyl)-5-phenylpiperidin-3-yl)oxy)phenyl)methanamine;
cis-(4-((1-(Methylsulfonyl)-5-phenylpiperidin-3-yl)oxy)phenyl)methanamine;
(1-((5-(Aminomethyl)thiophen-2-yl)sulfonyl)-5-phenylpiperidin-3-yl)(4-(methylsulfonyl)piperazin-1-yl)methanone;
(3-((-1-(Methylsulfonyl)-5-phenylpiperidin-3-yl)oxy)phenyl)methanamine;
cis-(3-((1-(Methylsulfonyl)-5-phenylpiperidin-3-yl)oxy)phenyl)methanamine;
(1-((3-(Aminomethyl)phenyl)sulfonyl)-5-phenylpiperidin-3-yl)(1,1-dioxidothiomorpholino)methanone;
cis-(1-((3-(Aminomethyl)phenyl)sulfonyl)-5-phenylpiperidin-3-yl)(1,1-dioxidothiomorpholino)methanone;
(4-((-1-(Methylsulfonyl)-5-phenylpiperidin-3-yl)sulfonyl)phenyl)methanamine;
cis-(4-((1-(Methylsulfonyl)-5-phenylpiperidin-3-yl)sulfonyl)phenyl)methanamine;
1-((3-(Aminomethyl)phenyl)sulfonyl)-5-phenylpiperidin-3-yl)(4-(methylsulfonyl)piperazin-1-yl)methanone;
cis-(1-((3-(Aminomethyl)phenyl)sulfonyl)-5-phenylpiperidin-3-yl)(4-(methylsulfonyl)piperazin-1-yl)methanone;
trans-(1-((3-(Aminomethyl)phenyl)sulfonyl)-5-phenylpiperidin-3-yl)(4-(methylsulfonyl)piperazin-1-yl)methanone;
(3-((-5-(Methylsulfonyl)-1-phenylpiperidin-3-yl)sulfonyl)phenyl)methanamine;
trans-(3-((5-(Methylsulfonyl)-1-phenylpiperidin-3-yl)sulfonyl)phenyl)methanamine;
(3-(3-(Aminomethyl)phenoxy)-5-phenylpiperidin-1-yl)(1,1-dioxidothiomorpholino)methanone;
trans-(3-(3-(Aminomethyl)phenoxy)-5-phenylpiperidin-1-yl)(1,1-dioxidothiomorpholino)methanone;

(1-((3-(Aminomethyl)phenyl)sulfonyl)-5-phenylpiperidin-3-yl)(1,1-dioxidothiomorpholino)methanone;

trans-(1-((3-(Aminomethyl)phenyl)sulfonyl)-5-phenylpiperidin-3-yl)(1,1-dioxidothiomorpholino)methanone;

1-((5-(Aminomethyl)thiophen-2-yl)sulfonyl)-5-(2-fluorophenyl)piperidin-3-yl)(4-(methylsulfonyl)piperazin-1-yl)methanone;

cis-(1-((5-(Aminomethyl)thiophen-2-yl)sulfonyl)-5-(2-fluorophenyl)piperidin-3-yl)(4-(methylsulfonyl)piperazin-1-yl)methanone;

(4-Fluoro-3-((-1-(methylsulfonyl)-5-phenylpiperidin-3-yl)oxy)phenyl)methanamine;

trans-(4-Fluoro-3-((-1-(methylsulfonyl)-5-phenylpiperidin-3-yl)oxy)phenyl)methanamine;

(3-((-1-(2-Fluorophenyl)-5-(methylsulfonyl)piperidin-3-yl)sulfonyl)phenyl)methanamine;

cis-(3-((1-(2-Fluorophenyl)-5-(methylsulfonyl)piperidin-3-yl)sulfonyl)phenyl)methanamine;

(4-Fluoro-3-((-5-(2-fluorophenyl)-1-(methylsulfonyl)piperidin-3-yl)oxy)phenyl)methanamine;

trans-(4-Fluoro-3-((5-(2-fluorophenyl)-1-(methylsulfonyl)piperidin-3-yl)oxy)phenyl)methanamine;

(1-((3-(Aminomethyl)phenyl)sulfonyl)-5-(trifluoromethyl)piperidin-3-yl)(morpholino)methanone;

cis-(1-((3-(Aminomethyl)phenyl)sulfonyl)-5-(trifluoromethyl)piperidin-3-yl)(morpholino)methanone;

3-((3-(Aminomethyl)phenyl)sulfonyl)-N,N-dimethyl-5-phenylpiperidine-1-carboxamide;

trans-3-((3-(Aminomethyl)phenyl)sulfonyl)-N,N-dimethyl-5-phenylpiperidine-1-carboxamide;

(1-((3-(Aminomethyl)phenyl)sulfonyl)-5-(trifluoromethyl)piperidin-3-yl)(1,1-dioxidothiomorpholino) methanone;

cis-(1-((3-(Aminomethyl)phenyl)sulfonyl)-5-(trifluoromethyl)piperidin-3-yl)(1,1-dioxidothiomorpholino) methanone;

(cis) (1-((5-(Aminomethyl)thiazol-2-yl)sulfonyl)-5-phenylpiperidin-3-yl)(morpholino) methanone;

(1-((5-(Aminomethyl)thiazol-2-yl)sulfonyl)-5-phenylpiperidin-3-yl)(morpholino) methanone;

(1-((3-(1-Aminoethyl)phenyl)sulfonyl)-5-phenylpiperidin-3-yl)(1,1-dioxidothiomorpholino)methanone;

trans-(1-((3-(1-Aminoethyl)phenyl)sulfonyl)-5-phenylpiperidin-3-yl)(1,1-dioxidothiomorpholino)methanone (1-((3-(1-Aminoethyl)phenyl)sulfonyl)-5-phenylpiperidin-3-yl)(morpholino)methanone;

cis-(1-((3-(1-Aminoethyl)phenyl)sulfonyl)-5-phenylpiperidin-3-yl)(morpholino)methanone;

trans-(1-((3-(1-Aminoethyl)phenyl)sulfonyl)-5-phenylpiperidin-3-yl)(morpholino)methanone ((3R,5S)-1-((3-(1-aminoethyl)phenyl)sulfonyl)-5-phenylpiperidin-3-yl)(morpholino)methanone;

(cis) (1-((3-(Aminomethyl)phenyl)sulfonyl)-5-(tert-butyl)piperidin-3-yl)(morpholino) methanone;

(1-((3-(Aminomethyl)phenyl)sulfonyl)-5-(tert-butyl)piperidin-3-yl)(morpholino) methanone;

(1-((3-(Aminomethyl)phenyl)sulfonyl)-5-(trifluoromethyl)piperidin-3-yl)(morpholino)methanone;

trans-(1-((3-(Aminomethyl)phenyl)sulfonyl)-5-(trifluoromethyl)piperidin-3-yl)(morpholino)methanone;

(1-((5-(Aminomethyl)thiazol-2-yl)sulfonyl)-5-phenylpiperidin-3-yl)(4-(methylsulfonyl)piperazin-1-yl)methanone;

cis-(1-((5-(Aminomethyl)thiazol-2-yl)sulfonyl)-5-phenylpiperidin-3-yl)(4-(methylsulfonyl)piperazin-1-yl) methanone (1-((6-(aminomethyl)pyrid-2-yl)sulfonyl)-5-phenylpiperidin-3-yl)(thiomorpholino-1,1-dioxide)methanone;

cis-(1-((6-(Aminomethyl)pyridin-2-yl)sulfonyl)-5-phenylpiperidin-3-yl)(1,1-dioxidothiomorpholino)methanone (1-((6-(aminomethyl)pyrid-2-yl)sulfonyl)-5-phenylpiperidin-3-yl)(morpholino)methanone;

cis-(1-((6-(Aminomethyl)pyrid-2-yl)sulfonyl)-5-phenylpiperidin-3-yl)(morpholino)methanone (1-((5-(Aminomethyl)thiazol-2-yl)sulfonyl)-5-phenylpiperidin-3-yl)(morpholino)methanone;

trans-(1-((5-(Aminomethyl)thiazol-2-yl)sulfonyl)-5-phenylpiperidin-3-yl)(morpholino)methanone (1-((5-(Aminomethyl)thiazol-2-yl)sulfonyl)-5-phenylpiperidin-3-yl)(1,1-dioxidothiomorpholino)methanone;

cis-(1-((5-(Aminomethyl)thiazol-2-yl)sulfonyl)-5-phenylpiperidin-3-yl)(1,1-dioxidothiomorpholino)methanone cis-(1-((2-(aminomethyl)pyridin-4-yl)sulfonyl)-5-phenylpiperidin-3-yl)(1,1-dioxidothiomorpholino)methanone;

trans-(1-((2-(aminomethyl)pyridin-4-yl)sulfonyl)-5-phenylpiperidin-3-yl)(1,1-dioxidothiomorpholino)methanone;

(1-((2-(aminomethyl)pyridin-4-yl)sulfonyl)-5-phenylpiperidin-3-yl)(1,1-dioxidothiomorpholino)methanone;

cis-(1-((5-(aminomethyl)pyridin-3-yl)sulfonyl)-5-phenylpiperidin-3-yl)(morpholino)methanone;

(1-((5-(aminomethyl)pyridin-3-yl)sulfonyl)-5-phenylpiperidin-3-yl)(morpholino)methanone;

cis-(1-((5-(aminomethyl)pyridin-3-yl)sulfonyl)-5-phenylpiperidin-3-yl)(1,1-dioxidothiomorpholino)methanone;

(1-((5-(aminomethyl)pyridin-3-yl)sulfonyl)-5-phenylpiperidin-3-yl)(1,1-dioxidothiomorpholino)methanone;

cis-(1-((4-(aminomethyl)pyridin-2-yl)sulfonyl)-5-phenylpiperidin-3-yl)(1,1-dioxidothiomorpholino)methanone;

(1-((4-(aminomethyl)pyridin-2-yl)sulfonyl)-5-phenylpiperidin-3-yl)(1,1-dioxidothiomorpholino)methanone;

cis-1-((4-(aminomethyl)pyridin-2-yl)sulfonyl)-5-cyclohexyl-N,N-dimethylpiperidine-3-carboxamide;

1-((4-(aminomethyl)pyridin-2-yl)sulfonyl)-5-cyclohexyl-N,N-dimethylpiperidine-3-carboxamide;

cis-(1-((4-(aminomethyl)pyridin-2-yl)sulfonyl)-5-cyclohexylpiperidin-3-yl)(morpholino)methanone;

(1-((4-(aminomethyl)pyridin-2-yl)sulfonyl)-5-cyclohexylpiperidin-3-yl)(morpholino)methanone;

cis-(1-((4-(aminomethyl)pyridin-2-yl)sulfonyl)-5-cyclohexylpiperidin-3-yl)(1,1-dioxidothiomorpholino) methanone;

(1-((4-(aminomethyl)pyridin-2-yl)sulfonyl)-5-cyclohexylpiperidin-3-yl)(1,1-dioxidothiomorpholino)methanone;

trans-(1-((6-(aminomethyl)pyridin-2-yl)sulfonyl)-5-phenylpiperidin-3-yl)(morpholino)methanone;

(1-((6-(aminomethyl)pyridin-2-yl)sulfonyl)-5-phenylpiperidin-3-yl)(morpholino)methanone;

trans-(1-((6-(aminomethyl)pyridin-2-yl)sulfonyl)-5-phenylpiperidin-3-yl)(1,1-dioxidothiomorpholino)methanone;

(1-((6-(aminomethyl)pyridin-2-yl)sulfonyl)-5-phenylpiperidin-3-yl)(1,1-dioxidothiomorpholino)methanone;

trans-(1-((6-(Aminomethyl)pyridin-2-yl)sulfonyl)-5-phenylpiperidin-3-yl)(4-(methylsulfonyl)piperazin-1-yl) methanone (1-((6-(aminomethyl)pyridin-2-yl)sulfonyl)-5-phenylpiperidin-3-yl)(4-(methylsulfonyl)piperazin-1-yl)methanone;

trans-(1-((5-(aminomethyl)thiazol-2-yl)sulfonyl)-5-phenylpiperidin-3-yl)(1,1-dioxidothiomorpholino)methanone;

(1-((5-(aminomethyl)thiazol-2-yl)sulfonyl)-5-phenylpiperidin-3-yl)(1,1-dioxidothiomorpholino)methanone;

trans-(1-((5-(aminomethyl)thiazol-2-yl)sulfonyl)-5-phenylpiperidin-3-yl)(4-(methylsulfonyl)piperazin-1-yl) methanone;

cis-(1-((5-(aminomethyl)thiazol-2-yl)sulfonyl)-5-phenylpiperidin-3-yl)(4-(methylsulfonyl)piperazin-1-yl) methanone (1-((5-(aminomethyl)thiazol-2-yl)sulfonyl)-5-phenylpiperidin-3-yl)(4-(methylsulfonyl)piperazin-1-yl)methanone;

cis-(5-((3-(aminomethyl)phenyl)sulfonyl)-1-cyclohexyl-N,N-dimethylpiperidine-3-carboxamide;

(5-((3-(aminomethyl)phenyl)sulfonyl)-1-cyclohexyl-N,N-dimethylpiperidine-3-carboxamide;

trans-5-((3-(aminomethyl)phenyl)sulfonyl)-1-cyclohexyl-N,N-dimethylpiperidine-3-carboxamide;

5-((3-(aminomethyl)phenyl)sulfonyl)-1-cyclohexyl-N,N-dimethylpiperidine-3-carboxamide;

trans-(5-((3-(aminomethyl)phenyl)sulfonyl)-1-cyclohexylpiperidin-3-yl)(morpholino)methanone;

(5-((3-(aminomethyl)phenyl)sulfonyl)-1-cyclohexylpiperidin-3-yl)(morpholino)methanone;

cis-(5-((3-(Aminomethyl)phenyl)sulfonyl)-1-cyclohexylpiperidin-3-yl)(morpholino)methanone;

cis-(5-((3-(Aminomethyl)phenyl)sulfonyl)-1-cyclohexylpiperidin-3-yl)(1,1-dioxidothiomorpholino)methanone (5-((3-(Aminomethyl)phenyl)sulfonyl)-1-cyclohexylpiperidin-3-yl)(1,1-dioxidothiomorpholino)methanone cis 1-((3-(aminomethyl)phenyl)sulfonyl)-5-(1,3-dioxan-2-yl)piperidin-3-yl)(1,1-dioxidothiomorpholino) methanone;

1-((3-(aminomethyl)phenyl)sulfonyl)-5-(1,3-dioxan-2-yl)piperidin-3-yl)(1,1-dioxidothiomorpholino)methanone;

cis 3-((3-(aminomethyl)phenyl)sulfonyl)-5-cyclohexyl-N,N-dimethylpiperidine-1-carboxamide;

3-((3-(aminomethyl)phenyl)sulfonyl)-5-cyclohexyl-N,N-dimethylpiperidine-1-carboxamide;

cis (3-((3-(aminomethyl)phenyl)sulfonyl)-5-cyclohexylpiperidin-1-yl)(1,1-dioxidothiomorpholino)methanone;

(3-((3-(aminomethyl)phenyl)sulfonyl)-5-cyclohexylpiperidin-1-yl)(1,1-dioxidothiomorpholino)methanone;

trans-(3-((3-(aminomethyl)phenyl)sulfonyl)-5-cyclohexylpiperidin-1-yl)(1,1-dioxidothiomorpholino)methanone;

1'-((4-(aminomethyl)pyridin-2-yl)sulfonyl)-[1,3'-bipiperidin]-5'-yl)(4-(methylsulfonyl)piperazin-1-yl)methanone;

cis-1'-((4-(aminomethyl)pyridin-2-yl)sulfonyl)-[1,3'-bipiperidin]-5'-yl)(4 (methylsulfonyl)piperazin-1-yl) methanone;

cis-(1'-((4-(Aminomethyl)pyridin-2-yl)sulfonyl)-[1,3'-bipiperidin]-5'-yl)(morpholino)methanone;

(1'-((4-(Aminomethyl)pyridin-2-yl)sulfonyl)-[1,3'-bipiperidin]-5'-yl)(morpholino)methanone;

cis-(1'-((4-(Aminomethyl)pyridin-2-yl)sulfonyl)-[1,3'-bipiperidin]-5'-yl)(1,1-dioxidothiomorpholino)methanone;

(1'-((4-(Aminomethyl)pyridin-2-yl)sulfonyl)-[1,3'-bipiperidin]-5'-yl)(1,1-dioxidothiomorpholino)methanone;

cis-(1'-((4-(Aminomethyl)pyridin-2-yl)sulfonyl)-[1,3'-bipiperidin]-5'-yl)(4-methylpiperazin-1-yl)methanone;

(1'-((4-(Aminomethyl)pyridin-2-yl)sulfonyl)-[1,3'-bipiperidin]-5'-yl)(4-methylpiperazin-1-yl)methanone;

cis-(1-((4-(Aminomethyl)pyridin-2-yl)sulfonyl)-5-morpholinopiperidin-3-yl)(morpholino)methanone;

(1-((4-(Aminomethyl)pyridin-2-yl)sulfonyl)-5-morpholinopiperidin-3-yl)(morpholino)methanone;

cis-(1-((4-(Aminomethyl)pyridin-2-yl)sulfonyl)-5-morpholinopiperidin-3-yl)(1,1-dioxidothiomorpholino) methanone;

(1-((4-(Aminomethyl)pyridin-2-yl)sulfonyl)-5-morpholinopiperidin-3-yl)(1,1-dioxidothiomorpholino) methanone;

cis-(1-((4-(Aminomethyl)pyridin-2-yl)sulfonyl)-5-morpholinopiperidin-3-yl)(4-(methylsulfonyl)piperazin-1-yl)methanone;

(1-((4-(Aminomethyl)pyridin-2-yl)sulfonyl)-5-morpholinopiperidin-3-yl)(4-(methylsulfonyl)piperazin-1-yl)methanone;

cis-1'-((4-(Aminomethyl)pyridin-2-yl)sulfonyl)-5'-(morpholine-4-carbonyl)-[1,3'-bipiperidin]-2-one;

1'-((4-(Aminomethyl)pyridin-2-yl)sulfonyl)-5'-(morpholine-4-carbonyl)-[1,3'-bipiperidin]-2-one;

cis-1'-((4-(Aminomethyl)pyridin-2-yl)sulfonyl)-5'-(1,1-dioxidothiomorpholine-4-carbonyl)-[1,3'-bipiperidin]-2-one;

1'-((4-(Aminomethyl)pyridin-2-yl)sulfonyl)-5'-(1,1-dioxidothiomorpholine-4-carbonyl)-[1,3'-bipiperidin]-2-one;

cis-1'-((4-(Aminomethyl)pyridin-2-yl)sulfonyl)-5'-(4-(methylsulfonyl)piperazine-1-carbonyl)-[1,3'-bipiperidin]-2-one; or 1'-((4-(Aminomethyl)pyridin-2-yl)sulfonyl)-5'-(4-(methylsulfonyl)piperazine-1-carbonyl)-[1,3'-bipiperidin]-2-one;

or a pharmaceutically acceptable salt or hydrate thereof and/or stereoisomer or racemic mixture thereof.

13. A pharmaceutical composition comprising a lysyl oxidase (LOX) enzyme-inhibiting compound according to claim 1 in a pharmaceutically acceptable carrier.

14. A method of inhibiting one or more enzymes of the family of lysyl oxidases, the method comprising administering an effective amount of a lysyl oxidase (LOX) enzyme-inhibiting compound according to claim 1.

15. The method according to claim 14, wherein the compound selectively inhibits 1 to 5 members of the LOX family of enzymes selected from LOX, LOXL1, LOXL2, LOXL3, or LOXL4.

16. The method according to claim 14, wherein the compound selectively or specifically inhibits LOX or LOXL2.

* * * * *